United States Patent
Sheps et al.

(10) Patent No.: US 11,890,190 B2
(45) Date of Patent: Feb. 6, 2024

(54) LOCATION INDICATION SYSTEM FOR IMPLANT-DELIVERY TOOL

(71) Applicant: Edwards Lifesciences Innovation (Israel) Ltd., Caesarea (IL)

(72) Inventors: Tal Sheps, Givat Shmuel (IL); Tal Hammer, Ramat Gan (IL); Tal Reich, Moledet (IL); Ehud Aviv, Costa Mesa, CA (US); Amir Gross, Tel Aviv-Jaffa (IL); Yaron Herman, Givat Ada (IL); Alexei Koifman, Melbourne (AU); Yuval Zipory, Modi'in (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 585 days.

(21) Appl. No.: 16/859,991

(22) Filed: Apr. 27, 2020

(65) Prior Publication Data

US 2020/0253730 A1  Aug. 13, 2020

Related U.S. Application Data

(60) Continuation of application No. 15/955,421, filed on Apr. 17, 2018, now Pat. No. 10,893,939, which is a
(Continued)

(51) Int. Cl.
*A61F 2/24* (2006.01)
*A61M 25/01* (2006.01)
(Continued)

(52) U.S. Cl.
CPC .......... *A61F 2/2436* (2013.01); *A61B 17/068* (2013.01); *A61F 2/2427* (2013.01);
(Continued)

(58) Field of Classification Search
CPC .......... Y02E 60/36; A61M 2025/0681; A61M 2025/015; A61M 29/00; A61M 25/0662;
(Continued)

(56) References Cited

U.S. PATENT DOCUMENTS

| | | |
|---|---|---|
| 3,604,488 A | 9/1971 | Wishart et al. |
| 3,656,185 A | 4/1972 | Carpentier |

(Continued)

FOREIGN PATENT DOCUMENTS

| | | |
|---|---|---|
| CN | 113331995 A | 9/2021 |
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Jocelin C Tanner
(74) *Attorney, Agent, or Firm* — Anya Adams

(57) ABSTRACT

A catheter, advanced toward an anatomical site, has a proximal end and a steerable distal end. An anchor is advanced through the catheter. An anchor driver drives the anchor out of the catheter's distal end, anchoring the anchor at the site. A first constraining member engages tissue, and inhibits, after the anchor has been driven out of the catheter and before the anchoring, movement of at least the anchor driver's distal end, on a first axis between the anchor driver's distal end and a site at which the first constraining member engages the tissue. A second constraining member inhibits, after the anchor has been driven out of the catheter and before the anchoring, movement of at least the anchor driver's distal end, on a second axis. Other embodiments are also described.

31 Claims, 65 Drawing Sheets

Related U.S. Application Data division of application No. 14/437,373, filed as application No. PCT/IL2013/050860 on Oct. 23, 2013, now Pat. No. 9,949,828.

(60) Provisional application No. 61/820,979, filed on May 8, 2013, provisional application No. 61/745,848, filed on Dec. 26, 2012, provisional application No. 61/717,303, filed on Oct. 23, 2012.

(51) Int. Cl.

| | | |
|---|---|---|
| *A61M 25/04* | (2006.01) | |
| *A61B 17/068* | (2006.01) | |
| *A61M 25/06* | (2006.01) | |
| *A61M 29/00* | (2006.01) | |
| *A61B 17/064* | (2006.01) | |
| *A61B 17/00* | (2006.01) | |
| *A61B 90/00* | (2016.01) | |
| *A61B 34/20* | (2016.01) | |
| *A61B 17/04* | (2006.01) | |

(52) U.S. Cl.
CPC .......... *A61F 2/2445* (2013.01); *A61F 2/2466* (2013.01); *A61M 25/0133* (2013.01); *A61M 25/0147* (2013.01); *A61M 25/04* (2013.01); *A61B 2017/00039* (2013.01); *A61B 2017/00044* (2013.01); *A61B 2017/00199* (2013.01); *A61B 2017/00327* (2013.01); *A61B 2017/00398* (2013.01); *A61B 2017/00455* (2013.01); *A61B 2017/00477* (2013.01); *A61B 2017/0409* (2013.01); *A61B 2017/0649* (2013.01); *A61B 2034/2051* (2016.02); *A61B 2090/066* (2016.02); *A61B 2090/0807* (2016.02); *A61B 2090/0811* (2016.02); *A61B 2090/3966* (2016.02); *A61M 25/06* (2013.01); *A61M 25/0662* (2013.01); *A61M 29/00* (2013.01); *A61M 2025/015* (2013.01); *A61M 2025/0681* (2013.01); *Y02E 60/36* (2013.01)

(58) Field of Classification Search
CPC .. A61M 25/06; A61M 25/04; A61M 25/0147; A61M 25/0133; A61F 2/2466; A61F 2/2445; A61F 2/2436; A61F 2/2427; A61B 34/20; A61B 17/068; A61B 2090/3966; A61B 2090/0811; A61B 2090/0807; A61B 2034/2051; A61B 2017/0649; A61B 2017/0409; A61B 2017/0477; A61B 2017/00455; A61B 2017/00398; A61B 2017/00327; A61B 2017/00199; A61B 2017/00044; A61B 2017/00039

See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,501,683 A | 3/1996 | Trott |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,674,279 A | 10/1997 | Wright et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,782,862 A | 7/1998 | Bonutti |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A * | 7/2000 | Altman .............. A61B 18/1492 606/41 |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |

(56) References Cited

U.S. PATENT DOCUMENTS

| | | |
|---|---|---|
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |

(56) References Cited

U.S. PATENT DOCUMENTS

| | | |
|---|---|---|
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,545,553 B2 | 10/2013 | Zipory et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |

(56) References Cited

U.S. PATENT DOCUMENTS

| | | |
|---|---|---|
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,724,084 B2 | 8/2017 | Groothuis et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0095139 A1* | 7/2002 | Keogh ............... A61B 17/0206 606/1 |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0208208 A1 | 11/2003 | Chu |
| 2003/0229350 A1 | 12/2003 | Kay |
| 2003/0229395 A1 | 12/2003 | Cox |
| 2003/0233142 A1 | 12/2003 | Morales et al. |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0220593 A1 | 11/2004 | Greenhalgh |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0187613 A1 | 8/2005 | Bolduc et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0245821 A1* | 11/2005 | Govari ............... A61B 34/20 600/429 |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0173251 A1* | 8/2006 | Govari ............... A61B 5/063 600/306 |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |

(56) References Cited

U.S. PATENT DOCUMENTS

| | | |
|---|---|---|
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0197858 A1 | 8/2007 | Goldfarb et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0265491 A1* | 11/2007 | Krag .............. A61B 34/74 600/37 |
| 2007/0270679 A1 | 11/2007 | Nguyen et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0082132 A1* | 4/2008 | Annest .............. A61N 1/3987 607/4 |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0187216 A1 | 7/2009 | Schmieding et al. |
| 2009/0222083 A1 | 9/2009 | Nguyen et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168827 A1 | 7/2010 | Schultz |
| 2010/0168845 A1 | 7/2010 | Wright |
| 2010/0174358 A1 | 7/2010 | Rabkin et al. |

(56) References Cited

U.S. PATENT DOCUMENTS

| | | |
|---|---|---|
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280604 A1 | 11/2010 | Zipory et al. |
| 2010/0280605 A1* | 11/2010 | Hammer ............ A61B 17/0401 623/2.11 |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1* | 5/2011 | Miller .................. A61B 17/068 623/2.17 |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0022557 A1 | 1/2012 | Cabiri et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0101571 A1 | 4/2012 | Thambar et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0197388 A1* | 8/2012 | Khairkhahan ........ A61F 2/2466 623/2.11 |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351906 A1 | 12/2015 | Hammer et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0262755 A1 | 9/2016 | Zipory et al. |

(56) References Cited

U.S. PATENT DOCUMENTS

| | | |
|---|---|---|
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2017/0325959 A1 | 11/2017 | Sheps et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | 2010085649 A1 | 7/2010 |
| WO | 2011051942 A1 | 5/2011 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

Odell JA et al., "Early Results o4yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

(56) References Cited

OTHER PUBLICATIONS

Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

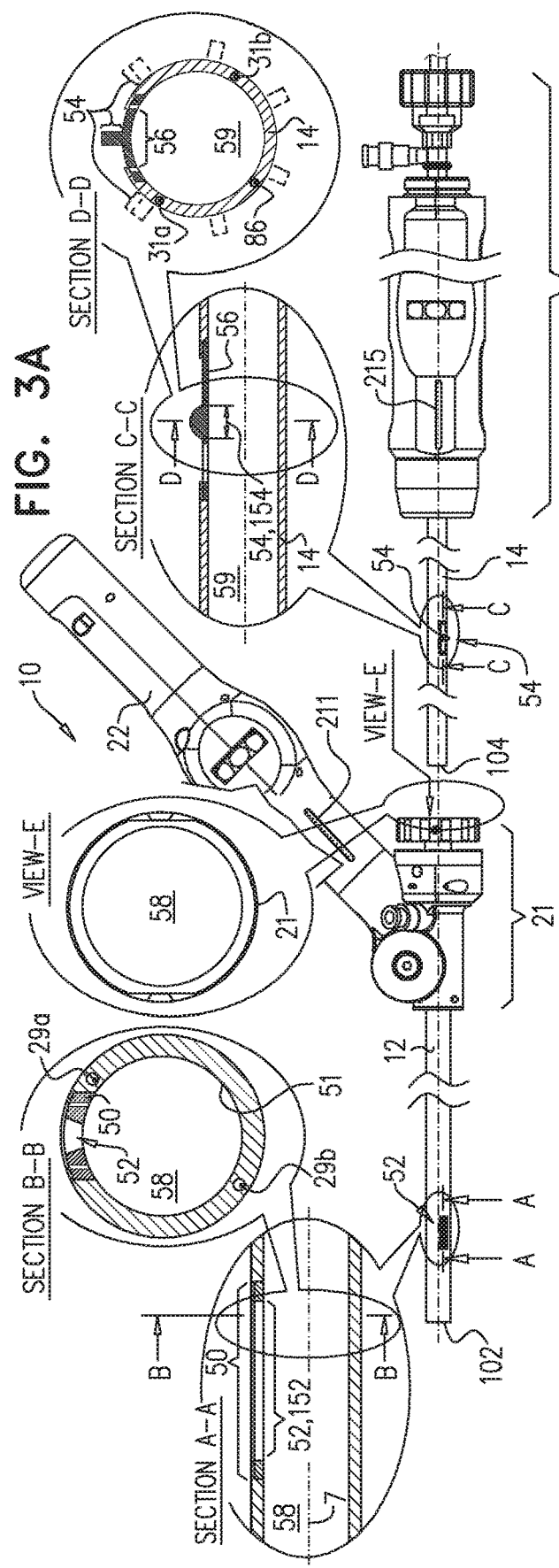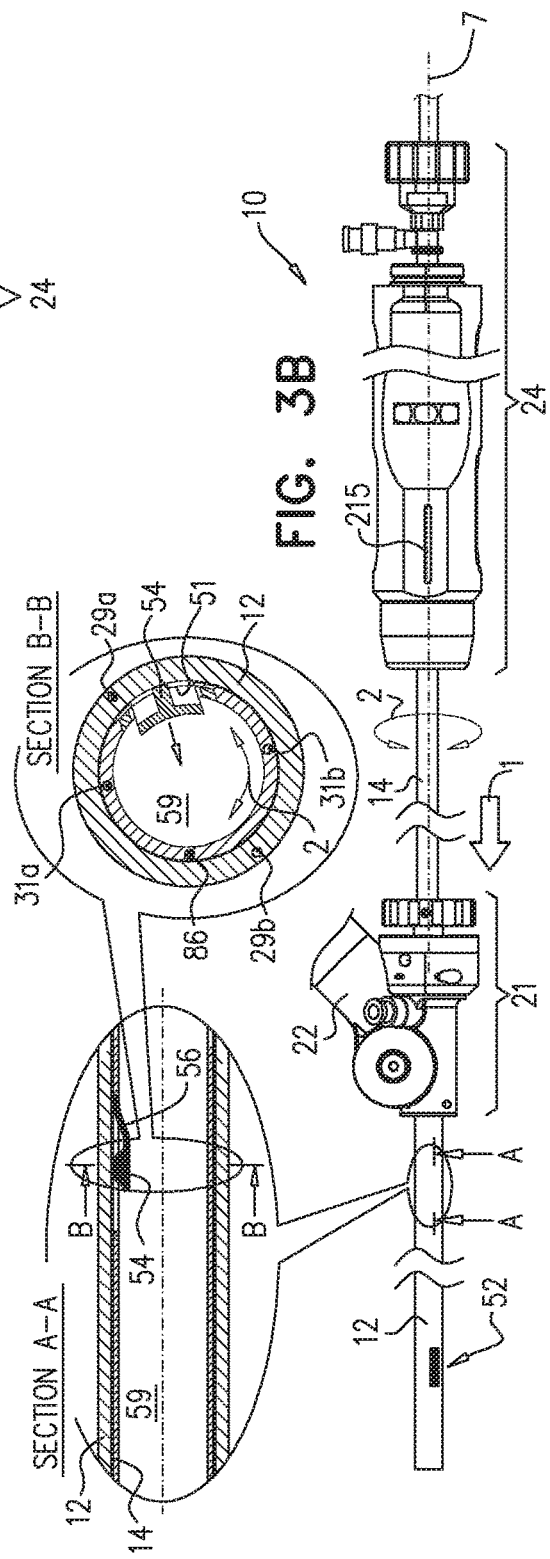

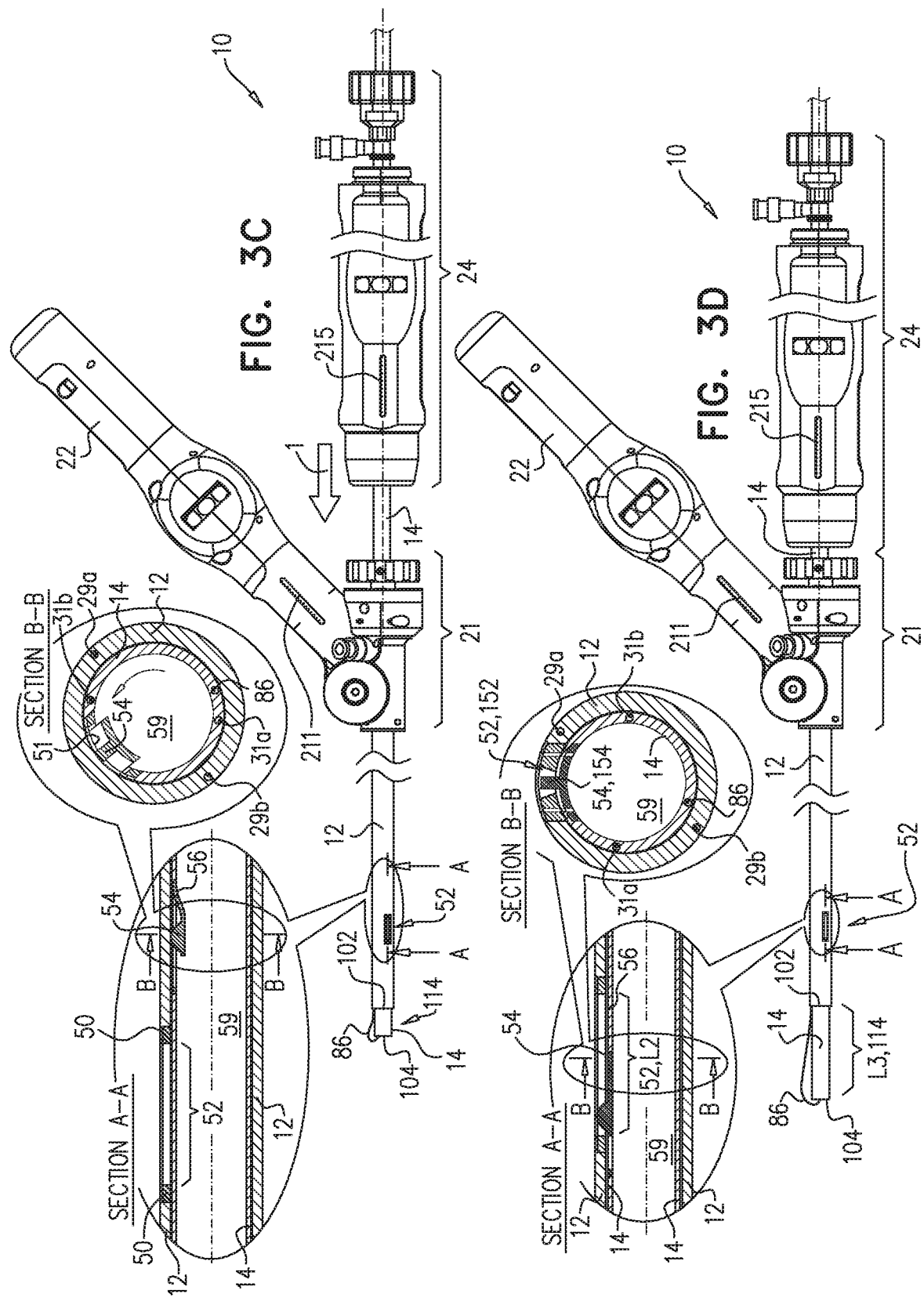

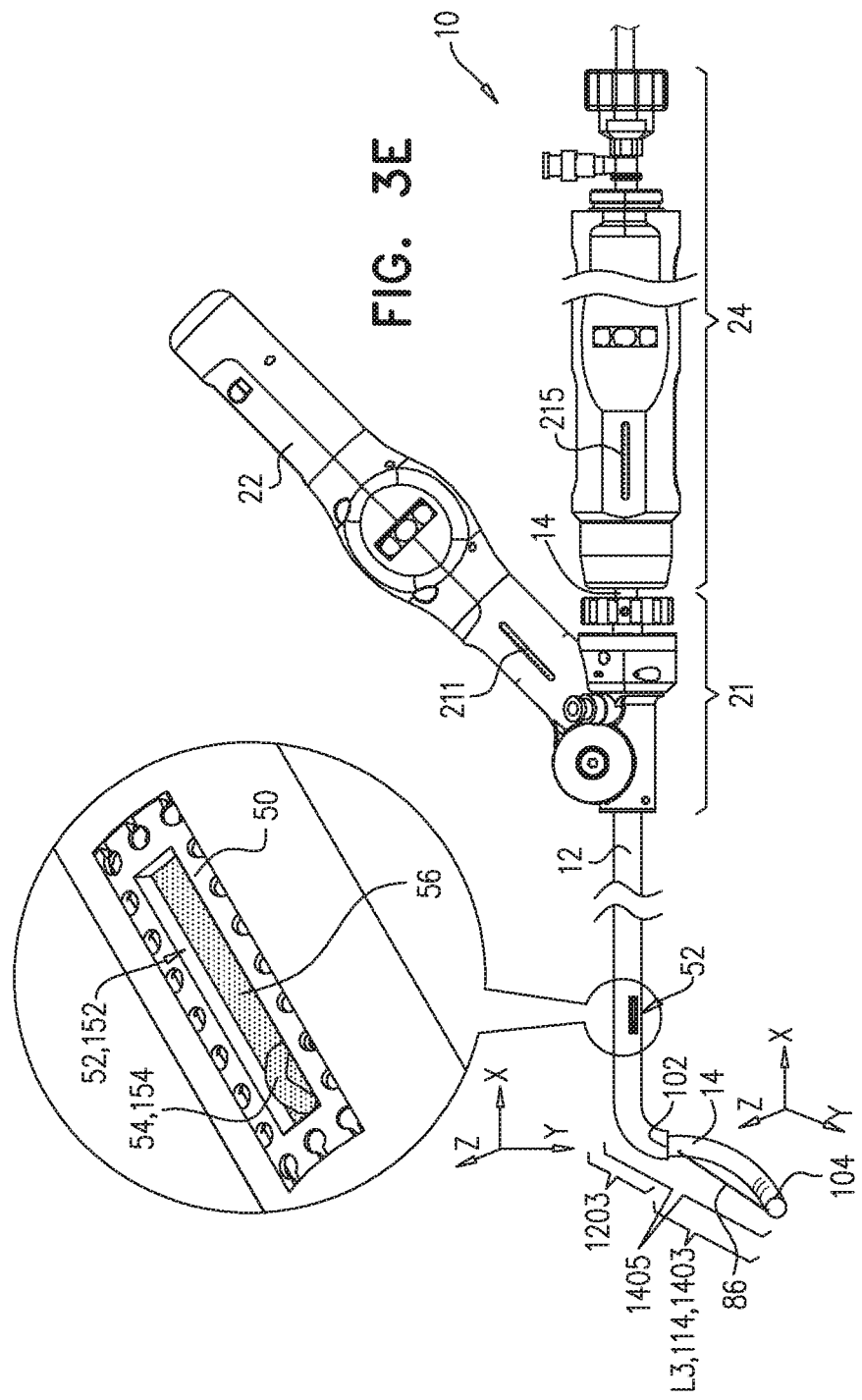

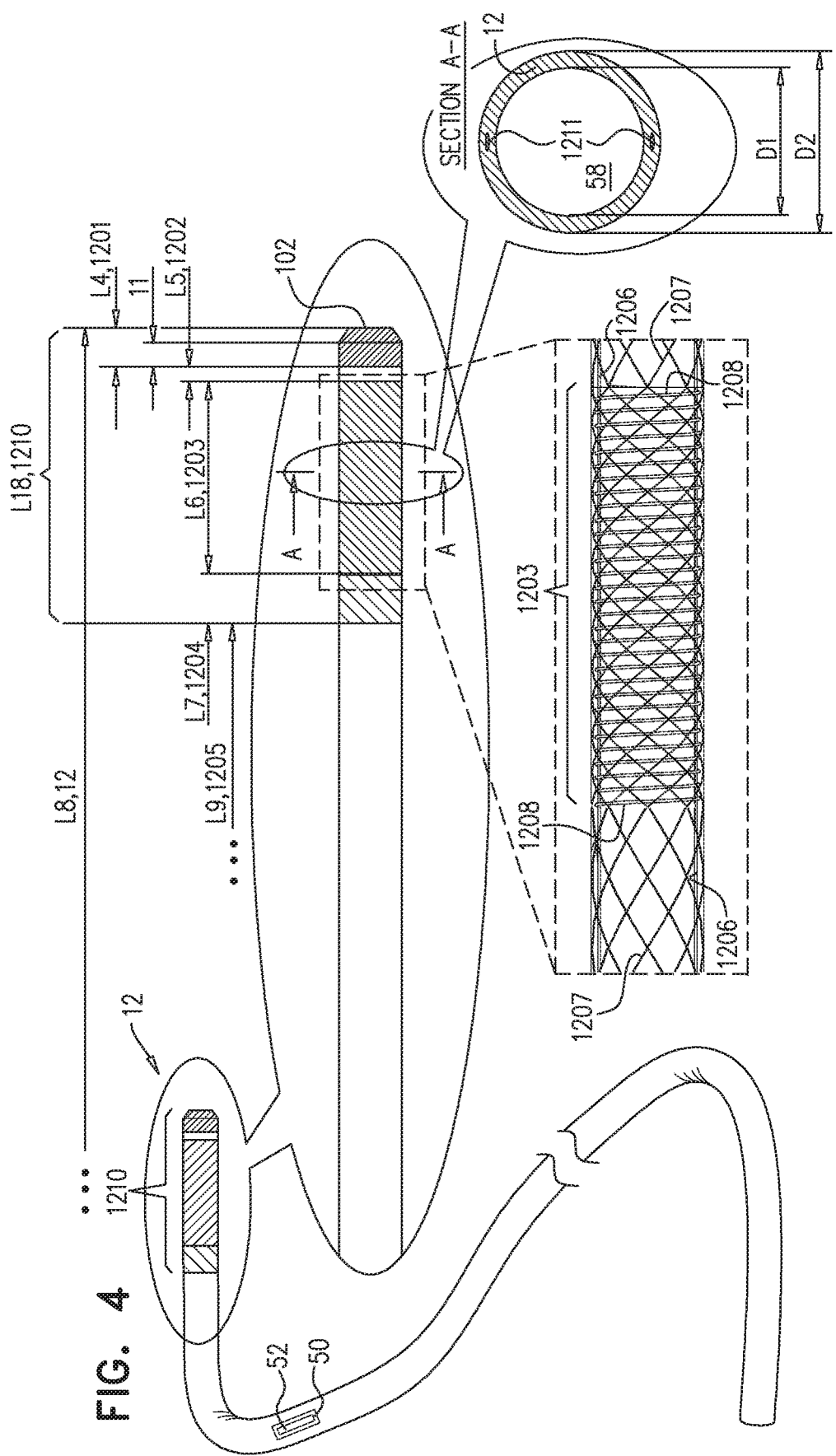

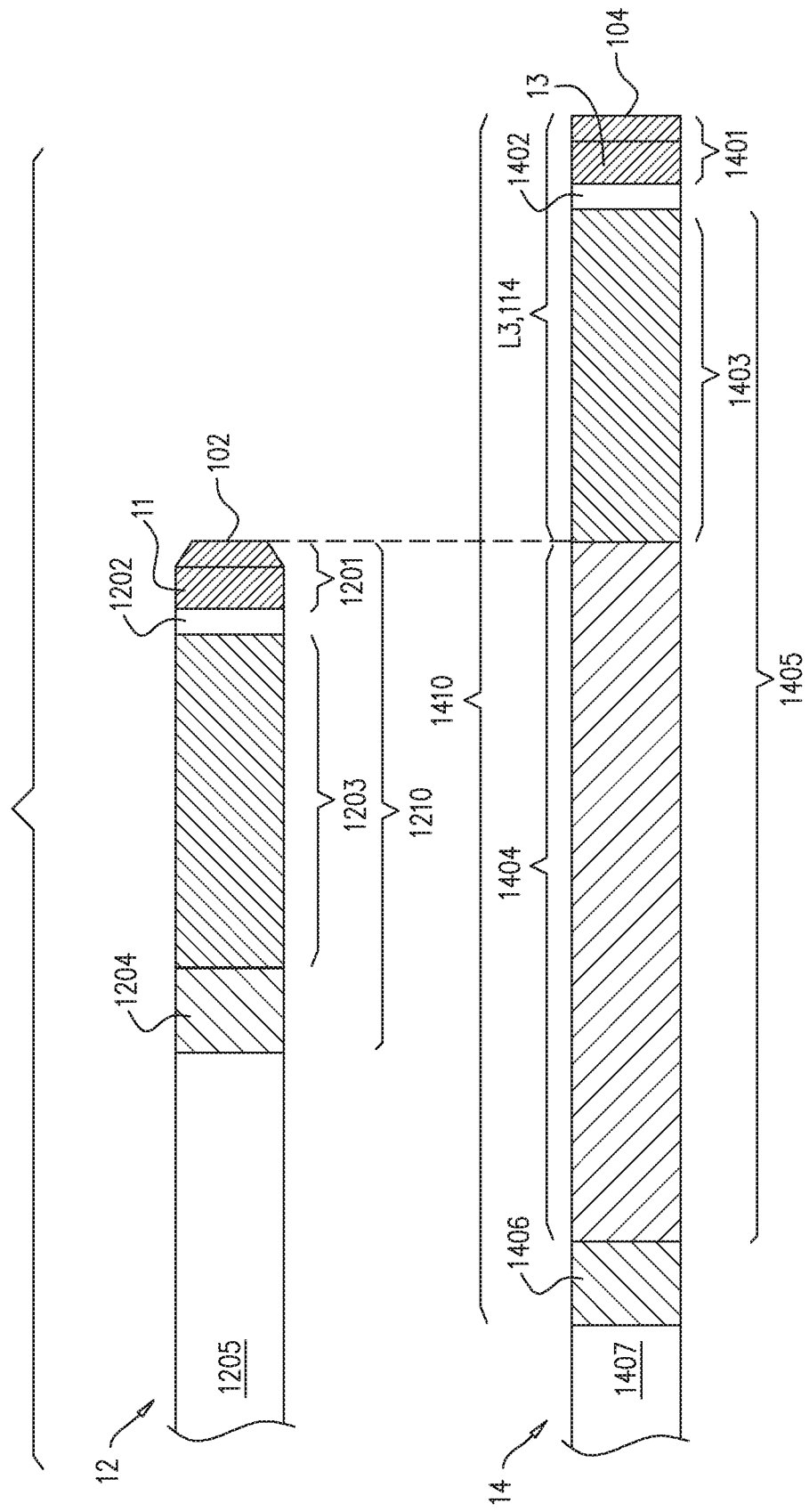

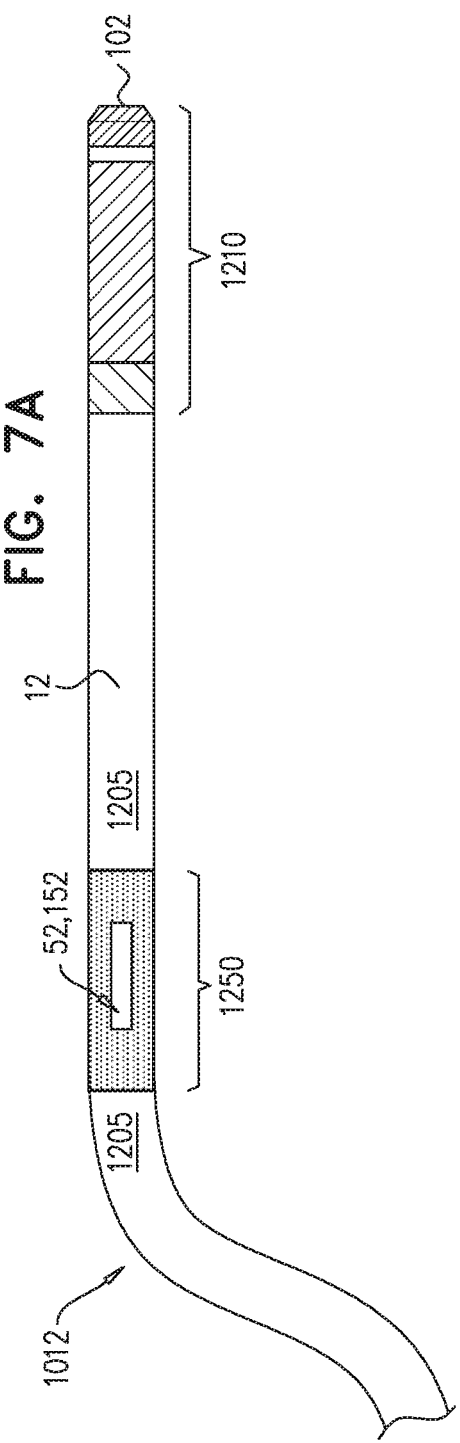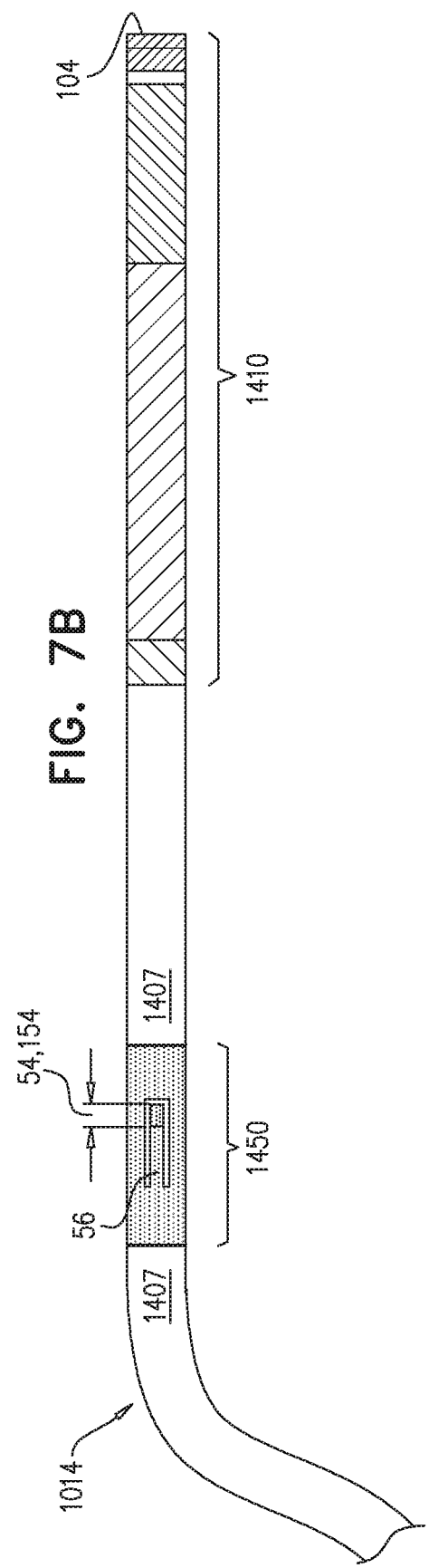

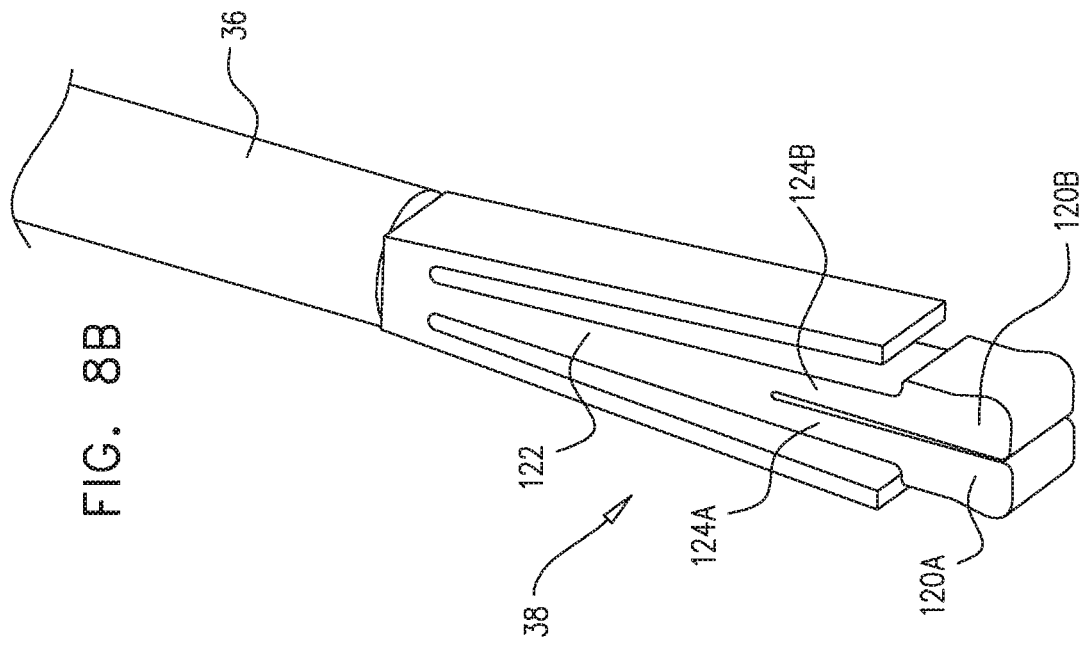
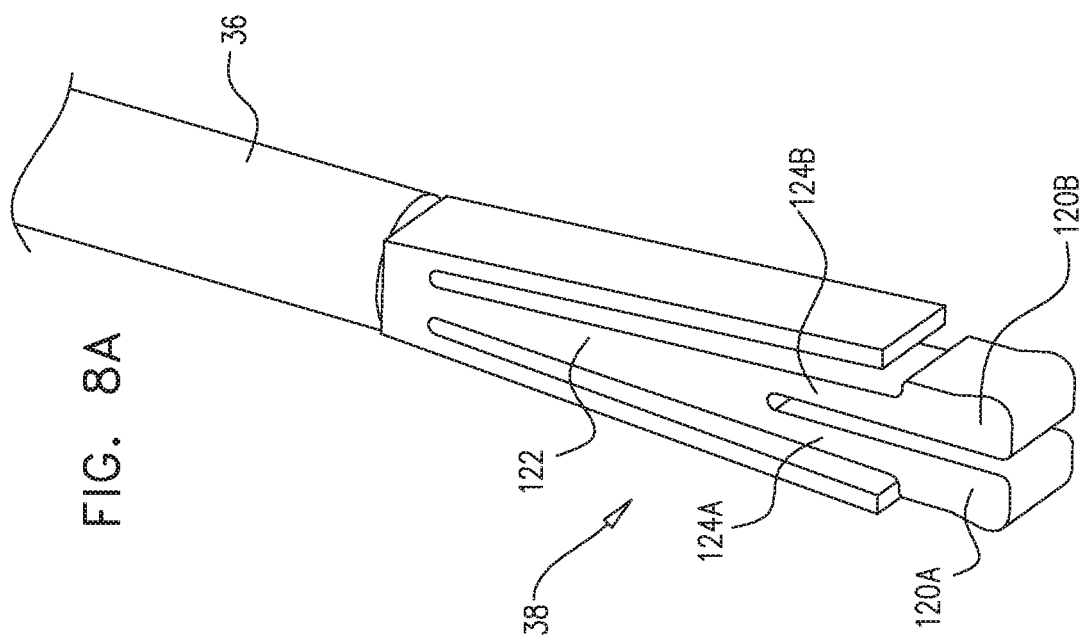

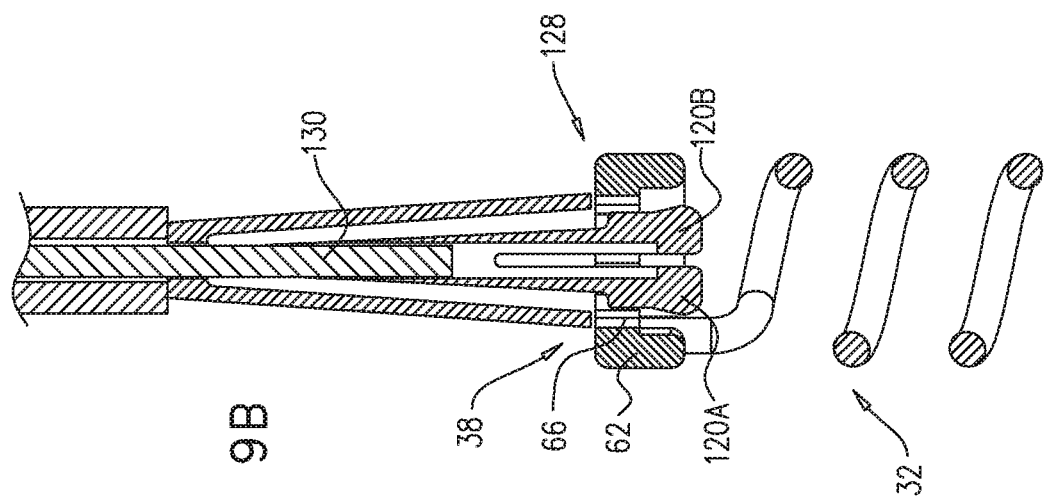
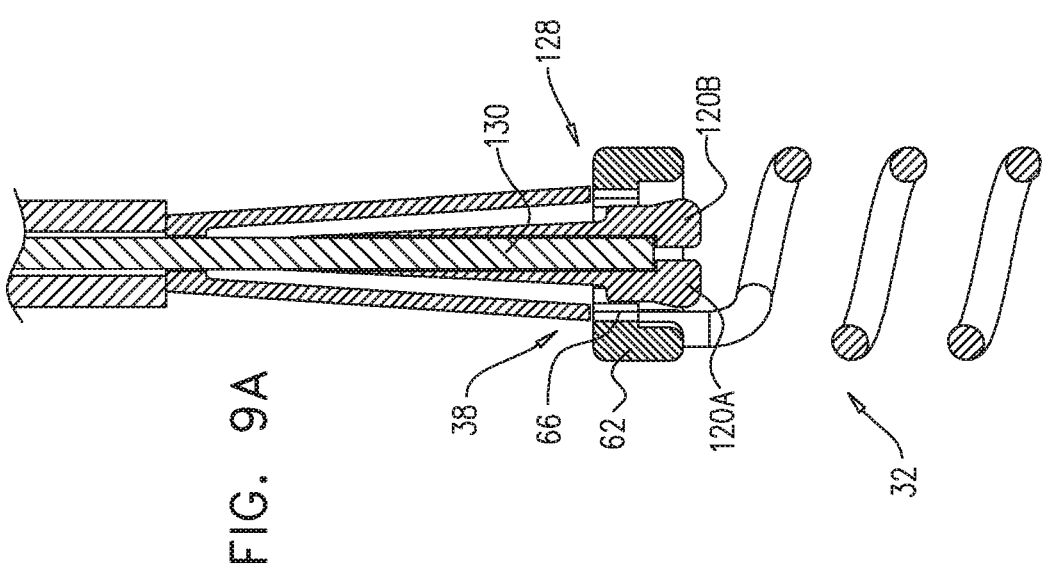

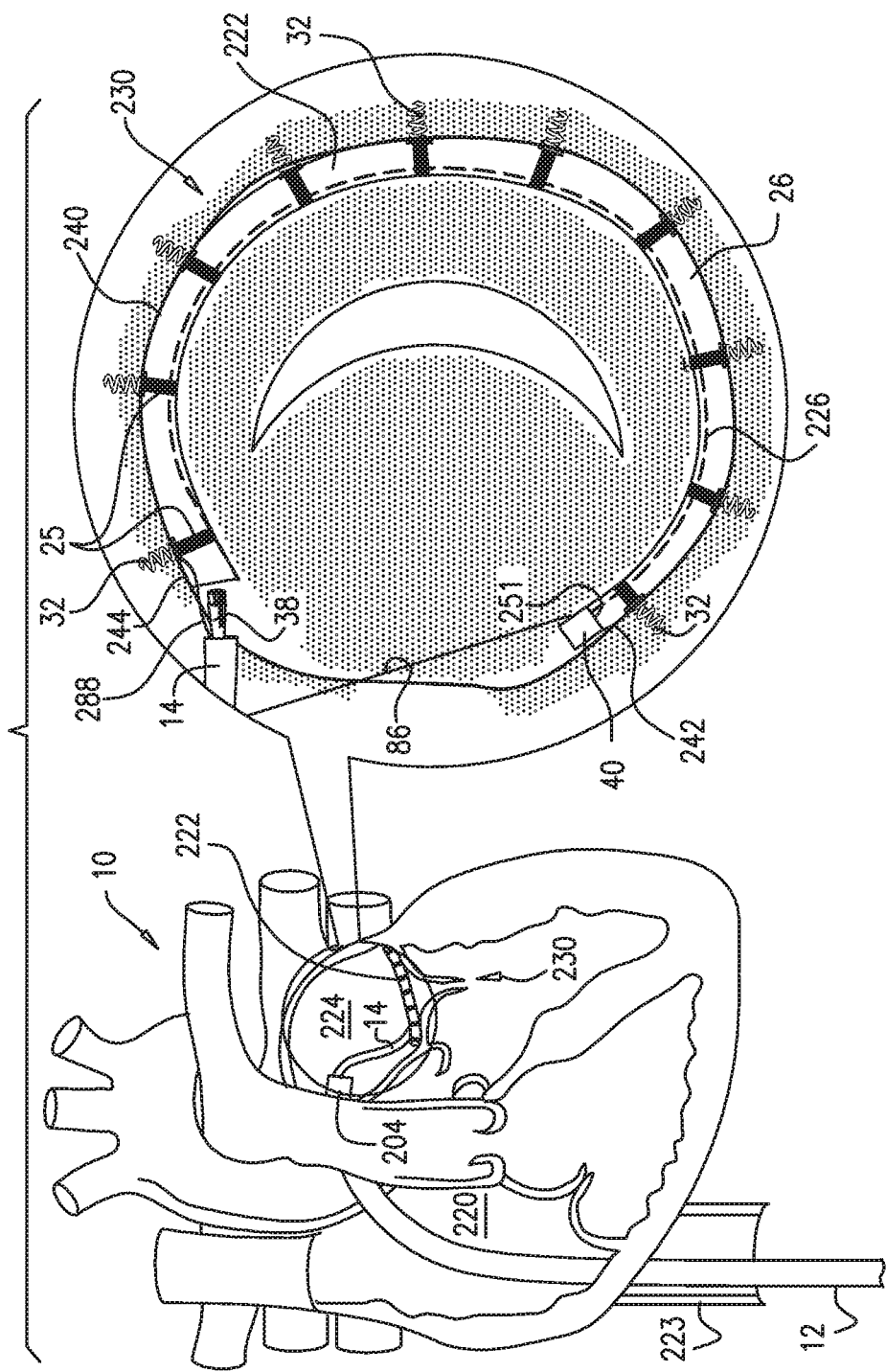

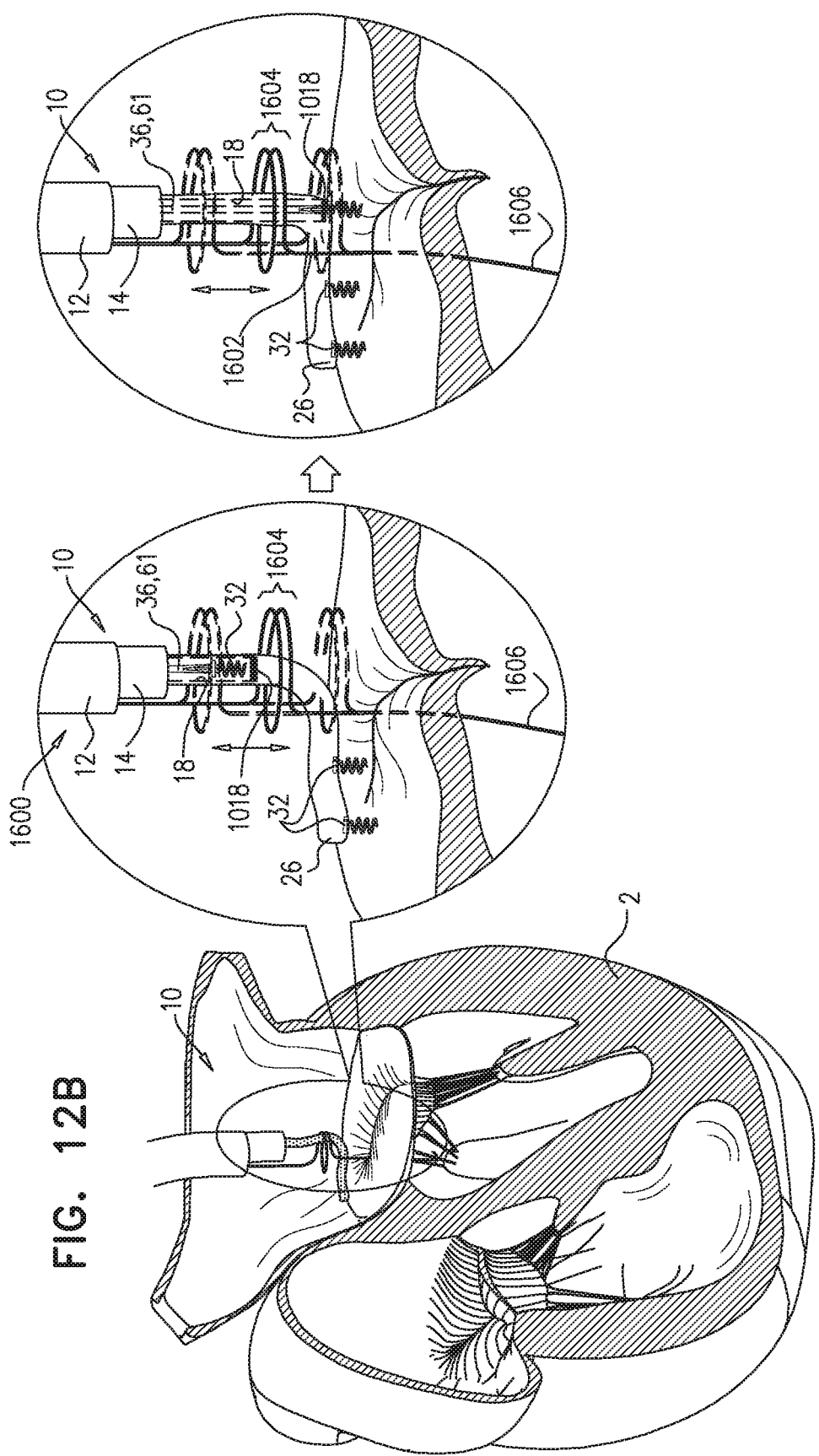

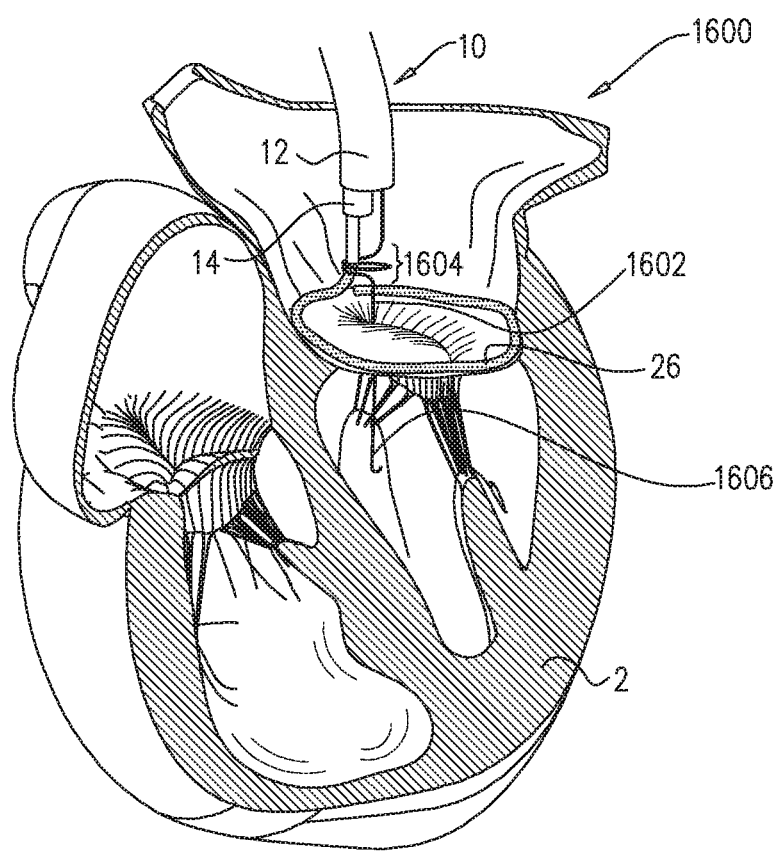

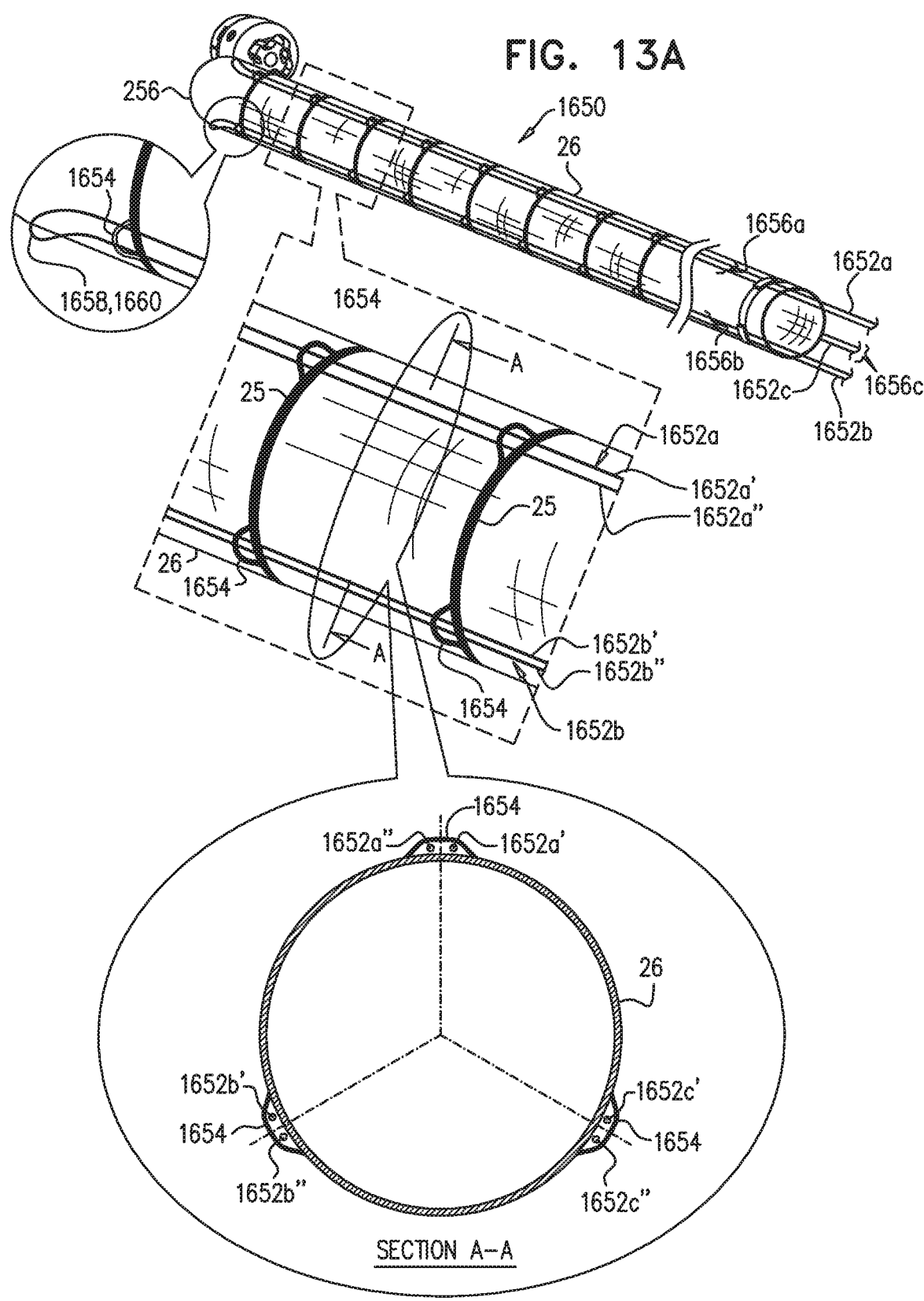

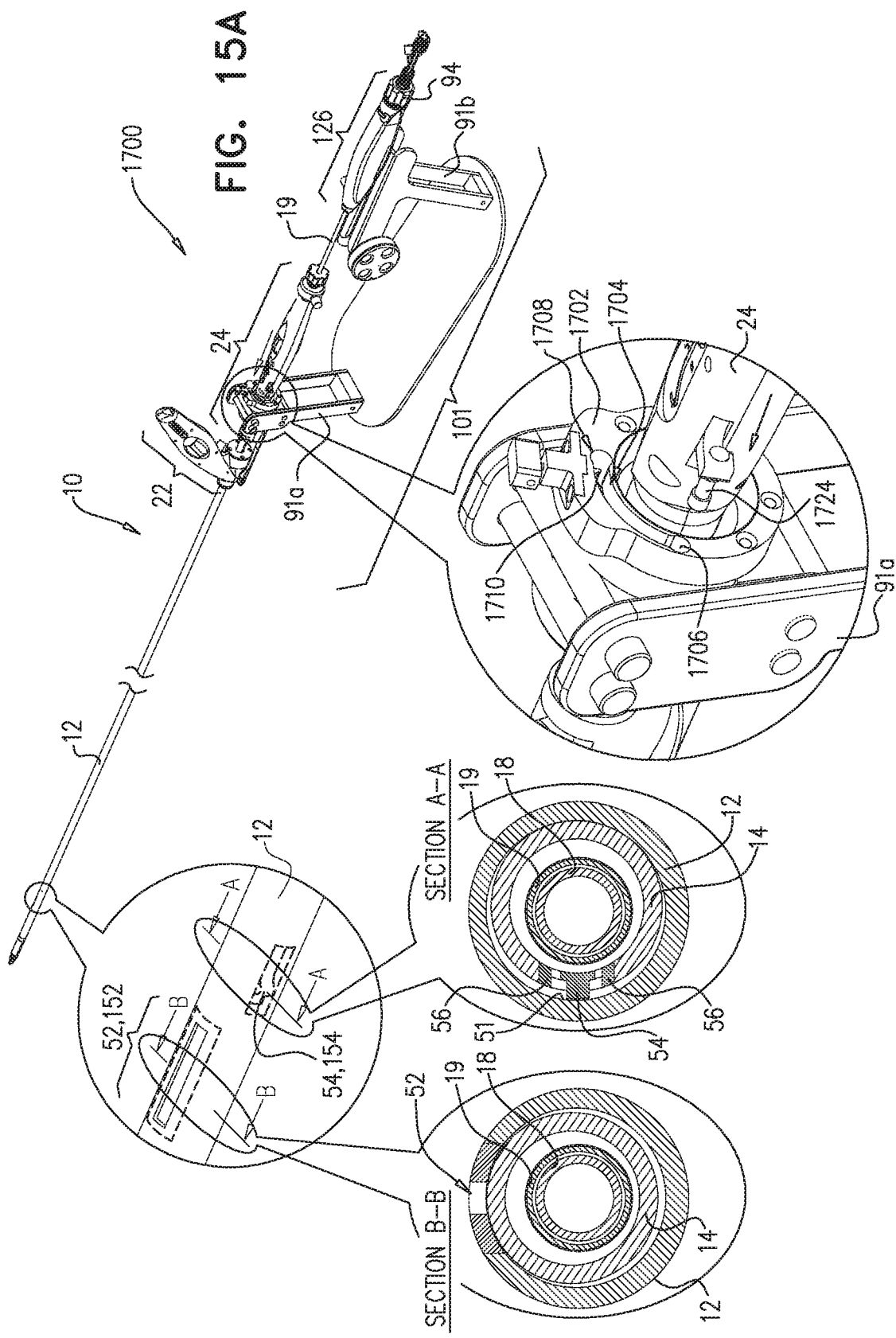

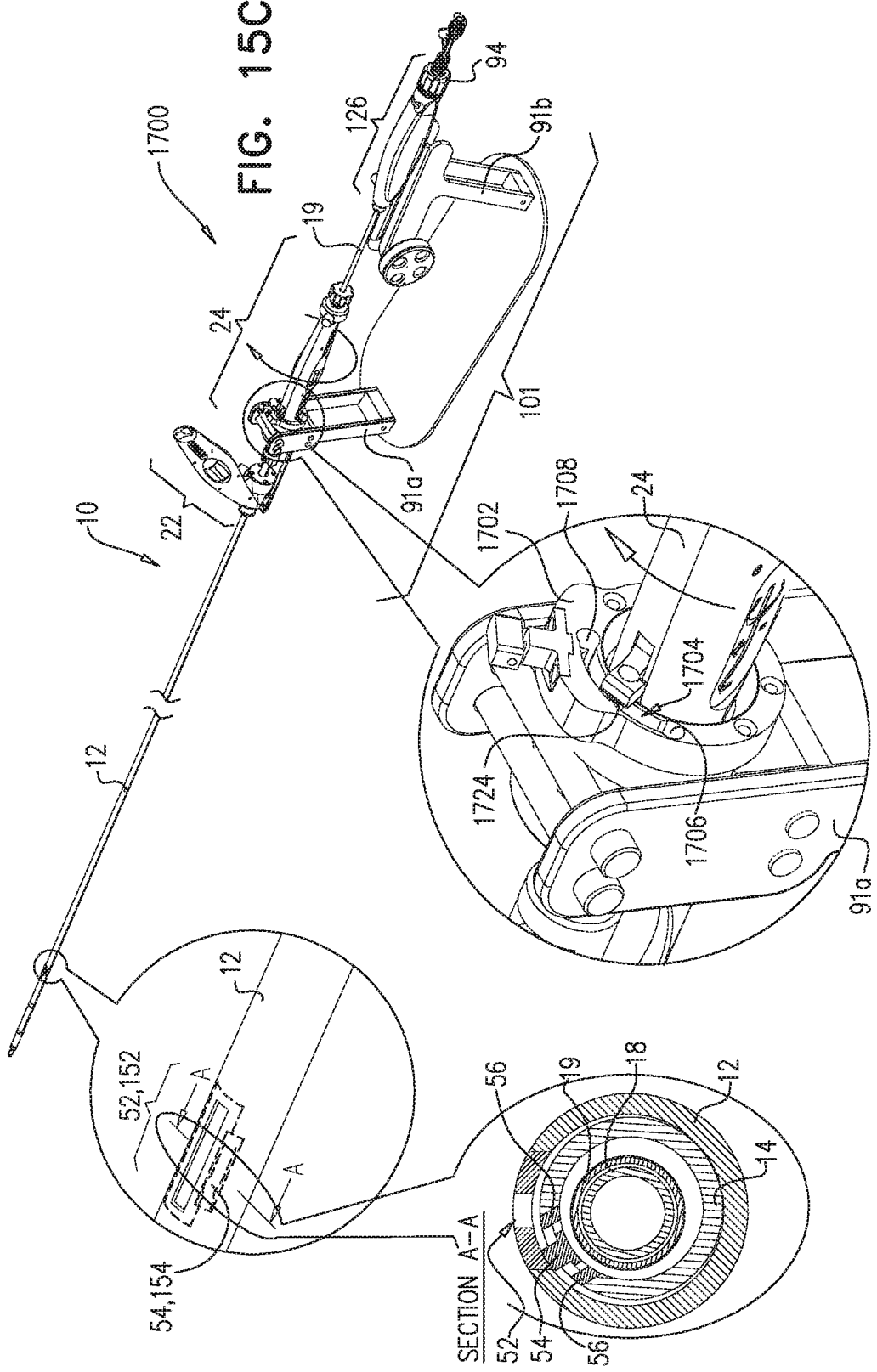

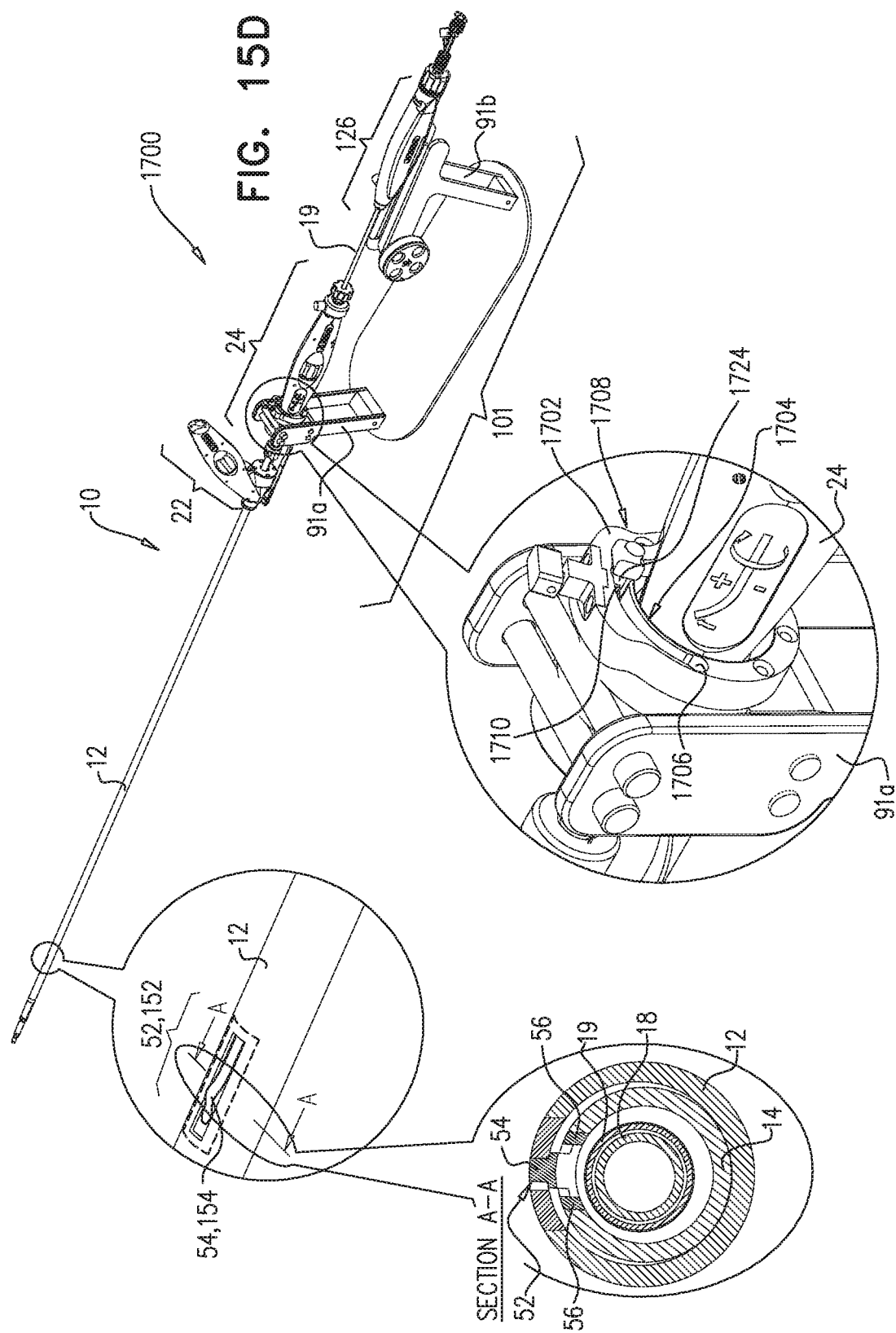

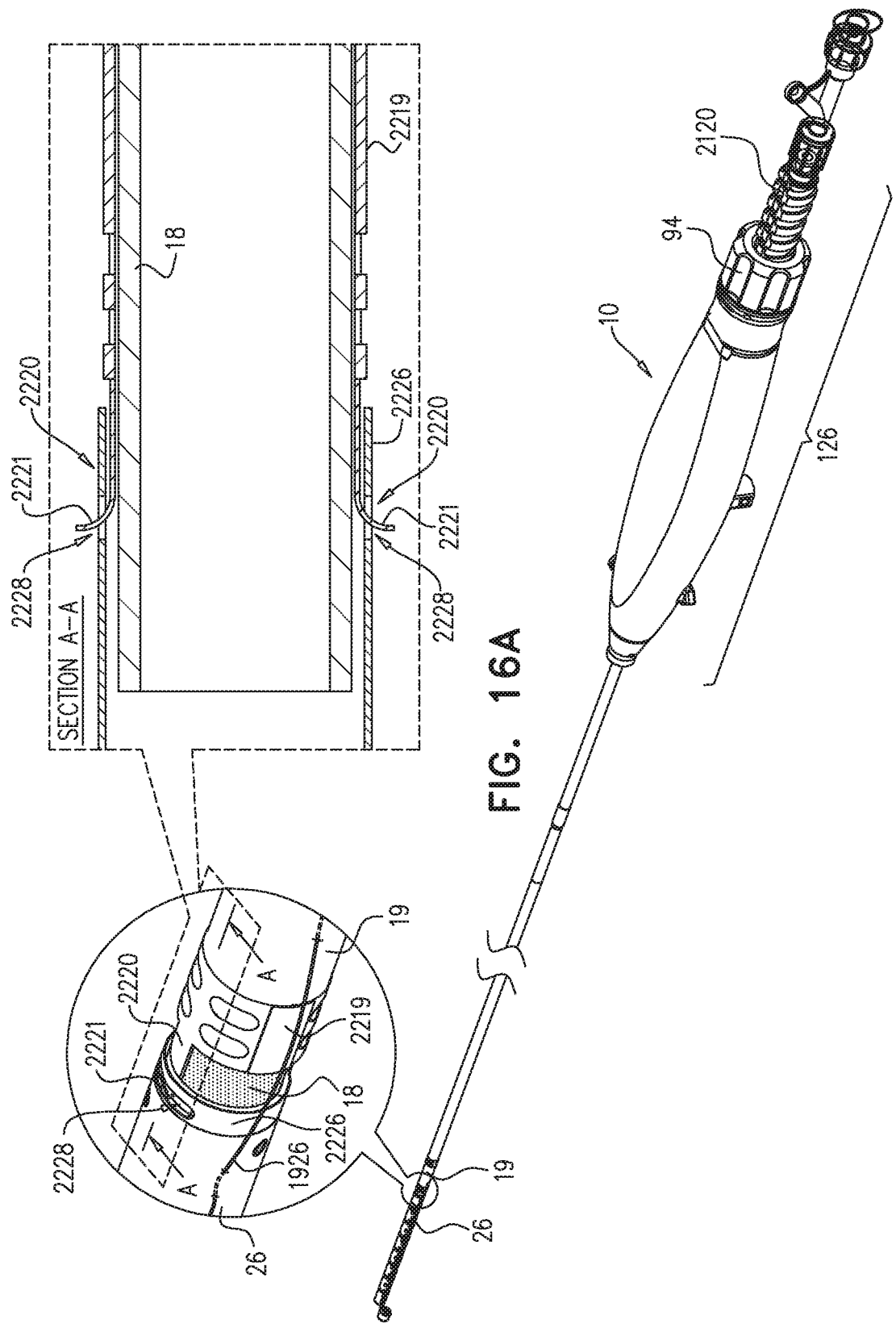

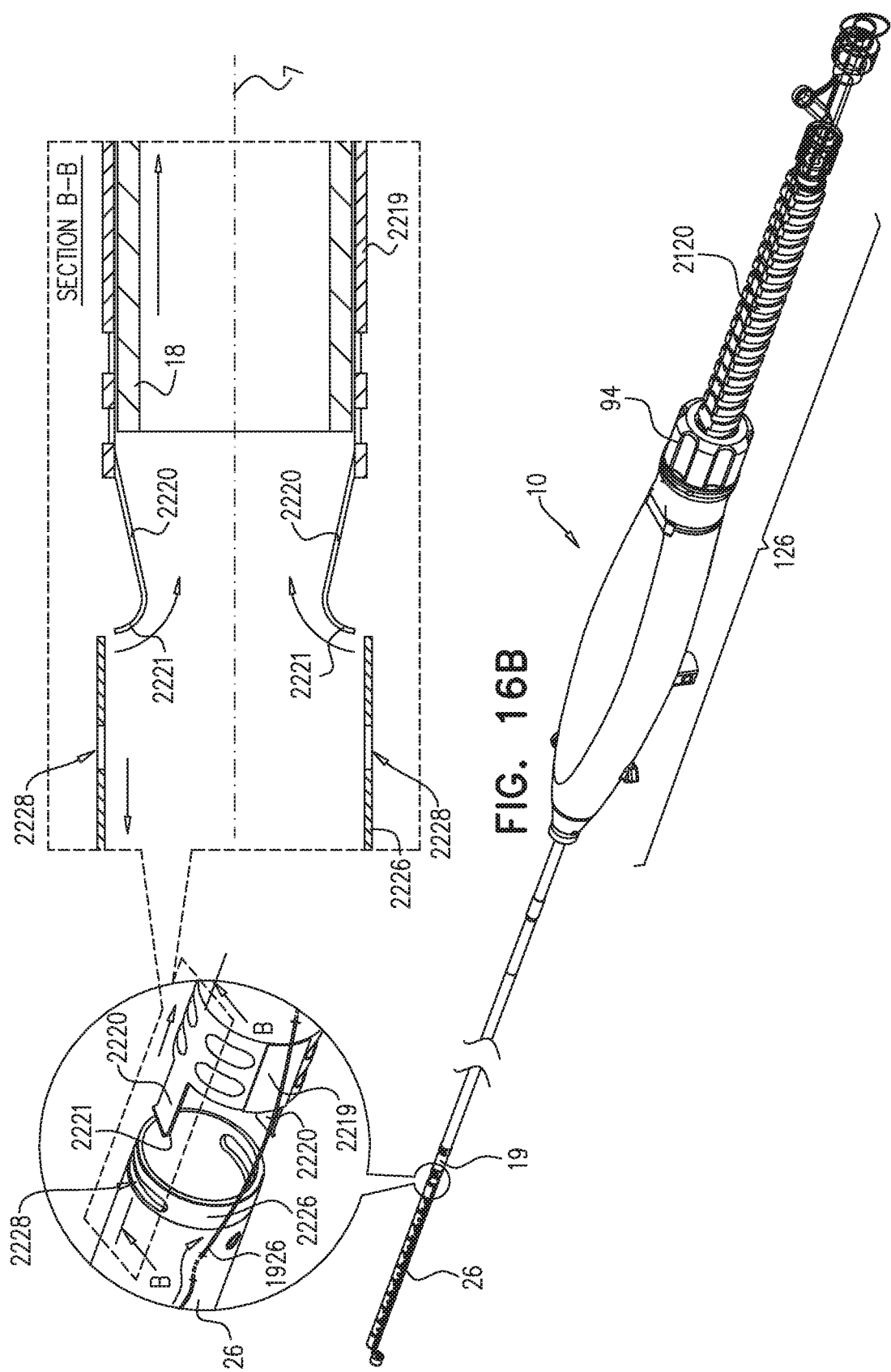

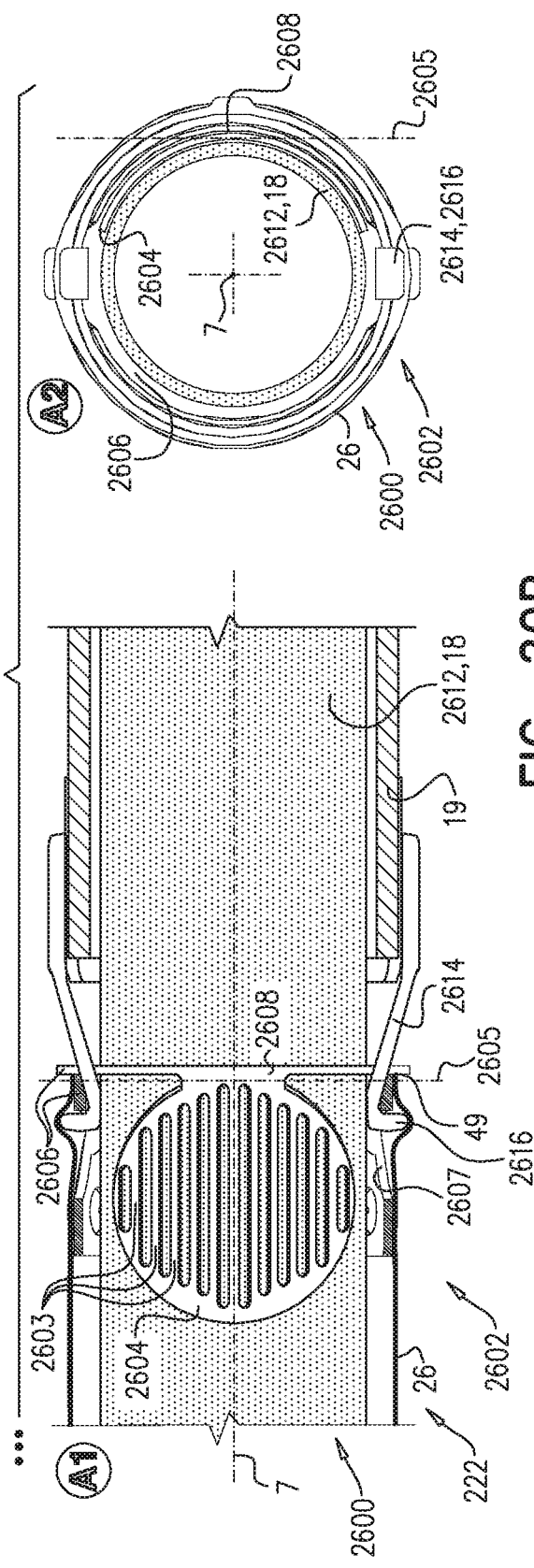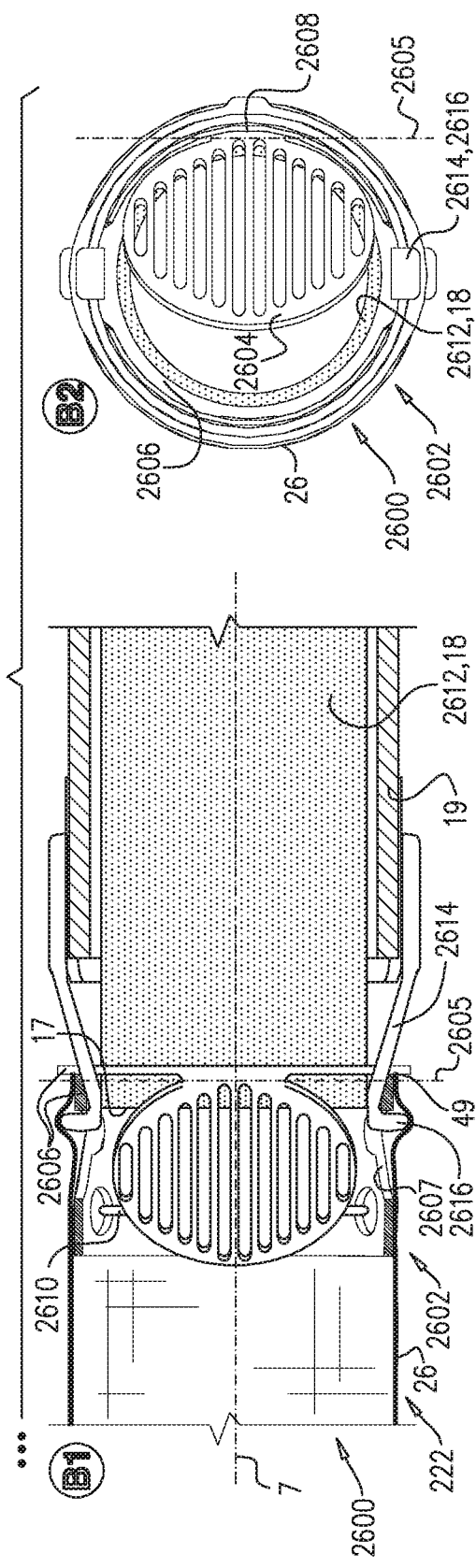

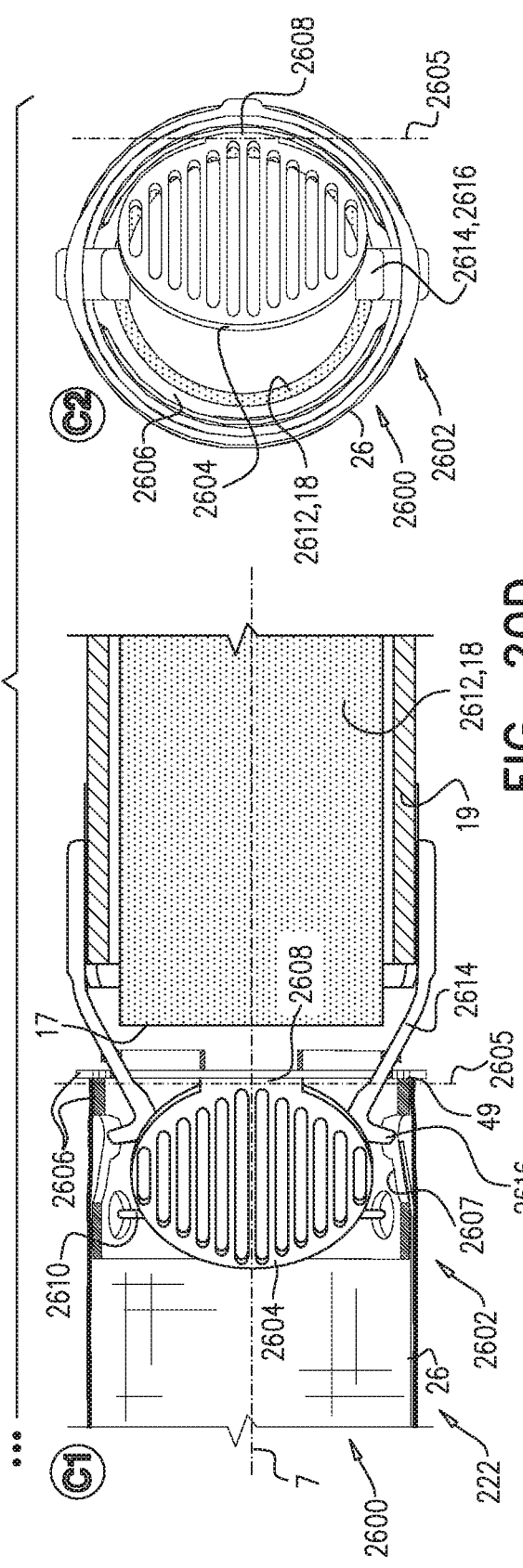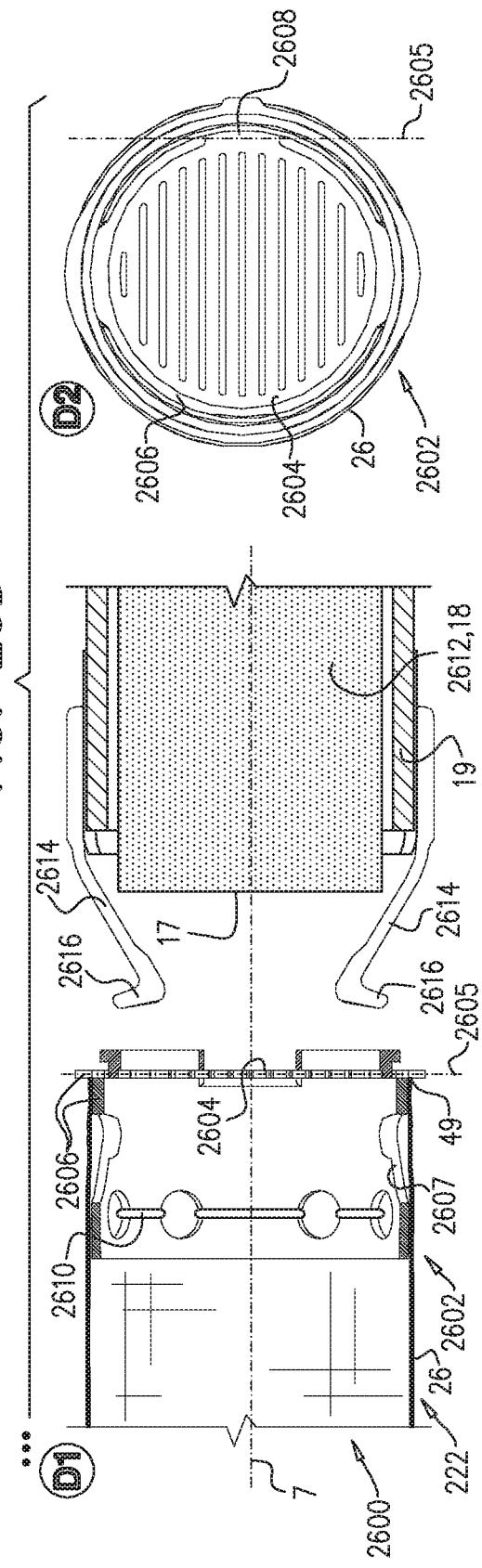

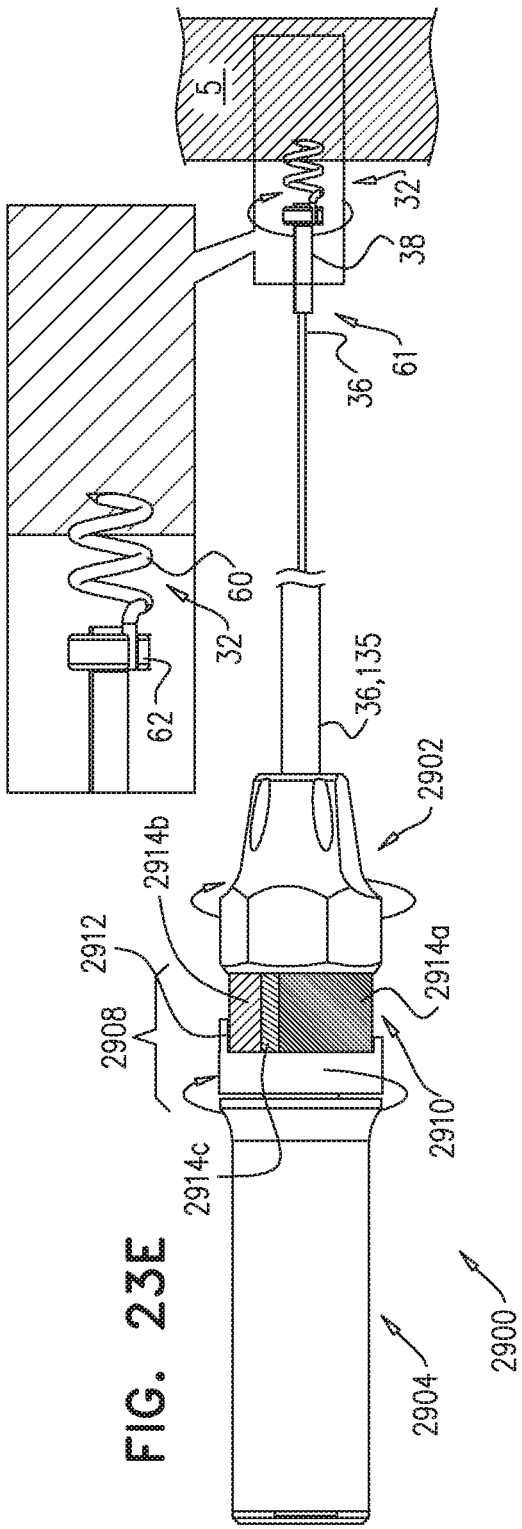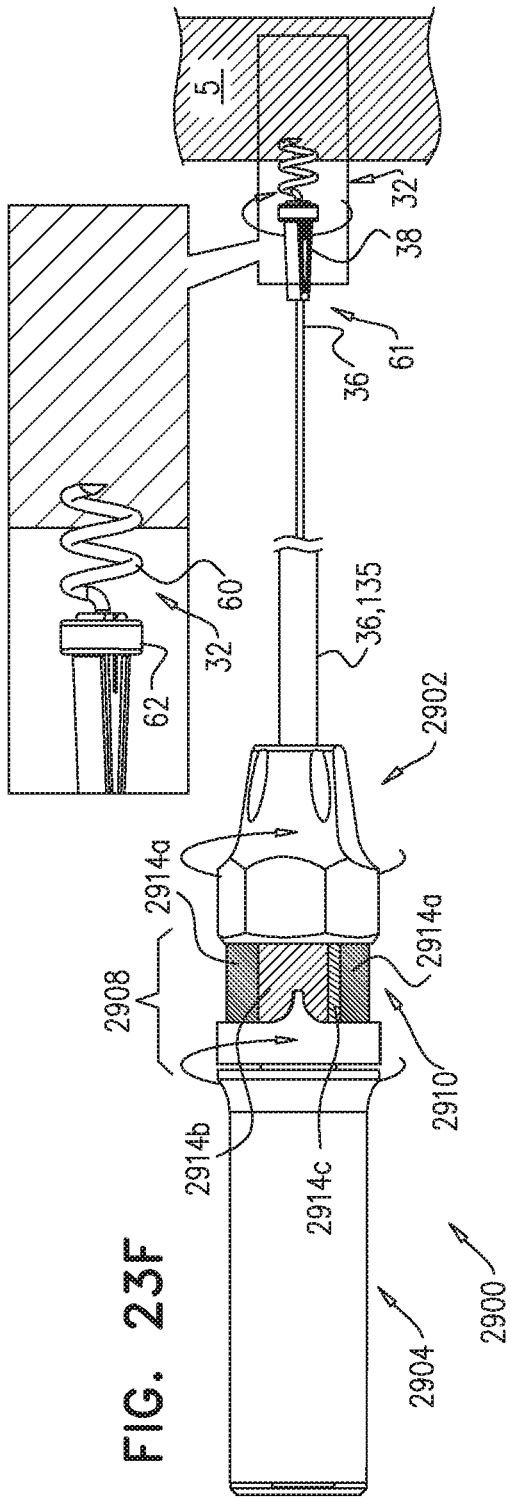

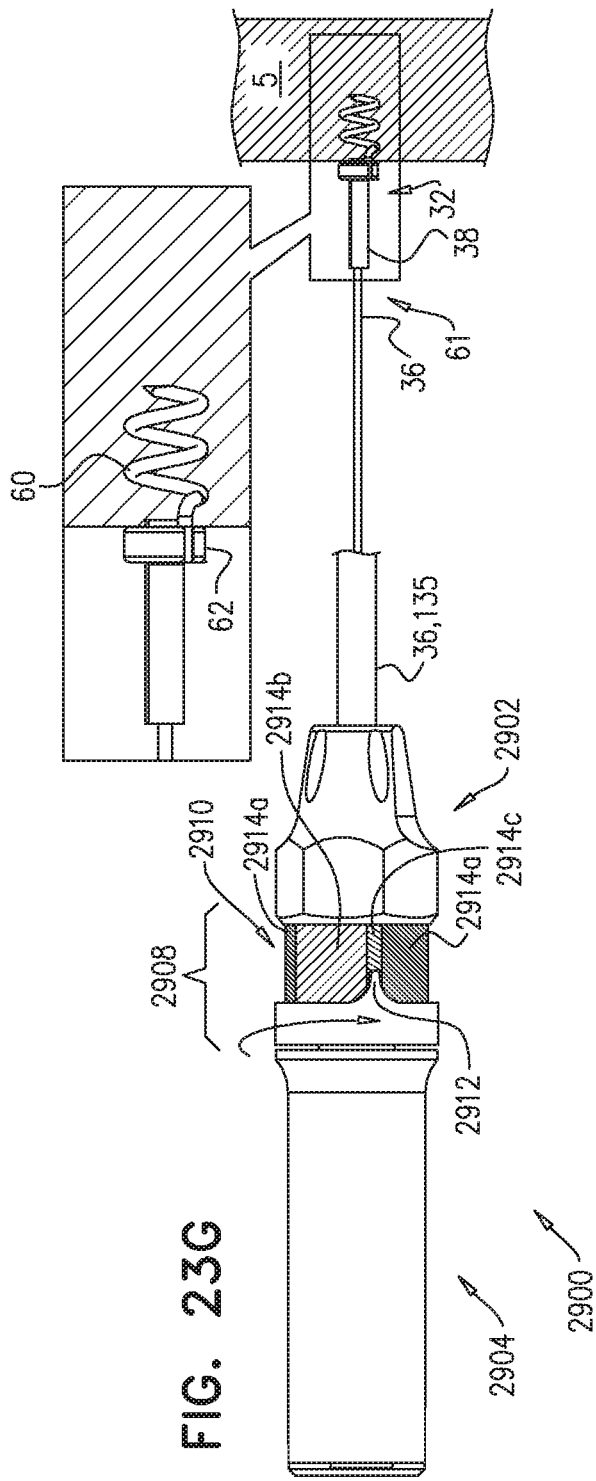
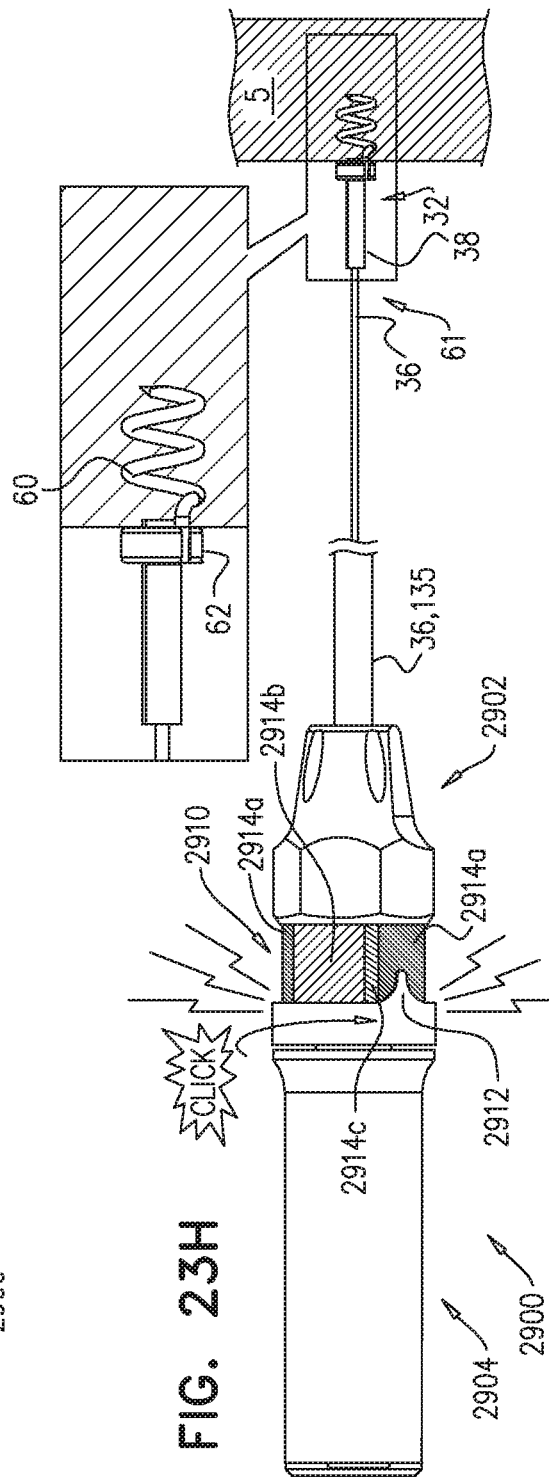

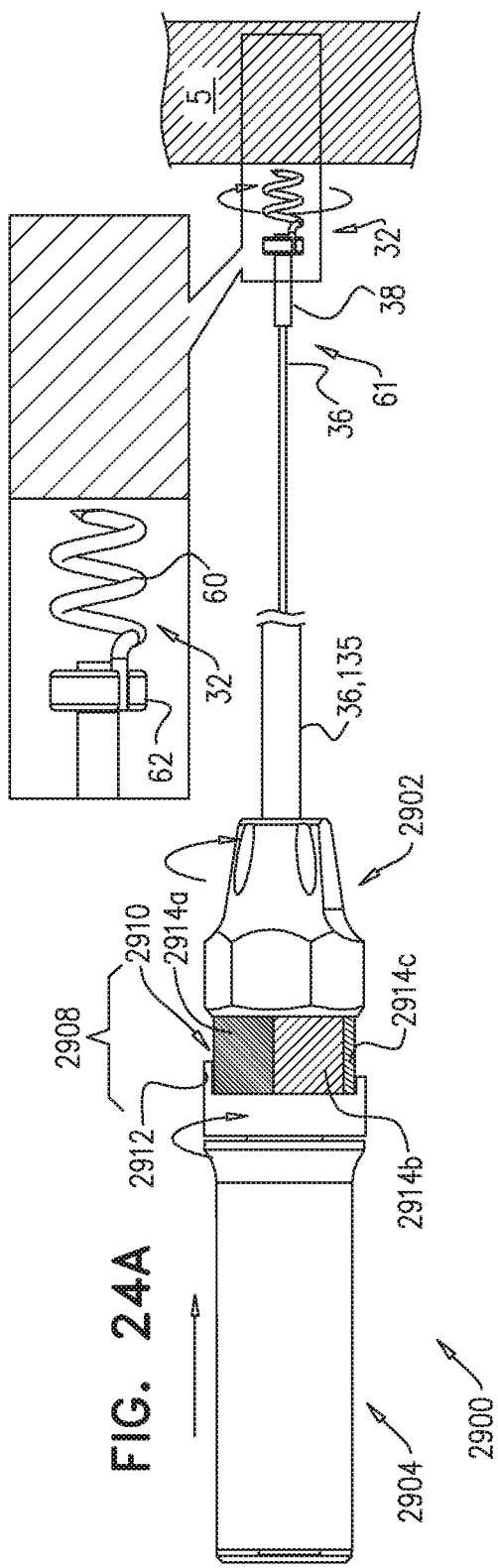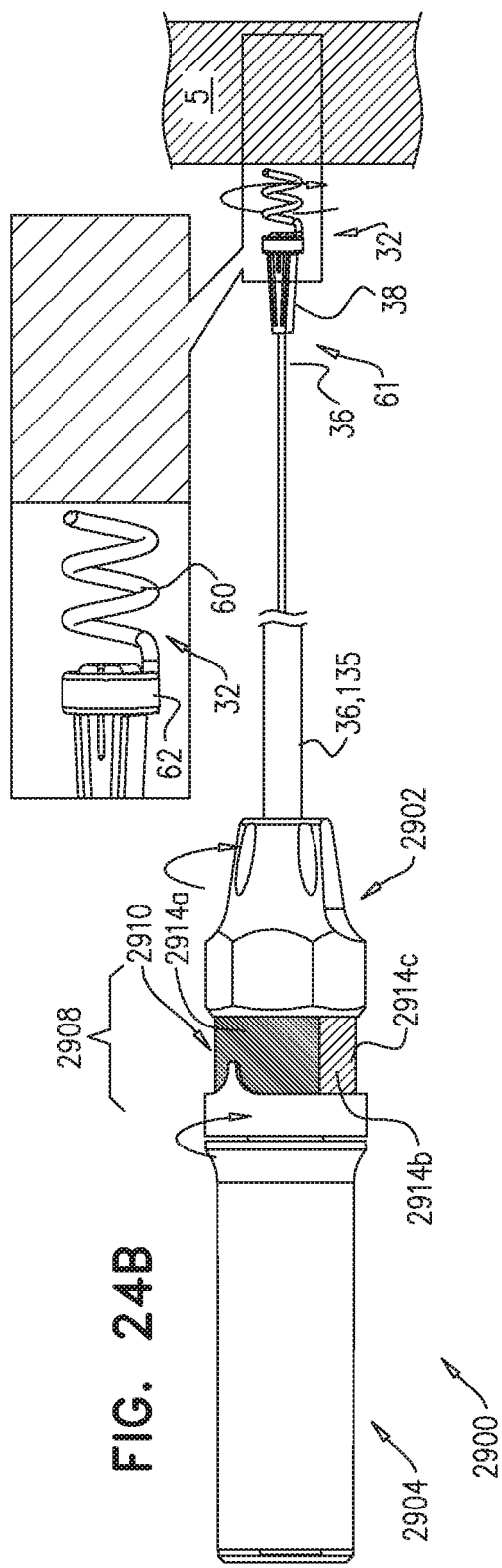

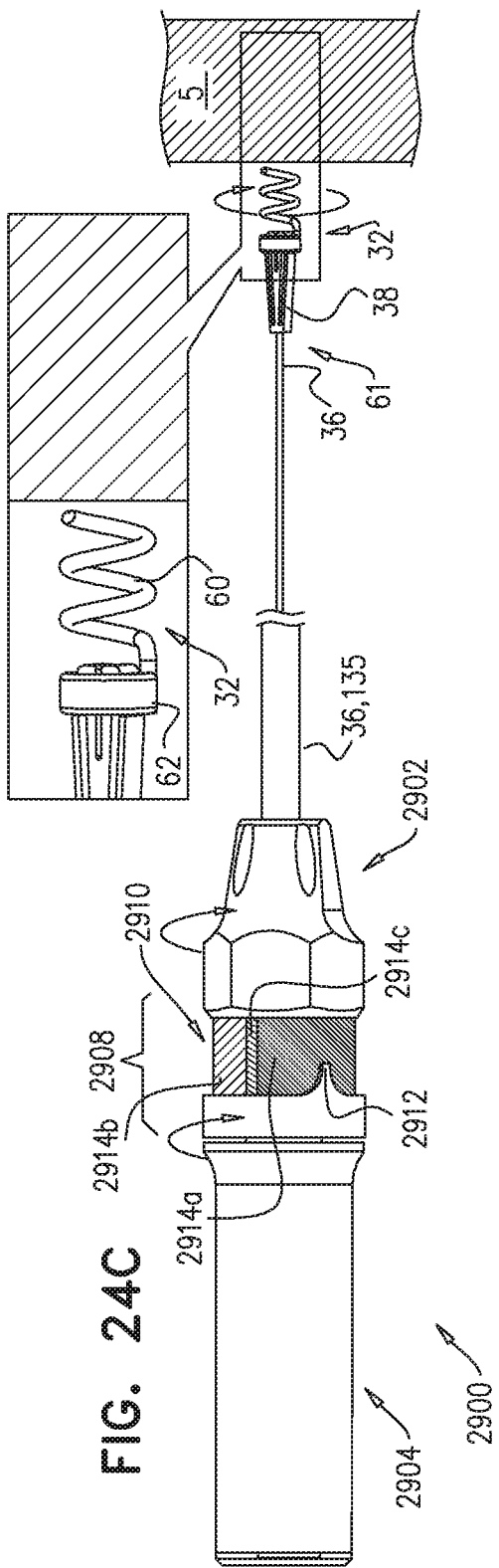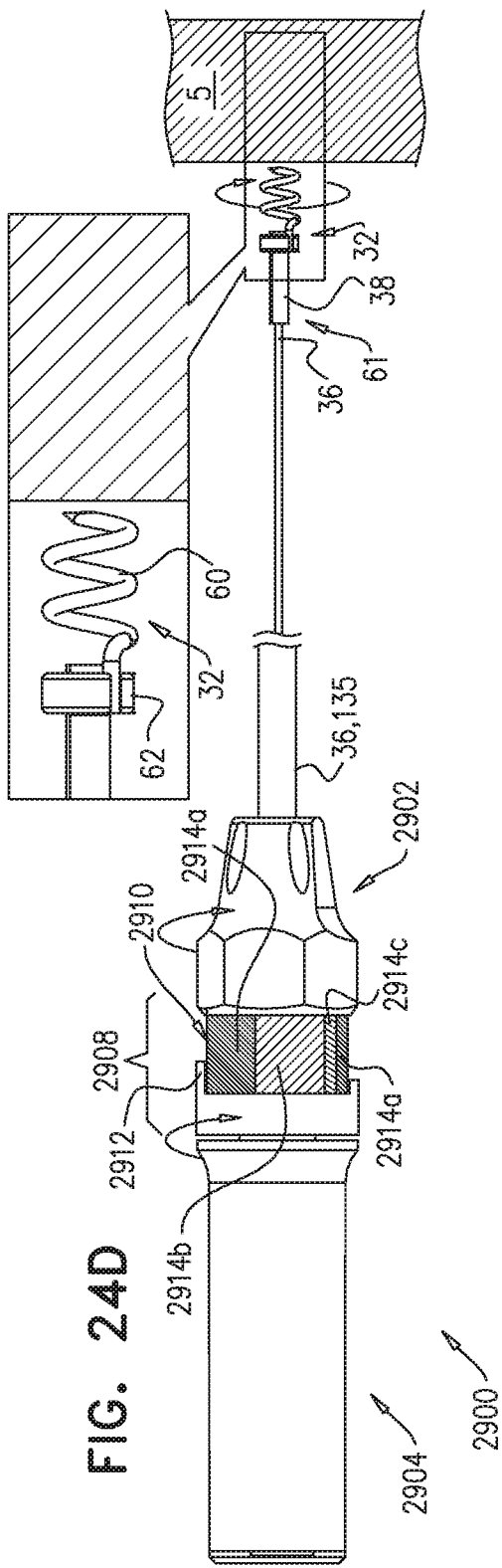

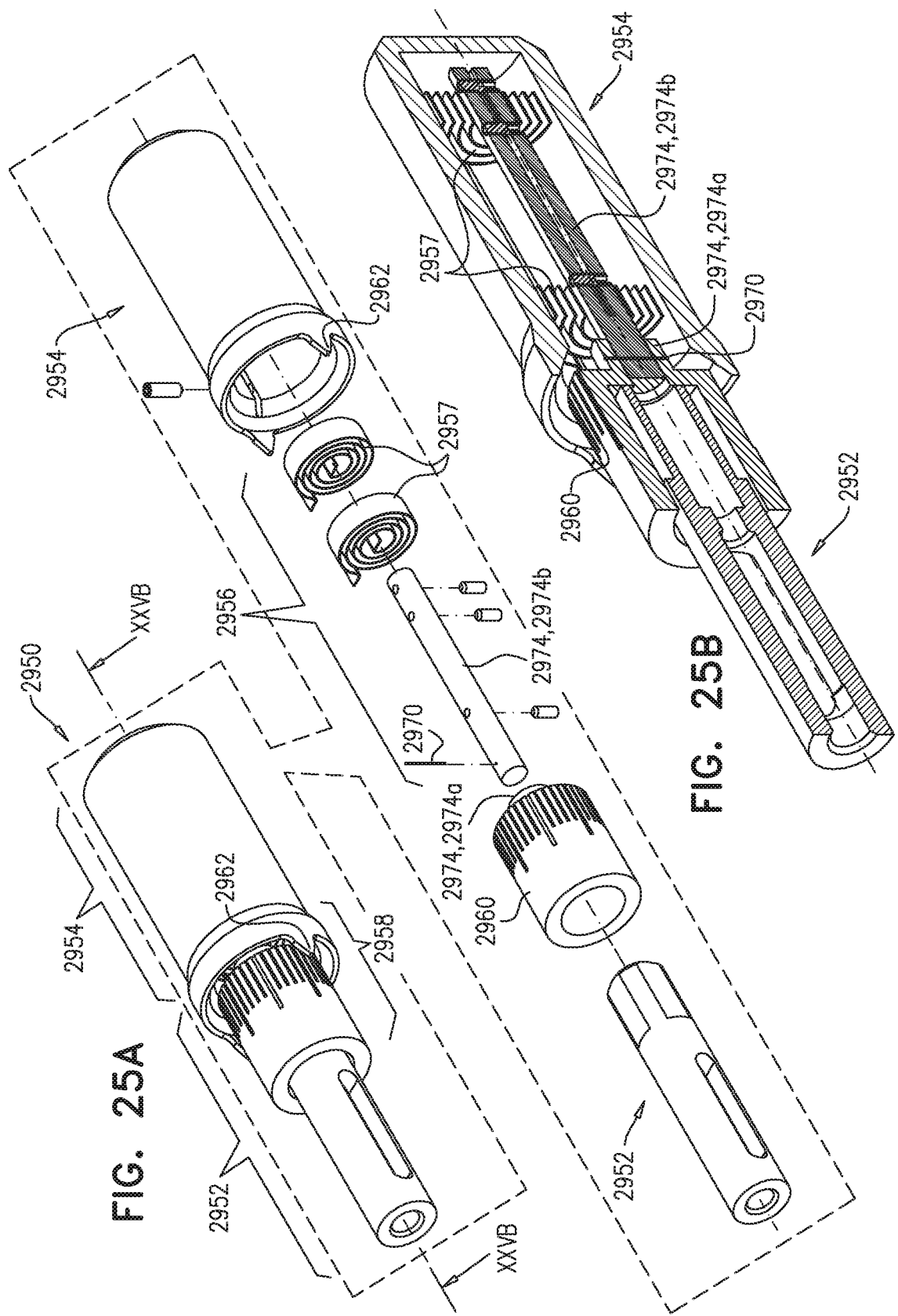

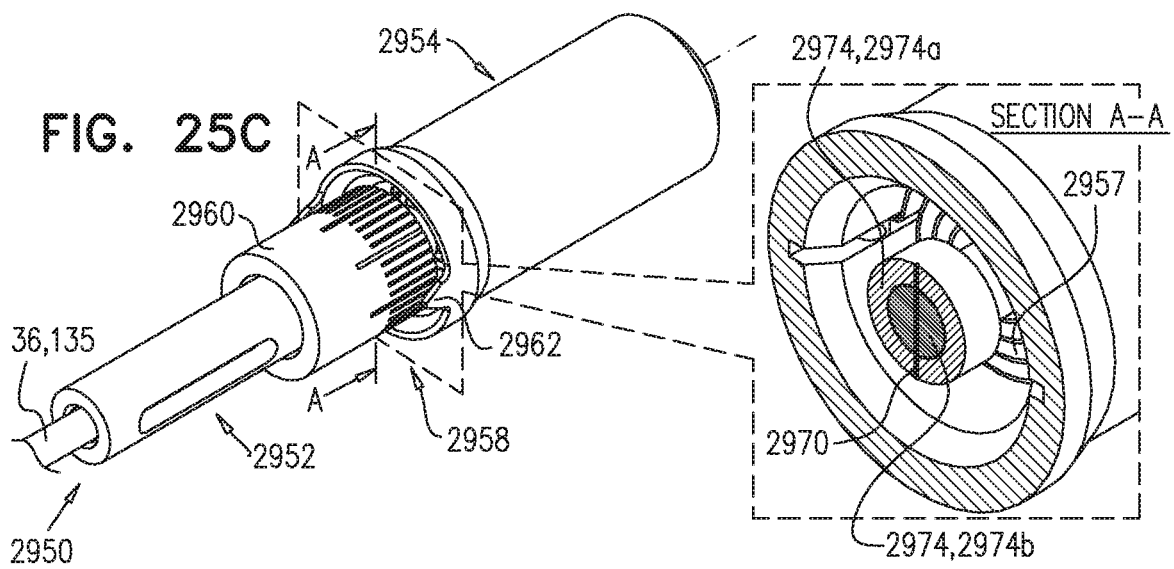
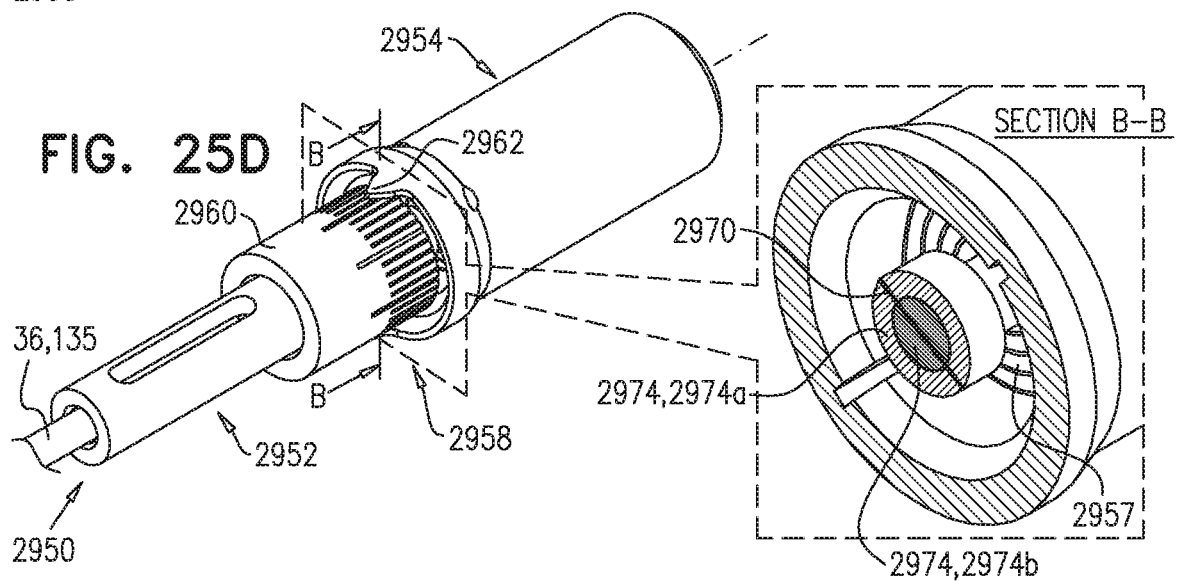
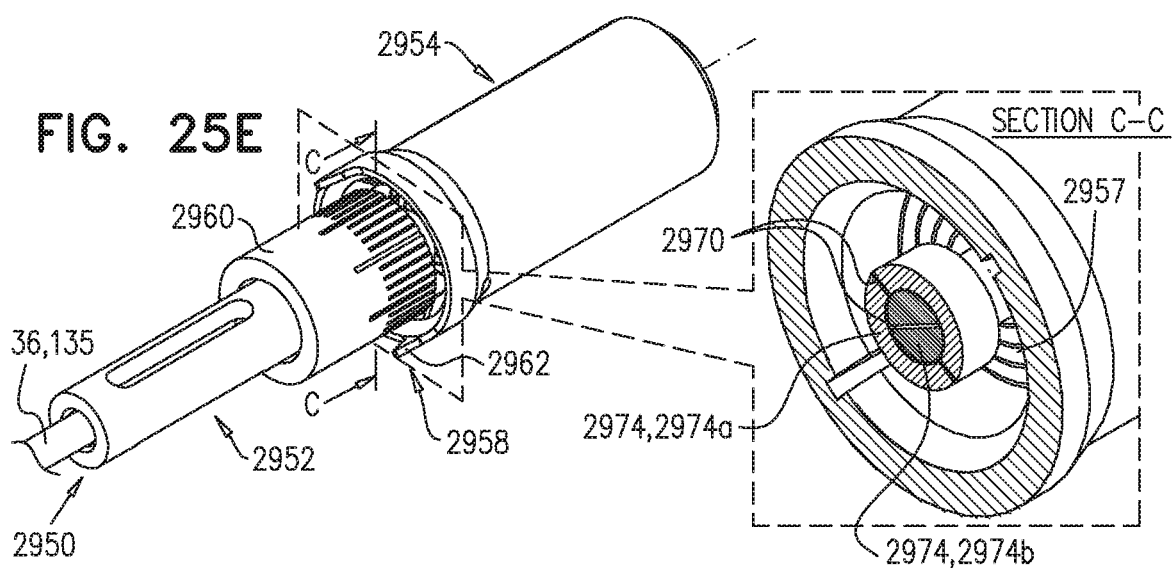

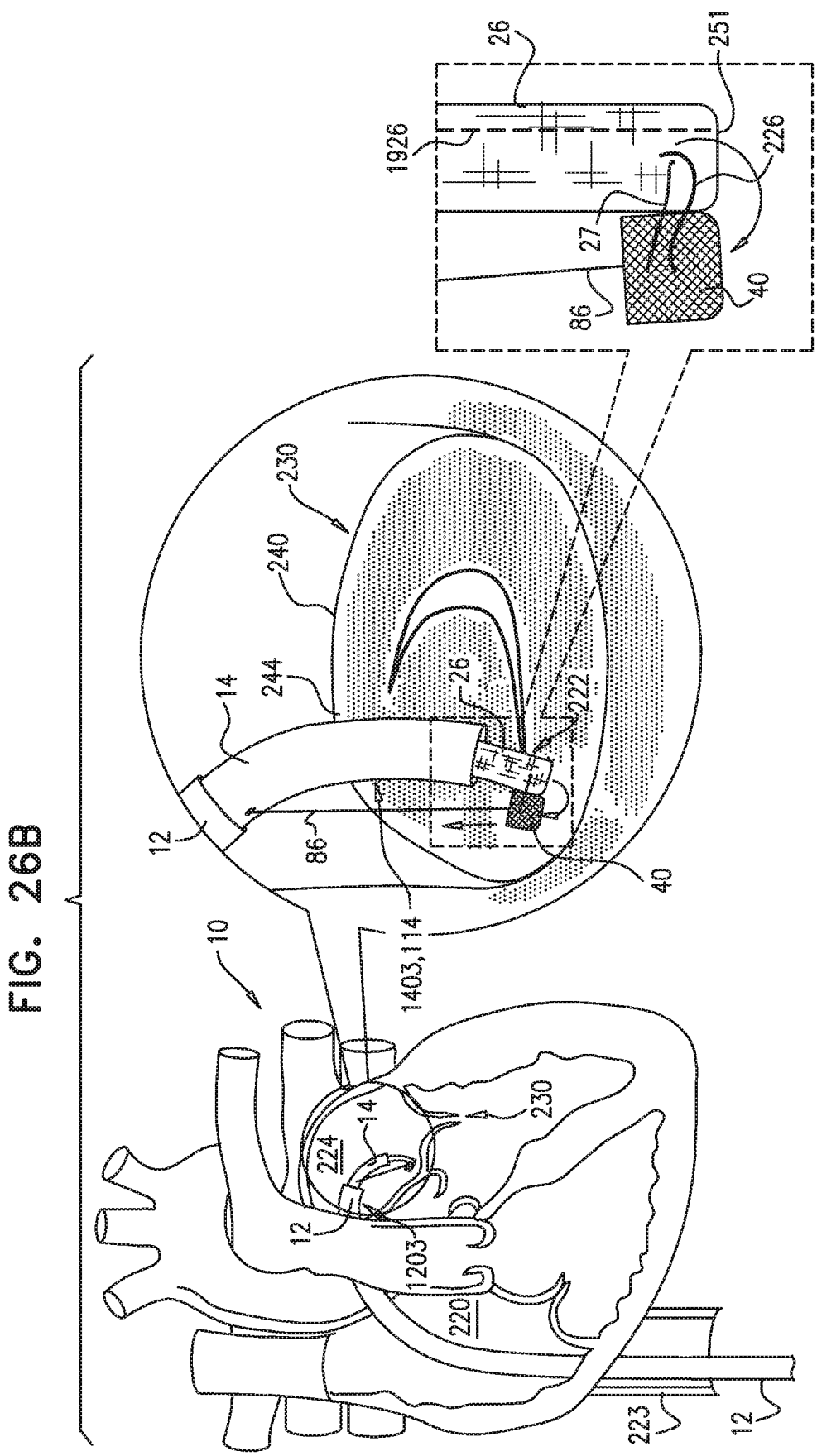

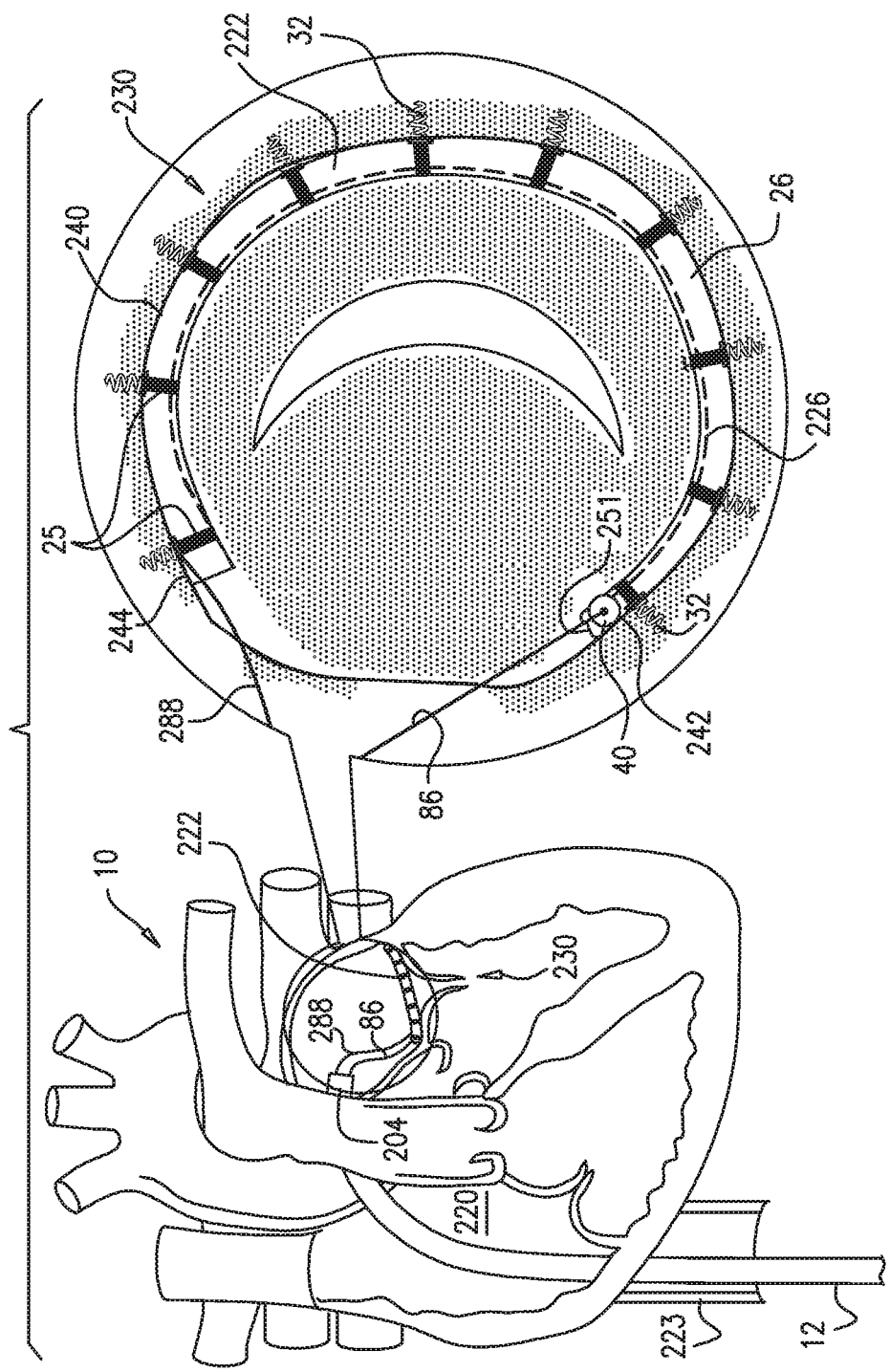

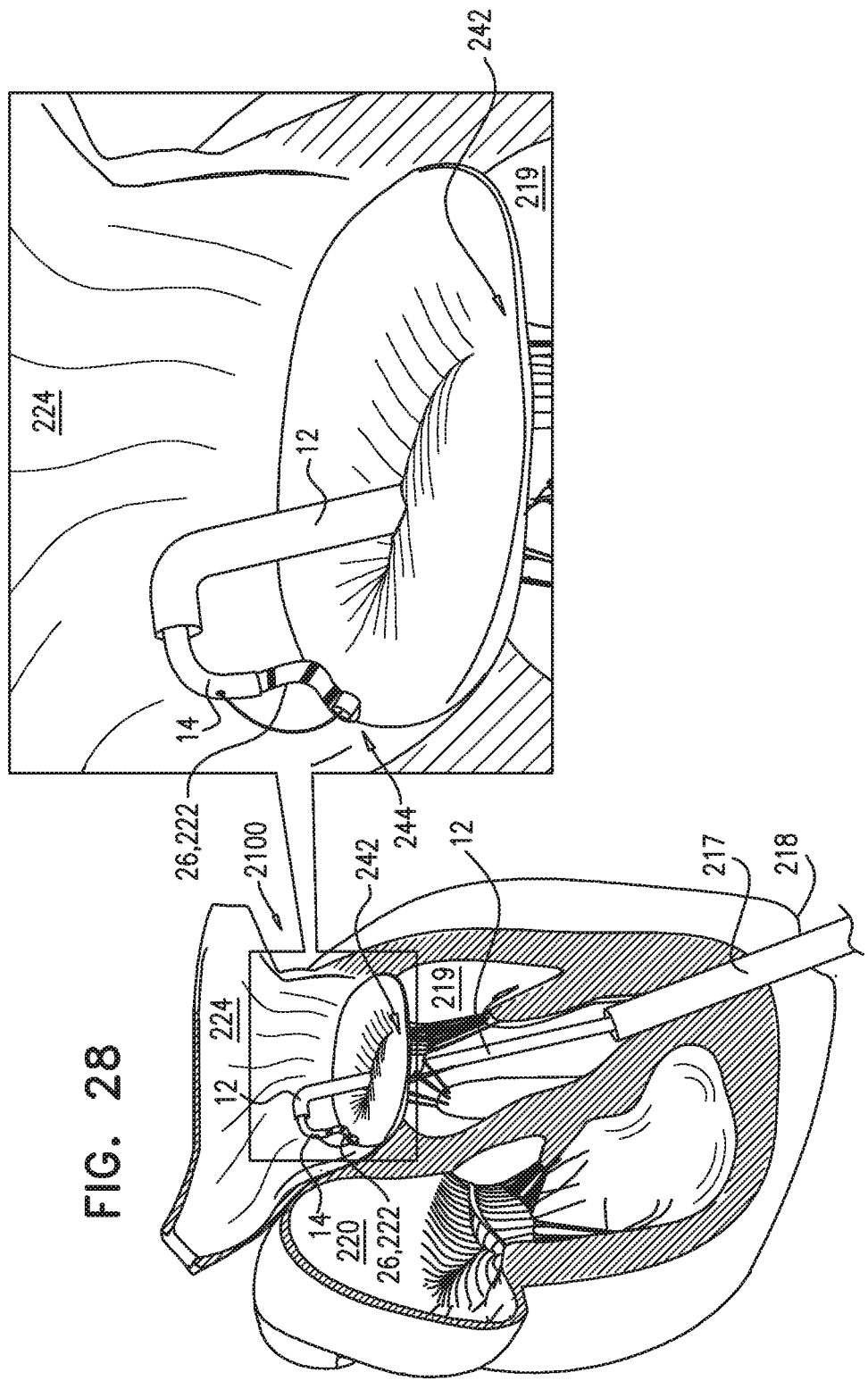

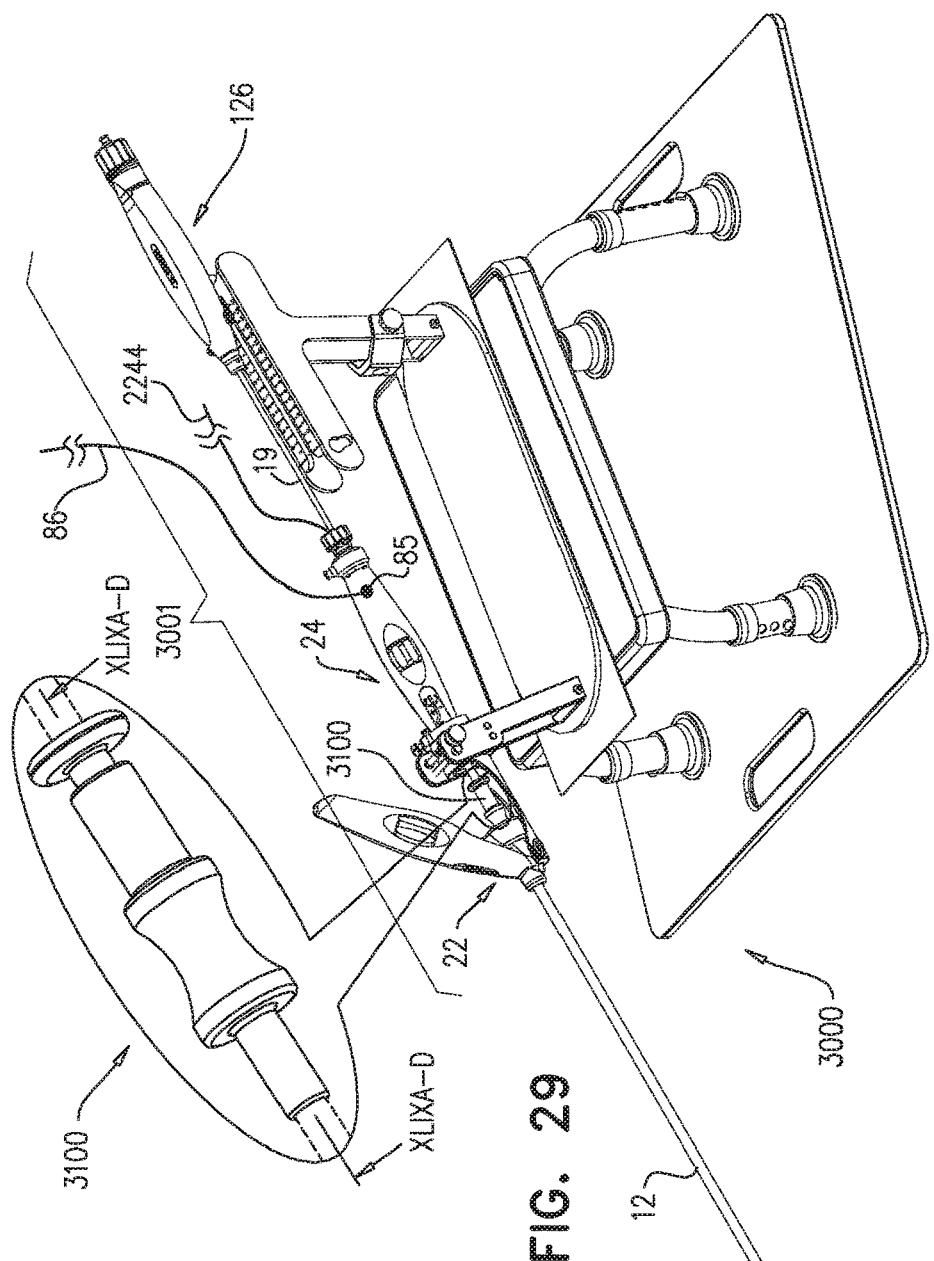
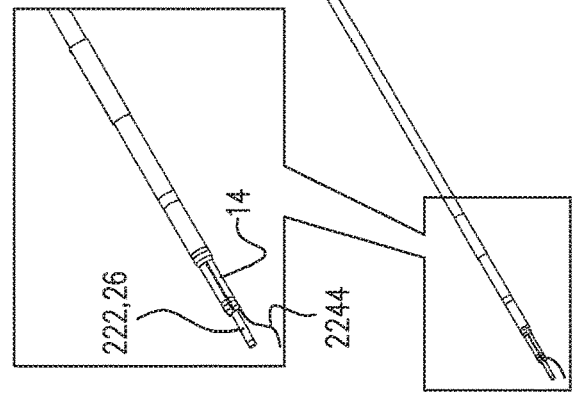
FIG. 29

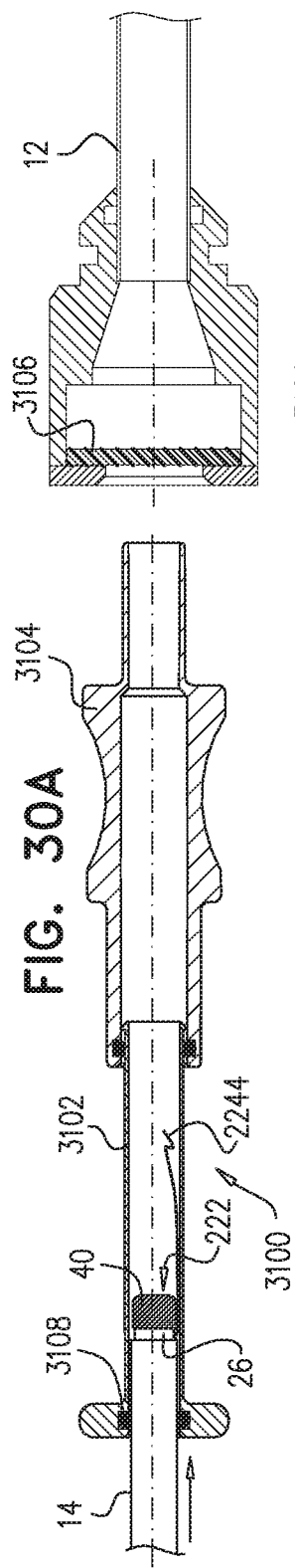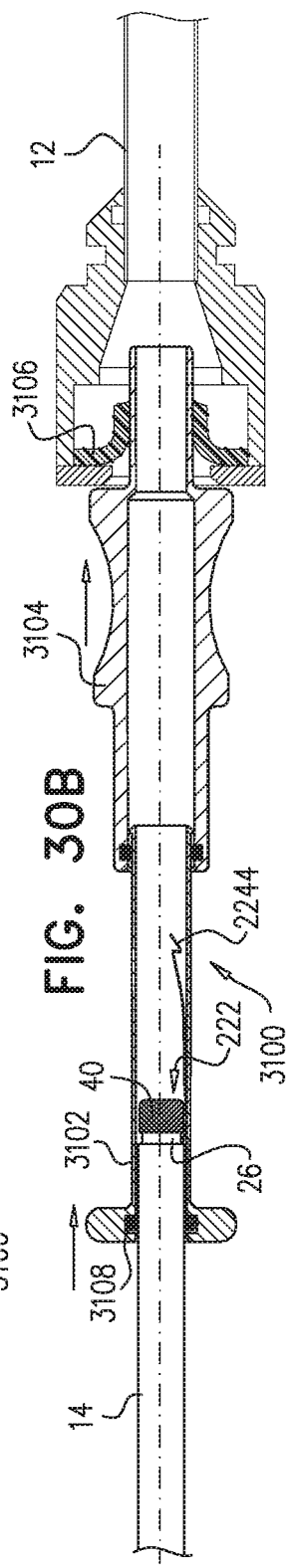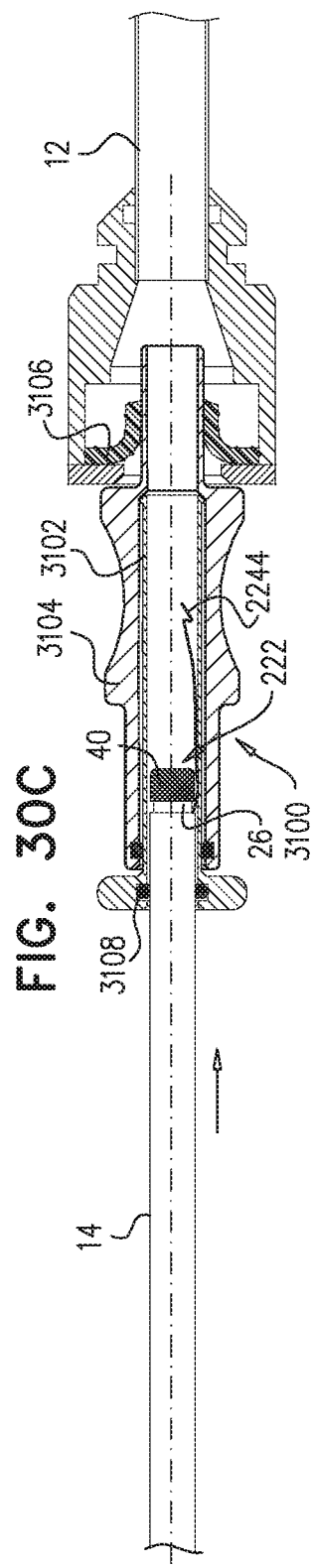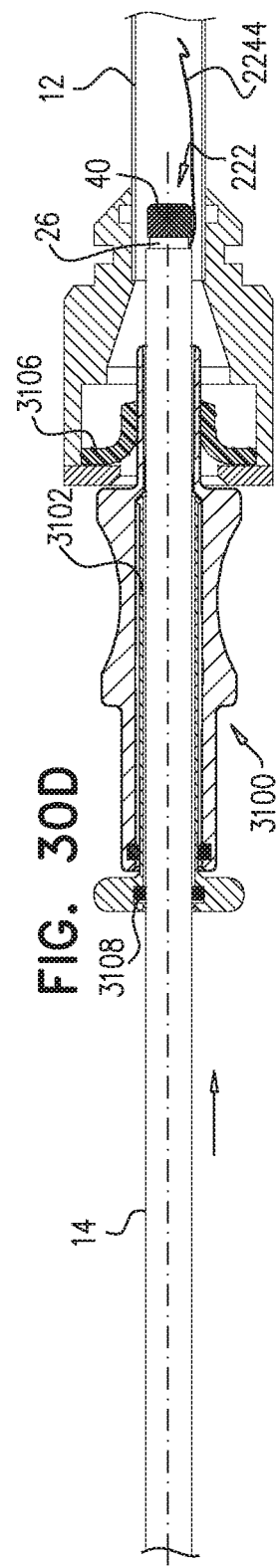

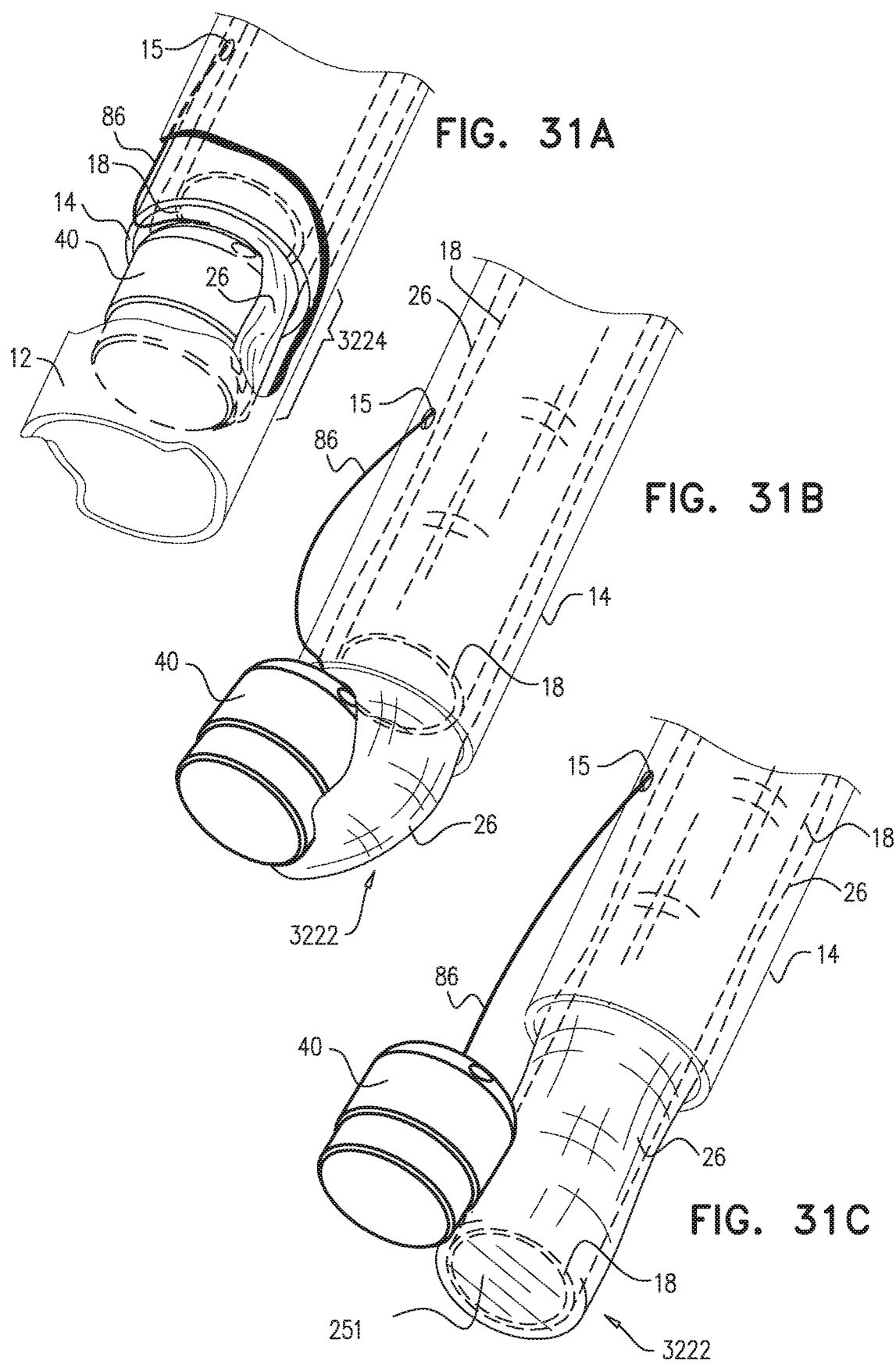

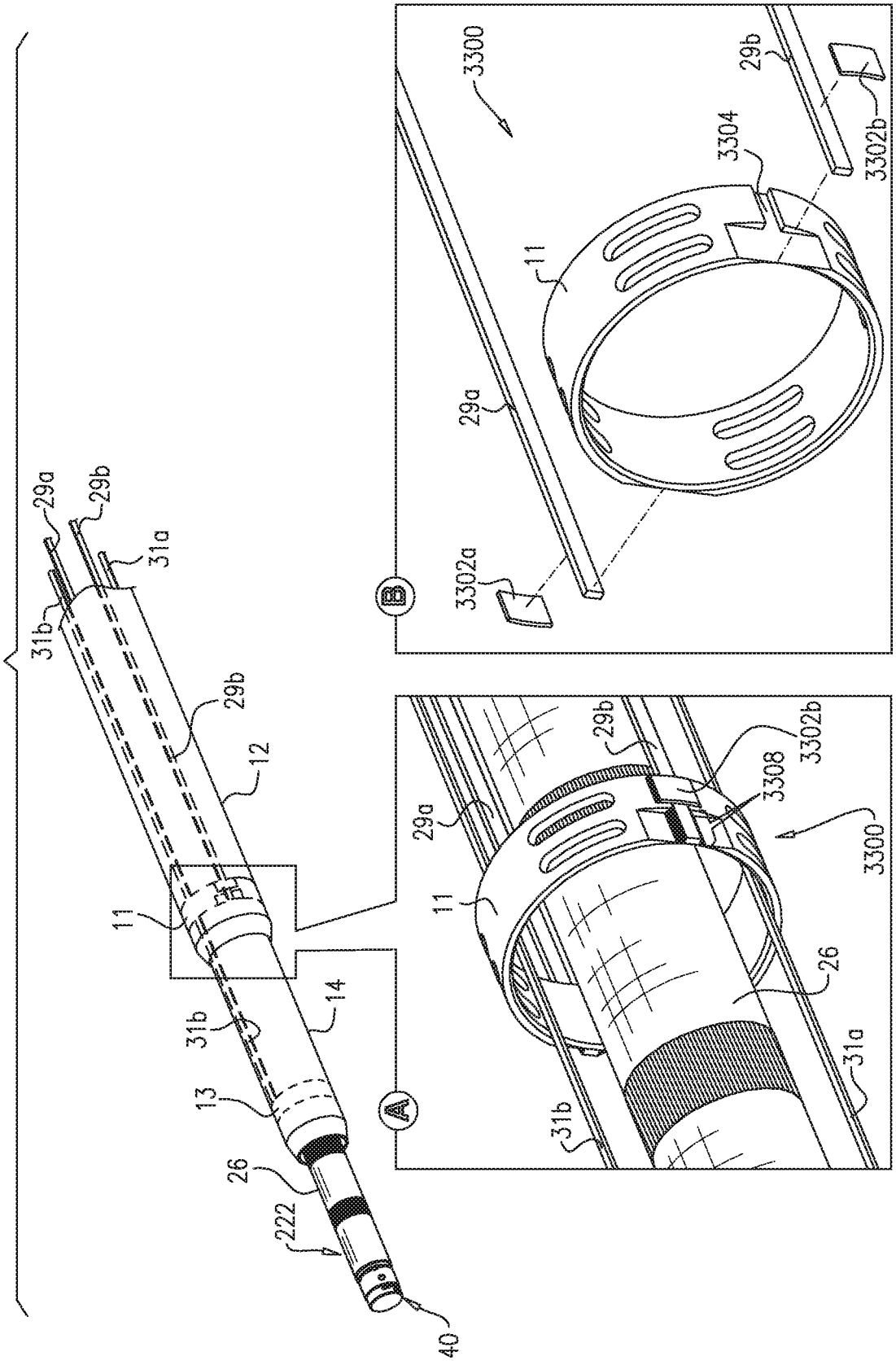

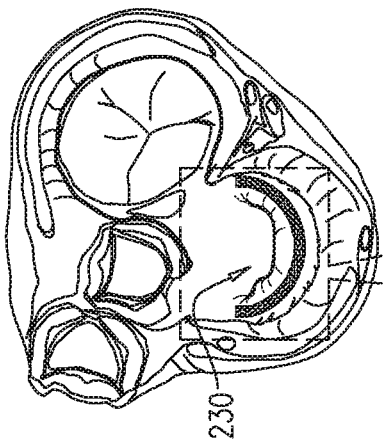
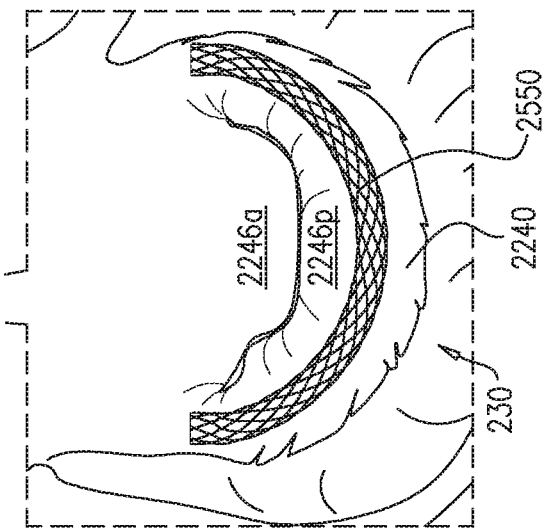
FIG. 35A
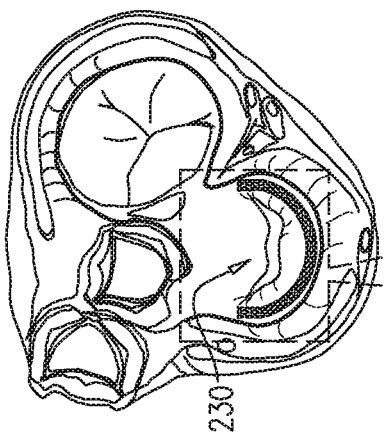
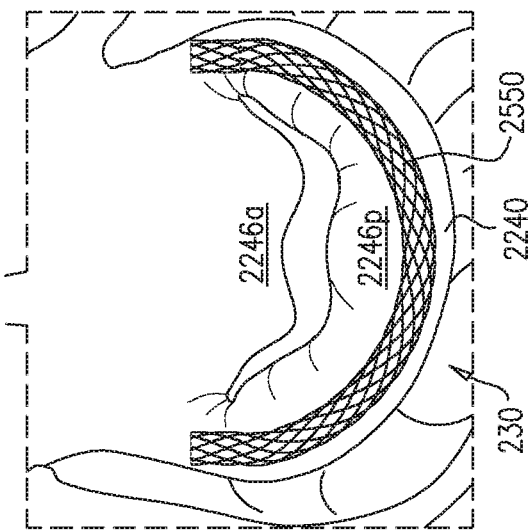
FIG. 35B
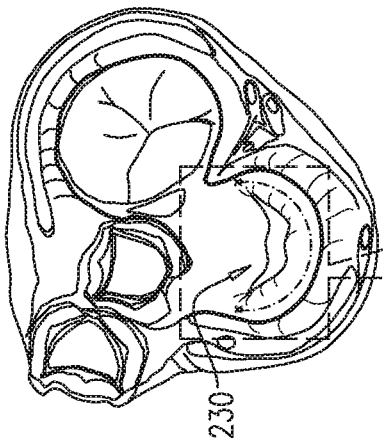
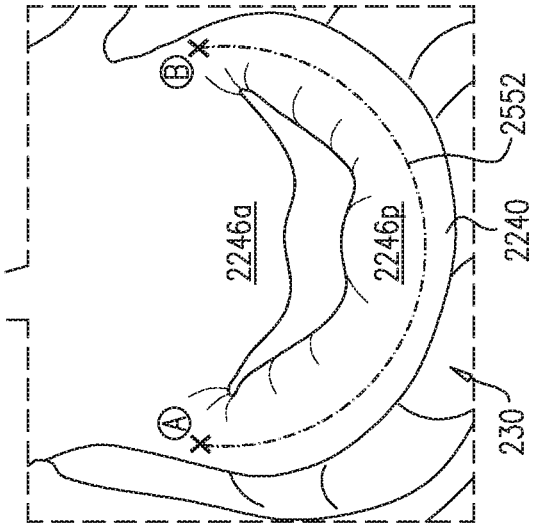
FIG. 35C

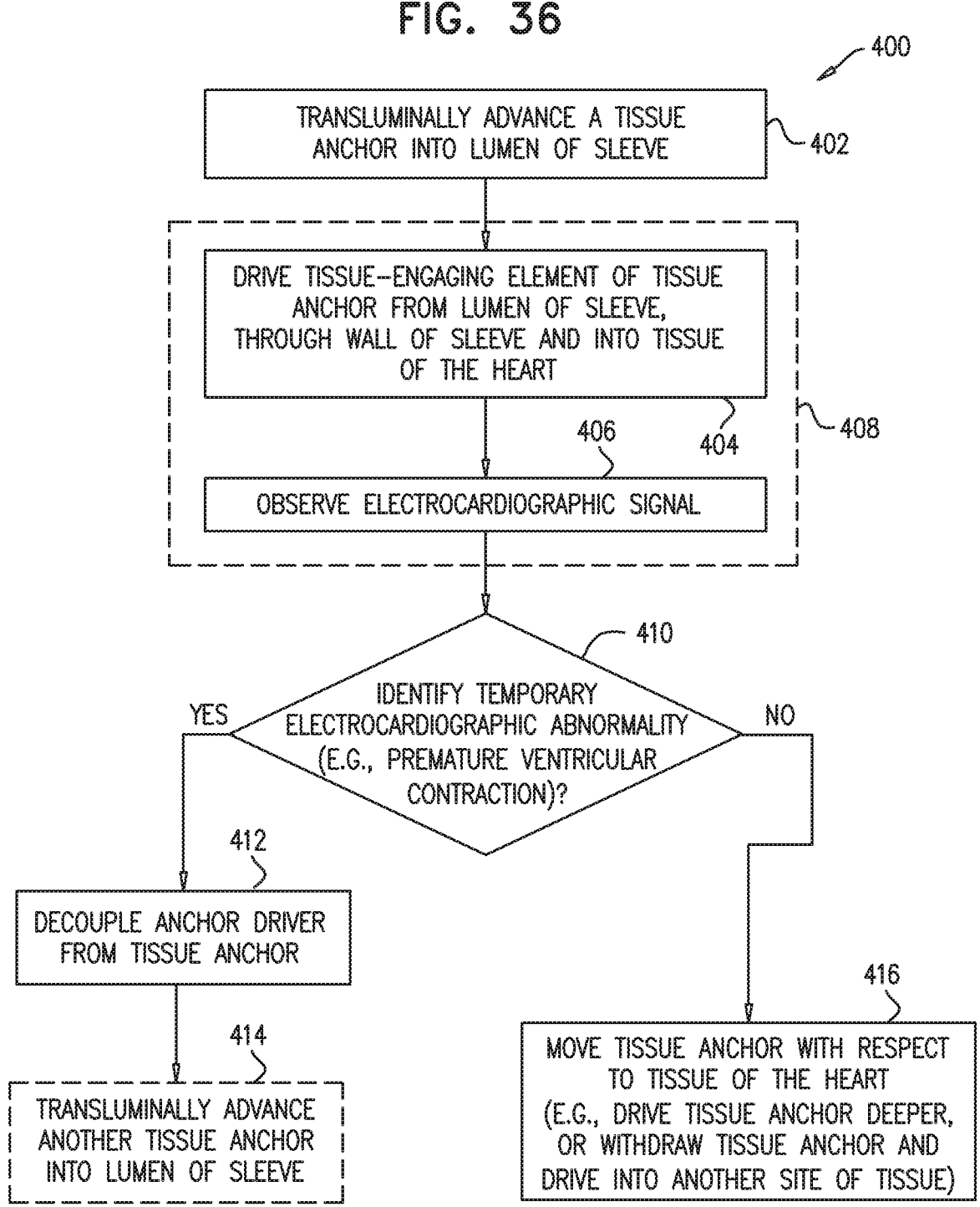

LOCATION INDICATION SYSTEM FOR IMPLANT-DELIVERY TOOL

CROSS-REFERENCES TO RELATED APPLICATIONS

The present application is a continuation of U.S. Ser. No. 15/955,421 to Sheps et al., entitled "Controlled steering functionality for implant-delivery tool," which published as US 2018/0228608, and which is Divisional of U.S. Ser. No. 14/437,373 to Sheps et al., entitled "Controlled steering functionality for implant-delivery tool," which published as US 2015/0272734, and which is the US National Phase of PCT application IL2013/050860 to Sheps et al., filed Oct. 23, 2013, entitled "Controlled steering functionality for implant-delivery tool," which published as WO 2014/064694, and which claims priority from:

U.S. Provisional Patent Application 61/717,303 to Sheps et al., titled "Controlled steering functionality for implant-delivery tool," filed Oct. 23, 2012;

PCT Patent Application PCT/IL2012/050451 to Sheps et al., titled "Controlled steering functionality for implant-delivery tool," filed on Nov. 8, 2012, which published as WO 2013/069019, and which claims priority from U.S. Provisional Patent Application 61/557,082 to Sheps et al., titled "Controlled steering functionality for implant-delivery tool," filed Nov. 8, 2011;

U.S. Provisional Patent Application 61/745,848 to Sheps et al., titled "Controlled steering functionality for implant-delivery tool," filed Dec. 26, 2012; and U.S. Provisional Patent Application 61/820,979 to Sheps et al., titled "Controlled steering functionality for implant-delivery tool," filed May 8, 2013.

The present application is related to:

U.S. patent application Ser. No. 14/027,934 to Zipory et al., titled "Over-wire rotation tool," filed Sep. 16, 2013, which published as US 2014/0018914, and issued as U.S. Pat. No. 9,474,606, and which is a Continuation of U.S. patent application Ser. No. 12/689,635 to Zipory et al., titled "Over-wire rotation tool", filed Jan. 19, 2010, which published as US 2010/0280604, and which issued as U.S. Pat. No. 8,545,553;

U.S. patent application Ser. No. 13/504,870 to Miller et al., titled "Tissue anchor for annuloplasty ring", which published as US 2012/0283757, which issued as U.S. Pat. No. 9,011,520, and which is a US National Phase application of PCT Patent Application PCT/IL10/00890, titled "Tissue anchor for annuloplasty ring", filed Oct. 28, 2010, which published as WO 2011/051942, and which is a Continuation-In-Part of U.S. patent application Ser. No. 12/608,316 to Miller et al., titled "Tissue anchor for annuloplasty ring", which published as 2011/0106247, and which issued as U.S. Pat. No. 8,277,502.

All of the above references are incorporated herein by reference.

FIELD OF THE INVENTION

The present invention relates in general to valve repair. More specifically, the present invention relates to repair of a cardiac valve of a patient using a steerable delivery tool.

BACKGROUND

Steerable catheters are typically used to access a body cavity of a patient since these steerable catheters are able to navigate through vasculature of the patient. Additionally, pre-shaped sheaths are used to deliver an implant to the body cavity in a particular orientation.

SUMMARY OF THE INVENTION

In some applications of the present invention, a multi-component tubular system is provided for accessing a heart of a patient. The system comprises one or more steerable guiding catheters configured for directing the passage of devices therethrough into the heart. The multi-component tubular system is configured to deliver an implant in a desired orientation to an annulus of a cardiac valve of the patient and to facilitate anchoring of the implant to the annulus. For some applications of the present invention, the guiding system is advanced transluminally or transthoracically accessing an atrium of the heart. Typically, the system comprises two or more steerable catheters. A first catheter has a distal portion that is steerable to a first desired spatial orientation. A second catheter is disposed within the first catheter and has a distal portion that is steerable to a second desired spatial orientation. The system provides techniques and relative-spatial-orientation-controlling devices for controlling the orientation of the distal portion of the second catheter with respect to the first catheter without substantially distorting the first spatial orientation of the distal portion of the first catheter. For some applications, the relative-spatial-orientation-controlling device comprises a rotational locking mechanism provided by components of the catheter system.

For some applications, the first catheter is configured to provide a slit at the distal portion thereof (i.e., a first component of the rotational locking mechanism), and the second catheter is configured to provide a depressible pin (i.e., a second component of the rotational locking mechanism) at a distal portion thereof. The second catheter is configured for advancement through a lumen of the first catheter. During the advancement, the pin is depressed by an inner wall of the first catheter. The pin is configured to return to a resting state in which the pin is not depressed, when the pin is aligned with the slit of the first catheter. Since the first catheter provides the slit at a distal portion thereof, the second catheter may be introduced within the lumen of the first catheter in any suitable rotational orientation with respect to the first catheter.

The distal portion of the first catheter may be steered in a suitable direction following advancement of the first catheter through vasculature of the patient. Following the advancement of the first catheter and steering of the distal portion of the first catheter in any one or more suitable planes, the second catheter is advanced through the first catheter. The second catheter is advanced through the first catheter until at least a distal-most portion of the distal portion of the second catheter is exposed from within the lumen of the first catheter. Depending on the relative rotational orientation of the second catheter with respect to the first catheter, the physician may need to rotate the second catheter in order to engage the pin with the slit and lock the second catheter with respect to the first catheter. Such locking enables steering of the distal portion of the second in any one or more suitable planes with respect to the distal portion of the first catheter in a manner which substantially maintains the spatial orientation of the first catheter during the steering of the second catheter. Additionally, the first catheter may be further steered without substantially disrupting the spatial orientation of the distal portion of the second catheter.

There is therefore provided, in accordance with an application of the present invention, apparatus for use with a subject, the apparatus including:
a catheter:
configured to be transluminally advanced toward an anatomical site of the subject, and
having a proximal end, a steerable distal end, and a longitudinal axis therebetween;
a tissue anchor, configured to be advanced through the catheter;
an anchor driver:
having a distal end that is reversibly couplable to the tissue anchor, and
configured to drive the tissue anchor through the catheter and out of the distal end of the catheter, and to anchor the tissue anchor at the anatomical site;
a first constraining member configured:
to engage tissue of the subject, and
to inhibit, after the anchor has been driven out of the distal end of the catheter and before the anchor has been anchored, movement of at least the distal end of the anchor driver, on a first axis between (1) the distal end of the anchor driver and (2) a site at which the first constraining member engages the tissue of the subject; and
a second constraining member configured to inhibit, after the anchor has been driven out of the distal end of the catheter and before the anchor has been anchored, movement of at least the distal end of the anchor driver, on a second axis.

In an application, the apparatus further includes a generally longitudinal implant, implantable at the anatomical site, and the first constraining member is slidably coupled to the implant such as to be slidable along an outer surface of the implant and along a longitudinal axis of the implant.

In an application, the first constraining member includes a wire, slidably coupled to the catheter such as to be longitudinally slidable with respect to the catheter.

In an application, the second constraining member includes an implant, advanceable through the catheter and implantable at the anatomical site.

In an application, the implant is configured to inhibit the movement on the second axis while (1) a first portion of the implant is anchored at the anatomical site and (2) the distal end of the anchor driver is disposed within a second portion of the implant, the second axis being between (1) the distal end of the anchor driver, and (2) a tissue site at which the first portion of the implant is anchored.

In an application, the wire is slidable longitudinally with respect to the implant, and is configured to contact tissue at the anatomical site.

In an application, the wire is shaped to define a loop that laterally circumscribes the implant.

In an application, the implant includes a plurality of eyelets disposed on a lateral surface thereof, and the wire is disposed within the eyelets and slidable out of the eyelets.

In an application, at least a portion of the wire is disposed between the catheter and the implant.

In an application, the wire is slidably coupled to, and decouplable from, the implant.

In an application:
the implant is shaped to define a lumen,
the apparatus further includes a channel, a distal end of the channel being slidable within the lumen,
the anchor driver is configured to drive the tissue anchor through the channel and into the lumen,
the distal end of the channel is coupled to a radiopaque marker,
at least a portion of the wire is configured to engage the tissue of the subject, at least the portion of the wire being radiopaque, and
the apparatus is configured, when the at least the portion of the wire is engaged with the tissue, to provide a fluoroscopically-identifiable arrangement that indicates a juxtaposition of the distal end of the channel with respect to the tissue.

There is further provided, in accordance with an application of the present invention, apparatus for use with a subject, the apparatus including:
a catheter configured to be transluminally advanced toward an anatomical site of the subject, and having a proximal end and a steerable distal end;
an annuloplasty implant:
advanceable through the catheter toward the anatomical site;
having a longitudinal axis,
being shaped to define a lumen, and
including a plurality of eyelets distributed longitudinally on an outer surface of the implant;
a tissue anchor, configured to be advanced through the catheter;
an anchor driver:
having a distal end that is:
reversibly couplable to the tissue anchor,
advanceable, while coupled to the tissue anchor, through the catheter, out of the distal end of the catheter, and into the lumen of the implant, and
configured to anchor the implant at the anatomical site using the anchor; and
a longitudinal guide:
having a tissue-engaging distal end portion, configured to be placed in contact with tissue of the subject,
disposed through the plurality of eyelets, and
slidable with respect to the plurality of eyelets such that the distal end portion of the longitudinal guide is:
slidable distally past a distal end of the implant, and
progressively slidable out of progressively proximal eyelets of the plurality of eyelets.

In an application, the apparatus further includes a channel, at least a distal portion of the channel being disposable coaxially within the lumen of the sleeve, a given position of a distal end of the channel within the lumen defining a respective portion of the sleeve to be anchored, and:
the anchor driver is configured to advance the anchor into the lumen of the implant via the channel, and to anchor the respective portion of the sleeve at the anatomical site,
a respective eyelet of the plurality of eyelets is disposed adjacent to each respective portion of the sleeve, and
the longitudinal guide is configured (i) to facilitate proximal sliding of the distal end portion thereof out of a given eyelet of the plurality of eyelets, and (ii) to inhibit any subsequent distal sliding of the longitudinal guide with respect to the plurality of eyelets from threading the distal end portion back into the given eyelet.

In an application, the distal end portion of the longitudinal guide is biased to protrude radially outward from the sleeve.

In an application:
at least the distal end portion of the guide is radiopaque,
the distal end of the channel includes a radiopaque marker, and
the apparatus is configured, when the distal end portion of the guide is in contact with the tissue, to provide a fluoroscopically-identifiable arrangement that indicates a juxtaposition of the distal end of the channel with respect to the tissue.

In an application:
the longitudinal guide includes a first longitudinal guide,
the plurality of eyelets includes a first plurality of eyelets, and
the apparatus further includes:
at least a second plurality of eyelets distributed longitudinally on the outer surface of the implant; and
at least a second longitudinal guide, disposed through the at least the second plurality of eyelets,
the first longitudinal guide and the second longitudinal guide being disposed at respective circumferential positions around the longitudinal axis of the implant.

In an application, the longitudinal guide is configured such that, when the distal end portion is in contact with the tissue and the longitudinal guide is moved distally, the distal end portion splays across the tissue away from the implant.

There is further provided, in accordance with an application of the present invention, apparatus for use with a subject, the apparatus including:
a catheter:
configured to be transluminally advanced, toward an anatomical site of the subject, and
having a proximal end, a steerable distal end, and a longitudinal axis therebetween;
an implant, advanceable through the catheter;
a tissue anchor, configured to be advanced through the catheter, and to anchor the implant to the anatomical site;
an anchor driver:
having a distal end that is reversibly couplable to the tissue anchor, and
configured to drive the tissue anchor through the catheter and out of the distal end of the catheter, and to anchor the tissue anchor at the anatomical site;
a first radiopaque marker, movable with respect to the catheter, the tissue anchor and the anchor driver; and
a second radiopaque marker, movable with respect to the catheter, the tissue anchor, the anchor driver, the implant, and the first radiopaque marker.

In an application, the apparatus further includes a channel, advanceable through the catheter, and:
the implant includes a sleeve that defines a lumen and a proximal opening into the lumen,
the channel is advanceable through the catheter and through the proximal opening into the lumen,
the distal end of the anchor driver is configured to be advanced the anchor through the channel and into the lumen,
In an application, one of the radiopaque markers selected from the group consisting of: the first radiopaque marker and the second radiopaque marker, is coupled to the channel.

In an application, the apparatus further includes at least one longitudinal guide member, and:
the longitudinal guide member:
is slidably coupled to the catheter and the sleeve,
has a tissue-engaging portion that is configured to be placed in contact with tissue of the subject, and
includes the second radiopaque marker, and
the first radiopaque marker is coupled to the channel.

In an application, the implant includes a third radiopaque marker.

In an application, the channel has a longitudinal axis, and the at least one longitudinal guide member is configured to provide radiopaque marking at more than one circumferential position around the longitudinal axis of the channel.

In an application, the at least one longitudinal guide member includes a plurality of longitudinal guide members, disposed at respective circumferential positions around the longitudinal axis of the channel.

In an application, the at least one longitudinal guide member includes a looped portion that is positionable so as to circumscribe the channel.

In an application, the first radiopaque marker is coupled to the implant.

There is further provided, in accordance with an application of the present invention, apparatus, including:
a catheter, transluminally advanceable to a valve of a heart of a subject;
an implant:
configured to be advanced distally through the catheter such that a distal end of the implant is placeable against tissue of the valve while a proximal end of the implant is disposed within the catheter, and
having a longitudinal axis between the distal end of the implant and the proximal end of the implant, and a lateral surface that circumscribes the longitudinal axis; and
a guidewire:
configured to be advanced distally through the catheter,
coupled to the implant such that at least a distal portion of the guidewire extends distally from a hole in the lateral surface of the implant, the distal portion of the guidewire being configured to be advanced between leaflets of the valve,
the apparatus being configured to mechanically bias the placement of the distal end of the implant against the tissue at least in part dependently on a distance along the longitudinal axis between the distal end of the implant and the hole.

In an application, the apparatus is configured to bias the placement of the distal end of the implant against the tissue at least in part dependently on a stiffness of the guidewire.

In an application, the guidewire is configured to engage a commissure of the valve, and the apparatus is configured, when the guidewire engages the commissure, to inhibit movement, on a plane of the valve, of the distal end of the implant outside of an arc centered on the commissure.

In an application, the guidewire is retractable through the hole and decouplable from the implant.

In an application:
the implant is shaped to define a lumen, the lateral surface of the implant circumscribing the lumen,
the apparatus further includes a tissue anchor, configured to be advanced distally through the catheter and into the lumen, and to anchor the distal end of the implant to the tissue against which the distal end of the implant is placed.

There is further provided, in accordance with an application of the present invention, a method, including:
transluminally advancing a catheter to a valve of a heart of a subject;
providing an implant and a guidewire, the implant having a longitudinal axis between a distal end of the implant and a proximal end of the implant, and a lateral surface that circumscribes the longitudinal axis;
transluminally advancing the implant and the guidewire through the catheter to the valve while at least a distal portion of the guidewire extends distally from a hole in the lateral surface of the implant;
moving the distal portion of the guidewire between leaflets of the valve and into contact with a commissure of the valve;
placing the distal end of the implant against tissue of the valve:
while a proximal end of the implant is disposed within the catheter, and while the position of the distal end of the implant against the tissue is mechanically biased by the contact of the guidewire and the commissure.

In an application, placing includes placing while the position of the distal end of the implant against the tissue is mechanically biased at least in part by a distance along the longitudinal axis between the distal end of the implant and the hole.

In an application, placing includes placing while the position of the distal end of the implant against the tissue is mechanically biased at least in part by a stiffness of the guidewire.

In an application, placing includes placing while the distal end of the implant is inhibited by the guidewire from moving, on a plane of the valve, outside of an arc centered on the commissure.

In an application, the method further includes, while the distal end of the implant is disposed against the tissue:
  advancing a tissue anchor into a lumen of the implant, the lumen being circumscribed by the lateral surface; and
  anchoring the implant to the tissue by driving the tissue anchor through the distal end of the implant and into the tissue.

In an application, the method further includes, subsequently to driving the tissue anchor through the distal end of the implant and into the tissue, withdrawing the guidewire through the hole, and removing the guidewire from the subject.

There is further provided, in accordance with an application of the present invention, apparatus, including:
  a first catheter having a steerable distal end portion, and including a first coupling at a longitudinal site of the first catheter, configured to be advanced transluminally into a subject;
  a second catheter having a steerable distal end portion configured to be advanced through the first catheter in any rotational orientation of the second catheter with respect to the first catheter, and to be advanced out of a distal end of the first catheter, the second catheter including a second coupling at a longitudinal site of the second catheter,
    the second coupling being configured to be advanced through the first catheter to the first coupling, and to be automatically intracorporeally locked to the first coupling upon the second catheter assuming a given rotational and longitudinal alignment with respect to the first catheter,
    the first coupling and the second coupling defining a distal locking mechanism having:
      an unlocked state in which the first coupling is not locked to the second coupling, and in which the second catheter is rotatable and longitudinally slidable within the first catheter, and
      a locked state in which the first coupling is locked to the second coupling, and in which the longitudinal site of the second catheter is (1) inhibited from rotating with respect to the longitudinal site of the first catheter, and (2) longitudinally slidable with respect to the longitudinal site of the first catheter;
  a first handle, coupled to a proximal end of the first catheter;
  a second handle, coupled to a proximal end of the second catheter; and
  a proximal locking mechanism, including:
    a third coupling, coupled to the first handle; and
    a fourth coupling, coupled to the second handle, and configured to be locked to the third coupling, the third coupling and the fourth coupling defining a proximal locking mechanism having an unlocked state in which the third coupling is not locked to the fourth coupling, and a locked state in which the third coupling is locked to the fourth coupling, and in which the proximal end of the second catheter is (1) inhibited from rotating with respect to the proximal end of the first catheter, and (2) inhibited from longitudinally sliding with respect to the proximal end of the first catheter.

In an application, the apparatus is configured such that, when a distal end of the second catheter is disposed within the first catheter, moving the proximal locking element into the locked state thereof moves the distal end of the second catheter out of the distal end of the first catheter.

In an application, the apparatus is configured such moving the proximal locking mechanism into the locked state thereof simultaneously moves the distal locking mechanism is in the locked state thereof.

In an application, the apparatus further includes an adjustment mechanism coupled to the proximal locking mechanism, and configured to longitudinally slide the first catheter with respect to the second catheter while the proximal locking mechanism is the locked state thereof.

In an application, while the first locking mechanism is in the locked state thereof and the second locking mechanism is in the locked state thereof, bending of the steerable distal end portion of the first catheter increases a length of the second catheter that is exposed from the distal end of the first catheter.

In an application, the adjustment mechanism is configured to facilitate maintenance of the amount of the second catheter that is exposed from the distal end of the first catheter.

In an application, the adjustment mechanism couples at least one of the couplings of the proximal locking mechanism to the handle to which the at least one of the couplings is coupled, and is configured to longitudinally slide the first catheter with respect to the second catheter by moving the at least one of the couplings with respect to the handle to which the at least one of the couplings is coupled.

In an application, the adjustment mechanism includes a control wheel.

In an application:
  the first handle is shaped to define a groove that includes the third coupling,
  the fourth coupling includes a protrusion configured to be inserted into the groove, and to be locked within the groove by the second handle being rotated with respect to the first handle.

In an application, the fourth coupling defines an extracorporeal indicator, configured to move correspondingly with the second coupling, and to provide an indication of an intracorporeal position of the second coupling with respect to the first steerable tube.

In an application, the second coupling is configured to revolve around a longitudinal axis of the second catheter in response to rotation of the second steerable tube, and the extracorporeal indicator is configured to revolve around the axis correspondingly with the second coupling.

In an application, the second coupling is configured to move longitudinally in response to longitudinal movement of the second catheter, and the extracorporeal indicator is configured to move longitudinally correspondingly with the second coupling.

In an application, the extracorporeal indicator is configured to indicate a locking state of the distal locking mechanism, the locking state selected from the group consisting of: the unlocked state and the locked state.

There is further provided, in accordance with an application of the present invention, a method, including:

placing an electrode in contact with a first anatomical site of the subject;

transluminally advancing, toward a heart of a subject, an implant including a sleeve that defines a lumen;

transluminally advancing, into the lumen of the sleeve, a tissue anchor having a helical tissue-engaging element that is mechanically and electrically coupled to an anchor driver;

moving a portion of the sleeve toward a second anatomical site of the subject and placing the tissue-engaging element at the second anatomical site;

while the tissue-engaging element is at the second anatomical site, using a control unit that is electrically coupled to the electrode and that is electrically coupled to the tissue-engaging element via the anchor driver, detecting a first electrical signal;

at least in part responsively to the first electrical signal, moving the portion of the sleeve toward a third anatomical site of the subject, and placing the tissue-engaging element in contact with the third anatomical site;

while the tissue-engaging element is in contact with the third anatomical site, using the control unit, detecting a second electrical signal; and at least in part responsively to the second electrical signal, anchoring the portion of the sleeve to the third anatomical site by using the anchor driver to drive the tissue-engaging element into the third anatomical site.

In an application, the method further includes, subsequently to anchoring the portion of the sleeve, electrically decoupling the tissue-engaging element from the anchor driver.

In an application, advancing the tissue anchor includes advancing a tissue anchor that includes stainless steel.

In an application, placing the tissue-engaging element at the second anatomical site includes placing the tissue-engaging element in contact with tissue at the second anatomical site, and detecting the first electrical signal includes detecting the first electrical signal while the tissue-engaging element is in contact with the tissue at the second anatomical site.

In an application:

placing the tissue-engaging element in contact with the third anatomical site includes placing the tissue-engaging element in contact with the third anatomical site (1) while at least part of the tissue-engaging element protrudes from the lumen through the portion of the sleeve, and (2) such that a gap exists between the portion of the sleeve and the third anatomical site, and using the anchor driver to drive the tissue-engaging element into the third anatomical site includes reducing the gap between the portion of the sleeve and the third anatomical site.

In an application, placing the tissue-engaging element in contact with the third anatomical site includes placing the tissue-engaging element in contact with the third anatomical site while (1) the entire tissue-engaging element protrudes through the portion of the sleeve, and (2) a proximal stem portion traverses the portion of the sleeve, the proximal stem portion (1) coupling the tissue-engaging element to a head of the tissue anchor, and (2) being disposed on a central longitudinal axis of the tissue anchor.

There is further provided, in accordance with an application of the present invention, apparatus, including:

an electrode, configured to be coupled to a subject;

a catheter, transluminally advanceable into a heart of the subject;

an implant, advanceable through the catheter into the heart of the subject, and including a sleeve shaped to define a lumen therethrough;

a channel, slidable within the catheter, a distal end portion of the channel being slidable within the lumen of the sleeve;

a tissue anchor:

slidable through the channel and into the lumen of the sleeve, and including (1) a distal electrically-conductive helical tissue-engaging element, configured to be screwed through the sleeve from the lumen, and to be anchored to tissue of the heart of the subject, and (2) a proximal electrically-conductive coupling head that is electrically coupled to the tissue-engaging element, and is configured to not pass through the sleeve;

an electrically-conductive anchor driver, having a proximal end, and a distal end that is mechanically and electrically couplable to and decouplable from the coupling head;

a control unit, electrically couplable to the electrode, and electrically couplable to the tissue-engaging element via the coupling head and the anchor driver, including a display, and circuitry configured, while the electrode is in contact with the subject and the tissue-engaging element is in contact with the tissue of the heart of the subject, to:

receive an electrical signal from the electrode and from the tissue-engaging element, and indicate via the display a position of the tissue-engaging element with respect to the heart of the subject.

In an application, the tissue anchor further includes a stem portion that couples the helical tissue-engaging element to the coupling head, and that is collinear with a central longitudinal axis of the tissue-engaging element.

In an application:

the tissue-engaging element is configured to be screwed through the sleeve from the lumen such that at least a portion of the tissue-engaging element is (1) disposed outside of the lumen, and (2) configured to be placed in contact with the tissue of the heart while (a) the coupling head is disposed within the lumen, and (b) a gap exists between the sleeve and the tissue, the control unit is configured to receive the electrical signal while the at least the portion of the tissue-engaging element is in contact with the tissue and the coupling head is disposed within the lumen, and the tissue anchor is configured to be subsequently screwed, by the anchor driver, into the tissue, and to responsively reduce the gap.

There is further provided, in accordance with an application of the present invention, apparatus, including:

a tubular member:

having a longitudinal axis, including a lateral wall shaped to define:

a primary lumen along the longitudinal axis, the lateral wall circumscribing the primary lumen, and a secondary lumen along the longitudinal axis, and within the lateral wall, and having a distal steerable portion;

a pull-wire disposed within the secondary lumen; and a pull-ring:

coupled to the distal steerable portion of the tubular member such that the pull-ring circumscribes the primary lumen, shaped to define a receptacle, coupled to a distal portion of the pull-wire, the distal portion of the pull-wire being disposed in the receptacle, the disposition of the distal portion of the pull-wire in the receptacle facilitating the coupling of the pull-wire to the pull-ring.

In an application, the receptacle includes a recess, and the apparatus further includes a cap that bridges the recess, the bridging of the cap over the recess further facilitating the coupling of the pull-wire to the pull-ring.

In an application, the receptacle includes an opening through which the guidewire is disposed, the disposition of the guidewire through the opening facilitating the coupling of the pull-wire to the pull-ring.

In an application, the distal portion of the pull-wire is welded to the pull-ring.

In an application, the distal portion of the pull-wire is welded to the receptacle.

In an application, the distal portion of the pull-wire includes a distal end of the pull-wire and the distal end of the pull-wire is welded to the pull-ring distally to the receptacle.

There is further provided, in accordance with an application of the present invention, apparatus, including:

a tube having a distal end and a tube lumen;

a marker coupled to the distal end of the tube, the marker being visible using imaging;

a guide shaped so as to define a looped portion, the looped portion surrounding and being slidable with respect to the tube at a distal portion of the tube, the looped portion being configured to abut against tissue of a patient, and the guide and the marker are configured to provide an indication of a position of the distal end of the tube with respect to the tissue during (1) the abutting of the looped portion against the tissue, and (2) alignment of the looped portion of the guide and the marker of the tube.

In an application, the apparatus further includes:

at least one tissue anchor; and an anchor deployment manipulator advanceable within the lumen of the tube, the anchor deployment manipulator being reversibly couplable to the at least one anchor and configured to deploy the anchor from within the tube in response to the indication of the position of the distal end of the tube.

In an application, the apparatus further includes an implant structure including a sleeve shaped so as to define a sleeve lumen, the tube is advanceable within the sleeve lumen, and the looped portion is configured to surround the distal portion of the tube by surrounding a portion of the sleeve.

There is further provided, in accordance with an application of the present invention, a method, including:

advancing toward tissue of a subject a tube having a distal end, a tube lumen, and a marker coupled to the distal end of the tube;

surrounding at least a distal portion of the tube with a looped portion of a guide;

sliding the looped portion of the guide with respect to the tube and toward a portion of tissue of a patient;

abutting the looped portion against the tissue of the patient;

providing an indication of a position of the distal end of the tube with respect to the tissue by:

using imaging to view an alignment between the marker and the looped portion; and sensing the abutting of the looped portion against the tissue of the patient.

In an application, advancing the tube includes advancing the tube surrounded by an implant structure including a sleeve shaped so as to define a sleeve lumen, and the tube is advanceable within the sleeve lumen, and the looped portion is configured to surround the distal portion of the tube by surrounding a portion of the sleeve.

In an application, the method further includes positioning the sleeve around an annulus of an atrioventricular valve of the patient.

In an application, sliding the looped portion of the guide includes advancing a linear section of the guide between leaflets of the atrioventricular valve.

In an application, the method further includes:

advancing an anchor deployment manipulator within the lumen of the tube, the anchor deployment manipulator being reversibly couplable to at least one anchor and using the deployment manipulator, deploying the anchor from within the tube in response to the providing the indication of the position of the distal end of the tube.

There is further provided, in accordance with an application of the present invention, apparatus, including:

an implant structure configured to treat a native atrioventricular valve of a patient, the implant structure including a sleeve having a lumen and at least a proximal end, the proximal end being shaped so as to define an opening;

a longitudinal element, having a distal end that is slidable within the lumen, and slidable out of lumen via the opening; and a closure element:

coupled to the implant structure in a vicinity of the at least one end, including a flap:

having (1) an open state and (2) a closed state in which the lumen is in reduced fluid communication with outside of the implant structure compared to when the flap is in the open state, and configured to be biased toward assuming the closed state, the apparatus being configured such that when the distal end of the longitudinal element is disposed within the lumen and distal to the closure element:

the flap is retained in the open state, and sliding of the distal end of the longitudinal element proximally past the closure element closes the flap.

In an application, the longitudinal element is shaped to define a channel that has a proximal end and a distal end, and is configured such that, when the distal end of the channel is disposed within the lumen of the sleeve and distal to the closure element, the proximal end of the channel is in fluid communication with the lumen of the sleeve.

In an application, the apparatus is configured to be implanted along an annulus of a mitral valve of the patient in a manner in which the implant structure is formed into at least a portion of an annuloplasty ring.

In an application, the closure element further includes a generally cylindrical frame, and the flap is articulatably coupled to the frame.

In an application, the flap is articulatably coupled to the frame so as to articulate around an articulation axis, and the flap is more flexible around an axis that is orthogonal to the articulation axis, than it is around an axis that is parallel to the articulation axis.

In an application, the apparatus further includes a reference-force tube, including one or more coupling elements at a distal end thereof, the coupling elements being reversibly couplable to the implant structure.

In an application, the coupling elements are reversibly couplable to the closure element.

In an application, the apparatus is configured such that when the coupling elements are coupled to the closure element:

when the distal end of the longitudinal element is disposed within the lumen and distal to the closure element, the longitudinal element inhibits the coupling elements from decoupling from the closure element, and sliding of the distal end of the longitudinal element proximally past the closure element automatically decouples the coupling elements from the closure element.

In an application, the coupling elements are configured to reversibly articulatably couple the reference-force tube to the implant structure.

In an application, the apparatus further includes a contracting mechanism, coupled to the implant structure and configured to contract at least a portion of the implant structure.

In an application, the contracting mechanism includes a rotatable structure, configured to contract the at least the portion by rotating in a first rotational direction.

In an application, the rotatable structure is configured to expand the implant structure in response to rotation of the rotatable structure in a second rotational direction that is opposite the first rotational direction.

There is further provided, in accordance with an application of the present invention, apparatus configured for providing percutaneous access to a body of a subject, including:

a first steerable catheter, including a first tubular member that is shaped to define a first lumen therethrough;

a second steerable catheter, including a second tubular member that is:

shaped to define a second lumen therethrough, and configured to be concentrically disposed within the first lumen of the first steerable tube;

a first coupling, disposed at a distal portion of the first catheter;

a second coupling, disposed at a distal portion of the second catheter, and couplable to the first coupling, coupling of the second coupling to the first coupling inhibiting rotation of at least the distal portion of the second catheter with respect to the distal portion of the first catheter;

a third coupling, disposed at a proximal portion of the first catheter;

a fourth coupling, disposed at a proximal portion of the second catheter, and couplable to the third coupling, coupling of the fourth coupling to the third coupling inhibiting rotation of at least the proximal portion of the second catheter with respect to the proximal portion of the first catheter.

In an application, the apparatus further includes an adjustment mechanism, coupled to at least one coupling selected from the group consisting of the third coupling and the fourth coupling, and configured, when the fourth coupling is coupled to the third coupling, to axially move the second catheter within the second lumen.

In an application, the adjustment mechanism is configured to adjust a distance between the selected coupling and the catheter at the proximal end of which the selected coupling is disposed.

In an application, the apparatus is configured such that as the third coupling couples to the fourth coupling, the second coupling simultaneously couples to the first coupling.

In an application, a distal portion of the first catheter defines the first coupling, and a distal portion of the second catheter defines the second coupling.

In an application:

a distal portion of the apparatus, including the distal portion of the first catheter and the distal portion of the second catheter, is configured to be advanced percutaneously into the body of the subject, and a proximal portion of the apparatus, including the proximal portion of the first catheter and the proximal portion of the second catheter, is configured to be disposed outside the body of the subject.

In an application:

the proximal portion of the first catheter includes a first handle, coupled to the third coupling, and the proximal portion of the second catheter includes a second handle, coupled to the fourth coupling.

In an application, the apparatus further includes an adjustment mechanism:

coupled to (1) at least one handle selected from the group consisting of the first handle and the second handle, and (2) at least one coupling selected from the group consisting of the third coupling and the fourth coupling, and configured to adjust a distance between the selected handle and the selected coupling.

In an application, the third coupling and the fourth coupling together define an indicator that indicates a state of coupling of the second coupling to the first coupling.

In an application, the apparatus is configured such that coupling of the fourth coupling to the third coupling inhibits longitudinal movement of at least the proximal portion of the second catheter with respect to at least the proximal portion of the first catheter.

In an application, the apparatus is configured such that when the first coupling is coupled to the second coupling, the distal portion of the second catheter is longitudinally slidable at least 5 mm with respect to the distal portion of the first catheter.

In an application, the apparatus is configured such that when the first coupling is coupled to the second coupling, the distal portion of the second catheter is longitudinally slidable between 5 mm and 15 mm with respect to the distal portion of the first catheter.

There is further provided, in accordance with an application of the present invention, a method, including:

transluminally advancing a steerable distal portion of a first catheter into a subject;

advancing at least part of a steerable distal portion of a second catheter through the first catheter and out of a distal end of the first catheter;

bending the steerable distal portion of the first catheter;

while the steerable distal portion of the first catheter is bent, advancing a first tissue anchor out of a distal end of the second catheter;

subsequently, at least partly straightening the steerable distal portion of the first catheter;

subsequently, moving the distal end of the second catheter distally away from the distal end of the first catheter; and subsequently, advancing a second tissue anchor out of the distal end of the second catheter.

There is further provided, in accordance with an application of the present invention, a method, including:

providing an implant including an adjusting mechanism that includes a housing that is reversibly coupled to a distal portion of a guide member;

percutaneously advancing the adjustable implant and at least the distal portion of the guide member through a catheter into a body of a subject;

moving the housing with respect to another portion of the implant by pulling the guide member proximally;

anchoring the implant to tissue of the subject;

advancing an adjustment tool distally along the guide member toward the implant; and adjusting the adjusting mechanism using the adjustment tool.

In an application, the other portion of the implant has a longitudinal axis, advancing the implant includes advancing the implant while the housing is disposed on the longitudinal axis, and moving the housing includes moving the housing away from the longitudinal axis.

In an application, moving the housing away from the longitudinal axis includes translating the housing away from the longitudinal axis.

In an application, advancing the implant includes advancing the implant while the housing is disposed at a distal end of the other portion of the implant, and anchoring the implant to the tissue of the subject includes, subsequently to moving the housing away from the longitudinal axis, anchoring the distal end of the other portion of the implant to the tissue.

In an application, the other portion of the implant includes a sleeve having a lumen, and anchoring the distal end includes driving an anchor, from within the lumen, through the distal end of the sleeve and into the tissue.

In an application, the method further includes, subsequently to driving the first anchor, driving a second anchor through a lateral wall of the sleeve and into the tissue.

There is further provided, in accordance with an application of the present invention, a method, including:

screwing at least part of a helical tissue-engaging element of a tissue anchor entirely through a portion of an implant;

screwing a distal end of the tissue-engaging element into a tissue such that there is a distance between the tissue and the portion of the implant; and subsequently, reducing the distance between the tissue and the portion of the implant by screwing the distal end of the tissue-engaging element deeper into the tissue.

In an application:

screwing the at least part of the helical tissue-engaging element entirely through the portion of the implant includes screwing at least one turn of the helical tissue-engaging element entirely through the portion of the implant, and screwing the distal end of the tissue-engaging element into the tissue includes screwing the distal end of the tissue-engaging element into the tissue such that the distance between the tissue and the portion of the implant is at least as great as a pitch of the helical tissue-engaging element.

In an application, screwing the at least part of the helical tissue-engaging element entirely through the portion of the implant includes screwing the entire helical tissue-engaging element entirely through the portion of the implant.

In an application, the portion of the implant includes a portion of a flexible sleeve of the implant, and reducing the distance includes reducing the distance without twisting the flexible sleeve.

There is further provided, in accordance with an application of the present invention, apparatus for use with an internal tissue of a subject, the apparatus including:

a tissue anchor, including a helical tissue-engaging element, configured to be anchored to the tissue by being screwed into the tissue;

a flexible, elongate anchor driver:

having a proximal end, and a distal end that is configured to be reversibly coupled to the tissue anchor, and advanced transluminally to the tissue of the subject, and being configured to transfer rotational force from the proximal end to the tissue anchor; and a tool:

including:

a distal portion that is couplable to the proximal end of the anchor driver, a proximal portion, rotatably coupled to the distal portion, and having a rest rotational position with respect to the distal portion, a variable-resistance mechanism, configured to progressively inhibit rotation of the proximal portion with respect to the distal portion, correspondingly with a rotational distance, from the rest rotational position, of the proximal portion with respect to the distal portion.

In an application, the variable-resistance mechanism includes a torsion spring.

In an application, the tool further includes an indicator that indicates at least one rotational position of the proximal portion with respect to the distal portion, that is not the rest rotational position.

In an application:

a pre-determined torque range is (i) sufficient to screw the tissue-engaging element into the tissue, and (ii) insufficient to over-tighten the tissue-engaging element within the tissue, and the apparatus is configured such that the indicator indicates at least a rotational position in which the inhibition of the rotation of the proximal portion with respect to the distal portion transfers, to the tissue anchor, torque that is within the pre-determined torque range.

In an application, the tool includes a torque-limiting mechanism, configured to rotationally disengage the proximal portion from the distal portion if the proximal portion becomes positioned at a rotational position with respect to the distal portion in which the inhibition of the rotation of the proximal portion with respect to the distal portion transfers, to the anchor, torque that is greater than the pre-determined range.

In an application, the torque-limiting mechanism is configured to rotationally disengage the proximal portion from the distal portion permanently.

In an application, the torque-limiting mechanism includes a shear pin that is configured to shear upon experiencing torque that is greater than the pre-determined range.

In an application, the torque-limiting mechanism is configured to rotationally disengage the proximal portion from the distal portion temporarily.

In an application:

the torque-limiting mechanism includes at least one socket, and at least one bearing configured to be seated in the socket, the tool is configured: to transfer torque from the proximal portion to the distal portion while the bearing is seated in the socket, and the bearing is configured to reversibly exit the socket upon experiencing torque that is greater than the pre-determined range.

In an application, the apparatus is configured such that the indicator further indicates at least a rotational position in which the inhibition of the rotation of the proximal portion with respect to the distal portion transfers, to the tissue anchor, torque that is smaller than the pre-determined torque range.

In an application, the apparatus is configured such that the indicator further indicates at least a rotational position in which the inhibition of the rotation of the proximal portion with respect to the distal portion transfers, to the tissue anchor, torque that is at an upper end of the pre-determined torque range.

There is further provided, in accordance with an application of the present invention, apparatus, including:

a catheter, a distal end thereof being percutaneously advanceable into a body of a subject;

a valve, disposed at a proximal end of the catheter, and configured to inhibit fluid flow proximally through the catheter;

an implant, configured to be advanced distally through the catheter; and an introducer, including:

a first tubular member, configured to receive at least a distal portion of the implant; and a second tubular member, telescopically coupled to the first tubular member, and configured to open the valve by a distal end of the second tubular member being advanced through the valve, the valve being configured to seal around the second tubular member.

In an application, the first tubular member includes an O-ring, configured to seal around the at least the distal portion of the implant when the at least the distal portion of the implant is received by the first tubular member.

There is further provided, in accordance with an application of the present invention, a method, including:

transluminally advancing, to a left atrium of a heart of a subject, an implant;

transluminally advancing, to the left atrium, a tissue anchor including a tissue-engaging element and a coupling head;

using an anchor driver, driving the tissue-engaging element through a portion of the implant and into tissue of the heart;

observing an electrocardiographic signal, and in response to the signal, performing an action selected from the group consisting of:

(1.) identifying a temporary electrocardiographic abnormality of the subject responsive to the driving of the tissue-engaging element into the tissue, and at least in part responsively to the identified abnormality, decoupling the anchor driver from the tissue anchor, and (2.) identifying an absence of a temporary electrocardiographic abnormality, and at least in part responsively to the identified absence, moving the tissue anchor with respect to the tissue.

In an application, detecting the temporary electrocardiographic abnormality includes detecting a premature ventricular contraction.

In an application, moving the tissue anchor with respect to the tissue includes driving the tissue-engaging element deeper into the tissue.

In an application:

driving the tissue-engaging element into the tissue includes driving the tissue-engaging element into a first site of the tissue, and moving the tissue anchor with respect to the tissue includes withdrawing the tissue-engaging element from the first site, and driving the tissue-engaging element into a second site of the tissue.

In an application:

withdrawing the tissue-engaging element from the first site includes withdrawing the tissue-engaging element from the first site without withdrawing the tissue-engaging element through the portion of the implant, and driving the tissue-engaging element into the second site includes moving the tissue-engaging element and the portion of the implant to the second site while the tissue-engaging element is disposed through the portion of the implant, and subsequently driving the tissue-engaging element into the second site.

In an application, decoupling the anchor driver from the tissue anchor includes decoupling the anchor driver from the tissue anchor, and subsequently advancing another tissue anchor via the channel and into the lumen.

There is further provided, in accordance with an application of the present invention, a method for use at an annulus of a heart valve of a subject, the method including:

anchoring a first portion of an annuloplasty implant at a first site of the annulus by driving a first tissue anchor into the annulus, the annuloplasty implant including a flexible member and a stiffening member that is stiffer than the flexible member;

subsequently, anchoring a second portion of the annuloplasty implant at a second site of the annulus by driving a second tissue anchor into the annulus while the second tissue anchor is:

inhibited, by the flexible member, from moving outside of a circle centered around the implanted first tissue anchor, and inhibited, by the stiffening member, from moving into the circle.

In an application, anchoring the second portion at the second site includes anchoring the second portion at a second site that is on a circular arc centered around the implanted first tissue anchor, while the stiffening member biases the second tissue anchor toward being disposed on the arc.

There is further provided, in accordance with an application of the present invention, a method, including:

using an imaging device, measuring a measurement of a posterior portion of an annulus of a native valve annulus in a pathological state;

selecting an adjustable annuloplasty band having a relaxed length that is within 10 percent of the measured measurement;

transluminally implanting the band to the posterior portion by anchoring a plurality of portions of the band to a respective plurality of tissue sites of the posterior portion using a respective plurality of tissue anchors; and contracting the posterior portion by contracting the band toward a contracted length thereof by drawing a contraction wire of the band into an adjustment mechanism of the band by actuating the adjustment mechanism.

In an application, transluminally implanting the band includes transluminally advancing the band in a linear state, and anchoring the plurality of portions includes anchoring the plurality of portions without reshaping the native valve annulus.

In an application, the method further includes, in response to the measured measurement, defining a number of portions of the band to be anchored to a respective tissue site using a respective tissue anchor.

There is further provided, in accordance with an application of the present invention, apparatus, including:

a catheter;

an implant, slidable through the catheter, and including a sleeve;

a reference-force member, slidable through the catheter, and configured such that sliding of the reference-force member distally through the catheter pushes the implant distally through the catheter; and a stiffening element:

stiffer than the sleeve, couplable to the sleeve so as to inhibit a flexibility of the sleeve, and couplable to the reference-force member such that movement of the reference-force member away from the sleeve decouples the stiffening element from the sleeve.

In an application, the sleeve is generally longitudinal, and the stiffening element is coupled to the sleeve at at least two longitudinal sites of the sleeve in a manner that increases a stiffness of the sleeve at least between the two sites.

In an application, the stiffening element is woven through the sleeve.

In an application, the stiffening element is couplable to the sleeve and to the reference-force member such that progressive proximal movement of the reference-force member away from the sleeve reduces the inhibition of the flexibility of progressively proximal portions of the sleeve.

In an application, the stiffening element is couplable to the sleeve and to the reference-force member such that progressive proximal movement of the reference-force member away from the sleeve decouples the stiffening element from progressively proximal portions of the sleeve.

In an application, the stiffening element is couplable to the sleeve by being woven a plurality of times through the sleeve, and the movement of the reference-force member away from the sleeve decouples the stiffening element from the sleeve by unweaving the stiffening element from the sleeve.

In an application, the stiffening element includes a stiffening wire.

In an application, the reference-force member includes a reference-force tube that defines a lumen therethrough.

In an application, the reference-force tube is reversibly couplable to the implant.

In an application, the sleeve defines a lumen, and, when the reference-force tube is coupled to the implant, the lumen of the reference-force tube is in fluid communication with the lumen of the sleeve.

In an application, the apparatus further includes a channel, and:
the channel is disposed through the reference-force tube,
a distal portion of the channel is disposed within the lumen of the sleeve, and
the reference-force tube is configured to facilitate proximal withdrawal of the channel out of the lumen of the sleeve by providing a reference distally-directed force to the implant.

There is further provided, in accordance with an application of the present invention, apparatus for use with a tissue of a subject, the apparatus including a tissue anchor, having a central longitudinal axis, and including:
a tissue-engaging element, shaped to define a helix around the central longitudinal axis, and configured to be screwed into the tissue of the subject by the tissue anchor being rotated;
a coupling head; and
a stem portion:
having a first end that is coupled to the tissue-engaging element, a second end that is coupled to the coupling head,
having a longitudinal axis, between the first end and the second end, that is disposed on and substantially parallel with the central longitudinal axis of the tissue anchor.

In an application, the apparatus further includes an implant, and the tissue anchor is configured to anchor the implant to the tissue by the helix passing from a first side of a portion of the implant, entirely through the portion of the implant, and into the tissue.

In an application, the tissue anchor is configured such that once the helix has passed from the first side of the portion of the implant, entirely through the portion of the implant, at least a portion of the stem portion is disposed through the portion of the implant.

In an application, the tissue anchor is configured such that:
while any portion of the helix is disposed through the portion of the implant, rotation of the tissue anchor moves the helix through the portion of the implant, and
while the stem portion is disposed through the portion of the implant, rotation of the tissue anchor does not move the stem portion through the portion of the implant.

There is further provided, in accordance with an application of the present invention, apparatus for anchoring an implant to a tissue of a subject, the apparatus including a tissue anchor, the tissue anchor:
including a helical tissue-engaging element and a coupling head, the helical tissue-engaging element defining a helix that has a radius from a central longitudinal axis thereof,
being configured to anchor the implant to the tissue by the tissue-engaging element penetrating, from a first side of a portion of the implant, through a penetration point in the portion of the implant and into the tissue, such that:
the portion of the implant is sandwiched between the coupling head and the tissue, and
when the portion of the implant is sandwiched between the coupling head and the tissue, the penetration point is disposed on the central longitudinal axis of the helical helix of the helical tissue-engaging element.

There is further provided, in accordance with an application of the present invention, apparatus to facilitate implantation of an implant at a tissue of a subject, the apparatus including:
a first tubular member, transluminally advanceable to the tissue;
an implant, slidable through the first tubular member, and including a sleeve that includes a flexible material;
a second tubular member, at least a distal portion of the second tubular member being slidable into and out of the sleeve;
an anchor, advanceable through at least the distal portion of the second tubular member, and including a helical tissue-engaging element; and
an extracorporeal portion:
coupled to the first tubular member, the implant, the second tubular member, and the anchor, and
configured to:
advance the implant and the second tubular member through the first tubular member, while the distal portion of the second tubular member is disposed inside of the sleeve;
slide the distal portion of the second tubular member proximally out of a portion of the sleeve;
advance the anchor through at least part of the second tubular member;
screw the entire tissue-engaging element through the flexible material of the portion of the sleeve;
subsequently, move the portion of the sleeve closer to the tissue; and
subsequently, screw the tissue-engaging element into the tissue.

There is further provided, in accordance with an application of the present invention, a method, including:
providing an implant including (1) a longitudinal element that defines a longitudinal axis, and (2) an adjusting mechanism coupled to the longitudinal element;
percutaneously advancing the implant distally, through a catheter, while the adjusting mechanism is disposed on the longitudinal axis;
exposing at least the adjusting mechanism from a distal end of the catheter; and subsequently, moving the adjusting mechanism away from the longitudinal axis.

In an application, advancing the implant includes advancing the implant while the adjusting mechanism is disposed at a distal portion of the longitudinal element.

In an application, moving the adjusting mechanism away from the longitudinal axis includes translating the adjusting mechanism laterally away from the longitudinal axis.

In an application, the method further includes, subsequent to moving the adjusting mechanism away from the longitudinal axis, advancing a tissue anchor through a lumen of the longitudinal element, past a coupling site of the adjusting mechanism to the longitudinal element.

In an application, advancing the implant includes advancing the implant while the adjusting mechanism is disposed distal to a distal end of the longitudinal element.

In an application, moving the adjusting mechanism away from the longitudinal axis includes moving the adjusting mechanism to become disposed laterally to the longitudinal element of the implant.

In an application, advancing the implant includes advancing the implant while the adjusting mechanism is pressed laterally into a region of the longitudinal element.

In an application, moving the adjusting mechanism away from the longitudinal axis includes translating the adjusting mechanism laterally away from the longitudinal axis by pushing a tubular member into the region of the other element.

The present invention will be more fully understood from the following detailed description of embodiments thereof, taken together with the drawings, in which:

BRIEF DESCRIPTION OF THE DRAWINGS

FIGS. 3A-E are schematic illustrations of cross-sectional images of components of the catheter system of FIGS. 1-2, in accordance with some applications of the present invention;

FIGS. 4-6 are schematic illustrations of components of the catheter system of FIGS. 1-2, in accordance with some applications of the present invention;

FIGS. 7A-B are schematic illustrations of components of the catheter system of FIGS. 1-2, in accordance with some other applications of the present invention;

FIGS. 8A-B are schematic illustrations of a rotating deployment element of an anchor deployment system in radially-expanded and radially-compressed states, respectively, in accordance with some applications of the present invention;

FIGS. 9A-B are schematic illustrations of the rotating deployment element of FIGS. 8A-B engaging a tool-coupling head of a tissue anchor, with the element in locked and unlocked states, respectively, in accordance with some applications of the present invention;

FIGS. 10A-I are schematic illustrations of a procedure for implanting an annuloplasty ring structure to repair a mitral valve, in accordance with some applications of the present invention;

FIGS. 12A-C are schematic illustrations of a navigational-based guidance system, which employs a guide shaped to define a looped portion, in accordance with some applications of the present invention;

FIGS. 13A-E are schematic illustrations of a navigational-based guidance system, which employs one or more longitudinal guides configured to facilitate guidance of an anchor driver to specific portions of the mitral valve by the guides contacting a surface of the mitral valve, in accordance with some applications of the invention

FIGS. 15A-D are schematic illustrations of an indicator and locking system comprising a protrusion and a housing, or cradle, shaped to define a groove, in accordance with some applications of the present invention;

FIGS. 16A-B are schematic illustrations of sleeve coupling elements which couple the annuloplasty ring structure to the multi-component tubular system, in accordance with an embodiment of the present invention;

FIGS. 19 and 20A-D are schematic illustrations of a closure mechanism for an annuloplasty ring structure, in accordance with some applications of the present invention;

FIGS. 21, 22, 23A-H, and 24A-D are schematic illustrations of a tool for use with an anchor driver, in accordance with some applications of the invention;

FIGS. 25 A-E are schematic illustrations of a tool for use with an anchor driver, in accordance with some applications of the invention;

FIGS. 26A-G are schematic illustrations of steps in the implantation of an annuloplasty ring structure to repair a mitral valve, in accordance with some applications of the invention;

FIG. 28 is a schematic illustration of a system used transapically to implant an annuloplasty ring structure at a mitral valve, in accordance with some applications of the present invention;

FIG. 29 is a schematic illustration of a multi-component tubular system providing one or more rotationally-controlled steering catheters configured for delivering an implant to a heart of a patient, in accordance with some applications of the invention;

FIGS. 30A-D are schematic illustrations of a telescopic introducer for facilitating introduction of a catheter and/or an annuloplasty ring structure into a proximal end of a catheter, in accordance with some applications of the invention;

FIGS. 31A-C are schematic illustrations of an annuloplasty ring structure, comprising a sleeve and an adjusting mechanism, in accordance with some applications of the invention;

FIGS. 32A-B are schematic illustrations of respective systems for coupling a pull ring of a catheter to pull wires, in accordance with some applications of the invention;

FIGS. 35A-C are schematic illustrations of a technique for sizing before implantation of an adjustable annuloplasty structure, in accordance with some applications of the invention; and FIG. 36 is a flow chart of at least some steps in a method for use with an implant, such as an annuloplasty ring structure, and a tissue anchor for anchoring the implant, in accordance with some applications of the invention.

DETAILED DESCRIPTION OF EMBODIMENTS

Figure 1:
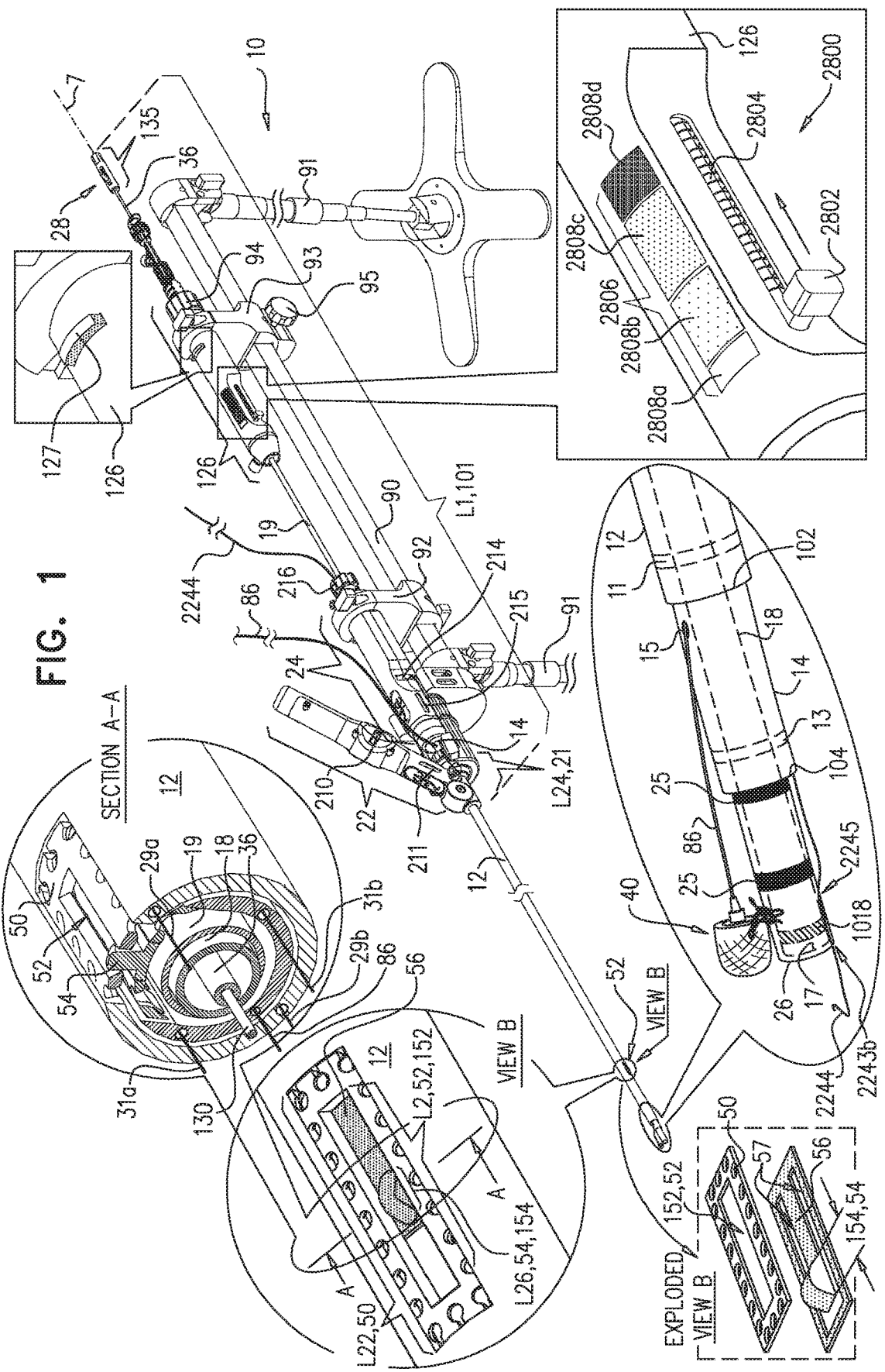
FIGS. 1-2 are schematic illustrations of multi-component tubular system for delivering and anchoring an implant and for controlling a relative spatial orientation of components of the catheter system, in accordance with some applications of the present invention.
Figure 2:
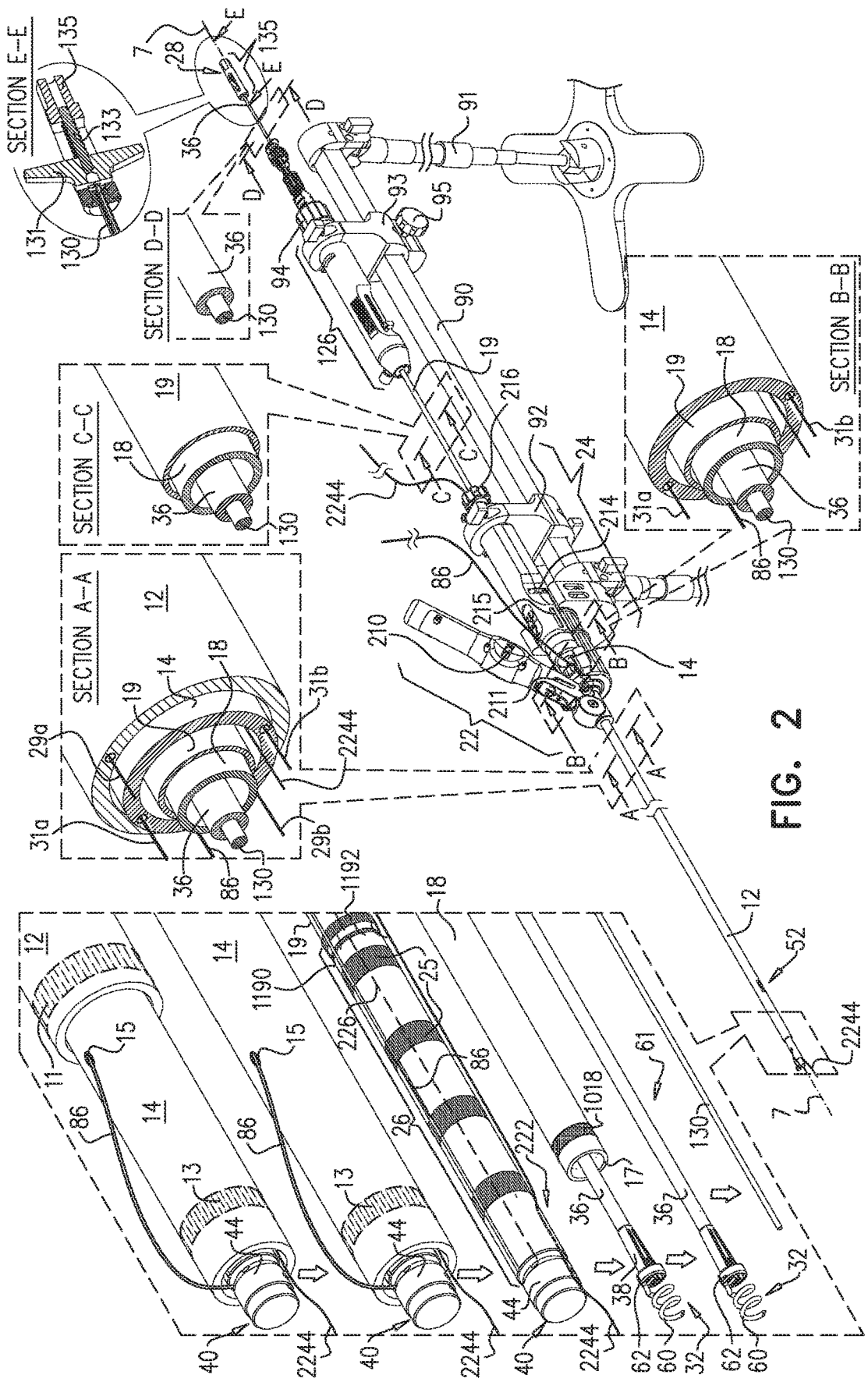

Reference is now made to FIGS. 1-2, which are schematic illustrations of a multi-component tubular system 10 providing one or more rotationally-controlled steering catheters configured for delivering an implant to a heart of a patient, in accordance with some applications of the present invention. System 10 provides an implant-delivery tool. Typically, system 10 comprises a first, outer catheter 12 comprising a sheath configured for advancement through vasculature of a patient. For some applications of the present invention, outer catheter 12 comprises a sheath configured for advancement through a femoral artery toward an interatrial septum of a heart of a patient. A distal steerable end portion of outer catheter 12 is configured to pass through the septum and be oriented in a desired spatial orientation. System 10 comprises a second catheter, or guide catheter 14, comprising a steerable distal end portion. Catheter 14 is configured for advancement through a lumen of outer catheter 12. Outer catheter 12 provides a first coupling 152 (e.g., a slit 52) at a distal portion thereof (e.g., a portion of catheter 12 that is proximal to the steerable distal end portion). Guide catheter 14 comprises a second coupling 154 (e.g., a depressible engager 54) that is coupled to a displaceable tab 56 coupled to a base. As is described herein, depressible engager 54 (or the second coupling 154) is configured so as to protrude within slit 52 (or the first coupling 152). Thus, slit 52 defines a second-coupling-receiving element.

First coupling 152 of catheter 12 defines a longer coupling, the second coupling 154 of catheter 14 defines a shorter coupling. The first and second couplings 152 and 154 of outer catheter 12 and guide catheter 14, respectively, enable axial advancement and rotational motion of guide catheter 14 through the lumen of outer catheter 12 until engager 54 of catheter 14 is aligned with and engages slit 52 of catheter 12, as will be described hereinbelow. As shown in cross-section A-A of FIG. 1, guide catheter 14 is configured to be concentrically disposed within a lumen of outer catheter 12. It is to be noted that the scope of the present invention includes catheter 12 providing the shorter coupling, and catheter 14 providing the longer coupling. For example, catheter 14 may be shaped so as to provide slit 52, and catheter 12 may comprise engager 54, which is configured to engage slit 52 of catheter 14.

As shown in the exploded view of view B, first coupling 152 is shaped so as to define slit 52. For some applications, slit 52 is provided by a metal frame 50, as shown. Metal frame 50 has a length L22 of between 7 and 15 mm, e.g., 13 mm. For such applications, a slit is created in material of catheter 12 (e.g., by creating a slit in the polymer material of catheter 12 during manufacturing of catheter 12), and frame 50 is coupled to catheter 12. Second coupling 154 comprises an engager 54 which comprises a protrusion disposed at a distal portion of displaceable tab 56 of a base of engager 54. The base of engager 54 is shaped so as to define slits 57 which form tab 56. Engager 54 is depressible when a force is applied thereto, and tab 56 facilitates movement of engager 54 in response to and in the absence of force applied to engager 54. For some applications, during manufacture of catheter 14, catheter 14 is manipulated in order to couple thereto engager 54 and tabs 56, e.g., engager 54 and tabs 56 are embedded within the polymer of catheter 14.

It is to be noted that although slit 52 and depressible engager 54 are shown on outer catheter 12 and guide catheter 14, respectively, at distal portions of catheters 12 and 14, slit 52 and engager 54 may be provided along any suitable portion of catheters 12 and 14, respectively (e.g., a respective proximal portions of catheters 12 and 14).

FIG. 2 shows the concentric relationship between components of tubular system 10 (in an exploded view on the left side of FIG. 2). As described hereinabove, a distal end portion of outer catheter 12 is steerable. The distal end portion of outer catheter 12 comprises a pull ring 11 that is coupled to two or more pull wires 29a and 29b, that are disposed within respective secondary lumens within a wall of catheter 12 (as shown in section A-A). As shown in the exploded view, guide catheter 14 is configured to be concentrically disposed within the lumen of catheter 12. As described hereinabove, the distal end portion of guide catheter 14 is steerable. The distal end portion of catheter 14 comprises a pull ring 13 that is coupled to two or more pull wires 31a and 31b, that are disposed within respective secondary lumens within a wall of catheter 14 (as shown in sections A-A and B-B).

Guide catheter 14 is steerable to a desired spatial orientation in order to facilitate advancing and implantation of an implant in a body cavity of the patient. As shown, the implant comprises an annuloplasty ring structure 222 comprising a flexible sleeve 26 (shown in the exploded view of FIG. 2). Sleeve 26 typically comprises a braided fabric mesh, e.g., comprising DACRON™. Sleeve 26 is typically configured to be placed only partially around a cardiac valve annulus (i.e., to assume a C-shape), and, once anchored in place, to be contracted so as to circumferentially tighten the valve annulus. Alternatively, the ring structure is configured to be placed entirely around the valve annulus. In order to tighten the annulus, annuloplasty ring structure 222 comprises a flexible elongated contracting member 226 that extends along sleeve 26. Elongated contracting member 226 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contracting member 226 comprises a braided polyester suture (e.g., Ticron). For some applications, contracting member 226 is coated with polytetrafluoroethylene (PTFE). For some applications, contracting member 226 comprises a plurality of wires that are intertwined to form a rope structure.

For applications in which system 10 is used to deliver an implant to the mitral valve of the patient, typically, outer catheter 12 is configured for initial advancement through vasculature of the patient until a distal end 102 of catheter 12 is positioned in the left atrium. The distal steerable end portion of catheter 12 is then steered such that distal end 102 of catheter 12 is positioned in a desired spatial orientation within the left atrium. The steering procedure is typically performed with the aid of imaging, such as fluoroscopy, transesophageal echo, and/or echocardiography. Following the steering of the distal end portion of catheter 12, guide catheter 14 (which houses annuloplasty ring structure 222) is advanced through catheter 12 in order to facilitate delivery and implantation of structure 222 along the annulus of the mitral valve. During the delivery, at least a portion of the steerable distal end portion of catheter 14 is exposed from distal end 102 of catheter 12 and is thus free for steering toward the annulus of the mitral valve, as is described hereinbelow.

Annuloplasty ring structure 222 further comprises an adjusting mechanism 40, which facilitates contracting and expanding of annuloplasty ring structure 222 so as to facilitate adjusting of a perimeter of the annulus and leaflets of the cardiac valve. Adjusting mechanism 40 is described in more detail hereinbelow. Adjusting mechanism 40 comprises a rotatable structure (e.g., a spool, as described hereinbelow) that is disposed within a housing 44. As shown in the enlarged image of FIG. 1, adjusting mechanism 40 is surrounded by a braided mesh and is coupled (e.g., by being sutured or otherwise coupled) to the braided mesh of sleeve 26. For some applications, adjusting mechanism 40 is coupled to an outer, lateral surface of sleeve 26. During delivery of sleeve 26 to the annulus of the cardiac valve, sleeve 26 and mechanism 40 are disposed within a lumen of catheter 14 and are aligned longitudinally with a longitudinal lumen of catheter 14. Such coupling of mechanism 40 to sleeve 26 allows mechanism 40 to transition from a state in which it is in line with the longitudinal axis of catheter 14 (FIG. 2) to a state in which it is disposed alongside sleeve 26 (FIG. 1). The positioning of adjusting mechanism 40 alongside a portion of sleeve 26 exposes a driving interface of the rotational structure to be accessed by a rotational tool that is guided toward adjusting mechanism 40 via a guide member 86.

A flexible, longitudinal guide member 86 (e.g., a wire) is coupled to a portion of adjusting mechanism 40 (e.g., a portion of the rotatable structure, as described hereinbelow). Guide member 86 is configured to facilitate guiding of a rotational tool via guide member 86 and toward the rotatable structure of adjusting mechanism 40. Typically, the rotational tool is configured to engage the rotatable structure of adjusting mechanism 40 following implantation of sleeve 26 along the annulus of the cardiac valve. Guide member 86 passes from adjusting mechanism 40, alongside a portion of the distal end portion of guide catheter 14, and into a secondary lumen in the wall of guide catheter 14, through an opening 15 in guide catheter 14. Guide member 86 passes through the secondary lumen of guide catheter 14 (as shown in sections A-A and B-B in FIG. 2) and has a proximal end that is accessible from outside the body of the patient. The secondary lumen in the wall of guide catheter 14 facilitates passage of guide member 86 through system 10 without interfering with the other concentrically-disposed elongate tubular members that pass concentrically through the lumen of guide catheter 14.

In addition, system 10 comprises a plurality of anchors 32, typically between about 5 and about 20 anchors, such as about 10 or about 16 anchors. Each anchor 32 comprises a tissue-engaging element 60 (e.g., a helical tissue-engaging element), and a tool-coupling head 62, fixed to one end of the tissue-engaging element. Only one anchor 32 is shown in FIG. 2 as being reversibly coupled to a deployment element 38 of a rotating anchor driver 36 of an anchor deployment manipulator 61. When sleeve 26 is disposed along the annulus of the cardiac valve, deployment manipulator 61 is configured to advance within a lumen of sleeve 26 and deploy each anchor 32 from within sleeve 26 through a wall of sleeve 26 and into cardiac tissue, thereby anchoring sleeve 26 around a portion of the valve annulus. The insertion of the anchors into the sleeve and deployment of the anchors into cardiac tissue is described in detail hereinbelow.

Typically, but not necessarily, anchors 32 comprise a biocompatible material such as stainless steel 316 LVM. For some applications, anchors 32 comprise nitinol. For some applications, anchors 32 are coated fully or partially with a non-conductive material.

Deployment manipulator 61 comprises anchor driver 36 and deployment element 38.

As shown in the exploded view of FIG. 2, sleeve 26 is disposed within a lumen of guide catheter 14. A force is applied to a proximal end of sleeve 26 by a distal end of a reference-force tube 19. As shown, an implant-decoupling channel 18 is advanceable within a lumen of reference-force tube 19 and through a lumen of sleeve 26 such that a portion of channel 18 that is disposed within the sleeve is coaxial with the sleeve. As shown in the enlarged image of FIG. 1, a distal end 17 of implant-decoupling channel 18 is disposed in contact with an inner wall of sleeve 26 at a distal end thereof. Additionally, a distal end portion of channel 18 comprises a radiopaque marker 1018. As shown, tube 19 and sleeve 26 are longitudinally and coaxially disposed with respect to each other.

Typically, anchor driver 36 advances within channel 18. For some applications, system 10 comprises a plurality of anchor drivers 36, each driver being coupled to a respective anchor 32. Each driver 36 is advanced within channel 18 in order to advance and implant anchor 32 in tissue. Following implantation of anchor 32, anchor 32 is decoupled from driver 36, as described herein, and driver 36 is removed from within channel 18. Subsequently, a new driver 36 coupled to another anchor 32 is then advanced within channel 18.

As will be described hereinbelow, a first anchor 32 is configured to be deployed through the wall of the sleeve into cardiac tissue, when sleeve 26 is positioned along the annulus of the valve. Following the deployment of the first anchor, a distal portion of sleeve 26 is slid distally off a portion of implant-decoupling channel 18. In order to decouple sleeve 26 distally from a portion of outer surface of channel 18, (1) a proximal force is applied to channel 18, while (2) reference-force tube 19 is maintained in place in a manner in which a distal end of tube 19 provides a reference force to sleeve 26 in order to facilitate freeing of a successive portion of sleeve 26 from around channel 18. Channel 18 is then positioned at a successive location within the lumen of sleeve 26 while either tube 19 and/or catheter 14 is steered toward a successive location along the annulus of the valve (as will be described hereinbelow). Consequently, the successive portion of sleeve 26 provides a free lumen for advancement of a successive anchor 32 and deployment of the anchor through the wall of the sleeve at the successive portion thereof. Such freeing of the successive portion of sleeve 26 creates a distance between successive anchors deployed from within the lumen of sleeve 26.

For some applications, sleeve 26 comprises a plurality of radiopaque markers 25, which are positioned along the sleeve at respective longitudinal sites. The markers may provide an indication in a radiographic image (such as a fluoroscopy image) of how much of the sleeve has been deployed at any given point during an implantation procedure, in order to enable setting a desired distance between anchors 32 along the sleeve. For some applications, the markers comprise a radiopaque ink.

Typically, at least a portion (e.g., at least three, such as all) of the longitudinal sites of the radiopaque markers are longitudinally spaced at a constant interval. Typically, the longitudinal distance between the distal edges of adjacent markers, and/or the distance between the proximal edges of adjacent markers, is set equal to the desired distance between adjacent anchors. For example, the markers may comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm. (If, for example, the distance were 6 mm and the length were 2 mm, the longitudinal gaps between adjacent markers would have lengths of 4 mm.)

Each anchor 32 is coupled to deployment element 38 of anchor driver 36. Anchor driver 36 comprises an elongate tube having at least a flexible distal end portion. The elongate tube of driver 36 extends within a lumen of channel 18, through system 10 toward a proximal end of a proximal handle portion 101 of system 10. The tube of anchor driver 36 provides a lumen for slidable advancement therethrough of an elongate rod 130. Rod 130 facilitates the locking and unlocking of anchor 32 to deployment element 38, as is described hereinbelow. As shown in Section E-E of FIG. 2, a proximal end of rod 130 is coupled to a component of an anchor-release mechanism 28 at a proximal end of system 10. Mechanism 28 comprises a housing 135 and a finger-engager 131 that is coupled to the proximal end of rod 130. Finger-engager 131 is coupled to a housing 135 via a spring 133 (section E-E of FIG. 2). A proximal end of the tube of anchor driver 36 is coupled to housing 135. As is described hereinbelow, the physician releases anchor 32 from deployment element 38 when finger-engager 131 is pulled proximally, thereby pulling rod 130 proximally.

For some applications, anchor driver 36 (e.g., rotation and/or proximal-distal movement thereof, and/or release of anchor 32) is electronically controllable, such as by using an extracorporeal controller and/or electric motor coupled to a proximal end of the anchor driver and/or housing 135, e.g., as described hereinbelow with reference to FIGS. 21-25E, and/or FIG. 34.

Proximal handle portion 101 is supported by a stand having support legs 91 and a handle-sliding track 90. Handle portion 101 comprises an outer-catheter handle 22, a guide-catheter handle 24, an implant-manipulating handle 126, and anchor-release mechanism 28. Handle 22 is coupled to a proximal end of outer catheter 12. Handle 24 is coupled to a proximal portion of guide catheter 14. Handle 126 is coupled to a proximal portion of reference-force tube 19, and linear movement of handle 126 with respect to handle 24 moves reference-force tube 19 (and thereby typically structure 222) through catheter 14. As described hereinabove, housing 135 of anchor-release mechanism 28 is coupled to a proximal portion of the tube of anchor driver 36. The relative positioning of each of the concentrically-disposed components of system 10 is shown in the exploded view and sections A-A, B-B, C-C, and D-D of FIG. 2.

The stand supporting proximal handle portion 101 may be moved distally and proximally to control a position of the entire multi-component system 10, particularly so as to adjust a distance of distal end 102 of catheter 12 from the interatrial septum. Handle 22 comprises a steering knob 210 that is coupled to steering wires 29a and 29b disposed within respective secondary lumens in the wall of outer catheter 12. Rotation of knob 210 adjusts a degree of tension of wires 29a and 29b which, in turn, apply a force to pull ring 11 at the distal end portion of outer catheter 12. Such force steers the distal end portion of catheter 12 within the atrium of the heart of the patient in a manner in which the distal end portion of catheter 12 is steered in a first plane that is parallel with the plane of the annulus of the valve (e.g., in a direction from the interatrial septum toward surrounding walls of the atrium). For some applications of the present invention, the distal end portion of catheter 12 may be pre-shaped so as to point downward toward the valve. For other applications, the distal end portion of catheter 12 may be pulled to assume an orientation in which the distal end portion points downward toward the valve. For yet other applications of the present invention, the distal end portion of catheter 12 is not made to point downward toward the valve.

Handle 24 is coupled to track 90 via a first mount 92. Mount 92 is slidable proximally and distally along track 90 in order to control an axial position of guide catheter 14 with respect to outer catheter 12. Mount 92 is slidable via a control knob 216. For example, control knob 216 of mount 92 controls the proximal and distal axial movement of the distal steerable portion of guide catheter 14 with respect to distal end 102 of outer catheter 12. Handle 24 comprises a steering knob 214 that is coupled to steering wires 31a and 31b disposed within respective secondary lumens in the wall of guide catheter 14. Rotation of knob 214 adjusts a degree of tension of wires 31a and 31b which, in turn, apply a force to pull ring 13 at the distal end portion of guide catheter 14. Such force steers the distal end portion of catheter 14 in a second plane within the atrium of the heart of the patient downward and toward the annulus of the cardiac valve. Typically, as described hereinbelow, the distal end portion of guide catheter 14 is steered in the second plane that is substantially perpendicular with respect to the first plane in which the distal end portion of outer catheter 12 is steered.

The combined steering of the respective distal end portions of catheters 12 and 14 directs sleeve 26 down toward the annulus (e.g., via the steering of the distal end portion of catheter 14) and along the perimeter of annulus (e.g., from the posterior section of the valve to the anterior section of the valve, and vice versa), via the steering of the distal end portion of catheter 12.

For some applications, handle 22 may be tilted by the operating physician, in order to further adjust a position of the distal end of catheter 12.

Figure 33:
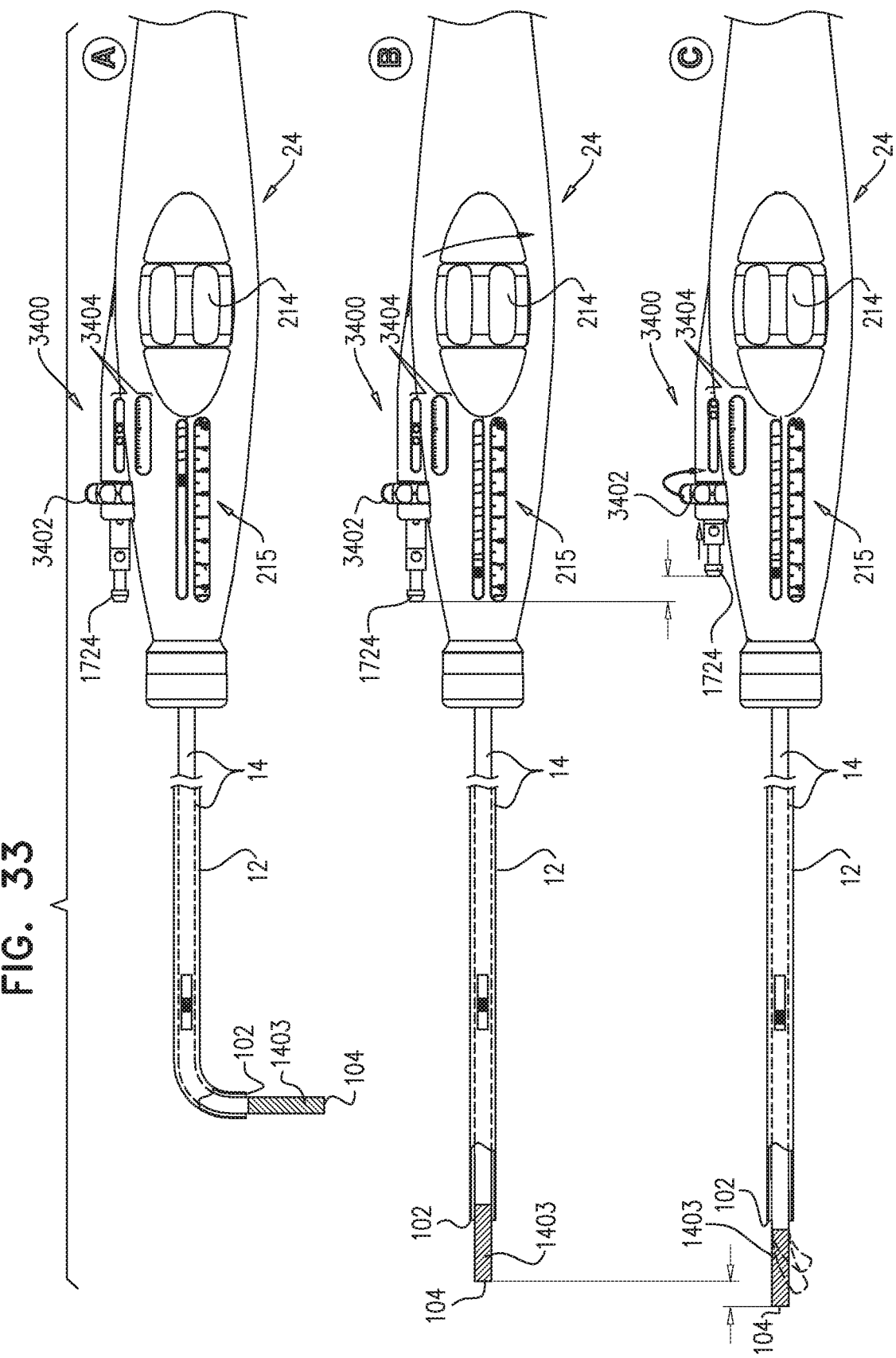
FIG. 33 is a schematic illustration of an adjustment mechanism for adjusting a relative axial position between coaxial catheters, in accordance with some applications of the invention.

For some applications, handle 22 comprises an indicator 211 that indicates a degree of steering (e.g., bending) of the distal end portion of catheter 12 that has been produced using knob 210. For some applications, handle 24 comprises an indicator 215 that indicates a degree of steering (e.g., bending) of the distal end portion of catheter 12 that has been produced using knob 214. FIG. 33 shows indicator 215 more clearly.

As described herein, first and second couplings 152 and 154 of outer catheter 12 and guide catheter 14, respectively (e.g., slit 52 and engager 54, respectively), provide a controlled steerable system in which, during the steering and bending of the distal end portion of guide catheter 14, the distal end portion of outer catheter 12 is maintained in its steered configuration, or in its spatial orientation, without substantially affecting the steering or the bending of the distal end portion of guide catheter 14. Thus, first and second couplings 152 and 154, respectively, minimize the effect of the distal end portion of outer catheter 12 on the steering and bending of catheter 14. That is, first and second couplings 152 and 154 of outer catheter 12 and guide catheter 14, respectively, collectively define a relative-spatial-orientation-controlling device which rotationally locks the relative spatial orientation of the steerable distal end portion and the bending section of outer catheter 12 with respect to the steerable distal end portion and the bending section of guide catheter 14.

Guide member 86 exits from the lumen in the wall of guide catheter 14 at a portion of handle portion 101 that is between handles 22 and 24.

Handle 126 is coupled to track 90 via a second mount 93. Mount 93 is slidable proximally and distally along track 90, in order to control an axial position of reference-force tube 19 and at least a proximal portion of sleeve 26 with respect to guide catheter 14. Mount 93 is slidable via a control knob 95. For example, control knob 95 of mount 93 controls the proximal and distal axial movement of the tube 19 and at least the proximal portion of sleeve 26 with respect to distal end 104 of guide catheter 14. Taken together with the steering of the distal end portion of guide catheter 14, such movement of tube 19 and at least the proximal portion sleeve 26 moves the proximal portion of sleeve 26 toward a desired portion of tissue of the annulus of the valve during deployment of anchors 32 from within the lumen of sleeve 26, as is described hereinbelow.

As is described hereinabove, in order to decouple sleeve 26 from a portion of an outer surface of channel 18, (1) channel 18 is pulled proximally, while (2) reference-force tube 19 is maintained in place. A proximal end of channel 18 is coupled to a knob 94 which adjusts an axial position of channel 18 proximally and distally with respect to reference-force tube 19 and sleeve 26.

Typically, handle portion 101 comprises a release-decision-facilitation member 127, such as a latch or button, that automatically engages when a given length of sleeve 26 has advanced off channel 18 (e.g., when channel 18 is at a given position with respect to tube 19); typically just before sleeve 26 becomes completely decoupled from channel 18. Engagement of member 127 inhibits proximal movement of channel 18 with respect to tube 19, thereby reducing a likelihood of (e.g., preventing) inadvertent release of sleeve 26. In order to release sleeve 26 (e.g., to decouple channel 18 from the sleeve), the operating physician must disengage member 127, such as by pushing the button, before continuing to withdraw channel 18 proximally. Typically, when engaged, member 127 also inhibits distal movement of channel 18 with respect to tube 19.

Handle portion 101 (comprising handles 22, 24, and 126 and anchor-release mechanism 28) has a length L1 of between 65 and 85 cm, e.g., 76 cm. Typically, as shown, a majority of the body portion of outer-catheter handle 22 is disposed at a non-zero angle with respect to a longitudinal axis 7 of the multiple components of system 10. The steering mechanism provided by handle 22 in order to steer the distal end portion of catheter 12 is disposed within the portion of handle 22 that is disposed at the non-zero angle with respect to axis 7. Handle 22 comprises an in-line tubular portion 21 which is longitudinally disposed in-line along axis 7 and coaxially with respect to handles 24 and 126 and release mechanism 28. Tubular portion 21 is shaped so as to define a lumen for inserting guide catheter 14 therethrough and subsequently into the lumen of outer catheter 12 (as is described hereinbelow with reference to FIG. 3A). Tubular portion 21 has a length L24 of between 7 and 11 cm, e.g., 7 cm. Such spatial orientation of the majority of handle 22 at an angle with respect to axis 7 reduces an overall functional length of handle portion 101.

Reference is now made to FIGS. 3A-E, which are schematic illustrations of the functional relationship between first and second couplings 152 and 154, respectively, and respective degrees of rotational freedom of guide catheter 14 with respect to outer catheter 12, in accordance with some applications of the present invention. It is to be noted that FIGS. 3A-E show a functional relationship between catheters 12 and 14, and, for clarity of illustration, does not show the concentric components disposed within a longitudinal lumen 59 of catheter 14 (i.e., reference-force tube 19, channel 18, anchor driver 36, and rod 130, as shown in FIGS. 1 and 2). FIG. 3A shows catheters 12 and 14 in a state prior to advancing catheter 14 through a lumen 58 of catheter 12. Sections A-A and B-B of FIG. 3A show slit 52, or first coupling 152, empty. Section C-C shows a portion of catheter 14 which provides engager 54, or second coupling 154. As described hereinabove with reference to FIG. 1, engager 54 is coupled to a depressible tab 56 which facilitates depressible movement of engager 54 when a force is applied thereto (e.g., at a later stage by an inner wall 51 of catheter 12 that surrounds lumen 58 when catheter 14 is advanced through lumen 58, as is described hereinbelow). As shown in section C-C of FIG. 3A, in the absence of a pushing force, tab 56 is disposed in parallel with longitudinal axis 7, and engager 54 is in a resting state thereof in which engager 54 is not in a depressed state and protrudes from an external surface of catheter 14.

As shown in sections A-A and B-B of FIGS. 3A-B, first coupling 152 is provided in a manner in which lumen 58 of catheter 12 is free from any protrusions. Additionally, inner wall 51 of catheter 12 is not shaped to define any interrupted portions, such as recessed portions, along a proximal portion of catheter 12 and extending toward distal end 102 of catheter 12, except for slit 52 at a distal portion thereof. Once catheter 12 is advanced through the vasculature of the patient, distal end 104 of catheter 14 is configured to enter a lumen provided by tubular portion 21 of handle 22, and subsequently, catheter 14 passes through lumen 58 of catheter 12. View E is a view of lumen 58 of catheter 12 from a proximal portion of tubular portion 21 of handle 22. Since lumen 58 is free from any protrusions or recessed portions, as described hereinabove, and since engager 54 is depressible by tab 56, catheter 14 is configured to enter lumen 58 of catheter 12 in any rotational configuration thereof. Catheter 14 is shown in section D-D in a manner in which engager is oriented at 12 o'clock, by way of illustration and not limitation. Catheter 14 may enter lumen 58 of catheter 12 in any rotational configuration thereof, therefore, engager 54 is shown in phantom in a plurality of orientations in section D-D, since catheter 14 may enter lumen 58 of catheter 12 in a rotational orientation in which engager 54 may be oriented in any given orientation with respect to inner wall 51 of catheter 12.

During the insertion of distal end 104 and the distal portion of catheter 14, the physician pushes down on engager 54 such that engager 54 fits within the lumen of catheter 12. In response to the pushing force on engager 54, tab 56 is pushed downward as well.

Typically, catheter 12 has an inner diameter (or the diameter of lumen 58) of between 6.5 and 7.0 mm (e.g., 6.85 mm). Typically, catheter 14 has an inner diameter (or the diameter of lumen 59) of between 4.7 and 5.3 mm (e.g., 5.1 mm). System 10, by providing slit 52 and depressible engager 54, provides a system in which the inner diameters of catheters 12 and 14 are maintained during given stages of the procedure. For example, engager 54 maintains the inner diameter of catheter 12 as catheter 14 is advanced within the lumen of catheter 12, and slit 52 maintains the inner diameter of catheter 14 once engager 54 pops up and is disposed within slit 52.

FIG. 3B shows the axial advancement of a distal portion of catheter 14 through the lumen of catheter 12 in the direction as indicated by arrow 1. Typically, the advancement of catheter 14 through catheter 12 is controlled by the physician who moves handle 24 axially closer to handle 22. During the advancement of catheter 14 through catheter 12, engager 54 is maintained in a pushed state (as shown in section A-A of FIG. 3B) by a pushing force applied thereto by inner wall 51 of catheter 12. As shown in section B-B of FIG. 3B, inner wall 51 of outer catheter 12 pushes on engager 54, in the direction as indicated by the radial arrow. In response to the force applied on engager 54 by inner wall 51 of catheter 12, engager 54 is pushed and tab 56 is displaced at a non-zero angle with respect to axis 7 in order to allow for depression of engager 54. During the depression of engager 54, engager 54 is pushed slightly within lumen 59 of catheter 14.

As described hereinabove, inner wall 51 of catheter 12 is smooth and uninterrupted by recesses or slits (except for slit 52 at the distal end of catheter 12). Typically, slit 52 has a length L2 (shown in view B of FIG. 1) of between 5 and 50 mm, e.g., between 10 and 25 mm, such as about 16 mm. A proximal-most end of slit 52 is disposed up to 120 mm (e.g., up to 100 mm) from distal end 102 of catheter 12. Catheter 12 is typically between 80 and 100 cm long. Thus, inner wall 51 of the proximal portion of catheter 12, until the proximal-most end of slit 52, is smooth and uninterrupted by recesses or slits. Taken together, the depressibility of engager 54 and such a smooth configuration of inner wall 51 of catheter 12 enables rotation of catheter 14 by 360 degrees (i.e., as indicated by arrow 2) within the lumen of catheter 12.

FIG. 3C shows further axial advancement of catheter 14 within the lumen of catheter 12. As described hereinabove, during the advancement, and prior to the engaging of engager 54 with slit 52 (as is described hereinbelow with reference to FIG. 3D), inner wall 51 pushes on engager 54 such that catheter 14 can be rotated to any suitable rotational orientation within outer catheter 12. For example, engager 54 is shown at 2 o'clock in section B-B of FIG. 3B, while engager 54 is shown at 11 o'clock in section B-B of FIG. 3C. Furthermore, prior to the engaging of engager 54 with slit 52 catheter 14 may be extracted from within the lumen of catheter 12.

FIG. 3C shows axial advancement of catheter 14 within catheter 12 in the distal direction, as indicated by arrow 1, in a manner in which engager 54 is about to engage with slit 52 at a distal portion of catheter 12. FIG. 3C shows a relative position of catheter 14 with respect to catheter 12 in a manner in which catheter 14 is not fully pushed within catheter 12. Handle 24 of catheter 14 is still distanced from handle 22 of catheter 12. However, catheter 14 is pushed distally sufficiently for distal end 104 and a portion of the distal end portion of catheter 14 to emerge from within catheter 12 and extend distally beyond distal end 102 of catheter 12.

Following further distal advancement of catheter 14 within catheter 12, and slight rotation of catheter 14 within the lumen of catheter 12, engager 54 of catheter 14 is aligned with slit 52 of catheter 12, as shown in FIG. 3D. In the absence of the pushing force of inner wall 51 of catheter 12 on engager 54, engager 54 returns to its resting state and protrudes within slit 52 so as to engage slit 52. That is, first coupling 152 is engaged with second coupling 154. As engager 54 returns to its resting state, tab 56 returns to a position in which it is parallel with respect to longitudinal axis 7.

FIG. 3D shows engager 54 in a distal-most position within slit 52, i.e., a fully-pushed state of catheter 14. As such, handles 24 and 22 are disposed adjacently to each other. In this state, an exposed distal end portion 114 of catheter 14 extends beyond distal end 102 of catheter 12. Typically, at least a portion of distal end portion 114 is steerable and bendable, as is described hereinbelow. Distal end portion 114 of catheter 14 has a length L3 of between 25 and 35 mm, e.g., 27.5 mm. As described hereinabove, slit 52 has a length L2 of between 5 and 50 mm, e.g., between 10 and 25 mm, such as about 20 mm.

Reference is now made to FIGS. 1 and 3D. As shown in view B of FIG. 1, engager 54 has a longitudinal length L26 of between 2 and 3 mm, e.g., 2 mm. Length L26 facilitates motion of engager 54 along length L2 of slit 52. A proximal-most end of engager 54 is disposed up to 120 mm (e.g., up to 80 mm) from distal end 104 of catheter 14. As described hereinabove, a proximal-most end of slit 52 is disposed up to 100 mm (e.g., up to 60 mm) from distal end 102 of catheter 12. Exposed distal end portion 114 of catheter 14 typically has a length L3 of between 20 and 35 mm, e.g., 27.5 mm.

For some applications, the combined lengths of first and second couplings 152 and 154, respectively, is less than 30 mm, e.g., less than 20 mm. For applications in which first coupling 152 (e.g., slit 52) is between 5 and 15 mm, and second coupling 154 (e.g., engager 54) is between 2 and 3 mm, the combined lengths of first and second couplings 152 and 154, respectively, is less than 50 mm, e.g., less than 20 mm.

Engager 54 has a longitudinal length L26 that is less than 30% (e.g., less than 20%) of the longitudinal length of catheter 14. Typically, however, as described hereinabove, engager 54 has a length L26 of between 2 and 3 mm. That is, engager 54 has a longitudinal length that is less than 2% (e.g., less than 1%) of the longitudinal length of catheter 14.

Reference is now made to FIGS. 3C-D. A portion of exposed distal end portion 114 extends beyond distal end 102 of catheter 12 prior to engager 54 engaging slit 52. The length L2 of slit 52 enables retraction of catheter 14 between 5 and 15 mm, proximally from the fully-pushed state of catheter 14. As catheter 14 is retracted proximally, engager 54 moves proximally within slit 52 until a proximal-most end of engager 54 contacts a proximal-most end of slit 52. When engager 54 is disposed at the proximal-most end of slit 52, the distal end portion exposed from within catheter 102 is between 10 and 30 mm, e.g., 20 mm. When catheter 14 is pushed distally, engager 54 moves distally within slit 52 until a distal-most end of engager 54 contacts a distal-most end of slit 52.

Reference is again made to FIG. 3D. In the state in which engager 54 is disposed within slit 52, catheter 14 is restricted from rotating within the lumen of catheter 12, and catheters 12 and 14 are thereby rotationally locked with respect to each other.

FIG. 3E shows catheter 12 and 14 in a state in which catheter 14 has been pushed fully within catheter 12 (i.e., a state in which engager 54 is disposed at a distal-most end of slit 52 and handle 24 is disposed adjacently to handle 22). As described hereinabove, during the fully-pushed state of catheter 14, exposed distal portion 114 extends beyond distal end 102 of catheter 12 and has a length L3 of between 25 and 35 mm, e.g., 30 mm. Additionally, as is described herein, at least a portion of distal end portion 114 is steerable and comprises an exposed bending section 1403 which is a portion of a collective distal bending section 1405 of catheter 14 (described hereinbelow with reference to FIGS. 5 and 6). A distal end portion of catheter 12 comprises a bending section 1203 (described hereinbelow with reference to FIGS. 4 and 6). A proximal portion of bending section 1405 of catheter 14 is bendable and disposed within the lumen of catheter 12 at bending section 1203 thereof.

The distal end portion of catheter 12 is steerable in a first plane (e.g., a plane that is parallel with respect to the cardiac valve of the patient). Bending section 1403 of exposed distal portion 114 (and additional portions of collective bending section 1405) is steerable in second plane that is substantially perpendicular to the first plane in which the distal end portion of catheter 12 is steerable (e.g., a plane that is perpendicular with respect to the valve of the patient). As shown, bending section 1203 of the steerable distal end portion of outer catheter 12 is maintained in its steered configuration, or in its spatial orientation, without substantially affecting the steering of exposed distal end portion 114 of guide catheter 14, nor of the bending of bending section 1403, nor of the collective bending section 1405 (including the proximal portion of bending section 1405 of catheter 14 that is disposed within the lumen of catheter 12 at bending section 1203 thereof). That is, first and second couplings 152 and 154, respectively, advantageously reduce the effect of the distal end portion of catheter 12 on the steering of section 114 and the bending of bending section 1405. That is, first and second couplings 152 and 154 of outer catheter 12 and guide catheter 14, respectively, collectively define a relative-spatial-orientation-controlling device which rotationally locks the relative spatial orientation of the steerable distal end portion and bending section 1203 of outer catheter 12 with respect to the steerable distal end portion and bending second 1405 of guide catheter 14, specifically of exposed bending section 1403.

Thus, for applications in which system 10 is used to treat the mitral valve, bending section 1203 of catheter 12 bends the steerable distal end portion of catheter 12 within the atrium in the first plane that is parallel with respect to the mitral valve. First and second couplings 152 and 154, respectively, enable (1) bending of bending section 1405 toward the valve in the second plane that is substantially perpendicular with respect to the first plane and to the plane of the mitral valve, while (2) restricting or minimizing the effect of the spatial orientation of bending section 1203 of catheter 12 on bending section 1405 of catheter 14.

Reference is now made to FIGS. 3A-E. It is to be noted that for some applications, slit 52 has a longitudinal length L2 of less than 20 cm, e.g., a length of less than 15 cm. That is, slit 52 has a longitudinal length L2 that is less than 30% (e.g., less than 20%) of the longitudinal length of catheter 12. Typically, however, as described hereinabove, slit 52 has a length L2 of between 5 and 15 mm, e.g., 10 mm. That is, slit 52 has a longitudinal length that is less than 2% (e.g., less than 1%) of the longitudinal length of catheter 12. For such applications, the proximal-most end of slit 52 is disposed up to 30 mm from distal end 102 of catheter 12.

It is to be noted that the scope of the present invention includes providing slit 52 and engager 54 at respective proximal portions of catheters 12 and 14, respectively. For such applications, a distal-most end of slit 52 is disposed up to 100 mm (e.g., up to 60 mm) from the proximal end of catheter 12 and a distal-most end of engager 54 is disposed up to 120 mm (e.g., up to 80 mm) from the proximal end of catheter 14.

Reference is now made to FIGS. 1, 2, and 3A-E. It is to be noted that first and second couplings 152 and 154, respectively, may be provided on any standard catheter. That is, coupling 152 comprises frame 50 which can be coupled to an external surface of any standard catheter (in which case, a corresponding slit would be made in the standard catheter). Additionally coupling 154 may be coupled to any standard catheter by coupling the base portion of coupling 154 to any standard catheter. Suitable adjustments to the standard catheter would be made to accommodate the displacing of tab 56 and engager 54 in response to pushing forces applied to engager 54.

Reference is now made to FIG. 4, which is a schematic illustration of catheter 12 comprising a multiple-durometer section 1210 at a distal steerable end portion of catheter 12, in accordance with some applications of the present invention. Multiple-durometer section 1210 has a length L18 of between 30 mm and 40 mm, e.g., 36 mm. Each section of multiple-durometer section 1210 has a respective durometer sections in Shore D, or scale D. Catheter 12 comprises a uniform durometer section 1205 that is disposed proximal to multiple-durometer bending section 1210. Typically, multiple durometer section 1210 and uniform durometer section 1205 comprise an elastic tubular polymer 1206 (e.g., sequences of polyamide 12 segments (PA12) and polytetramethylene glycol segments (PTMG), polyether block amide, or PEBA) that defines the tubular structure of catheter 12. Polymer 1206 has mechanical and dynamic properties which impart flexibility, impact resistance, energy return, and fatigue resistance to catheter 12.

As shown in the cross-sectional image, catheter 12 provides a wall which defines lumen 58. The inner wall of catheter 12 (which defines lumen 58) is coated with a friction-reducing liner comprising polytetrafluoroethylene (PTFE) so as to reduce friction during the sliding of catheter 14 through lumen 58 of catheter 12. The wall of catheter 12 is shaped so as to define secondary lumens 1211, which are typically spaced apart from each other by 180 degrees. A respective pull wire 29a and 29b (not shown in FIG. 4 for clarity of illustration, but are shown in FIGS. 1 and 2) is advanced through each lumen 1211. The inner walls of each secondary lumen 1211 is coated with a friction-reducing liner comprising polytetrafluoroethylene (PTFE) so as to reduce friction during the sliding of respective wires 29a and 29b therethrough.

Typically, catheter 12 has an inner diameter D1 (or the diameter of lumen 58) of between 6.5 and 7.0 mm (e.g., 6.85 mm) and outer diameter D2 of between 8.0 and 9.0 mm (e.g., 8.3 mm).

It is to be noted that even though catheter 12 has multiple durometer segments, inner and outer diameters D1 and D2, respectively, remain constant along a longitudinal length L8 of catheter 12 (with the exception of outer diameter D2 being tapered at the distal end portion of section 1201, as is described hereinbelow).

Typically, catheter 12 has a longitudinal length L8 of between 800 and 900 mm, e.g., between 853 and 867 mm, e.g., 860 mm. Uniform durometer section 1205 has a length L9 that is between 770 and 860 mm, e.g., 824 mm. Tubular polymer 1206 extends an entire length L8 of catheter 12. Catheter 12 is surrounded by a braided mesh 1207, which typically comprises a flexible metal (e.g., stainless steel 304 or nitinol). Typically, braided mesh 1207 extends along the length of catheter 12 until a proximal portion at which the pull wires 29a and 29b (not shown for clarity of illustration) are exposed from within lumens 1211 at a proximal section of catheter 12, e.g., between 823 and 837 mm (e.g., 830 mm) from distal end 102 of catheter 12.

Section 1210 comprises a distal pull-ring section 1201 in which pull ring 11 is disposed. Typically, a distal-most portion of section 1201 is tapered so as to facilitate atraumatic advancement of catheter 12 through the vasculature of the patient. Section 1201 has a length of between 4 and 5 mm (e.g., 4.5 mm) and has a durometer of between 45 D and 63 D (e.g., 55 D). Such a durometer of section 1201 imparts more hardness and rigidity to the distal portion of catheter 12 in which pull ring 11 is disposed, such that portion 1201 supports ring 11 and protects the distal portion of catheter 12 from the impact of forces applied thereto during the pulling of pull ring 11 by the pull wires. Typically, pull ring 11 has a length of between 2.5 and 2.6 mm, e.g., 2.54 mm. A distal transition section 1202 is disposed proximal to section 1201 and has a length L5 of between 1 and 2 mm (e.g., 1.5 mm) and has a durometer of between 63 D and 72 D (e.g., 72 D). The relatively high durometer of section 1202 imparts hardness to section 1202 such that pull ring 11 is supported and maintained in place during the pulling of pull ring 11 by the pull wires. Thus, section 1202 helps overcome high tensile forces acting on the distal end of catheter 12.

Catheter 12 provides bending section 1203 proximally adjacent to section 1202. As shown in the enlarged image, bending section 1203 comprises a coil 1208 which is embedded within the tubular polymer 1206. Typically, coil 1208 comprises a flexible metal (e.g., stainless steel 304 or nitinol). Coil 1208 imparts efficient and durable bending to bending section 1203. Additionally, polymer 1206 at bending section 1203 has a durometer of between 25 D and 45 D (e.g., 35 D) which provides a degree of softness that facilitates bending of the distal steerable portion of catheter 12 at bending section 1203. Bending section 1203 has a length L6 of between 22 and 27 mm, e.g., 25 mm.

Typically, bending section 1203 has a maximum bending angle between 120 and 140 degrees (e.g., 127 degrees). That is, bending section 1203 can bend between 0 and 140 degrees. For some applications, bending section 1203 has a pre-shaped angle of between 40 and 55 degrees (e.g., 45 degrees) so as to reduce force applied to bending section 1203 of catheter 12 by pull wires 29a and 29b.

It is to be noted that only tubular polymer 1206 and braided mesh 1207 extend proximally and distally beyond bending section 1203.

Proximally adjacent to bending section 1203 is a transition section 1204 having a length L7 of between 4 and 6 mm (e.g., 5 mm). Proximally adjacent to transition section 1203 is uniform durometer section 1205. Uniform durometer section 1205 has a durometer of between 63 D and 72 D (e.g., 72 D). Transition section 1204 has a durometer of between 35 D and 55 D (e.g., 45 D) so as to provide a transition from the relatively low durometer of bending section 1203 to the relatively high durometer of uniform durometer section 1205.

FIG. 4 shows the relative position of slit 52 with respect to distal end 102 of catheter 12. As described hereinabove, a proximal-most end of slit 52 is disposed up to 100 mm (e.g., up to 60 mm) from distal end 102 of catheter 12.

Typically, the spatial orientation of bending section 1203 is determined by pulling on pull wires 29a and 29b that are disposed within lumens 1211 (wires 29a and 29b are not shown for clarity of illustration). Bending section 1203, for some alternative applications of the present invention, may be pre-shaped (e.g., at 45 degrees with respect to a transverse plane provided by opposing pull wires 29a and 29b) to assume a given spatial orientation and the spatial orientation of section 1203 is additionally determined by pulling on pull wires 29a and 29b.

Figure 5:
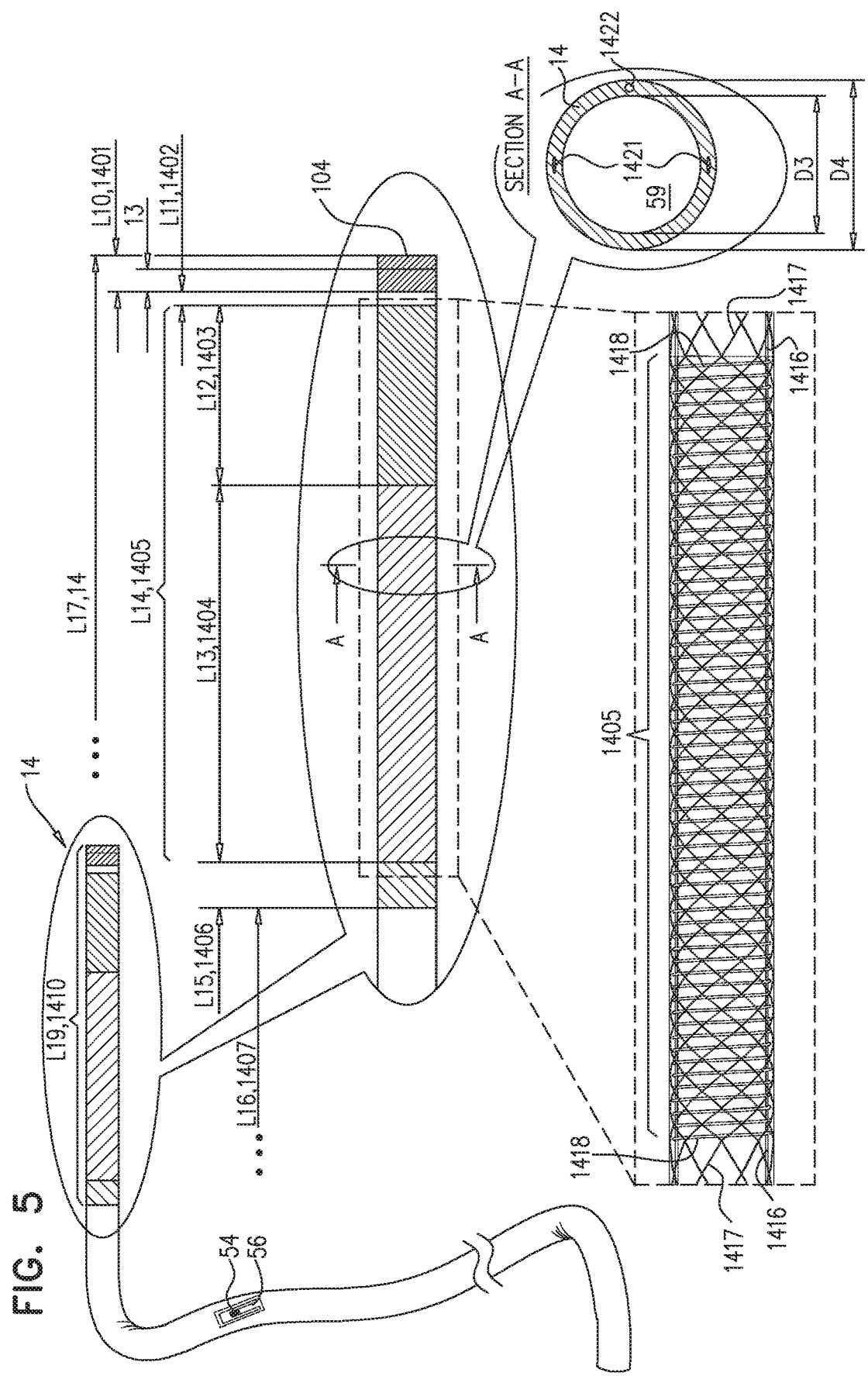

Reference is now made to FIG. 5, which is a schematic illustration of catheter 14 comprising a multiple-durometer section 1410 at a distal steerable end portion of catheter 14, in accordance with some applications of the present invention. Multiple-durometer section 1410 has a length L19 of between 70 mm and 80 mm, e.g., 74 mm. Each section of multiple-durometer section 1410 has a respective durometer sections in Shore D, or scale D. Catheter 14 comprises a uniform durometer section 1407 that is disposed proximal to multiple-durometer bending section 1410. Typically, multiple durometer section 1410 and uniform durometer section 1407 comprise an elastic tubular polymer 1416 (e.g., sequences of polyamide 12 segments (PA12) and polytetramethylene glycol segments (PTMG), polyether block amide, or PEBA) that defines the tubular structure of catheter 14. Polymer 1416 has mechanical and dynamic properties which impart flexibility, impact resistance, energy return, and fatigue resistance to catheter 14.

As shown in the cross-sectional image, catheter 14 provides a wall which defines lumen 59. The inner wall of catheter 14 (which defines lumen 59) is coated with a friction-reducing liner comprising polytetrafluoroethylene (PTFE) so as to reduce friction during the sliding of tube 19 (not shown for clarity of illustration, but shown in FIGS. 1 and 2) through lumen 59 of catheter 14. The wall of catheter 14 is shaped so as to define secondary lumens 1421, which are typically spaced apart from each other by 180 degrees. A respective pull wire 31a and 31b (not shown in FIG. 5 for clarity of illustration, but are shown in FIGS. 1 and 2) is advanced through each lumen 1421. The inner walls of each secondary lumen 1421 is coated with a friction-reducing liner comprising polytetrafluoroethylene (PTFE) so as to reduce friction during the sliding of respective wires 31a and 31b therethrough. Additionally, the wall of catheter 14 is shaped so as to define a secondary lumen 1422 for passage therethrough of guide member 86 (not shown in FIG. 5 for clarity of illustration, but are shown in FIGS. 1 and 2). The inner wall of secondary lumen 1422 is coated with a friction-reducing liner comprising polytetrafluoroethylene (PTFE) so as to reduce friction during the sliding of guide member 86 therethrough.

Typically, catheter 14 has an inner diameter D3 (or the diameter of lumen 59) of between 4.7 and 5.3 mm (e.g., 5.1 mm) and outer diameter D4 of between 6.3 and 6.9 mm (e.g., 6.5 mm or 6.7 mm).

It is to be noted that even though catheter 14 has multiple durometer segments, inner and outer diameters D3 and D4, respectively, remain constant along a longitudinal length L17 of catheter 14.

Typically, catheter 14 has a length L17 of between 1000 and 1500 mm, e.g., between 1190 and 1210 mm, e.g., 1200 mm. Uniform durometer section 1407 has a length L16 that is between 900 and 1400 mm, e.g., between 1110 and 1130 mm, e.g., 1126 mm. Tubular polymer 1416 extends an entire length L17 of catheter 14. Catheter 14 is surrounded by a braided mesh 1417, which typically comprises a flexible metal (e.g., stainless steel 304 or nitinol). Typically, braided mesh 1417 extends along the length of catheter 14 until a proximal portion at which the pull wires 31a and 31b (not shown for clarity of illustration) are exposed from within lumens 1421 at a proximal section of catheter 14, e.g., between 993 and 1007 mm (e.g., 1000 mm) from distal end 104 of catheter 14.

Section 1410 comprises a distal pull-ring section 1401 in which pull ring 13 is disposed. Section 1401 has a length of between 3.5 and 4.5 mm (e.g., 4.04 mm) and has a durometer of between 45 D and 63 D (e.g., 55 D). Such a durometer of section 1401 imparts more hardness and rigidity to the distal portion of catheter 14 in which pull ring 13 is disposed, such that portion 1401 supports ring 13 and protects the distal portion of catheter 14 from the impact of forces applied thereto during the pulling of pull ring 13 by the pull wires. Typically, pull ring 13 has a length of between 2.5 and 2.6 mm, e.g., 2.54 mm. A distal transition section 1402 is disposed proximal to section 1401 and has a length L11 of between 1 and 2 mm (e.g., 1.5 mm) and has a durometer of between 63 D and 72 D (e.g., 72 D). The relatively high durometer of section 1402 imparts hardness to section 1402 such that pull ring 13 is supported and maintained in place during the pulling of pull ring 13 by the pull wires. Thus, section 1402 helps overcome high tensile forces acting on the distal end of catheter 14.

Catheter 14 provides collective bending section 1405 proximally adjacent to section 1402. As shown in the enlarged image, bending section 1405 comprises a coil 1418 which is embedded within the tubular polymer 1416. Typically, coil 1418 comprises a flexible metal (e.g., stainless steel 304 or nitinol). Coil 1418 imparts efficient and durable bending to bending section 1405. Bending section 1405 has a length L14 of between 60 and 70 mm, e.g., 62 mm. Collective bending section 1405 comprises exposed bending section 1403 and a proximal bending section 1404.

Reference is now made to FIG. 6, which is a schematic illustration of a relative spatial orientation of the steerable distal end portions of catheters 12 and 14, respectively. Typically, in a fully-pushed state of catheter 14 within catheter 12, as described hereinabove, catheter 14 provides exposed distal end portion 114 that extends beyond distal end 102 of catheter 12. Distal end portion 114 comprises exposed bending section 1403. In the fully-pushed state of catheter 14, exposed bending section 1403 is configured to be exposed from and extend beyond distal end 102 of catheter 12, while at least a distal portion of proximal bending section 1404 is configured to remain concentrically disposed within the lumen of catheter 12 in general alignment with bending section 1203 of catheter 12, as indicated by the broken line in FIG. 6.

Reference is now made to FIGS. 5 and 6. Polymer 1416 at exposed bending section 1403 (in FIG. 5) has a durometer of between 20 D and 35 D (e.g., 25 D) which provides a degree of softness at exposed bending section 1403 that facilitates bending of second 1403. Additionally, proximal bending section 1404 has a durometer of between 25 D and 45 D (e.g., 35 D) which provides a degree of softness at exposed bending section 1404 that facilitates bending of second 1404. It is to be noted that the durometer of proximal bending section 1404 is higher than the durometer of exposed bending section 1403. Since the durometer of proximal bending section 1404 of catheter 14 is generally similar to the durometer of bending section 1203 of catheter 12, the steering of the distal end portion of catheter 14 (and of exposed distal portion 114) and the bending of bending section 1405 of catheter 14 (especially the bending of exposed bending section 1403) does not substantially influence the bending and spatial orientation of bending section 1203 at the distal end portion of catheter 12 when catheter 14 is disposed within catheter 12.

Typically, bending section 1405 has a maximum bending angle between 100 and 140 degrees (e.g., 117 degrees). That is, bending section 1405 can bend between 0 and 140 degrees. For some applications, at least a portion of bending section 1405 has a pre-shaped angle of between 40 and 55 degrees (e.g., 45 degrees) so as to reduce force applied to bending section 1405 of catheter 14 by pull wires 31a and 31b.

Reference is again made to FIG. 5. It is to be noted that only tubular polymer 1416 and braided mesh 1417 extend proximally and distally beyond bending section 1405.

Proximally adjacent to bending section 1405 is a transition section 1406 having a length L15 of between 4 and 6 mm (e.g., 5 mm). Proximally adjacent to transition section 1406 is uniform durometer section 1407. Uniform durometer section 1407 has a durometer of between 63 D and 72 D (e.g., 72 D). Transition section 1406 has a durometer of between 35 D and 55 D (e.g., 45 D) so as to provide a transition from the relatively low durometer of proximal bending section 1404 of bending section 1405 to the relatively high durometer of uniform durometer section 1407. FIG. 5 shows the relative position of slit engager 54 with respect to distal end 104 of catheter 14. As described hereinabove, a proximal-most end of engager 54 is disposed up to 120 mm (e.g., up to 80 mm) from distal end 104 of catheter 14.

Typically, the spatial orientation of bending section 1405 is determined by pulling on pull wires 31a and 31b that are disposed within lumens 1421 (wires 31a and 31b are not shown for clarity of illustration). Bending section 1405, for some alternative applications of the present invention, may be pre-shaped to assume a given spatial orientation and the spatial orientation of section 1405 is additionally determined by pulling on pull wires 31a and 31b.

Reference is now made to FIG. 7A, which is a schematic illustration of a catheter 1012 as described hereinabove with regard to catheter 12 with reference to FIG. 4, with the exception that catheter 1012 comprises a tubular portion 1250 that is shaped so as to define slit 52 described herein, in accordance with some applications of the present invention. Tubular portion 1250 comprises a flexible or rigid metal segment that is shaped to provide first coupling 152. For some applications, slit 52 is created in tubular portion 1250. For other applications, frame 50 (described hereinabove with reference to FIG. 1) is coupled to tubular portion 1250 in alignment with a slit generated therein.

During manufacture of catheter 1012, tubular portion 1250 is positioned longitudinally and coaxially between segments of section 1205 of catheter 1012. That is, a portion of section 1205 is cut in order to generate intermediate free ends, and tubular portion 1250 is attached at respective free ends thereof to the intermediate free ends of section 1205. For some applications, catheter 1012 is not cut, but rather catheter 1012 is comprised of two separate parts, each having free ends which are each coupled to section 1250. For some applications, the intermediate free ends are coupled to respective metal segments, and tubular portion 1250 is coupled to the metal segments at the intermediate free ends of catheter 12 by being welded to the metal segments.

Typically, but not necessarily, the metal of portion 1250 is covered by plastic or the polymer of catheter 12, described hereinabove with reference to FIG. 4.

Typically, the pull wires of catheter 12 described hereinabove with reference to FIG. 2, run through secondary lumens in the wall of tubular portion 1250, or adjacently to the wall of portion 1250.

It is to be noted that tubular portion 1250 may be coupled to any suitable catheter known in the art.

Reference is now made to FIG. 7B, which is a schematic illustration of a catheter 1014 as described hereinabove with regard to catheter 14 with reference to FIG. 5, with the exception that catheter 1014 comprises a tubular portion 1450 that is shaped so as to define engager 54 and tab 56 described herein, in accordance with some applications of the present invention. Tubular portion 1450 comprises a flexible or rigid metal segment that is shaped to provide second coupling 154. That is, tubular portion 1450 provides slits 57 (as shown in FIG. 1) which define tab 56 and engager 54. Thus, for some applications, tubular portion 1450 and tab 56 are constructed from a single unit by creating slits in tubular portion 1450, and the protrusion of engager 54 is welded or otherwise coupled to a distal end of tab 56. For other applications, coupling 154 comprises a base which defines tab 56 and provides engager 54, and the base is coupled to tubular portion 1450.

During manufacture of catheter 1014, tubular portion 1450 is positioned longitudinally and coaxially between segments of section 1407 of catheter 1014. That is, a portion of section 1407 is cut in order to generate intermediate free ends, and tubular portion 1450 is attached at respective free ends thereof to the intermediate free ends of section 1407. For some applications, catheter 1014 is not cut, but rather catheter 1012 is comprised of two separate parts, each having free ends which are each coupled to section 1250. For some applications, the intermediate free ends are coupled to respective metal segments, and tubular portion 1450 is coupled to the metal segments at the intermediate free ends of catheter 14 by being welded to the metal segments.

Typically, but not necessarily, the metal of portion 1450 is covered by plastic or the polymer of catheter 14, described hereinabove with reference to FIG. 5.

Typically, the pull wires of catheter 14 described hereinabove with reference to FIG. 2, run through secondary lumens in the wall of tubular portion 1450, or adjacently to the wall of portion 1450.

It is to be noted that tubular portion 1450 may be coupled to any suitable catheter known in the art.

Reference is made to FIGS. 8A-B, which are schematic illustrations of rotating deployment element 38, as described hereinabove with reference to FIG. 2, in radially-expanded and radially-compressed states, respectively, in accordance with some applications of the present invention. For some applications, rotating deployment element 38 is shaped so as to define at least two prongs 124A and 124B that extend in a distal direction from a proximal base 122 of the deployment element. Engagement elements 120A and 120B extend in a distal direction from prongs 124A and 124B, respectively. The engagement elements are typically male, and, for example, may together have a cross-sectional shape that is rectangular, e.g., square. Optionally, rotating deployment element 38 comprises more than two prongs and two engagement elements, e.g., three or four of each.

Rotating deployment element 38 is typically configured to assume a radially-expanded state as its resting state, as shown in FIG. 8A. In this expanded state, engagement elements 120A and 120B, as well as prongs 124A and 124B, are positioned apart from one another. In this state, the engagement elements are shaped and sized to engage coupling head 62 of anchor 32, as shown, for example, in FIG. 2.

As shown in FIG. 8B, the rotating deployment element 38 assumes a radially-compressed state, when the engagement elements and prongs are squeezed together, such as by passing through the engaging opening of coupling head 62 of anchor 32.

Reference is now made to FIGS. 9A-B, which are schematic illustrations of rotating deployment element 38 engaging coupling head 62 of anchor 32, with the element 38 in locked and unlocked states, respectively, in accordance with an application of the present invention. In accordance with this application, rotating deployment element 38 comprises a locking mechanism 128, which is configured to selectively assume locked and unlocked states. When locking mechanism 128 assumes the locked state, the locking mechanism prevents disengagement of rotating deployment element 38 from the anchor which rotating deployment element 38 currently engages. This locking allows deployment element 38 to proximally withdraw anchor 32 if necessary, without coming disengaged therefrom. Disengagement is thus prevented even upon withdrawal of the rotating deployment element in the proximal direction. When the locking mechanism assumes the unlocked state, the locking mechanism does not prevent disengagement of the rotating deployment element from the anchor upon withdrawal of rotating deployment element 38 in the proximal direction. The rotating deployment element thus can be disengaged and withdrawn from the anchor in a proximal direction. It is noted that even when the locking mechanism assumes the unlocked state, the rotating deployment element generally does not disengage from the anchor unless the rotating deployment element is withdrawn in the proximal direction. As mentioned above with reference to FIG. 8A, rotating deployment element 38 is typically configured to assume a radially-expanded state as its resting state. In this radially-expanded state, engagement elements 120A and 120B are positioned apart from each other, and engage coupling head 62 of anchor 32.

For some applications, locking mechanism 128 comprises elongate rod 130. In order to cause the locking mechanism to assume the locked position, rod 130 is advanced distally between engagement elements 120A and 120B. The rod holds the engagement elements in their radially-expanded state, as described hereinabove with reference to FIG. 8A, thereby preventing the engagement elements from assuming the radially-compressed state shown in FIG. 8B and disengaging from the anchor. In the radially-expanded state, the engagement elements engage a proximal engaging surface 66 of coupling head 62 of anchor 32. In order to cause locking mechanism 128 to assume the unlocked state, rod 130 is withdrawn proximally from between engagement elements 120A and 120B. As a result, the engagement elements may assume the radially-compressed state shown in FIGS. 8B and 13B, when deployment element 38 is withdrawn in the proximal direction. In the radially-compressed state, the engagement elements do not engage the coupling head of the anchor.

Movement of rod 130 proximally and distally is described hereinabove with reference to FIG. 2. As shown in Section E-E of FIG. 2, a proximal end of rod 130 is coupled to a component of an anchor-release mechanism 28 at a proximal end of system 10. Mechanism 28 comprises a housing 135 and a finger-engager 131 that is coupled to the proximal end of rod 130. Finger-engager 131 is coupled to a housing 135 via a spring 133 (section E-E of FIG. 2). A proximal end of the tube of anchor driver 36 is coupled to housing 135. As is described hereinbelow, the physician releases anchor 32 from deployment element 38 when finger-engager 131 is pulled proximally, thereby pulling rod 130 proximally. When rod 130 is moved proximally, the distal portion of rod 130 is removed from between engagement elements 120A and 120B, and elements 120A and 120B assume the unlocked state described hereinabove.

Providing this selective, actively-controllable engagement and release of the anchor allows rotating deployment element 38 to be used to unscrew an already-deployed anchor from the tissue, and/or to proximally withdraw an anchor, without deployment element 38 unintentionally disengaging from the anchor head. Such unscrewing or proximal withdrawal may allow an anchor to be repositioned if it is initially coupled to the tissue in an incorrect location. Rotating deployment element 38 is capable of performing this redeployment for both (a) the anchor that has been most recently deployed into the tissue, and to which the deployment element 38 is still coupled, and (b) an anchor that was previously deployed, and from which deployment element 38 has already been decoupled (and, optionally, even after another anchor has subsequently been deployed). In the latter case, deployment element 38 re-engages the anchor that is to be redeployed. For some applications, such re-engaging occurs when deployment element 38, in its compressed state, reenters the opening of coupling head 62 and coupling elements 120A and 120B are allowed to assume their radially-expanded states (e.g., such as by advancing rod 130 therebetween).

Reference is now made to FIGS. 10A-I, which are schematic illustrations of a procedure for implanting an annuloplasty ring structure 222 to repair a mitral valve 230, in accordance with an application of the present invention. This procedure is one exemplary procedure that can be performed using system 10.

Annuloplasty ring structure 222 is used to repair a dilated valve annulus of an atrioventricular valve, such as mitral valve 230. For some applications, the annuloplasty ring is configured to be placed only partially around the valve annulus (e.g., to assume a C-shape), and, once anchored in place, to be contracted so as to circumferentially tighten the valve annulus. The annuloplasty ring comprises flexible sleeve 26 and a plurality of anchors 32. Anchor deployment manipulator 61 is advanced into a lumen of sleeve 26, and, from within the lumen, deploys the anchors through a wall of the sleeve and into cardiac tissue, thereby anchoring the sleeve around a portion of the valve annulus. For some application, annuloplasty ring structure 222 is implemented using techniques described in U.S. application Ser. No. 12/437,103, filed May 7, 2009 which published as US 2010/0286767, and which issued as U.S. Pat. No. 8,715,342, and/or U.S. application Ser. No. 12/689,635, filed Jan. 19, 2010 which published as US 2010/0280604, and which issued as U.S. Pat. No. 8,545,553, both of which are assigned to the assignee of the present application and are incorporated herein by reference. As described hereinabove, annuloplasty ring structure 222 comprises adjusting mechanism 40. The adjusting mechanism comprises a rotatable structure, such as a spool, arranged such that rotation of the rotatable structure contracts the implant structure. The implant further comprises a longitudinal member, such as a wire, which is coupled to the adjusting mechanism. A rotation tool is provided for rotating the rotatable structure. The tool is configured to be guided along (e.g., over, alongside, or through) the longitudinal member, to engage the rotatable structure, and to rotate the rotatable structure in response to a rotational force applied to the tool.

Figure 10A:
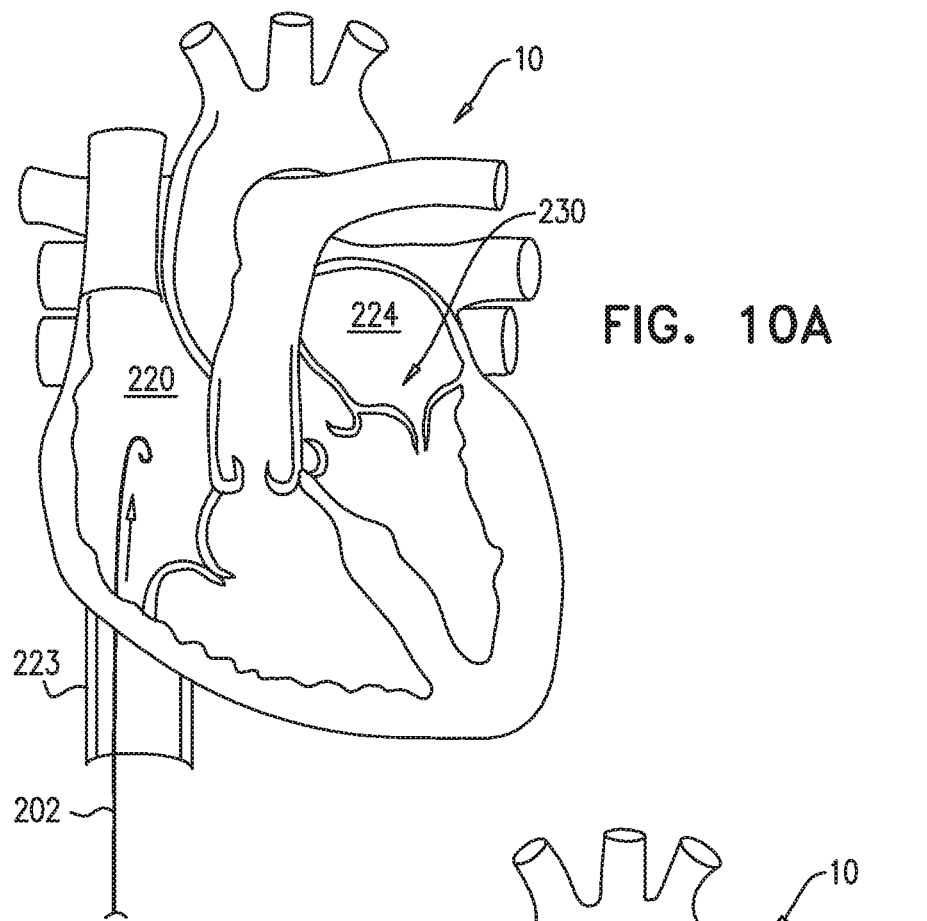

As shown in FIG. 10A, the procedure typically begins by advancing a semi-rigid guidewire 202 into a right atrium 220 of the patient. The procedure is typically performed with the aid of imaging, such as fluoroscopy, transesophageal echo, and/or echocardiography.

Figure 10B:
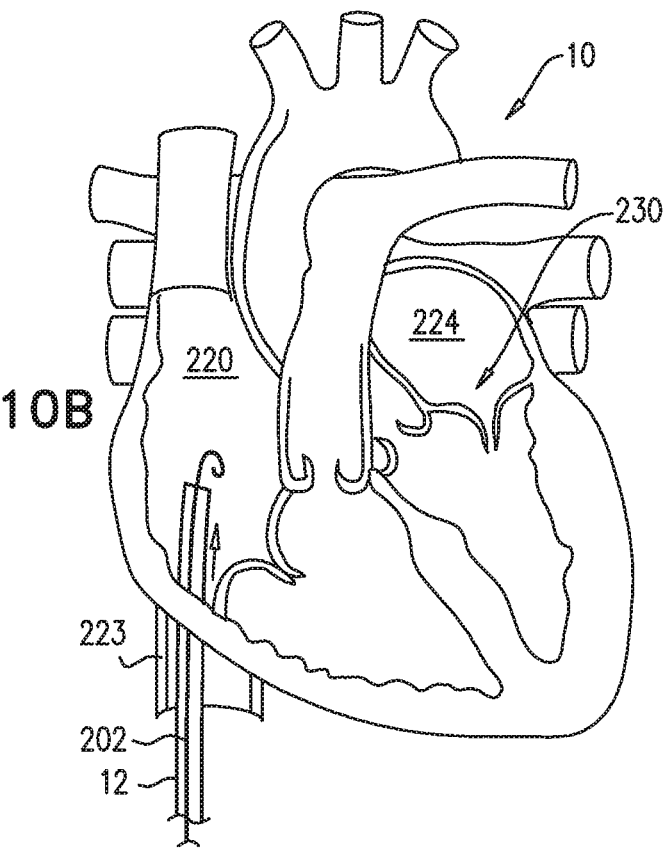

As show in FIG. 10B, guidewire 202 provides a guide for the subsequent advancement of outer catheter 12 therealong and into the right atrium. Once a distal portion of catheter 12 has entered the right atrium, guidewire 202 is retracted from the patient's body. Catheter 12 typically comprises a 14-24 F sheath, although the size may be selected as appropriate for a given patient. Catheter 12 is advanced through vasculature into the right atrium using a suitable point of origin typically determined for a given patient. For example:

catheter 12 may be introduced into the femoral vein of the patient, through an inferior vena cava 223, into right atrium 220, and into a left atrium 224 transseptally, typically through the fossa ovalis;

catheter 12 may be introduced into the basilic vein, through the subclavian vein to the superior vena cava, into right atrium 220, and into left atrium 224 transseptally, typically through the fossa ovalis; or catheter 12 may be introduced into the external jugular vein, through the subclavian vein to the superior vena cava, into right atrium 220, and into left atrium 224 transseptally, typically through the fossa ovalis.

For some applications of the present invention, catheter 12 is advanced through inferior vena cava 223 of the patient (as shown) and into right atrium 220 using a suitable point of origin typically determined for a given patient.

Figure 10C:
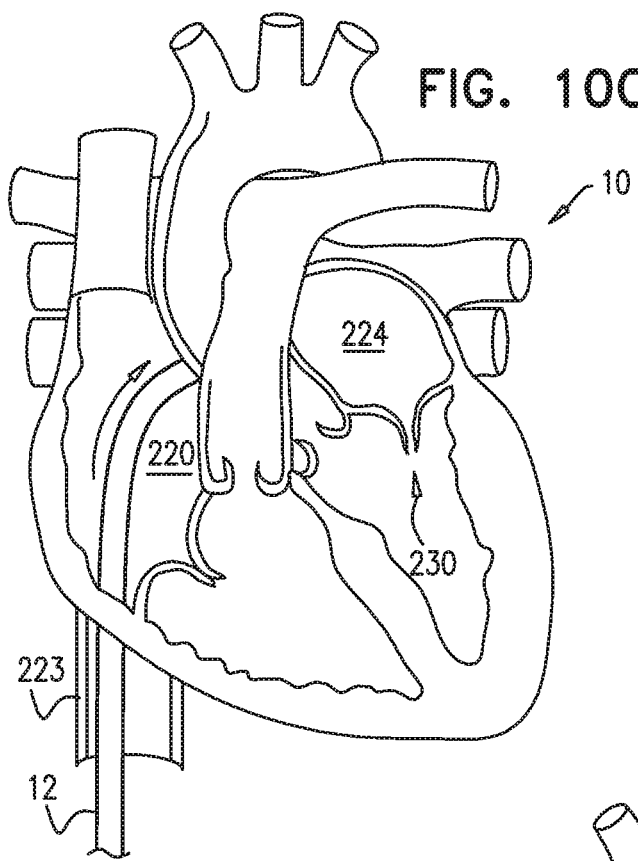

Catheter 12 is advanced distally until the sheath reaches the interatrial septum, and guidewire 202 is withdrawn, as shown in FIG. 10C.

Figure 10D:
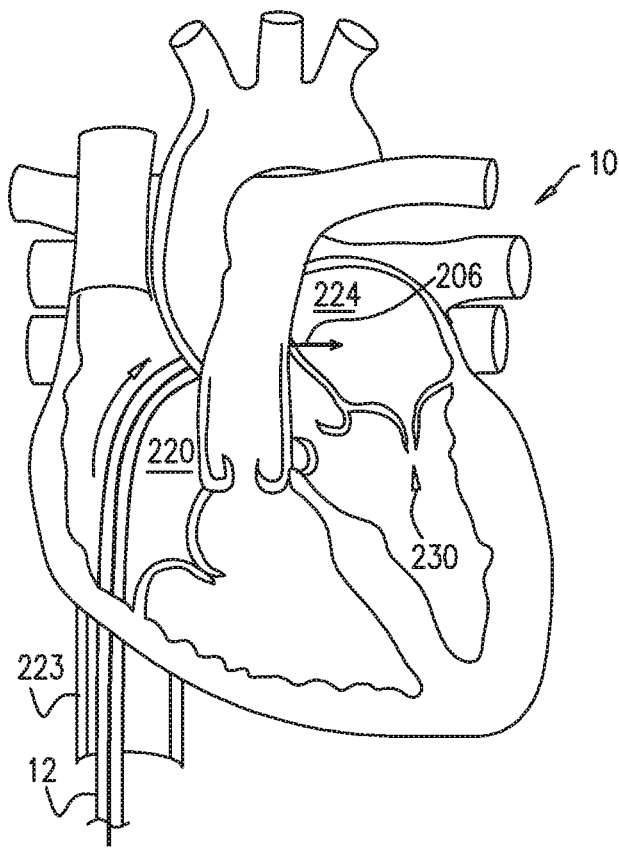

As shown in FIG. 10D, a resilient needle 206 and a dilator (not shown) are advanced through catheter 12 and into the heart. In order to advance catheter 12 transseptally into left atrium 224, the dilator is advanced to the septum, and needle 206 is pushed from within the dilator and is allowed to puncture the septum to create an opening that facilitates passage of the dilator and subsequently catheter 12 therethrough and into left atrium 224. The dilator is passed through the hole in the septum created by the needle. Typically, the dilator is shaped to define a hollow shaft for passage along needle 206, and the hollow shaft is shaped to define a tapered distal end. This tapered distal end is first advanced through the hole created by needle 206. The hole is enlarged when the gradually increasing diameter of the distal end of the dilator is pushed through the hole in the septum. As shown in FIG. 4, for example, a distal-most end 102 of catheter 12 is tapered so as to facilitate passage of the distal portion of catheter 12 through the opening in the septum.

Figure 10E:
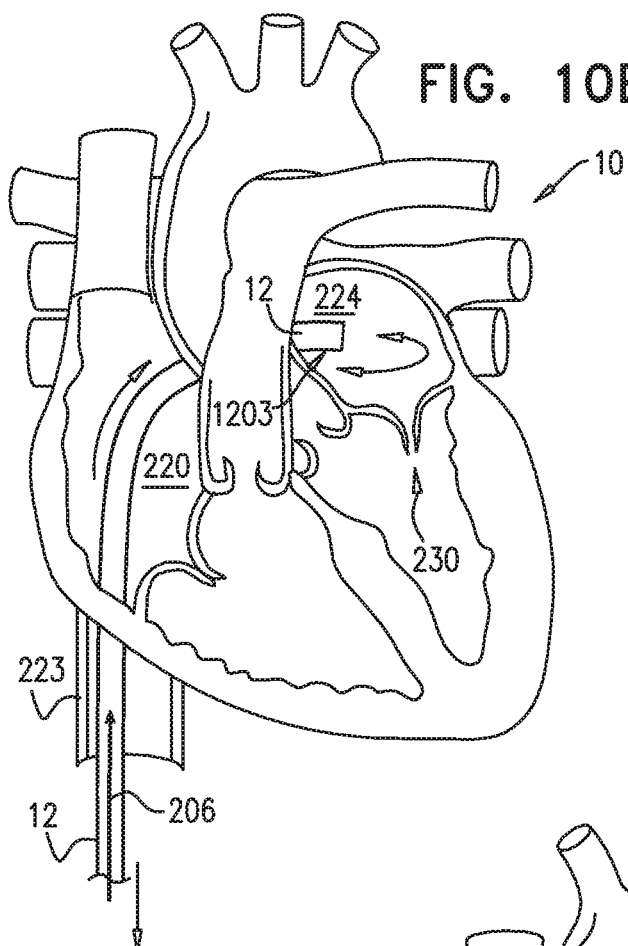

The advancement of catheter 12 through the septum and into the left atrium is followed by the extraction of the dilator and needle 206 from within catheter 12, as shown in FIG. 10E. Once the distal portion of catheter 12 is disposed within atrium 224, the steerable distal end portion of catheter 12 (which includes at least a portion of bending section 1203, as described hereinabove with reference to FIGS. 4 and 6) is steered in a first plane that is parallel to a plane of the annulus of mitral valve 230. Such steering moves the distal end portion of catheter 12 in a direction from the interatrial septum toward surrounding walls of the atrium, as indicated by the arrow in atrium 224. As described hereinabove, steering of the distal portion of catheter 12 is performed via steering knob 210 of handle 22 in handle portion 101 (in FIGS. 1 and 2).

Figure 10F:
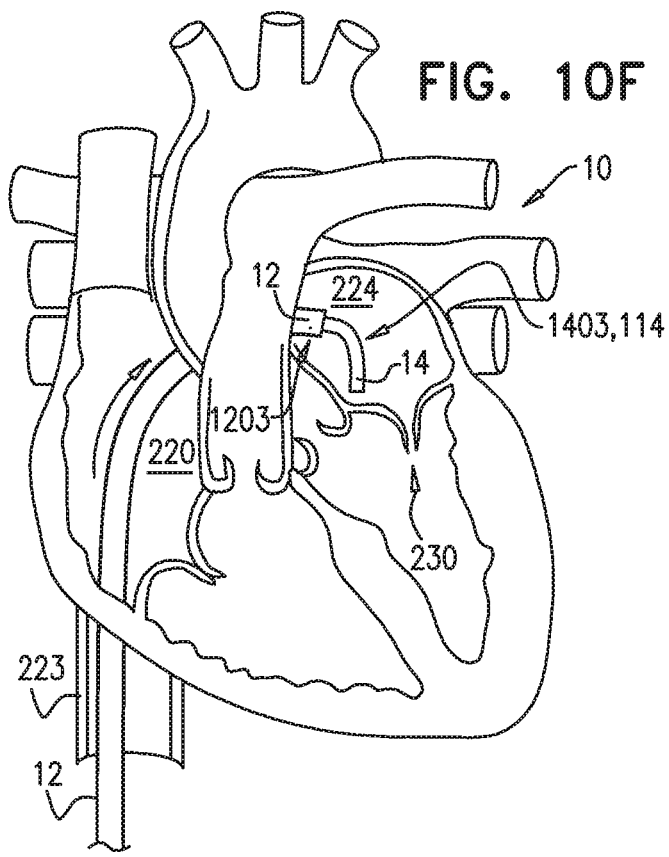

As shown in FIG. 10F, annuloplasty ring structure 222 (not shown for clarity of illustration, with anchor deployment manipulator 61 therein) is advanced through guide catheter 14, which is in turn, advanced through catheter 12 into left atrium 224. As shown in FIG. 10F, exposed distal end portion 114 of catheter 14 extends beyond distal end 102 of catheter 12. Exposed distal end portion 114 is then (1) steered toward the annulus of valve 230 along a plane that is perpendicular with respect to the steering plane of catheter 12 and that is perpendicular with respect to valve 230, and is (2) bent, via bending section 1403 (as described hereinabove with reference to FIGS. 5 and 6) toward valve 230. As described hereinabove, steering of the distal portion of catheter 14 is performed via steering knob 214 of handle 24 in handle portion 101 (in FIGS. 1 and 2).

Figure 10G:
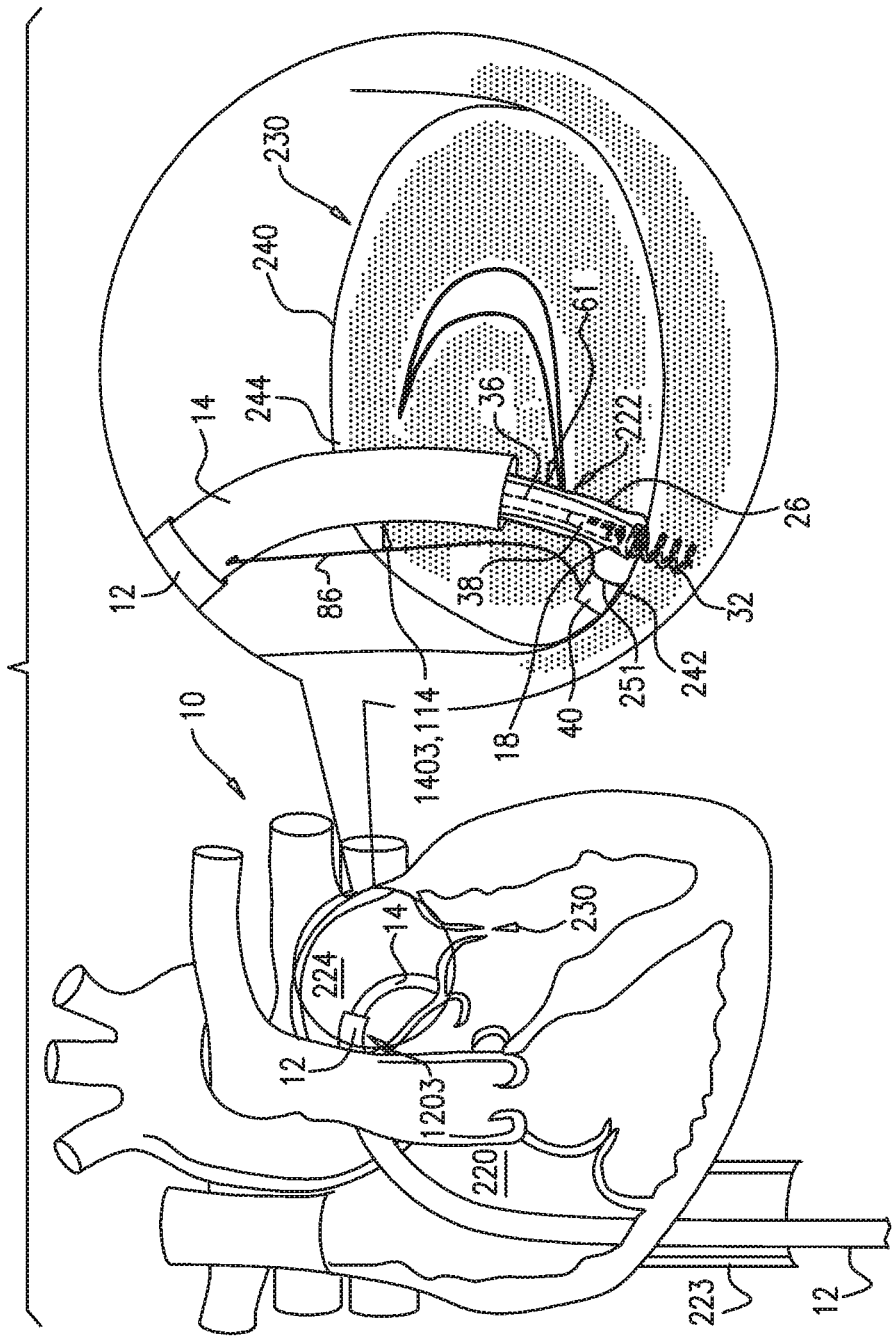

As shown in FIG. 10G, a distal end 251 of sleeve 26 is positioned in a vicinity of a left fibrous trigone 242 of an annulus 240 of mitral valve 230. (It is noted that for clarity of illustration, distal end 251 of sleeve 26 is shown schematically in the cross-sectional view of the heart, although left trigone 242 is in reality not located in the shown cross-sectional plane, but rather out of the page closer to the viewer.) Alternatively, the distal end of sleeve 26 is positioned in a vicinity of a right fibrous trigone 244 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Once positioned at the desired site near the selected trigone, deployment manipulator 61 deploys a first anchor 32 through the wall of sleeve 26 (by penetrating the wall of the sleeve in a direction in a direction parallel to a central longitudinal axis of deployment manipulator 61, or anchor driver 36, through the distal end of channel 18, and/or parallel to central longitudinal axis of tissue-engaging element 60 of anchor 32) into cardiac tissue near the trigone, using the techniques described hereinabove with reference to FIGS. 8A-B and 9A-B. Following the deployment of anchor 32 in the cardiac tissue, deployment element 38 is decoupled from anchor 32 by moving rod 130 proximally, as described hereinabove with reference to FIGS. 2, 8A-B, and 9A-B.

Anchors 32 are typically deployed from a distal end of manipulator 61 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Typically, anchors 32 are deployed from the distal end of manipulator 61 into the cardiac tissue in a direction parallel to the central longitudinal axis through the distal end of manipulator 61. Such an angle is typically provided and/or maintained by channel 18 being more rigid than sleeve 26. Distal end 17 (shown in FIG. 2) of channel 18 is typically brought close to the surface of the cardiac tissue (and the wall of sleeve 26 that is disposed against the surface of the cardiac tissue), such that little of each anchor 32 is exposed from channel 18 before penetrating the sleeve and the tissue. For example, distal end 17 of channel 18 may be placed (e.g., pushed) against the wall of the sleeve, sandwiching the sleeve against the cardiac tissue.

For some applications, this placement of distal end 17 of channel 18 against the cardiac tissue (via the wall of the sleeve), stabilizes the distal end during deployment and anchoring of each anchor 32, and thereby facilitates anchoring. For some applications, pushing of distal end 17 against the cardiac tissue (via the wall of the sleeve) temporarily deforms the cardiac tissue at the site of contact. This deformation may facilitate identification of the site of contact using imaging techniques (e.g., by identifying a deformation in the border between cardiac tissue and blood), and thereby may facilitate correct positioning of the anchor.

For some applications of the present invention, anchors 32 may be deployed from a lateral portion of manipulator 61.

Figure 10H:
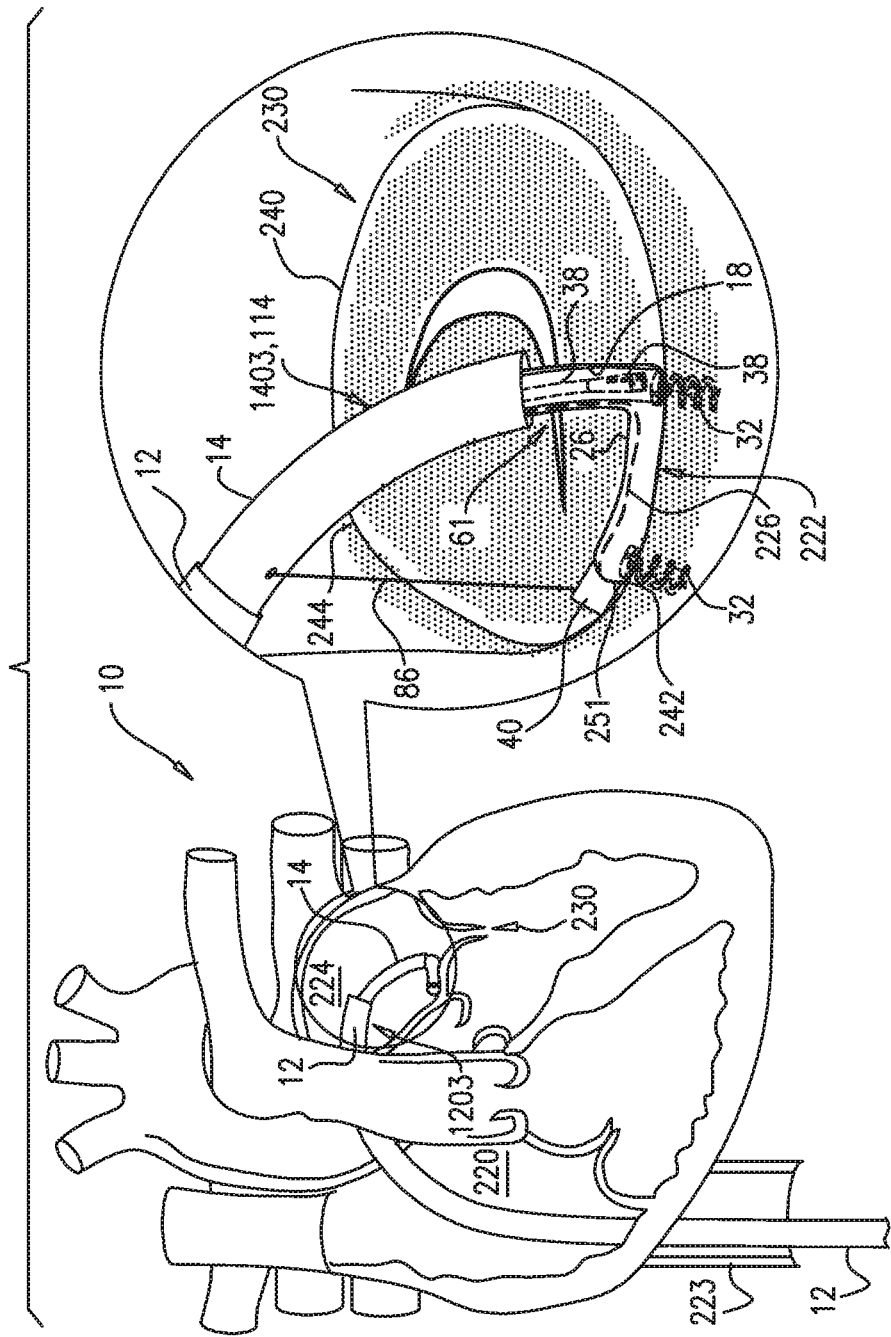

Reference is now made to FIGS. 10G and 2. Following the deployment of the first anchor, a distal portion of sleeve 26 is decoupled from a portion of implant-decoupling channel 18. In order to decouple the portion of sleeve 26 from outer surface of channel 18, (1) channel 18 is pulled proximally, while (2) reference-force tube 19 is maintained in place in a manner in which a distal end of tube 19 provides a reference force to sleeve 26 in order to facilitate retraction freeing of a successive portion of sleeve 26 from around channel 18. In order to decouple sleeve 26 from the outer surface of channel 18, (1) channel 18 is pulled proximally, while (2) reference-force tube 19 is maintained in place. An indicator (such as indicator 2120 described in PCT patent application PCT/IL2012/050451 to Sheps et al., which published as WO/2013/069019, which is incorporated herein by reference) on handle 126 provides an indication of how much channel 18 is withdrawn from within sleeve 26 (i.e., how much the delivery tool is decoupled from sleeve 26, and how much the sleeve has advanced off channel 18 and against tissue). A proximal end of channel 18 is coupled to a knob 94 (FIG. 2) which adjusts an axial position of channel 18 proximally and distally with respect to reference-force tube 19 and sleeve 26. As shown in FIG. 10H, deployment manipulator 61 is repositioned along annulus 240 to another site selected for deployment of a second anchor 32. Reference is now made to FIGS. 1 and 10H. Such repositioning of manipulator 61 is accomplished by:

(1) the steering of the distal end portion of catheter 12 (e.g., by steering knob 210 of handle 22) in the first plane that is parallel with respect to annulus 240 of valve 230 to a desired spatial orientation and in a manner which bends bending section 1203 of catheter 12, (2) the steering of the distal end portion of portion of catheter 14 (e.g., by steering knob 214 of handle 24) in the second plane that is perpendicular with respect to annulus 240 of valve 230 to a desired spatial orientation, and in a manner which bends bending section 1405 of catheter 14 (specifically bending section 1403), (3) by axially moving catheter 14 with respect to catheter 12 via knob 216, (4) by axially moving the stand supporting handles 22 and 24 to move both catheters 12 and 14, (5) by moving tube 19 and sleeve 26 axially by sliding mount 93 along track 90 via knob 95, and/or (6) by moving channel 18 relative to tube 19 by actuating knob 94.

Typically, the first anchor is deployed most distally in the sleeve (generally at or within a few millimeters of the distal tip of the sleeve), and each subsequent anchor is deployed more proximally, such that the sleeve is gradually decoupled from channel 18 of deployment manipulator 61 in a distal direction during the anchoring procedure (i.e., channel 18 is withdrawn from within sleeve 26, and handle 126 is moved distally so as to retract the tool to make the successive proximal portion sleeve 26 ready for implantation of a subsequent anchor). The already-deployed first anchor 32 holds the anchored end of sleeve 26 in place, so that the sleeve is drawn from the site of the first anchor towards the site of the second anchor. Typically, as sleeve 26 is decoupled from channel 18, deployment manipulator 61 is moved generally laterally along the cardiac tissue, as shown in FIG. 10H. Deployment manipulator 61 deploys the second anchor through the wall of sleeve 26 into cardiac tissue at the second site. Depending on the tension applied between the first and second anchor sites, the portion of sleeve 26 therebetween may remain tubular in shape, or may become flattened, which may help reduce any interference of the ring with blood flow.

As shown in FIG. 10I, deployment manipulator 61 is repositioned along the annulus to additional sites, at which respective anchors are deployed, until the last anchor is deployed in a vicinity of right fibrous trigone 244 (or left fibrous trigone 242 if the anchoring began at the right trigone). Alternatively, the last anchor is not deployed in the vicinity of a trigone, but is instead deployed elsewhere in a vicinity of the mitral valve, such as in a vicinity of the anterior or posterior commissure. Then, system 10 is removed, leaving behind guide member 86. A rotation tool is then threaded over and advanced along guide member 86 toward adjusting mechanism 40, and is used to rotate the spool of adjusting mechanism 40 in order to tighten structure 222 by adjusting a degree of tension of contracting member 226 (not shown in FIG. 10I, but (i) advancing of a rotation tool over guide member 86 is described with reference to FIG. 26G, mutatis mutandis, and (ii) rotating the spool of member 40 is described hereinbelow with reference to FIG. 11).

Once the desired level of adjustment of structure 222 is achieved (e.g., by monitoring the extent of regurgitation of the valve under echocardiographic and/or fluoroscopic guidance), the rotation tool and guide member 86 are removed from the heart. For some applications, a distal portion of guide member 86 may be left within the heart of the patient and the proximal end may be accessible outside the body, e.g., using a port. For such applications, adjusting mechanism 40 may be accessed at a later stage following initial implantation and adjustment of ring structure 222.

For some applications, a re-access wire 288 may be provided, coupled to a proximal portion of the implant (e.g., a portion of the implant that is deployed last), such as to a last anchor 32 (as shown in FIG. 10I) or sleeve 26, such that, upon anchoring, the wire extends proximally, e.g., out of the body of the subject, such as via catheter 14 and/or catheter 12. Should it be determined, after implantation (e.g., and after adjustment) of annuloplasty ring structure 222, that one or more anchors 32 requires adjustment or retrieval, re-access wire 288 facilitates guidance of an anchor-manipulation tool to annuloplasty ring structure 222 and/or into the lumen thereof. For example, such an anchor-manipulation tool may comprise an anchor-manipulation tool described in a PCT patent application to Herman et al, titled "Percutaneous tissue anchor techniques", filed on even date herewith, and incorporated herein by reference. Apparatus and techniques described in the present patent application may be used in combination with apparatus and techniques described in said PCT patent application to Herman et al, titled "Percutaneous tissue anchor techniques".

As shown, sleeve 26 of ring structure 222 comprises a plurality of radiopaque markers 25, which are positioned along the sleeve at respective longitudinal sites to indicate anchor-designated target areas. The markers may provide an indication in a radiographic image (such as a fluoroscopy image) of how much of sleeve 26 has been deployed at any given point during an implantation procedure, in order to enable setting a desired distance between anchors 32 along the sleeve 26.

For some applications, and as shown in FIG. 10I, anchors 32 are deployed at longitudinal sites of sleeve 26 at which radiopaque markers 25 are disposed (e.g., the anchors are driven through a radiopaque ink of the radiopaque markers). Alternatively, anchors 32 may be deployed at longitudinal sites of sleeve 26 between markers 25. For example, when dispensing sleeve 26 from channel 18 (i.e., when advancing sleeve 26 with respect to channel 18 and/or withdrawing channel 18 from sleeve 26), the appearance of a marker 25 at the distal end of channel 18 (e.g., the marker 25 becoming aligned with marker 1018 of channel 18) may indicate that a correct length of sleeve 26 has been dispensed. Subsequent limited movement of the channel with respect to the sleeve may occur. For example, when channel 18 is placed against the annulus, the channel may tension the portion of sleeve 26 between the previously-deployed anchor and the distal end of the channel (e.g., as described with reference to FIG. 26D), such that when the anchor is deployed, it passes through the sleeve slightly proximally to the marker 25 (e.g., 1-2 mm proximally to the marker).

Alternatively, annuloplasty ring structure 222 is implanted by right or left thoracotomy, mutatis mutandis.

For some applications of the present invention, following implantation of sleeve 26 along the annulus, an excess portion of sleeve 26 may be present at the proximal portion of sleeve. In such applications, following removal of manipulator 61, a cutting tool (not shown) may be advanced within channel 18 and into the lumen of the excess portions of sleeve 26 (e.g., from within sleeve 26) in order to cut the sleeve proximal to the proximal-most-deployed anchor 32.

Figure 11:
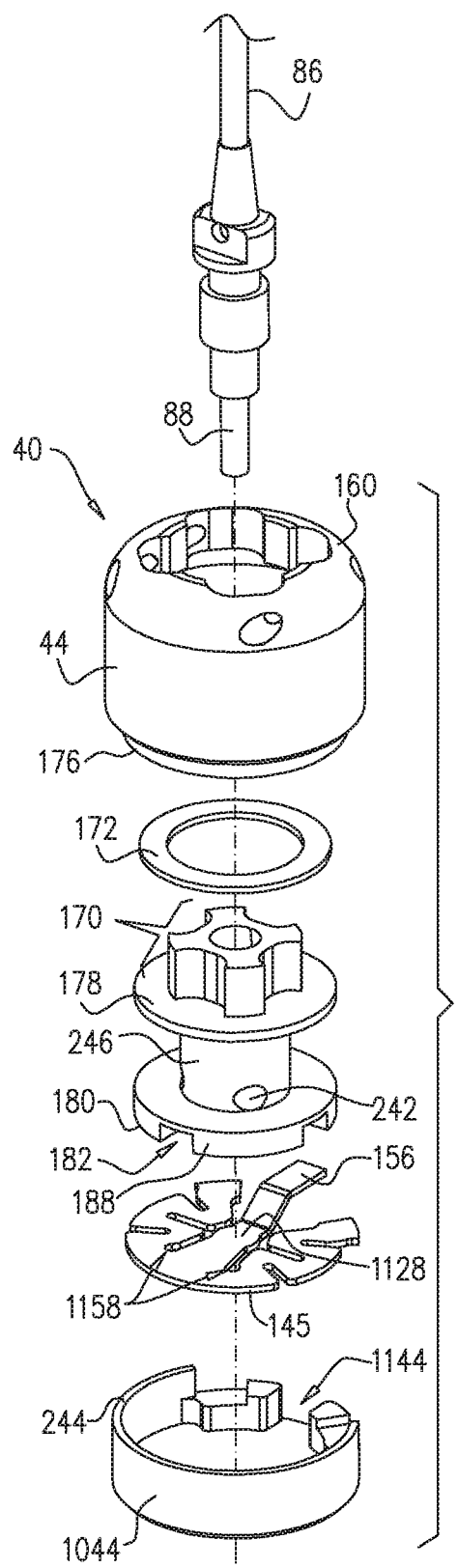
FIG. 11 is a schematic illustration of components of a rotational adjusting mechanism, in accordance with some applications of the present invention.

Reference is now made to FIG. 11, which is a schematic illustration showing a relationship among individual components of adjusting mechanism 40, in accordance with some applications of the present invention. Adjusting mechanism 40 is shown as comprising spool housing 44 which defines an upper surface 160 and a lower surface 176 defining a recessed portion (as described with regard to recess 142 with reference to FIG. 3). A spool 246 is configured to be disposed within housing 44 and defines an upper surface 178, a lower surface 180, and a cylindrical body portion disposed vertically between surfaces 178 and 180. The cylindrical body portion of spool 246 is shaped so as to define a channel which extends from a first opening at upper surface 178 to a second opening at lower surface 180.

Typically, spool 246 is configured to adjust a perimeter of annuloplasty ring structure 222 by adjusting a degree of tension of contracting member 226 that is coupled at a first portion of member 226 to spool 246. As described hereinabove, contracting member 226 extends along sleeve 26 and a second portion of contracting member 226 (i.e., a free end portion) is coupled to a portion of sleeve 26 such that upon rotation of the spool in a first rotational direction, the portion of sleeve 26 is pulled toward adjusting mechanism 40 in order to contract annuloplasty ring structure 222. It is to be noted that the contraction of structure 222 is reversible. That is, rotating spool 246 in a second rotational direction that opposes the first rotational direction used to contract the annuloplasty structure, unwinds a portion of contracting member 226 from around spool 246. Unwinding the portion of contracting member 226 from around spool 246 thus feeds the portion of contracting member 226 back into a lumen of sleeve 26 of structure 222, thereby slackening the remaining portion of contracting member 226 that is disposed within the lumen sleeve 26. Responsively, the annuloplasty structure gradually relaxes and expands (i.e., with respect to its contracted state prior to the unwinding).

Lower surface 180 of spool 246 is shaped to define one or more (e.g., a plurality, as shown) of recesses 182 which define structural barrier portions 188 of lower surface 180.

It is to be noted that any suitable number of recesses 182 may be provided, e.g., between 1 and 10 recesses. For some applications, but not necessarily, recesses 182 are provided circumferentially with respect to lower surface 180 of spool 246.

Typically, spool 246 comprises a locking mechanism 145. For some applications, locking mechanism 145 is coupled, e.g., welded, at least in part to a lower surface of spool housing 44. Typically, locking mechanism 145 defines a mechanical element having a planar surface that defines slits 1158. The surface of locking mechanism 145 may also be curved, and not planar. Locking mechanism 145 is shaped to provide a protrusion 156 which projects out of a plane defined by the planar surface of the mechanical element. The slits define a depressible portion 1128 of locking mechanism 145 that is disposed in communication with and extends toward protrusion 156.

In a resting state of locking mechanism 145 (i.e., a locked state of spool 246), protrusion 156 is disposed within a recess 182 of spool 246. Additionally, in the locked state of spool 246, protrusion 156 is disposed within the recess of housing 44.

Depressible portion 1128 is aligned with the opening at lower surface 180 of spool 246 and is moveable in response to a force applied thereto by a distal force applicator 88 that extends in a distal direction from a distal portion of longitudinal guide member 86. That is, distal force applicator 88 is configured to be disposed within the channel of spool 246. A distal end of applicator 88 is configured to push on depressible portion 1128 in order to move depressible portion 1128 downward so as to disengage protrusion 156 from within a recess 182 of spool and to unlock spool 246 from locking mechanism 145.

It is to be noted that the planar, mechanical element of locking mechanism 145 is shown by way of illustration and not limitation and that any suitable mechanical element having or lacking a planar surface but shaped to define at least one protrusion may be used together with locking mechanism 145.

A cap 1044 is provided that is shaped so as to define a planar surface and an annular wall having an upper surface 244 that is coupled to, e.g., welded to, lower surface 176 of spool housing 44. The annular wall of cap 1044 is shaped so as to define a recessed portion 1144 of cap 1044 that is in alignment with the recessed portion of spool housing 44. Locking mechanism 145 is disposed between lower surface 180 of spool 246 and the planar surface of cap 1044.

In an unlocked state of adjusting mechanism 40, protrusion 156 of locking mechanism 145 is disposed within recessed portion 1144 of cap 1044. In the unlocked state, force applicator 88 extends through spool 246 and pushes against depressible portion 1128 of locking mechanism 145. The depressible portion is thus pressed downward, freeing protrusion 156 from within a recess 182 defined by structural barrier portions 188 of the lower portion of spool 246. Additionally, protrusion 156 is freed from within the recessed portion of spool housing 44. As a result, adjusting mechanism 40 is unlocked, and spool 246 may be rotated with respect to spool housing 44.

Cap 1044 functions to restrict distal pushing of depressible portion 1128 beyond a desired distance so as to inhibit deformation of locking mechanism 145. For applications in which adjusting mechanism 40 is implanted in heart tissue, cap 1044 also provides an interface between adjusting mechanism 40 and the heart tissue. This prevents interference of heart tissue on adjusting mechanism 40 during the locking and unlocking thereof. Additionally, cap 1044 prevents damage to heart tissue by depressible portion 1128 as it is pushed downward.

Spool 246 is shaped so as to define a rotation-facilitating head 170, or a driving interface. A rotation tool (not shown) is configured to slide distally along guide member 86 to engage head 170 of spool 246. The rotation tool is configured to rotate spool 246 by applying rotational force to head 170. A friction-reducing ring 172 is disposed between upper surface 178 of spool 246 and the inner surface of upper surface 160 of spool housing 44.

For some applications, as described herein, guide member 86 is not coupled to spool 246. For such applications the rotation tool used to rotate spool 246 may be shaped to provide a distal force applicator (similar to distal force applicator 88) configured to unlock spool 246 from locking mechanism 145. During the unlocked state, spool 246 may be bidirectionally rotated.

Following rotation of spool 246 such that contracting element 226 is pulled sufficiently to adjust the degree of tension of contracting element 226 so as treat tissue of the ventricle as described herein, spool 246 is then locked in place so as to restrict rotation of spool 246. Force applicator 88 is removed from within the channel of spool 246, and thereby, depressible portion 1128 returns to its resting state. As depressible portion 1128 returns to its resting state, protrusion 156 is introduced within one of the plurality of recesses 182 of lower surface 180 of spool 246 and within the recess of housing 44, and thereby restricts rotation of spool 246.

Spool 246 is shaped so as to provide a hole 242 or other coupling mechanism for coupling a first portion of contracting element 226 to spool 246, and thereby to adjusting mechanism 40.

Figure 12A:
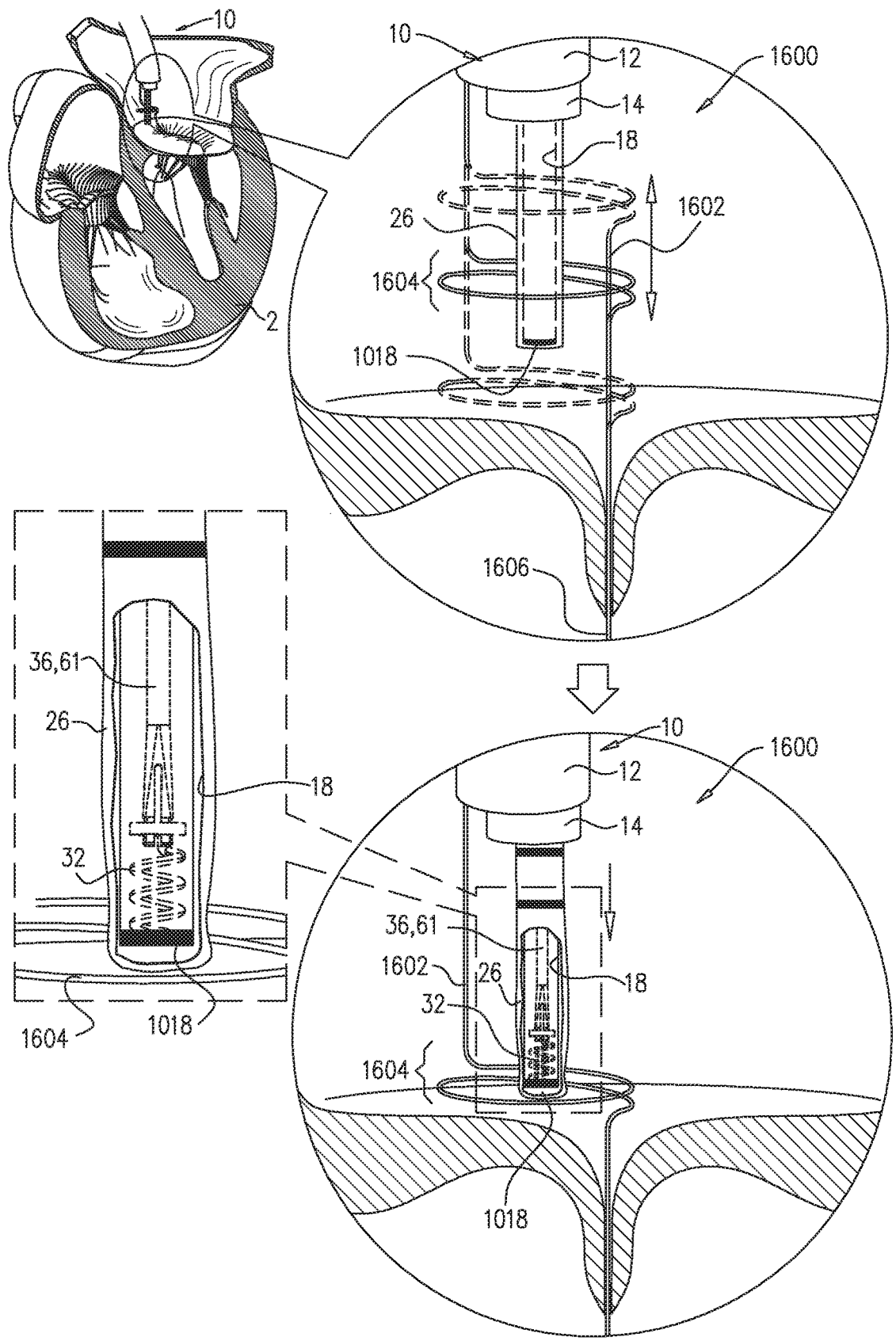

Reference is now made to FIGS. 12A-C, which are schematic illustrations of a navigational-based guidance system 1600, which employs a guide 1602 shaped to define a looped portion 1604 configured to facilitate guidance of manipulator 61, and thereby anchors 32, to specific portions of the annulus by contacting a surface of the valve (e.g., the annulus of the valve), in accordance with some applications of the present invention. Guide 1602 comprises a flexible material (e.g., a flexible metal such as nitinol or stainless steel) and is shaped so as to provide (a) a proximal generally-straight, or linear, section, (b) looped portion 1604, which loops around (i.e., circumscribes) and is slidable proximally and distally along a portion of sleeve 26, and (c) a distal generally-straight, or linear, section 1606.

The proximal straight section is configured to extend through any tube of system 10, (e.g., between outer catheter 12 and guide catheter 14 (and thereby also between catheter 12 and sleeve 26), or within a designated secondary lumen in a wall of either catheter 12 or 14). Looped portion 1604 is configured to assume a loop shape by shape memory, or is simply looped around a portion of sleeve 26, and thereby around a portion of channel 18 within sleeve 26. Looped portion 1604 is slidable proximally and distally along sleeve 26 when a respective force is applied to a proximal portion of guide 1602. Distal straight section 1606 of guide 1602 is configured to be disposed at least in part in a ventricle of the patient (e.g., the left ventricle, as shown). A proximal portion of distal straight section 1606 (i.e., the portion of distal straight section 1606 that is distal to loop 1604) extends between the leaflets of the atrioventricular valve (e.g., the mitral valve, as shown by way of illustration and not limitation). For some applications, and as shown, distal straight section 1606 is configured to have an end which is disposed as a J-loop in the ventricle. Alternatively, for some applications, distal straight section 1606 extends through the ventricle and out the aorta through vasculature of the patient until the end of the section 1606 is disposed outside the body of the patient, in a manner in which guide 1602 assumes an arteriovenous loop in which an end of the proximal straight section is exposed at a venous access location of the patient, and the end of distal straight portion 1606 is exposed at an arterial access location of the patient.

When the operating physician intends to implant one of anchors 32 at a targeted location along the annulus, the physician pushes distally on guide 1602 in order that looped portion 1604 travels distally toward the annulus (FIG. 12A). Distal migration of looped portion 1604 into the ventricle is prevented by the shape of the coapting leaflets. Looped portion 1604 is shaped such that it cannot pass through the leaflets, and thereby abuts tissue of the valve. Looped portion 1604 thereby comprises a tissue-engaging portion of guide 1602 that is configured to be placed in contact with the tissue. Thus, when the physician pushes distally on guide 1602 and feels resistance, the physician knows that looped portion 1604 has reached the annulus. In addition to the distal pushing of guide 1602, the distal end portion of channel 18 is pushed distally, under fluoroscopic guidance, toward the annulus in order to advance sleeve 26, as described hereinabove. The operating physician views marker 1018 of channel 18 under the fluoroscopic guidance. Once the physician feels resistance from looped portion 1604, sees via the imaging that looped portion 1604 cannot be pushed further, and sees via the imaging, marker 1018 of channel 18 in line with looped portion 1604, the physician knows that the distal end of channel 18 is indeed at the annulus, and then can deploy anchor 32, as described hereinabove. That is, while looped portion 1604 is disposed against tissue of the valve, marker 1018 and looped portion 1604 provide a fluoroscopically-identifiable arrangement that indicates a juxtaposition of the distal end of the channel with respect to the tissue.

For some applications, guide 1602 further facilitates guidance of anchor driver 36 by inhibiting movement of at least the distal end of channel 18 (and thereby movement of at least the distal end of anchor driver 36). For example, when portion 1606 is disposed between leaflets of the valve (e.g., at a commissure or elsewhere), guide 1602 may inhibit movement of catheter 14, channel 18, and/or driver 36 away from the site at which the guide engages tissue.

When the operating physician wishes to deploy a subsequent anchor 32 into tissue of the annulus, the operating physician pulls on guide 1602 such that looped portion 1604 advances proximally, as shown in FIG. 12B. Then, a successive portion of sleeve 26 is advanced toward the annulus, as described hereinabove with reference to FIG. 2. That is, (1) a proximal force is applied to channel 18, while (2) reference-force tube 19 is maintained in place in a manner in which a distal end of tube 19 provides a reference force to sleeve 26 in order to facilitate freeing of a successive portion of sleeve 26 from around channel 18. Channel 18 is then positioned at a successive location within the lumen of sleeve 26 while either tube 19 and/or catheter 14 is steered toward a successive location along the annulus of the valve. Then, looped portion 1604 is pushed distally along with channel 18, in order to provide the physician with the guidance described hereinabove. Once the distal end of system 10 is at the appropriate location along the annulus, the physician deploys the successive anchor, as shown in FIG. 12B.

FIG. 12C shows the operation of system 1600 following deployment of a majority of the anchors in order to anchor sleeve 26 to the annulus.

As described hereinabove, guide 1602 may inhibit movement of at least the distal end of channel 18, and thereby movement of at least the distal end of anchor driver 36 (e.g., a portion of the guide that extends between leaflets at a commissure may inhibit movement of the distal end of the channel away from the commissure). As described in more detail hereinbelow (e.g., with reference to FIG. 26D, mutatis mutandis), following deployment of at least one anchor, sleeve 26 inhibits movement of the distal end of anchor driver 36 by providing a maximum distance that the distal end of the driver may be disposed from the previously-deployed anchor. It is to be noted, therefore, that:

(1) a guide 1602 comprises a first constraining member configured to inhibit movement of the distal end of anchor driver 36 on a first axis (e.g., an axis between (i) the distal end of the anchor driver, and (ii) the guide and/or the site at which the guide engages tissue); and (2) sleeve 26 comprises a second constraining member configured to inhibit movement of the distal end of the anchor driver on a second axis (e.g., an axis between (i) the distal end of the anchor driver, and (ii) a previously-deployed anchor).

Reference is made to FIGS. 13A-E, which are schematic illustrations of a navigational-based guidance system 1650, which employs one or more longitudinal guides 1652 configured to facilitate guidance of channel 18, and thereby anchor driver 36 and anchors 32, to specific portions of annulus 240 by the guides contacting a surface of the valve (e.g., the annulus, commissure, and/or leaflets of the valve), in accordance with some applications of the invention. Guide 1652 comprises a flexible material (e.g., a flexible metal such as nitinol or stainless steel). A plurality of eyelets 1654 are disposed along a lateral outer surface of sleeve 26, and each guide 1652 (e.g., a distal portion thereof) is disposed within at least some of the eyelets (e.g., the guide is threaded through the eyelets). Eyelets 1654 typically comprise suture or fabric.

Typically, eyelets 1654 are arranged in longitudinal rows 1656 along the length of sleeve 26, and each guide 1652 is disposed within the eyelets of a respective row. FIGS. 13A-E show system 1650 comprising three guides 1652 (e.g., a first guide 1652a, a second guide 1652b, and a third guide 1652c) and three respective rows of eyelets (e.g., a first row 1656a, a second row 1656b, and a third row 1656c; indicated but not visible in FIG. 13A) within which the guides are disposed. Typically, the eyelets of each row are disposed at the same longitudinal site as a corresponding eyelet of each other row. As described hereinabove, for some applications sleeve 26 comprises a plurality of radiopaque markers 25, which are positioned along the sleeve at respective longitudinal sites. For some applications the eyelets of each row are disposed at the same longitudinal site as a corresponding radiopaque marker (e.g., as shown in FIGS. 13A-E). Alternatively, the eyelets may be disposed between radiopaque markers. Guides 1652 are disposed at respective circumferential positions around sleeve 26 (e.g., the longitudinal axis thereof). In FIGS. 13A-E, each of the three guides is shown as being disposed at about 120 degrees around sleeve 26 from the adjacent guides, but the scope of the invention includes other arrangements, such as two guides disposed opposite each other.

It is to be noted that, when sleeve 26 is advanced through catheter 14, at least part of each guide 1652 is disposed between the sleeve and the catheter (e.g., see FIGS. 13B-E).

For some applications, and as shown in FIGS. 13A-E, each guide 1652 comprises a wire with a looped portion 1658 such that the guide has (1) two parallel linear portions of the wire, and (2) the looped portion at a distal end portion 1660 of the guide. The reference numeral of each parallel linear portion of each wire is designated ' or ". For example, guide 1652a is shown as comprising a wire having parallel linear portions 1652a' and 1652a", and guide 1652b is shown as comprising a wire having parallel linear portions 1652b' and 1652b".

For some applications, and as shown in FIGS. 13A-E, distal end portion 1660 of each guide 1652 is biased (e.g., shape-set) to protrude radially outward from sleeve 26. Such biasing may confer a desired behavior on the guide, e.g., during distal movement of the guide. For example, when the guide is moved distally against tissue, the biasing may facilitate splaying of the guide over the tissue (e.g., as described hereinbelow). Alternatively or additionally, after the guide has been withdrawn proximally from a given eyelet, when the guide is subsequently moved distally again, the biasing may inhibit (e.g., prevent) re-threading of the guide into the given eyelet.

Figure 13B:
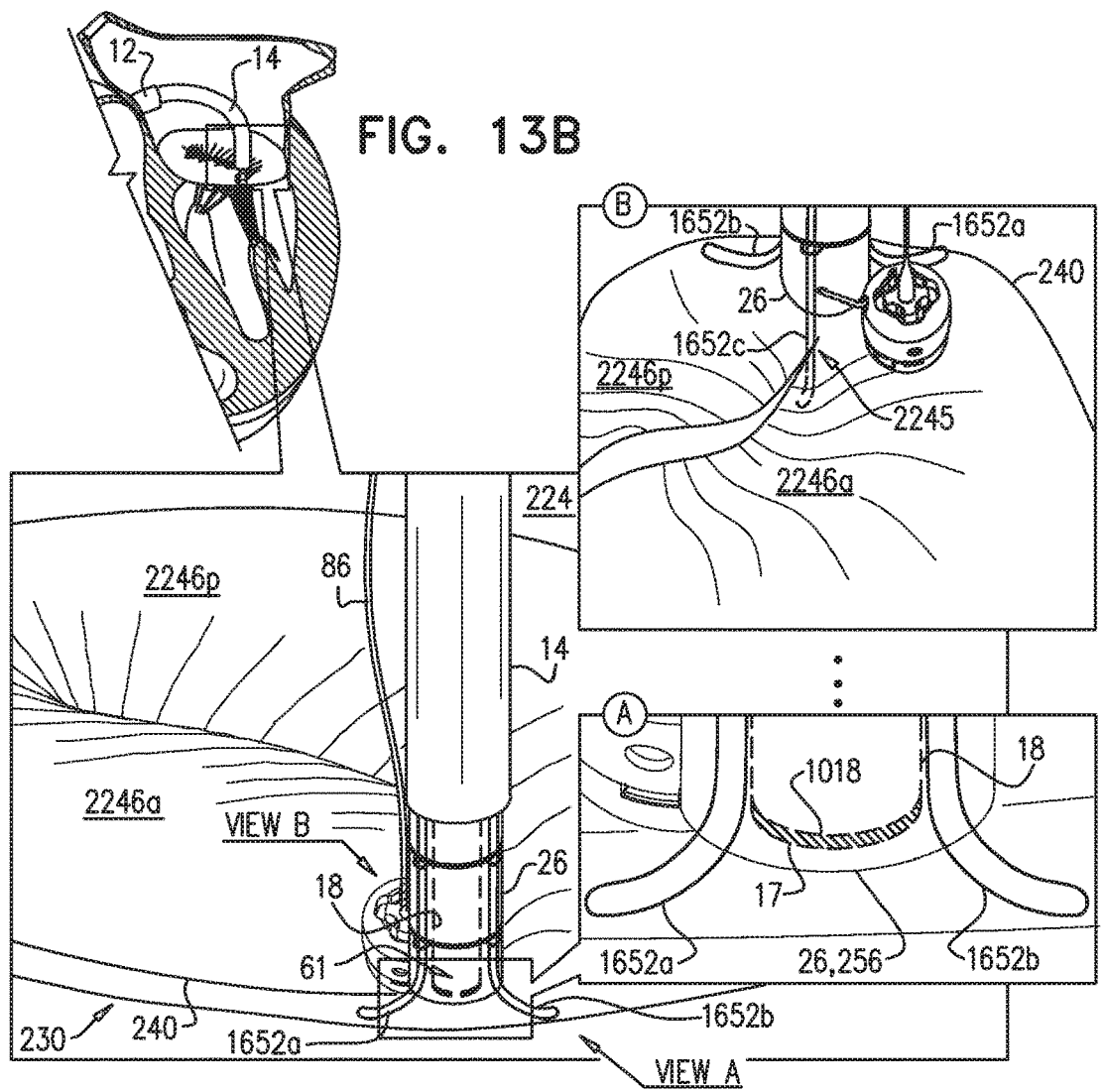

Sleeve 26 is configured to be advanced distally out of catheter 14 and anchored to annulus 240 using anchors 32 as described elsewhere herein (e.g., with reference to FIGS. 10A-I and/or 26A-28), mutatis mutandis. Distal end 251 of sleeve 26 is placed against tissue of the valve (e.g., annulus 240), in advance of the distal end being anchored to the annulus (FIG. 13B). It is to be noted that, as described elsewhere herein, channel 18 is disposed within sleeve 26, and distal end 17 of the channel sandwiches the distal end of the sleeve against the tissue. It is to be further noted that guides 1652 are disposed at respective circumferential positions around channel 18 (e.g., the longitudinal axis thereof).

Guides 1652 are placed (e.g., pushed) against tissue of the valve, e.g., by virtue of being already disposed distally to distal end 251 of sleeve 26, or by being advanced distally after the distal end of the sleeve has itself been placed against tissue of the valve. Each guide 1652 (e.g., looped portion 1658 thereof) thereby comprises a tissue-engaging portion that is configured to be placed in contact with tissue of the subject.

In one or more ways, the behavior of guides 1652 in response to being placed against the tissue of the valve facilitates guidance of sleeve 26, and channel 18 therewithin (e.g., positioning of the sleeve and channel on the annulus). For example:

Resistance of a guide to being pushed further distally may indicate that the guide is in contact with tissue that resists forces applied by the guide. For example, the distal end of the guide may be abutting annulus 240 and/or a wall of atrium 224. Conversely, lack of resistance of a guide to being pushed further distally may indicate that the distal end of the guide is not in contact with tissue that resists forces applied by the guide. For example, the distal end of the guide may be moving between leaflets 2246a and 2246p of the valve (e.g., at a commissure 2245), and/or may be pushing a leaflet 2246 downward (e.g., into the ventricle). Such resistance (or lack thereof) may be detected mechanically (e.g., as tactile feedback to the operating physician and/or by an extracorporeal control unit).

Similarly, the position, orientation and/or shape of a guide (e.g., with respect to one or more other guides, sleeve 26, channel 18, catheter 14, tissue of the valve, etc.) may indicate against what, if anything, the guide is disposed. Imaging techniques such as fluoroscopy may be used to identify this position, orientation and/or shape of the guide. For example, if the distal end of a guide is positioned at the same height (i.e., at the same place on a superior-inferior axis of the subject) as the distal end of channel 18, this may indicate that the channel (and thereby sleeve 26) and the guide abut the same surface (e.g., annulus 240). Conversely, if the distal end of the guide is positioned lower than the distal end of channel 18, this may indicate that the channel (and thereby sleeve 26) is disposed against annulus, while the guide has passed toward or into the ventricle. Movement (e.g., beating) of the guide may indicate that the guide is disposed against a leaflet of the valve, and that the leaflet is moving the guide as the heart beats. Such imaging may be facilitated by one or more components comprising radiopaque markings. For example, distal end 17 of channel 18 may comprise radiopaque marker 1018, e.g., as described with reference to FIGS. 12A-C. For some applications, each guide 1652 has different radiopaque markings, so as to facilitate identification during imaging.

One or more of the guides 1652 may inhibit movement of the distal end of channel 18 (and thereby sleeve 26). For example, if a guide extends between leaflets at a commissure 2245, the guide may inhibit movement of the distal end of channel 18 away from the commissure (e.g., as described in a different context with reference to FIGS. 14A-B, mutatis mutandis).

Guides 1652 may be configured and/or selected, either collectively or individually, such that the guides behave in a particular manner upon interaction with tissue. For example, the guides may be configured and/or selected to be (1) sufficiently rigid so as to provide tactile feedback upon abutting tissue, and/or (2) sufficiently flexible so as to splay over tissue, not to damage tissue, and/or to be movable by beating leaflets.

FIG. 13B shows distal end 251 of sleeve 26 having been placed against annulus 240 of the subject in a vicinity of left fibrous trigone 242. Guides 1652a and 1652b have been pushed distally, and have splayed across annulus 240, e.g., due to resistance of the annulus (see view A of FIG. 13B). As described hereinabove, this may be detected mechanically and/or by imaging. Guide 1652c, which has also been pushed distally, extends between leaflets 2246 at commissure 2245 (see view B of FIG. 13B). As described hereinabove, this may be detected mechanically and/or using imaging. The position, orientation and/or shape of each guide, alone and/or in combination with the other guides and/or elements indicates that the distal end 251 of sleeve 26 is positioned against firm tissue that is close to commissure 2245, which for some applications is the preferred position for anchoring of the distal end of the sleeve. Identification (e.g., mechanically and/or by imaging) of which guide is in which position may further indicate the rotational orientation of sleeve 26.

Figure 13C:
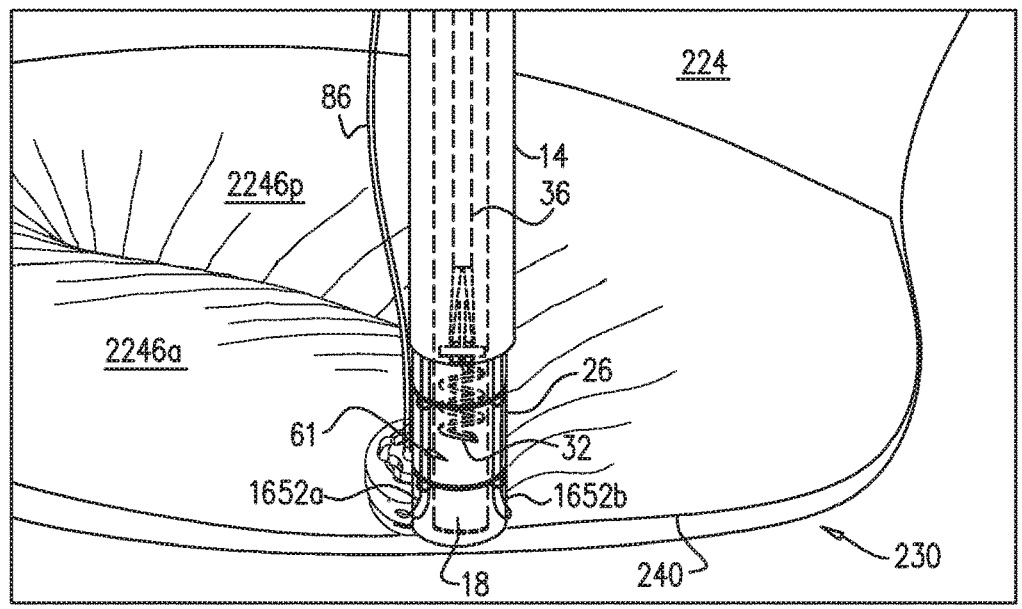
Figure 13D:
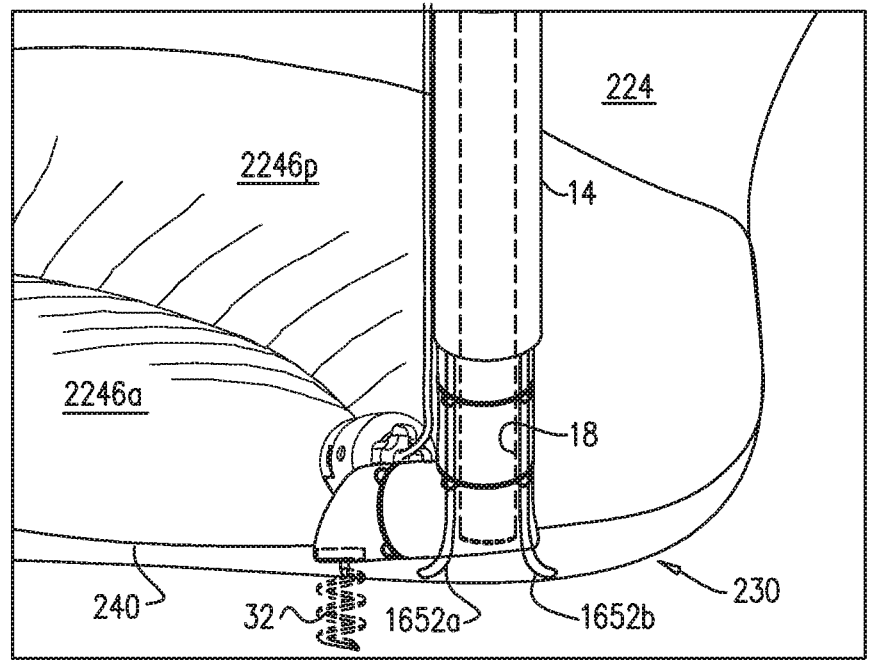
Figure 13E:
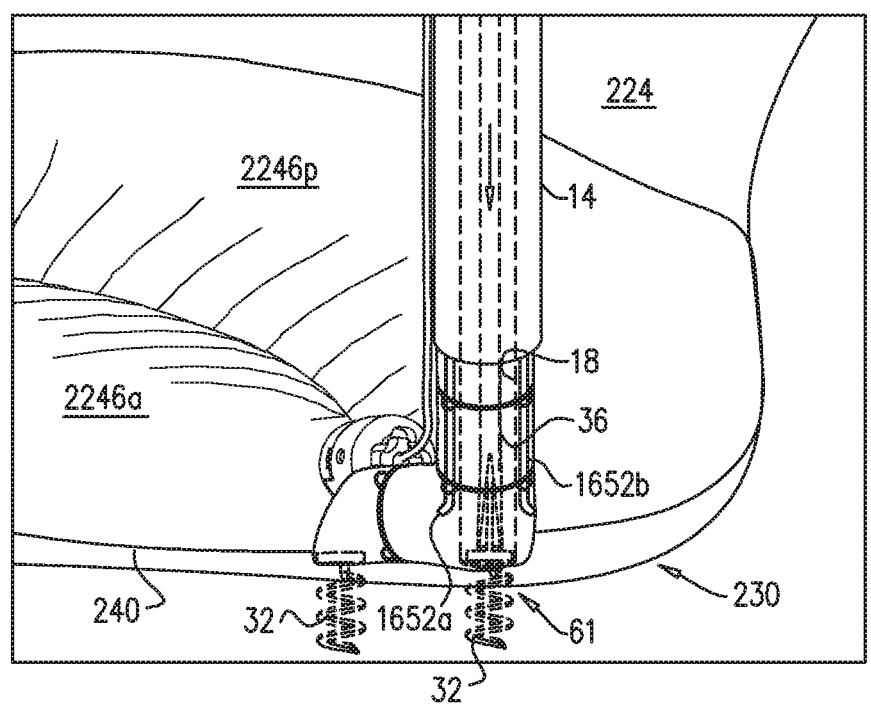

As shown in FIG. 13C, once the desired position has been identified, an anchor 32 (e.g., a first anchor) is delivered via channel 18, and is used to anchor distal end 251 of sleeve 26, as described elsewhere herein (e.g., with reference to FIGS. 10A-I and/or 26A-28, mutatis mutandis). For some applications, and as shown in FIG. 13C, one or more of guides 1652 may be withdrawn slightly proximally before anchoring, e.g., so as to reduce a likelihood of inadvertently anchoring the guide to the tissue. Subsequently, sleeve 26 is advanced further distally out of catheter 14, channel 18 is withdrawn proximally out of the sleeve, and another portion of the sleeve is sandwiched between channel 18 and tissue of the valve (FIG. 13D). Guides 1652 are typically moved proximally with respect to sleeve 26 (e.g., the guides may be kept still with respect to other elements while sleeve 26 is advanced distally with respect to channel 18 and the guides). Subsequently, guides 1652 are again used to facilitate positioning of channel 18, and thereby the portion of the sleeve that is sandwiched against the tissue. This process is repeated for each anchor, typically until sleeve 26 is fully implanted.

As described hereinabove, guides 1652 may inhibit movement of at least the distal end of channel 18, and thereby movement of at least the distal end of anchor driver 36 (e.g., a guide that extends between leaflets at a commissure may inhibit movement of the distal end of the channel away from the commissure). As described in more detail hereinbelow (e.g., with reference to FIG. 26D, mutatis mutandis), following deployment of at least one anchor, sleeve 26 inhibits movement of the distal end of anchor driver 36 by providing a maximum distance that the distal end of the driver may be disposed from the previously-deployed anchor. It is to be noted, therefore, that:

(1) a guide 1652 comprises a first constraining member configured to inhibit movement of the distal end of anchor driver 36 on a first axis (e.g., an axis between (i) the distal end of the anchor driver, and (ii) the guide and/or the site at which the guide engages tissue); and (2) sleeve 26 comprises a second constraining member configured to inhibit movement of the distal end of the anchor driver on a second axis (e.g., an axis between (i) the distal end of the anchor driver, and (ii) a previously-deployed anchor).

Figure 14A:
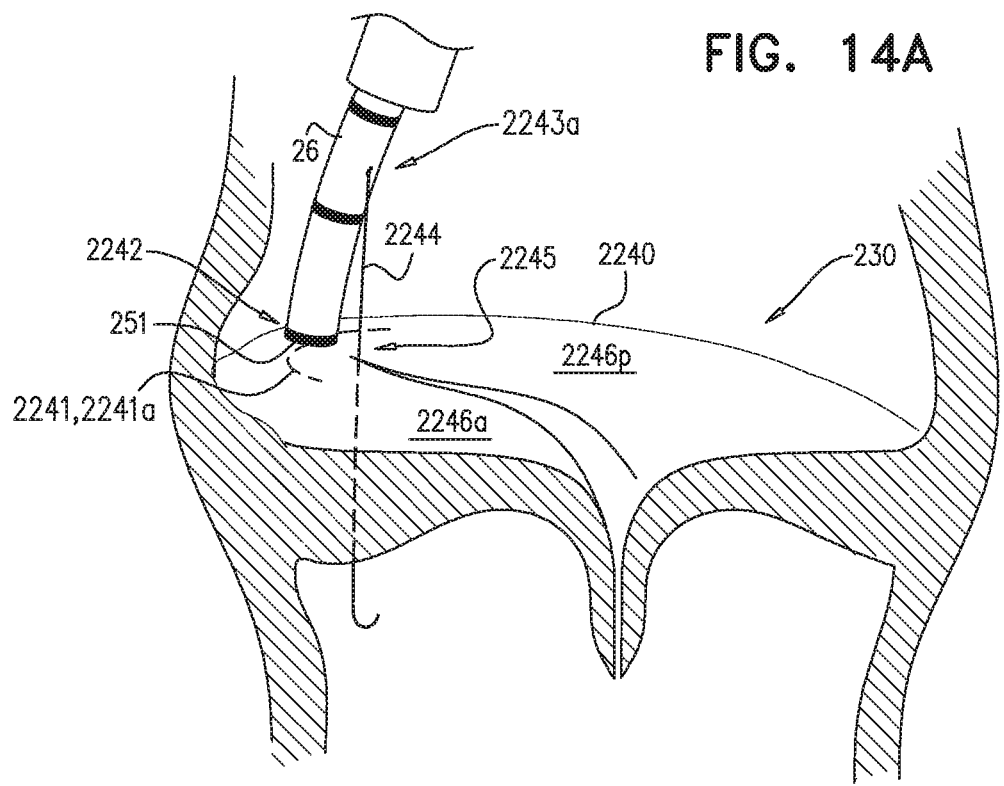
FIGS. 14A-B are schematic illustrations of techniques for positioning a distal end of a sleeve of an annuloplasty structure, at an annulus of a mitral valve, in accordance with some applications of the invention.
Figure 14B:
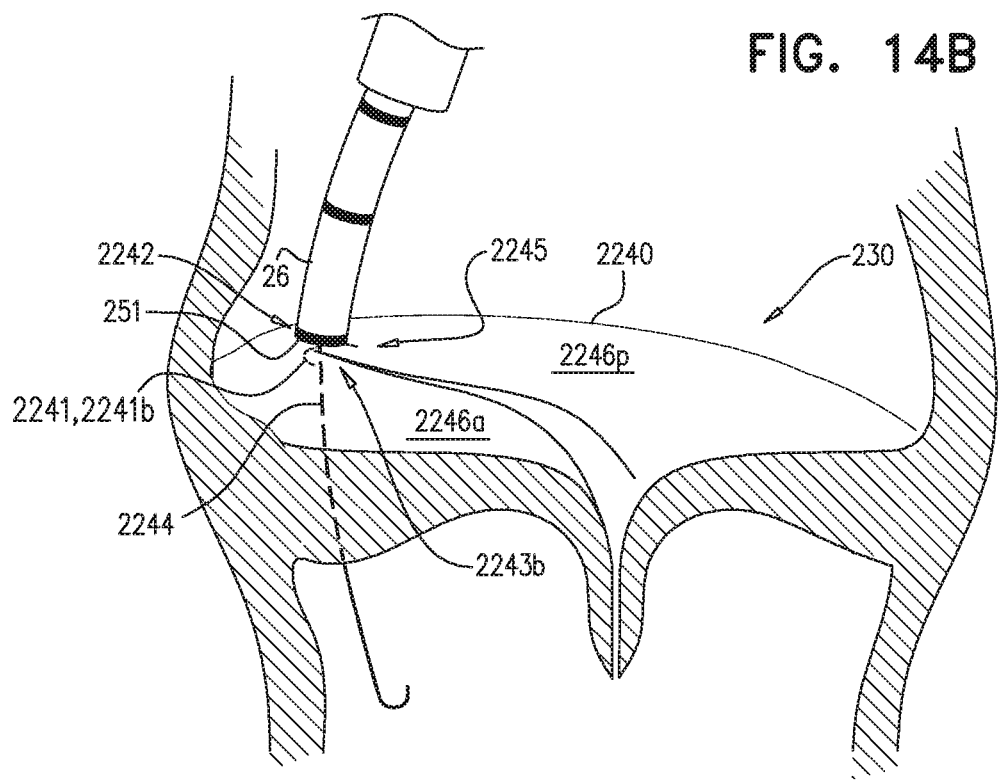

Reference is made to FIGS. 14A-B, which are schematic illustrations of a technique for positioning distal end 251 of sleeve 26 of an annuloplasty structure, at an annulus of mitral valve 230, in accordance with some applications of the invention. For clarity, adjusting mechanism 40 is not shown in FIGS. 14A-B. As described with reference to FIG. 10G, distal end 251 is typically positioned in a vicinity of a fibrous trigone 2242 of annulus 2240 of the mitral valve. To facilitate this positioning, a guidewire 2244 extends out from sleeve 26, and is disposed between leaflets 2246 (e.g., posterior leaflet 2246p and anterior leaflet 2246a), typically at commissure 2245 of the valve. Guidewire 2244 is at least partly stiff, and provides resistance, which facilitates positioning of end 251. For example, guidewire 2244 may bias end 251 to be disposed at a site in an arc (e.g., a circular arc) 2241 around commissure 2245, the arc including fibrous trigone 2242 and/or a site in a vicinity of the fibrous trigone. Guidewire 2244 may also provide tactile feedback to the operating physician. A first anchor is deployed into the cardiac tissue, thereby anchoring end 251 of sleeve 26, e.g., as described hereinabove. Typically, guidewire 2244 is retracted into sleeve 26 (and further typically removed from the sleeve entirely), before subsequent anchors are deployed.

FIG. 14A shows an embodiment in which guidewire 2244 (e.g., at least a distal portion thereof) extends distally from a point 2243a (e.g., a hole) in a lateral surface (e.g., a lateral wall) of sleeve 26, and FIG. 14B shows an embodiment in which guidewire 2244 extends from a point 2243b (e.g., a hole) in a distal end 251 of the sleeve. The radius of arc 2241 may be adjusted by selecting the stiffness of guidewire 2244, and/or the "exit position" in which the guidewire extends from sleeve 26. For example, the radius of arc 2241 may be increased by selecting (1) a more flexible guidewire 2244, and/or (2) an "exit position" position that is further proximally along sleeve 26. It is to be noted that arc 2141a (FIG. 14A) has a larger radius than does arc 2141b (FIG. 14B).

In addition to mechanical effects such as biasing of the position of sleeve 26 and providing tactile feedback, guidewire 2244 may also facilitate positioning of sleeve 26 by facilitating imaging. For example, the presence of guidewire 2244 in and/or the shape thereof (e.g., bending due to being pressed into the commissure) may be visible in fluoroscopic imaging, and may be used to facilitate identification of the position and angle of sleeve 26 with respect to tissues.

For some applications, instead of extending from sleeve 26, a similar functionality may be obtained by guidewire 2244 extending from catheter 14, or from reference-force tube 19, such as from a secondary lumen thereof.

Guidewire 2244 extends proximally from sleeve 26, typically to outside of the body of the subject (e.g., as shown in FIGS. 1 and 2). Guidewire 2244 is typically removed by pulling subsequent to the deployment of one or more tissue anchors, e.g., subsequent to the deployment of the first tissue anchor, and before the deployment of subsequent tissue anchors. Typically, guidewire 2244 exits a point 2245 in the lateral wall of sleeve 26 close to point 2243a or 2243b (FIG. 1 shows points 2243a and 2245), and extends proximally along the outside of sleeve 26. For some applications, guidewire 2244 extends out of the body of the subject by passing between reference-force tub 19 and catheter 14, as shown in FIGS. 1 and 2. Alternatively, a secondary lumen is provided in the wall of reference-force tube 19 or catheter 14, via which guidewire 2244 extends out of the body of the subject.

The guides described hereinabove with reference to FIGS. 12A-14B are described, for some applications, as inhibiting movement of at least the distal end of channel 18, and thereby movement of at least the distal end of anchor driver 36. It is to be noted that inhibition of this movement means resisting this movement to some degree, and does not necessarily mean prevention of such movement.

Reference is now made to FIGS. 15A-D, which are schematic illustrations of an indicator and locking system 1700 comprising (1) a protrusion 1724 coupled to guide-catheter handle 24, and (2) a housing 1702, or cradle, shaped to define a groove 1704 configured to receive protrusion 1724, in accordance with some applications of the present invention. System 1700 is configured to provide an indication, at a proximal location outside the body of the patient, of the state of coupling of first and second couplings 152 and 154 of outer catheter 12 and guide catheter 14, respectively (i.e., when engager 54 is received within slit 52 at the distal end portions of catheters 14 and 12, respectively). Additionally, system 1700 is configured to rotationally lock catheter 12 to catheter 14, and to longitudinally lock at least proximal portions of catheters 12 and 14, as described hereinbelow.

Housing 1702 comprises a handle portion that is coupled to a proximal end of catheter 12. As shown, groove 1704 is shaped so as to define a curved groove along a lateral portion of housing 1702. Groove 1704 extends between 45 and 135 rotational degrees, e.g., 90 degrees, as shown.

As described hereinabove with reference to FIGS. 1-2, proximal handle portion 101 is supported by a stand having support legs 91 (i.e., first leg 91a and second leg 91b, as shown in FIGS. 15A-D). As shown in FIGS. 15A-D, first leg 91a (which is configured to receive guide-catheter handle 24) provides housing 1702. As described hereinabove, guide catheter 14 is first advanced within the lumen of outer catheter 12 when the physician places the distal end of catheter 14 within the lumen of catheter 12 (via outer-catheter handle 22) and advances handle 24 (coupled to the proximal end of catheter 14) toward handle 22, as indicated by the arrow in FIG. 15A. As described hereinabove with reference to FIGS. 3A-B, since the lumen of catheter 12 is free from any protrusions or recessed portions, and since engager 54 is depressible by tab 56, catheter 14 is configured to enter the lumen of catheter 12 in any rotational configuration thereof. As handle 24 is advanced toward handle 22, protrusion 1724 of handle 24 advances toward groove 1704. Groove 1704 is shaped to provide a protrusion-access location 1706 and a protrusion-locking location 1708, which locations are typically but not necessarily spaced 90 degrees apart. Protrusion-locking location 1708 is shaped to provide a depressible locking element 1710 which comprises a depressible pin to lock protrusion 1724 in place, as is described hereinbelow.

Figure 15B:
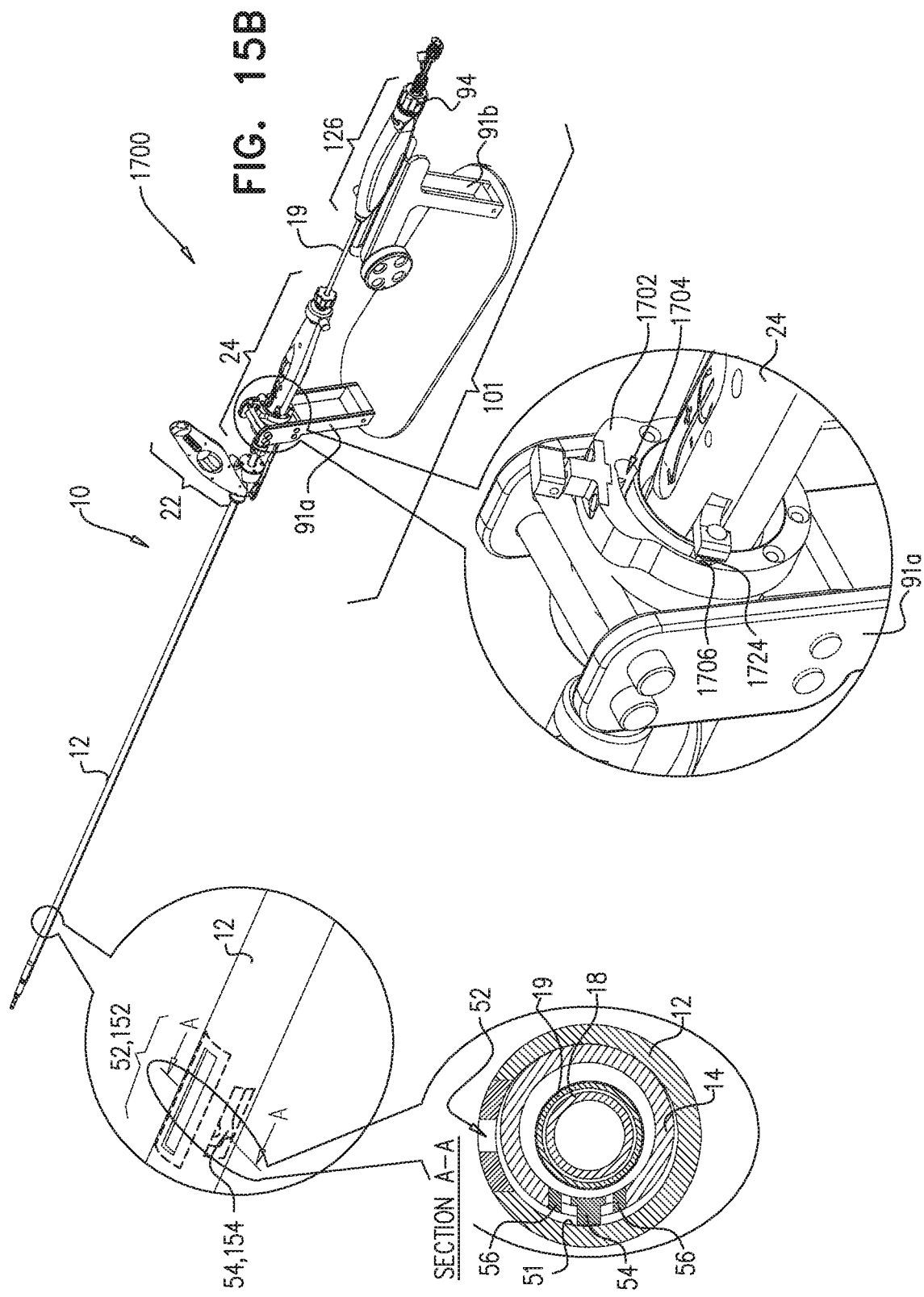

As shown in FIG. 15B, when handle 24 has been pushed distally toward handle 22, protrusion 1724 advances toward groove 1704 in order to engage protrusion-access location 1706 thereof. Depending on the rotational orientation of handle 24 with respect to handle 22, the physician may need to rotate handle 24 to bring protrusion 1724 in alignment with protrusion-access location 1706 of groove 1704. Once protrusion 1724 is in alignment with protrusion-access location 1706, handle 24 is further pushed distally in order to engage protrusion 1724 with protrusion-access location 1706 of groove 1704. Once protrusion 1724 is located within protrusion-access location 1706 of groove 1704, engager 54 is disposed in proximity with (e.g., in a distal location in the vicinity of) slit 52. As shown in the enlarged image at the distal end portion of system 10 and in section A-A, when protrusion 1724 is located within protrusion-access location 1706 of groove 1704, engager 54 of catheter 14 is rotationally offset with respect to slit 52 of catheter 12 by 90 degrees, by way of illustration and not limitation (i.e., the degrees between protrusion-access location 1706 and protrusion-locking location 1708).

FIG. 15C shows rotation of catheter 14 with respect to catheter 12, in response to rotation of handle 24 in the direction indicated by the arrow. As handle 24 is rotated, protrusion 1724 slides within groove 1704 toward protrusion-locking location 1708, as shown in the enlarged image of a portion of handle 24. As shown in the enlarged section of the distal end portion of system 10 and in section A-A, as protrusion 1724 is being advanced toward protrusion-locking location 1708, engager 54 is closer to slit 52 and is rotationally offset with respect to slit 52 by fewer degrees than when protrusion 1724 is located at protrusion-access location 1706.

FIG. 15D shows system 1700 following the rotation of handle 24 to position protrusion 1724 within protrusion-locking location 1708, in order to rotationally lock catheter 12 to catheter 14 in addition to the rotational locking of catheters 12 and 14 provided by insertion of engager 54 within slit 52, as shown the enlarged section of the distal end portion of system 10 and in section A-A. As protrusion 1724 advances toward location 1708, protrusion 1724 pushes locking element 1710. For some applications, locking element 1710 is spring-loaded, and is configured to return to a resting state (as shown in FIG. 15D) in the absence of force applied thereto. Thus, once protrusion 1724 has advanced beyond locking element 1710 into protrusion-locking location 1708, element 1710 returns to its resting state to prevent protrusion from returning toward protrusion-access location 1706. That is, locking element 1710 is only depressible when protrusion 1724 is advanced from protrusion-access location 1706 toward protrusion-locking location 1708. In such a manner, groove 1704, protrusion 1724, and locking element 1710 of system 1700 (1) rotationally lock catheters 12 and 14, and (2) longitudinally lock (i.e., inhibit relative longitudinal movement of) at least proximal portions of catheters 12 and 14. System 1700 also prevents accidental movement of handle 24 with respect to handle 22.

Typically, when protrusion 1724 couples to housing 1702 (e.g., when protrusion 1724 locks into protrusion-locking location 1708), coupling 154 simultaneously couples to coupling 152.

Reference is again made to FIGS. 1, 3A-E, and 15A-D. For some applications, two pairs of couplings are thereby provided: (pair 1) couplings 152 and 154 at a distal portion of catheters 12 and 14, respectively, and (pair 2) housing 1702 and protrusion 1724 at a proximal portion of the catheters. Pair 1 thereby define a distal locking mechanism, and pair 2 thereby define a proximal locking mechanism. It should be noted that, whereas couplings 152 and 154 typically facilitate some longitudinal sliding of the distal end of catheter 14 with respect to the distal end of catheter 12 (as described hereinabove), housing 1702 and protrusion 1724 typically inhibit (e.g., prevent) longitudinal movement of the proximal end of catheter 14 with respect to the proximal end of catheter 12.

Reference is now made to FIGS. 16A-B, which are schematic illustrations of one or more sleeve-coupling elements 2220 which couple sleeve 26 to reference-force tube 19, in accordance with an embodiment of the present invention. As shown, a distal end of tube 19 is coupled to a ring 2219, e.g., a metal ring, which is shaped so as to define one or more male coupling elements 2220. Each element 2220 is shaped so as to define a distal projection 2221. A proximal end of sleeve 226 is coupled to a ring 2226, e.g., a metal ring, shaped so as to define one or more openings 2228 configured to receive a respective one of the one or more projections 2221, as shown in FIG. 16A. For some applications, the proximal end of sleeve 26 is not coupled to ring 2226, but rather projections 2221 puncture through the fabric of sleeve 26.

For some applications, coupling elements 2220 are configured to have a natural tendency (e.g., to be biased) to flex inwards toward a central longitudinal axis 7 of tube 19. When channel 18 is positioned within the lumen of sleeve 26, and through rings 2219 and 2226, channel 18 pushes coupling elements 2220 outwards and away from axis 7, thereby causing coupling elements 2220 to engage sleeve 26 via openings 2228. For example, coupling elements 2220 may be curved to define outwardly-directed ends (i.e., projections 2221) that fit within openings 2228 or push against or pierce sleeve 26. Such fitting within openings 2228 or pushing against or piercing, engages sleeve 26, which, as mentioned above, may comprise braided or woven fabric. Upon removal of channel 18 from within sleeve 26 and beyond ring 2226, coupling elements 2220 are allowed to assume their natural inwardly-flexed position, thereby releasing sleeve 26 from coupling elements 2220 (i.e., when elements 2220 move away from openings 2228), and decoupling the sleeve from reference-force tube 19 and implant-decoupling channel 18. Reference-force tube 19 may then be withdrawn proximally from sleeve 26.

For some applications, a stiffening element 1926 is threaded through sleeve 26, so as to provide controllably-variable stiffness to sleeve 26. For example, one or more generally stiff stiffening elements 1926, e.g., a wire or a suture, is woven one or more times (e.g., a plurality of times) through sleeve 26 to provide the stiffness, and subsequently be removed at the conclusion of the implantation procedure when the stiffness is no longer useful.

Since channel 18 holding manipulator 61 and components that are slidable therein are deflectable and steerable, stiffening element 1926 helps maintain the relative positioning of channel 18 and manipulator 61 with respect to sleeve 26 in order to prevent manipulator 61 from deploying an anchor through sleeve 26 in a vicinity of contracting member 226. That is, stiffening element 1926 helps maintain the shape and integrity of structure 26 (e.g., prevents flailing and/or kinking of sleeve 26). Stiffening element 1926 helps ensure that the anchors are deployed through sleeve 26 without interfering with contracting member 226. For some applications, stiffening element 1926 additionally or alternatively facilitates positioning of portions of sleeve 26 and/or anchors 32, such as positioning of subsequent portions and/or anchors following positioning of previous portions and/or anchors (e.g., as described with reference to FIGS. 26D-E).

Figure 19:
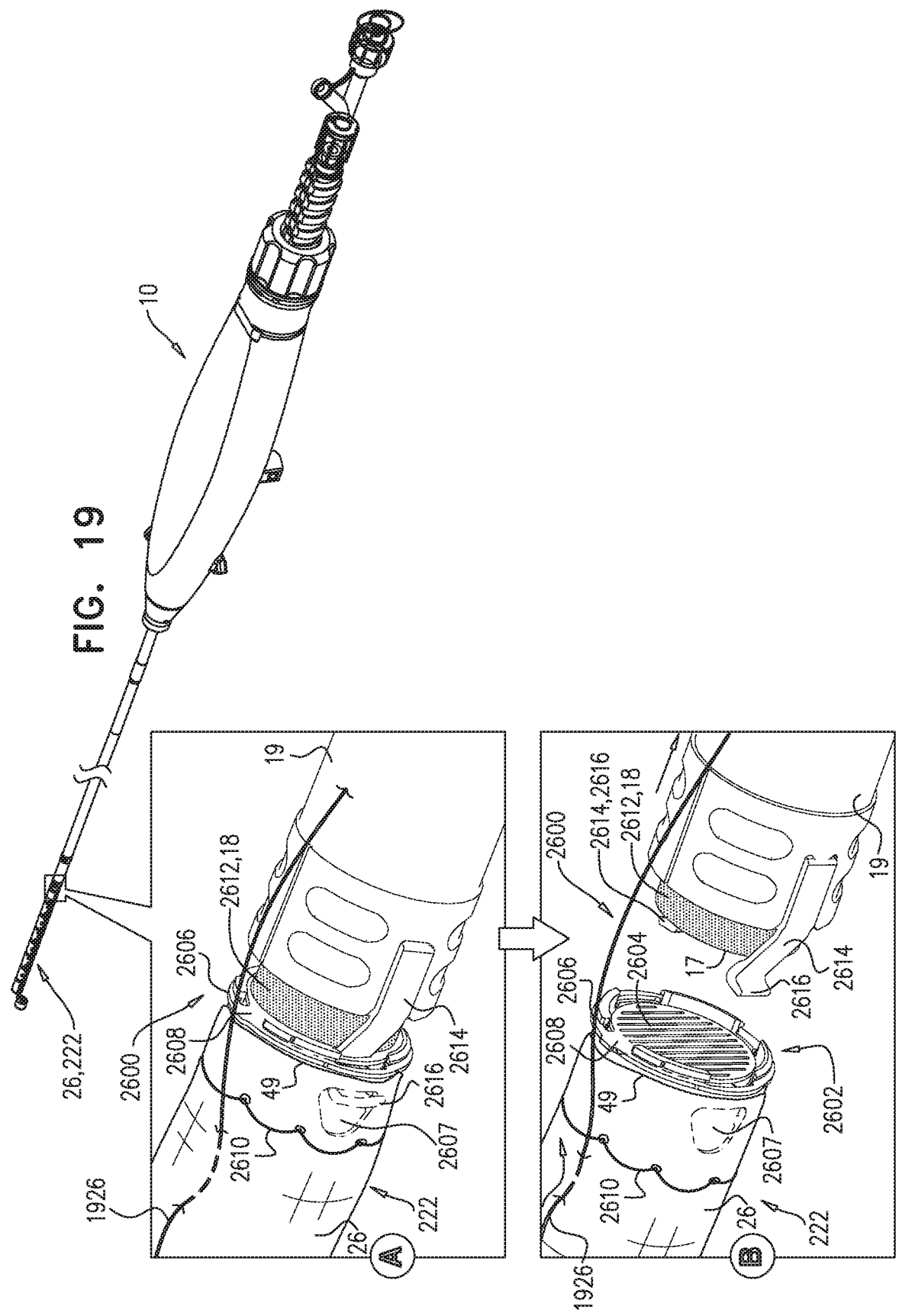

For some applications, element 1926 is removed from sleeve 26 by being pulled by an operating physician, e.g., using a tool. For other applications, element 1926 is coupled to another portion of system 10, such as a portion of channel 18, manipulator 61, or a component that is slidable within a lumen of manipulator 61, and is removed by being pulled either by the channel or the manipulator or any component thereof. For some applications, stiffening element 1926 (e.g., a proximal end thereof) is coupled to reference-force tube 19, and is pulled out of sleeve 26 (e.g., unthreaded from the sleeve) following release of the sleeve, as tube 19 is withdrawn proximally (e.g., as shown in FIGS. 16A-B and 19).

For some applications, stiffening element 1926 may comprise more than one component, at least one of the components being removed from sleeve 26, and at least one of the components remaining within the sleeve. For some applications, such stiffening elements may facilitate loading of the stiffening element into sleeve 26, removal of the stiffening element (or an element thereof) from the sleeve. For example, stiffening element 1926 may comprise a relatively flexible tube, and a relatively stiff rod within the tube, the rod being pulled out of the tube in order to reduce the stiffness of the stiffening element and the sleeve. For some applications, stiffening element 1926 may comprise a plurality of relatively stiff tubes, arranged in series, and a longitudinal member (e.g., a wire or a suture) disposed through the tubes, and fixedly coupled to at least one of the tubes (e.g., a tube at the end of the series). When the longitudinal member is under tension, the tubes are held together (e.g., resembling one long tube), and the stiffening element is generally stiff along its overall length. When the longitudinal member is released and/or removed, the tubes may separate, and although each tube remains relatively stiff, the stiffening element becomes less stiff along its overall length. For some applications, such a stiffening element resembles a trick collapsing "magic wand".

For some applications, the controllably-variable stiffness of sleeve 26 is provided by stiffening element 1926 becoming less stiff (e.g., without mechanically removing the stiffening element). For example, the stiffening element may be configured to become less stiff and/or to dissolve at least in part over time and/or in response to being disposed within the body of the subject (e.g., due to temperature or body fluids). Alternatively or additionally, the stiffening element may comprise a shape-memory or shape-change material having a transition temperature, the stiffening element being delivered in a configuration (e.g., a shape) that is relatively stiff, and transitioning (e.g., in response to provided electromagnetic, electrical, and/or heat energy) to a configuration (e.g., a shape) that is relative flexible.

Figure 17:
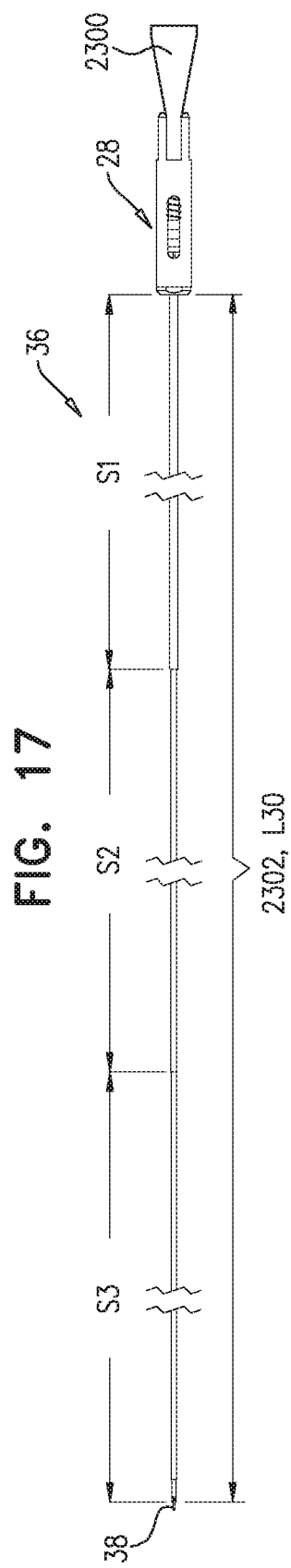
FIG. 17 is a schematic illustration of an anchor driver, in accordance with some applications of the present invention.

Reference is now made to FIG. 17, which is a schematic illustration of anchor driver 36, as described hereinabove, coupled to a torque-limiting apparatus 2300, in accordance with some applications of the present invention. For some applications, torque-limiting apparatus 2300 is coupled to (or discrete from and couplable to) a proximal end of anchor driver 36 in order to provide an indication of the torque delivered to and/or amount of rotations of any of the tissue anchors described herein such that the anchor is not deployed too deep within tissue. In such a manner, torque-limiting apparatus 2300 prevents damage of the tissue and/or of the sleeve of the annuloplasty structure. For some applications, torque-limiting apparatus 2300, as is known for conventional screwdrivers, to prevent over-application of torque. Alternatively or additionally, for some applications, anchor deployment system 10 comprises a sensor (e.g., a torque transducer), for measuring the resistance to rotation of any of the tissue anchors described herein. When the measured resistance exceeds a threshold value, the system generates a signal alerting the surgeon, and/or discontinues rotation of anchor driver 36. For example, the measured resistance may increase as the coupling head of the anchor (e.g., coupling head 2310 of anchor 2332, described with reference to FIGS. 18A-C) contacts, and tightens against, the material (e.g., fabric) of the sleeve of the annuloplasty ring structure.

As shown, anchor driver 36 has a shaft 2302 having a length L30 of between 150 and 170 cm, e.g., 168 cm. Driver 36 is divided into three sections, as shown by way of illustration and not limitation. A distal-most section S3 of driver 36 has an outer diameter of between 0.2 and 0.25 cm, e.g., 0.211 cm; an intermediate section S2 has an outer diameter of between 0.14 and 0.15 cm, e.g., 0.149 cm; a proximal-most section S1 has an outer diameter of between 0.12 and 0.14 cm, e.g., 0.137 cm.

For some applications, torque-limiting apparatus 2300 has a torque range of between 0.2 and 20 Ncm, e.g., 0.5-5 Ncm, such as 0.7-1.2 Ncm, e.g., 0.8 Ncm. For some applications, a ratio between an anchor driver working length (cm) to torque (Ncm) is typically, but not necessarily 168/0.8, or 210. For some applications, a ratio between an outer diameter of anchor driver 36 (cm) to torque (Ncm) is typically, but not necessarily (0.137–0.149)/0.8, or 0.1713-0.1863. For some applications, torque-limiting apparatus 2300 has, or is configurable to have, one or more torque ratios described hereinbelow with respect to FIGS. 18A-C.

Figure 18A:
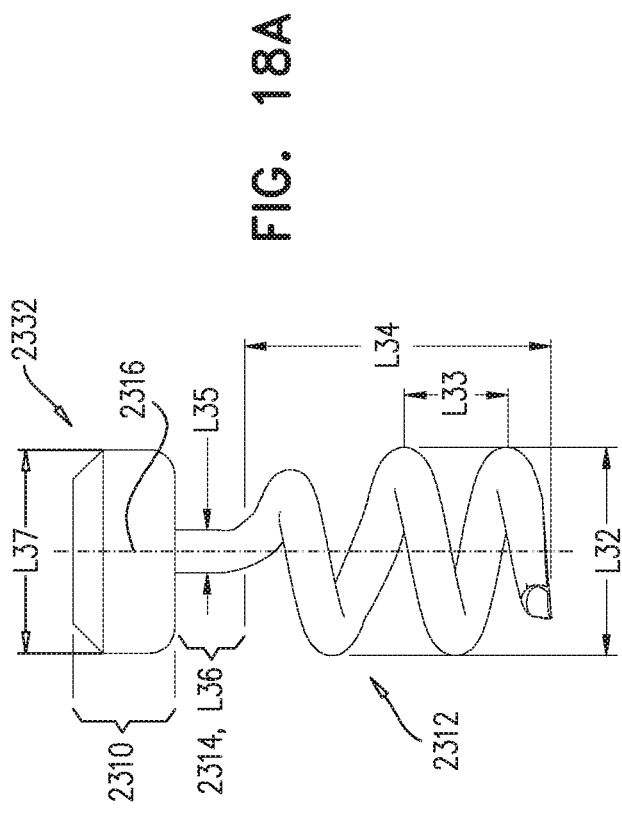
FIGS. 18A-C are schematic illustrations of a tissue anchor and techniques for use therewith, in accordance with some applications of the present invention.
Figure 18B:
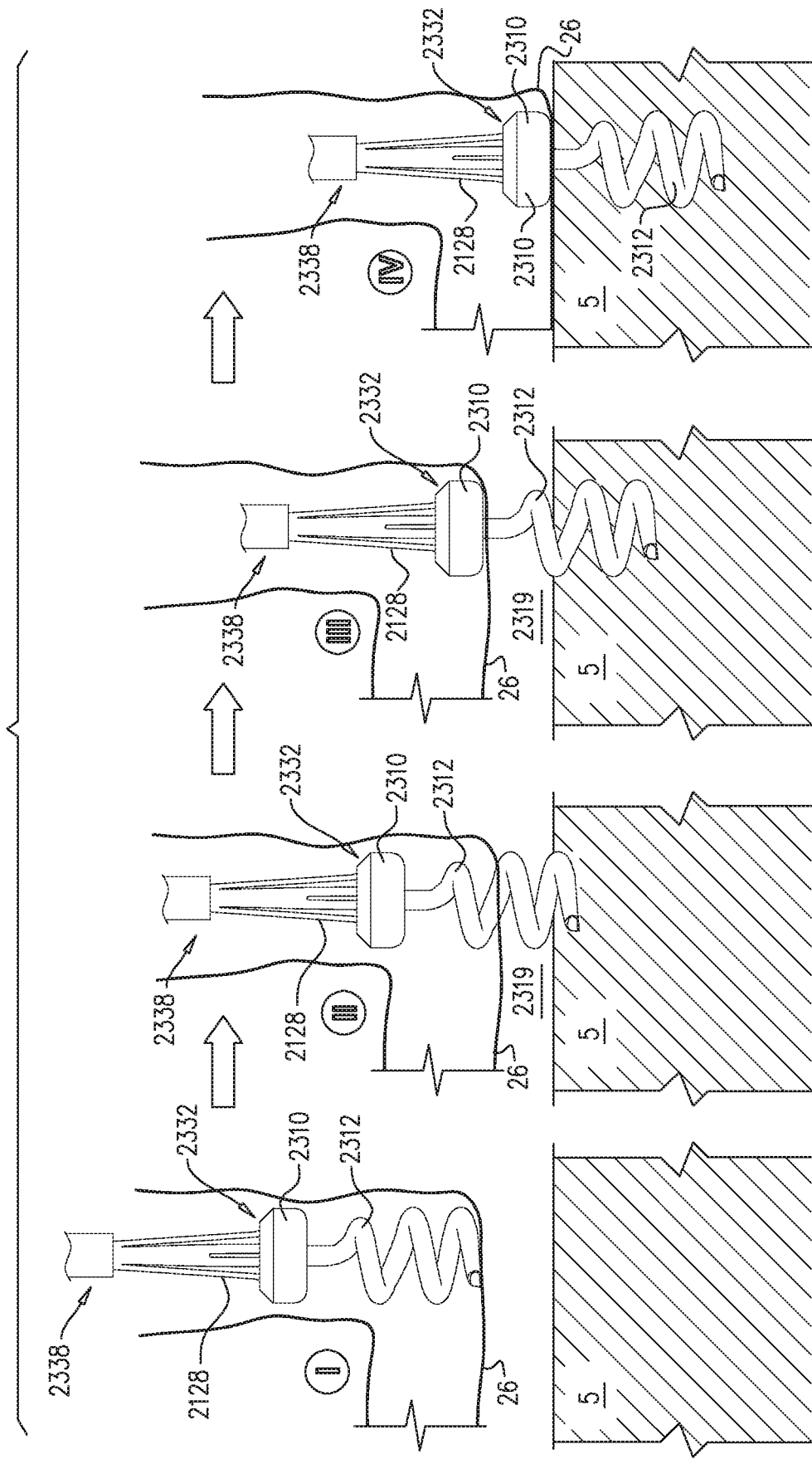
Figure 18C:
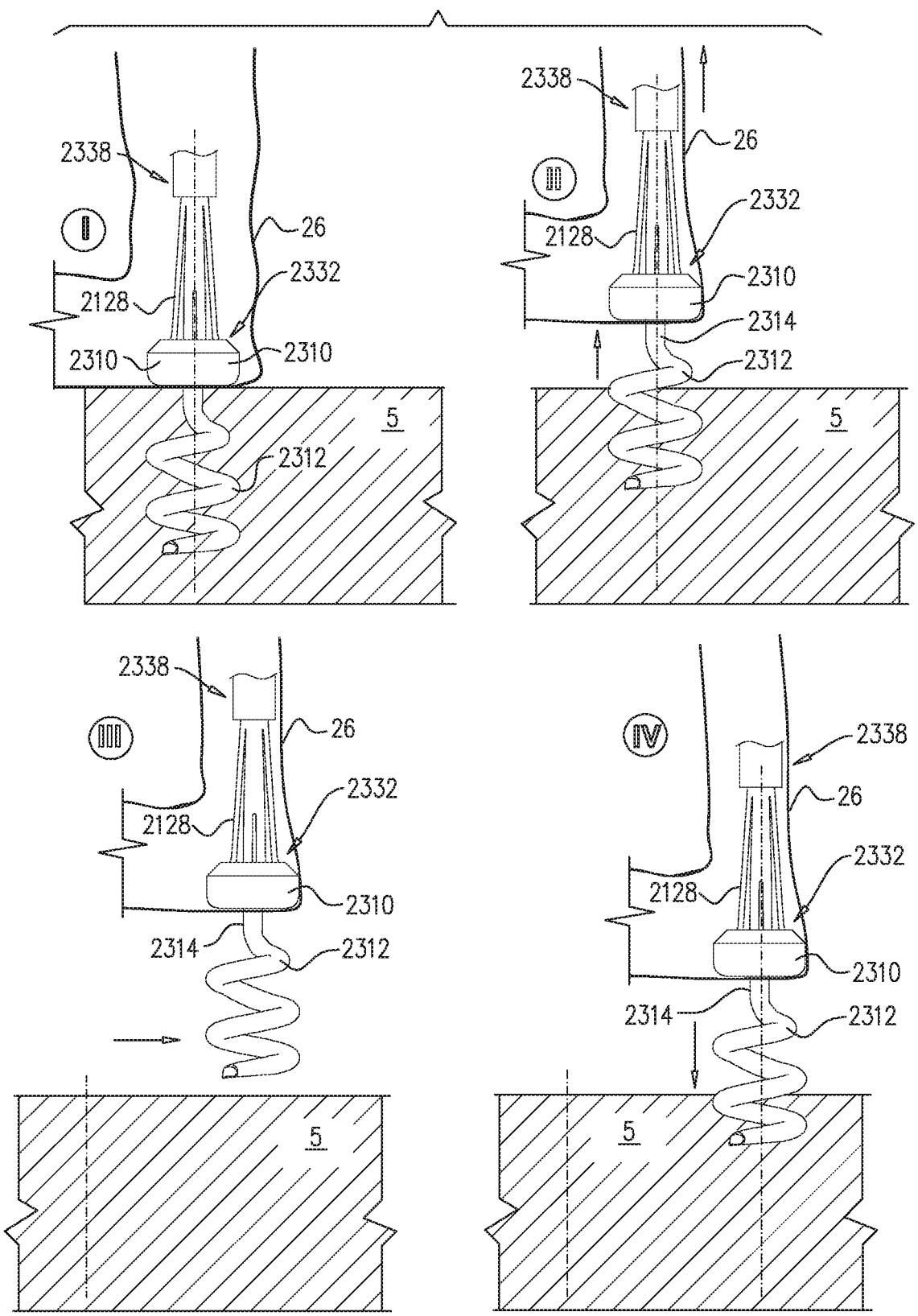

Reference is made to FIGS. 18A-C, which are schematic illustrations of a tissue anchor 2332, and techniques for use therewith, configured for anchoring sleeve 26 described hereinabove, in accordance with some applications of the present invention. Anchor 2332 has a coupling head 2310 configured to be coupled to a deployment element 2338, which has a locking mechanism 2128 disposed at a distal end thereof. Typically, deployment element 2338 and locking mechanism 2128 respectively comprise deployment element 38 and locking mechanism 128, described hereinabove. For some applications, coupling head 2310 is alternatively or additionally configured to be coupled to, and/or used with, deployment manipulator 61, deployment element 38, and/or anchor driver 36 described hereinabove. Anchor 2332 provides a tissue-engaging element 2312 (e.g., a helical tissue-engaging element, as shown, or a screw). For some applications of the invention, anchor 32 described hereinabove, comprises anchor 2332 and/or anchors 32 and 2332 are interchangeable.

A proximal portion of tissue-engaging element 2312 comprises a vertical proximal stem portion 2314, which is substantially parallel with a central longitudinal axis 2316 of tissue anchor 2322, the central longitudinal axis being defined by tissue-engaging element 2312. For example, stem portion may be disposed at less than 10 degrees of deflection with respect to axis 2314, such as disposed parallel to axis 2314. Portion 2314 is disposed substantially centrally with respect to tissue anchor 2332 (e.g., with respect to tissue-engaging element 2312). Typically, portion 2314 is disposed on axis 2316, and is coupled to coupling head 2310 on axis 2316. Proximal stem portion 2314 couples tissue-engaging element 2312 to coupling head 2310. Central longitudinal axis 2316 typically comprises and/or is collinear with a central longitudinal axis of tissue-engaging element 2312, and further typically defines an axis around which anchor 2332 (e.g. element 2312 thereof) is configured to rotate when driven into tissue.

Vertical proximal stem portion 2314 typically has a length L36 of 0.2-0.7 mm, and is typically more than 1.3 times as great as (e.g., between 2 and 10 times as great as, such as between 2 and 4 times as great as) a thickness of the fabric of sleeve 26. During anchoring of sleeve 26 by anchor 2332 (e.g., as shown in FIG. 18B), such a configuration of the positioning of portion 2314 at the center of coupling head 2310 facilitates rotation of tissue anchor 2332 with respect to sleeve 26 in a manner that prevents twisting of sleeve 26 during rotation. That is, once tissue-engaging element 2312 has passed far enough through sleeve 26 such that portion 2314 traverses the wall of the sleeve (as shown in stage (iii) of FIG. 18B), portion 2314 rotates freely within the wall of the sleeve.

Such a configuration allows (1) tissue-engaging element 2312 to engage the cardiac tissue while protruding from sleeve 26, such that when the tissue-engaging element engages the tissue, a gap 2319 exists between the sleeve and the tissue (e.g., if the tissue-engaging element protrudes at least one turn through the sleeve, gap 2319 is at least as great as a pitch L33 of the tissue-engaging element); and (2) anchor 2332 to subsequently be driven into the cardiac tissue, such that coupling head 2310 draws sleeve 26 closer to the cardiac tissue (i.e., reduces and/or closes gap 2319), without distorting (e.g., twisting, kinking, buckling, etc.) the sleeve (as shown by the transition from stage (iii) to stage (iv) of FIG. 18B). For some such applications, anchor 2332, tissue-engaging element 2312, and/or portion 2314 act as an integral washer and/or a screw with an integral washer, as is known in the hardware art.

Depending on one or more characteristics of sleeve 26 (e.g., strength and flexibility), for some applications, vertical proximal stem portion 2314 is disposed slightly away from axis 2316, such as within 1 mm of axis 2316, and/or within 3 mm of axis 2316. For such applications, reversible and non-destructive deformation of sleeve 26 may occur as portion 2314 revolves (e.g., "wiggles") around axis 2316.

Coupling head 2310 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Anchor driver 36 of FIG. 17 has a deployment element 38 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided by coupling head 2310 of anchor 2332 of FIGS. 18A-C.

Anchor 2332 (e.g., element 2312 thereof) has an anchor helix diameter L32 of between 0.1 and 0.5 cm, e.g., 0.25 cm. Anchor 2332 has an anchor helix pitch L33 of between 0.05 and 0.3 cm, e.g., 0.12 cm. Anchor 2332 has an anchor helix length L34 of between 0.3 and 0.9 cm, such as 0.3 and 0.65 cm, e.g., 0.55 cm. Anchor 2332 has a helix wire thickness L35 of between 0.02 and 0.1 cm, e.g., 0.05 cm. Typically, coupling head 2310 has a width L37 (e.g., a diameter) that is at least 50 percent as great as helix diameter L32. For example, width L37 may be generally equal to, or greater than, diameter L32. Further typically, L37 is at least twice as great as L35, such as at least four times as great as L35.

For some applications of the invention, torque-limiting apparatus 2300, coupled to anchor driver 36 (e.g., as described in FIG. 17), prevents over-rotation of the anchor, penetration of tissue-engaging element 2312 too deep into tissue, and/or damage to the tissue.

For some applications, a ratio between diameter L32 of the helix of anchor 2332 (cm) to torque (Ncm) is typically, but not necessarily 0.25/0.8, or 0.3125. For some applications, a ratio between pitch L33 of anchor 2332 (*cm*) to torque (Ncm) is typically, but not necessarily 0.12/0.8, or 0.15. For some applications, a ratio between length L34 of the helix of anchor 2332 (cm) to torque (Ncm) is typically, but not necessarily 0.35/0.8, or 0.4375. For some applications, a ratio between thickness L35 of the wire forming anchor 2332 (*cm*) to torque (Ncm) is typically, but not necessarily 0.05/0.8, or 0.0625.

Typically, but not necessarily, anchor 2332 comprises a biocompatible material such as stainless steel 316 LVM. For some applications, anchor 2332 comprises nitinol. For some applications, anchor 2332 is coated with a non-conductive material, typically while the distal tip of the tissue-engaging element remains uncoated.

Reference is made to FIGS. 19 and 20A-D, which are schematic illustrations of a system 2600 comprising a closure mechanism 2602 for closing opening 2226 at proximal end 49 of sleeve 26, in accordance with some applications of the invention. Closure mechanism 2602 is coupled to sleeve 26 (e.g., described hereinabove with respect to annuloplasty ring structure 222) in a vicinity of (e.g., at) proximal end 49, such as by being sutured to sleeve 26 using one or more sutures 2610.

Closure mechanism 2602 comprises a flap 2604 (e.g., a door) that has an open state (e.g., as shown in FIG. 20A) and a closed state (e.g., as shown in FIG. 20D), and is configured to be biased toward assuming the closed state. When flap 2604 is in the closed state, the lumen of sleeve 26 is in reduced communication with outside of the sleeve compared to when the flap is in the open state. Typically, closure mechanism comprises a frame 2606 to which flap 2604 is articulatably coupled at an articulation point 2608, and flap 2604 is elastically biased toward assuming the closed state, e.g., by the frame, the articulation point, and the flap comprising a continuous piece of shape-memory material such as nitinol. Typically, frame 2606 is generally cylindrical, which reinforces the proximal end of sleeve 26. For some applications, closure element 2602 comprises (e.g., is coated with) an anti-thrombotic agent.

When a portion of a longitudinal element 2612, such as distal end 17 of implant-decoupling channel 18, is disposed within the lumen of sleeve 26, flap 2604 is held in the open state. For applications in which longitudinal element 2612 comprises implant-decoupling channel 18, channel 18 thereby provides a working channel between outside the body of the subject, and the lumen of sleeve 26, such as for delivery of anchors 32, as described hereinabove. When the longitudinal element is removed from the lumen (e.g., slid out of a proximal opening of the sleeve, the flap automatically moves toward the closed state).

Typically, sleeve 26 is reversibly couplable to reference-force tube 19 (e.g., described hereinabove with reference to FIGS. 1-2) via one or more coupling elements 2614 (e.g., sleeve-coupling elements) which are coupled to a distal end of the reference-force tube. Each coupling element 2614 is shaped to define a distal projection 2616, which is configured to be disposed within a respective negative space, such as a recess or a hole 2607 in frame 2606, thereby coupling the coupling element to closure element 2602, and thereby to sleeve 26. Typically, frame 2606 is generally cylindrical, and hole 2607 is defined in a lateral portion of the cylindrical shape. For some applications, coupling elements 2614 comprise coupling elements 2220, described hereinabove with reference to FIGS. 16A-B, mutatis mutandis. Typically, coupling elements 2614 are configured to have a natural tendency (e.g., to be biased) to flex inward toward central longitudinal axis 7 of tube 19, e.g., as described for coupling elements 2220 with reference to FIGS. 16A-B, mutatis mutandis.

For some applications, and as shown in FIGS. 19-20D, each hole 2607 is larger than a respective projection 2616. For such applications, hole 2607 typically has a longitudinal length along axis 7 that is greater than that of projection 2616, such that each projection is slidable longitudinally (i.e., parallel to axis 7) within its respective hole. This configuration provides a degree of freedom of movement, such as articulation, between reference-force tube 19 and structure 222 while the reference force tube is coupled to the structure. Such a configuration typically facilitates sliding of reference-force tube 19 and structure 222 through bends in a catheter, such as catheter 14, described hereinabove.

When coupling elements 2614 are coupled to closure element 2602 (i.e., when projection 2614 is disposed in hole 2607) and the distal end of longitudinal element 2612 (e.g., distal end 17 of channel 18) is disposed within the lumen of sleeve 26 and distal to closure element 2612, the longitudinal element inhibits the coupling elements from decoupling from the closure element (e.g., as shown in FIG. 20A). When the distal end of the longitudinal element is slid proximally past closure element 2602 (and proximally past coupling elements 2614), the coupling elements automatically decouple from the closure element by flexing inward toward the central longitudinal axis of tube 19 (e.g., as shown in FIG. 20C), thereby allowing tube 19 to become decoupled from sleeve 26 (e.g., as shown in FIG. 20C). Reference-force tube 19 may then be withdrawn proximally from sleeve 26. As shown in FIG. 19, for some applications in which a stiffening element 1926 is threaded through sleeve 26 (e.g., as described with reference to FIGS. 16A-B), the stiffening element (e.g., a proximal end thereof) is coupled to reference-force tube 19, such that the stiffening element is removed (e.g., unthreaded) from sleeve 26 as the reference-force tube is withdrawn proximally.

Thereby, system 2600 facilitates:

(1) when distal end 17 of channel 18 is disposed within the lumen of sleeve 26 of implant structure 222 (*a*) coupling of reference-force tube 19 to sleeve 26, and (b) fluid communication between a proximal end of channel 18 (e.g., a proximal end of the lumen thereof) and the lumen of the sleeve, and (2) when the distal end of channel 18 is withdrawn past closure element 2612 (e.g., withdrawn from the lumen of the sleeve), (a) automatic closure of proximal end 49 of sleeve 26 of implant structure 222, and (b) automatic decoupling of reference-force tube 19 from the sleeve of the implant structure.

FIGS. 20A-D show sequential steps in the withdrawn of channel 18 from the lumen of sleeve 26, and thereby the automatic closure of the proximal end of the sleeve, and the automatic decoupling of the reference-force tube from the sleeve. Views A1, B1, C1, and D1 of FIGS. 20A-D, respectively, show a first cutaway parallel to longitudinal axis 7, and views A2, B2, C2, and D2 show respective second cutaways orthogonal to the respective first cutaway (e.g., showing, inter alia, closure element 2602 as seen from within sleeve 26).

As shown in FIG. 20A, for some applications, flap 2604 is configured to bend when in the open state, such that the flap conforms to the curvature of the wall of channel 18 and/or the curvature of a portion of structure 222 (e.g., a portion of sleeve 26 and/or a portion of frame 2606), so as to fit (e.g., snugly) between the channel and the portion of the structure. For example, and as shown in FIGS. 19-20D, flap 2604 may comprise a plurality of struts 2603 (labeled in FIG. 20A) that define a plurality of slits therebetween, such that the flap is more flexible around an axis that is orthogonal to an axis 2605 around which the flap articulates, than it is around an axis that is parallel to axis 2605. For such applications, flap 2604 is typically arcuate in the open state thereof. For some applications, flap 2604 comprises a plurality of independently flexible portions. For example, whereas FIGS. 19-20D show each strut 2603 being constrained at both ends thereof, for some applications, each strut is constrained at only one end thereof, e.g., the struts are constrained at one side of flap 2604, such that the flap resembles a comb.

For some applications, closure element 2602 is configured to reduce fluid communication between the inside of sleeve 26 (e.g., the lumen of the sleeve) and the outside of the sleeve (e.g., the atrium of the heart), when sleeve 26 is implanted in the heart. For some applications, the closure element is configured to provide the implant (e.g., structure 222) with a continuous outer surface, e.g., with no substantial gaps, such as in order to facilitate tissue growth thereon. For some applications, such as for applications in which the implant (e.g., structure 222) comprises multiple components (such as a sleeve and tissue anchors), the closure element facilitates general unification and/or integration of the multiple components, such as throughout the lifetime of the implant, e.g., at least in part irrespective of the stability of the individual components.

Reference is again made to FIGS. 1, 16A-B and 19-20D. For applications in which sleeve-coupling elements are used to couple reference-force tube 19 to sleeve 26, and in which the presence of channel 18 prevents decoupling thereof, during retraction of the channel from the sleeve, release decision facilitation member 127 (FIG. 1) typically automatically engages before (e.g., just before) the channel reaches the point at which the sleeve-coupling elements automatically decouple from the sleeve.

Reference is again made to FIGS. 1, 16A-B and 19-20D. The sleeve-coupling elements described, which couple sleeve 26 to reference-force tube 19, facilitate testing of the anchoring of the sleeve by anchors 32. For example, following implantation of each anchor, the operating physician may pull the reference-force tube proximally by pulling handle 126 proximally, in order to feel the strength of implantation. (Similarly, the operating physician may pull on anchor driver 36 while it is still coupled to the anchor that it has been used to implant.) For some applications, a force gauge 2800 (FIG. 1) is provided on handle 126, comprising a knob 2802 that is slidably coupled to the handle. Rather than pulling directly on handle 126, the operating physician pulls knob 2802 proximally. An elastic member 2804 (e.g., a spring) transfers force from knob 2802 to handle 126 such that the pulling force transferred to the handle is indicated by the position of the knob relative to a marker 2806 (e.g., a scale or color-code). Alternatively or additionally, gauge 2800 may comprise a load cell or a strain gauge. Gauge 2800 is configured to indicate when a pre-determined acceptable force has been applied to handle 126 (and thereby to sleeve 26)—i.e., to indicate that acceptable anchoring has been achieved. For example, a series of color-coded regions 2808 may be provided, whereby:

(1) when knob 2802 is disposed adjacent to a first region 2808a, gauge 2800 indicates a resting state (e.g., no proximal pulling force is being applied to handle 126);

(2) when knob 2802 is disposed adjacent to a second region 2808b, gauge 2800 indicates that a modest force is being applied to handle 126, the modest force being less than that required to liberate a properly-anchored anchor from the tissue;

(3) when knob 2802 is disposed adjacent to a third region 2808c, gauge 2800 indicates that a significant force is being applied to handle 126, the significant force being greater than the modest force, and indicative of a properly-anchored anchor; and (4) a fourth region 2808d indicates a maximum recommended force to apply to handle 126 (i.e., the operating physician should not move knob 2802 past or adjacent to fourth region 2808d).

Thereby, in addition to transferring force via member 2804 to handle 126, knob 2802 functions as a pointer. Therefore, the operating physician may understand that an anchor (e.g., the most recently implanted anchor) that is liberated from the tissue in which it is implanted before knob 2802 reaches third region 2808c, was not anchored sufficiently and/or correctly. For some applications, gauge 2800 has a safety mechanism similar to that of tool 2900, whereby if the maximum recommended force is exceeded, knob 2802 "jumps" (e.g., member 2804 temporarily decouples from the knob), such that force is temporarily not transferred from the knob to handle 126. For some application, the safety mechanism may be considered to be a clutch mechanism.

Figure 21:
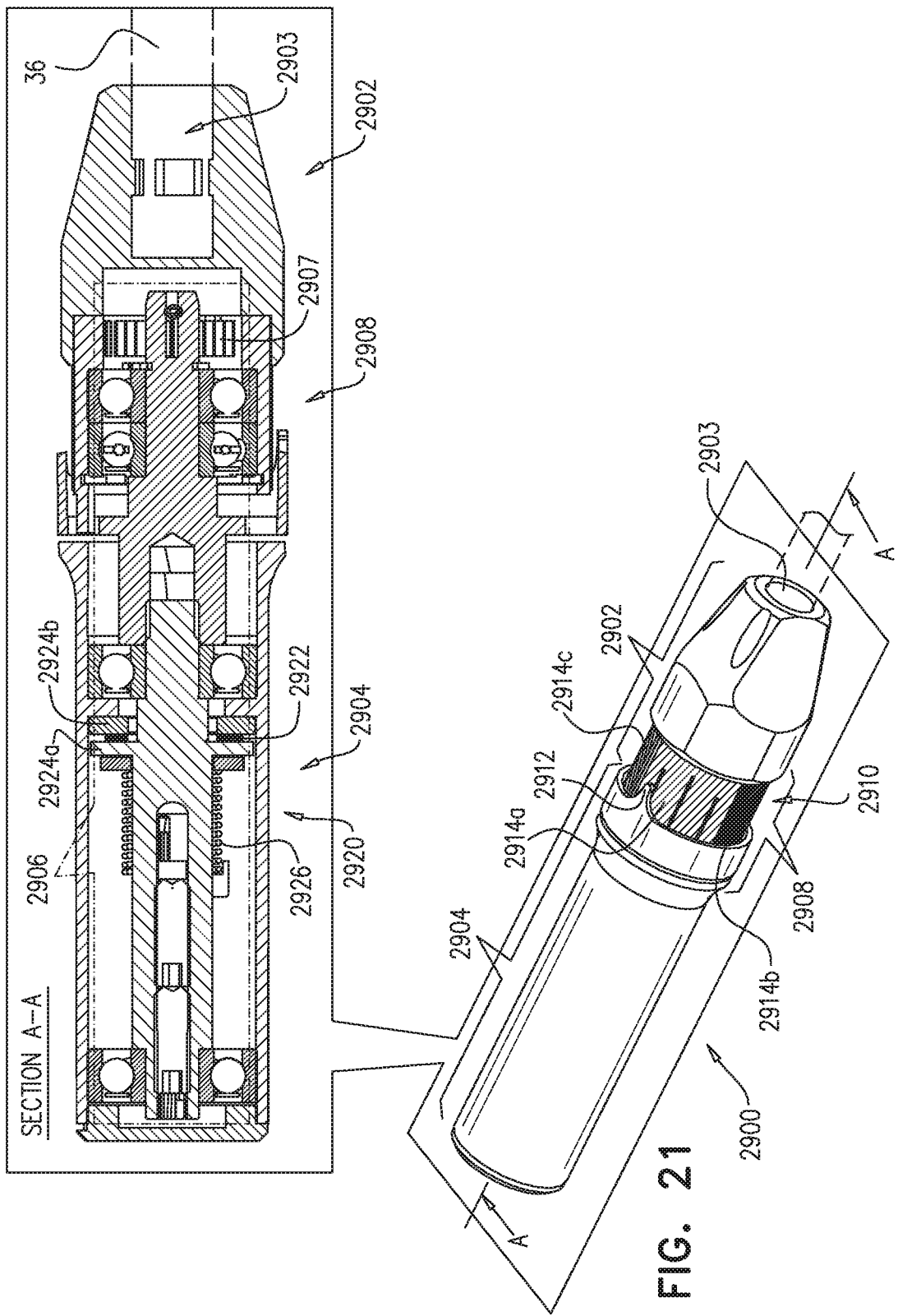
Figure 22:
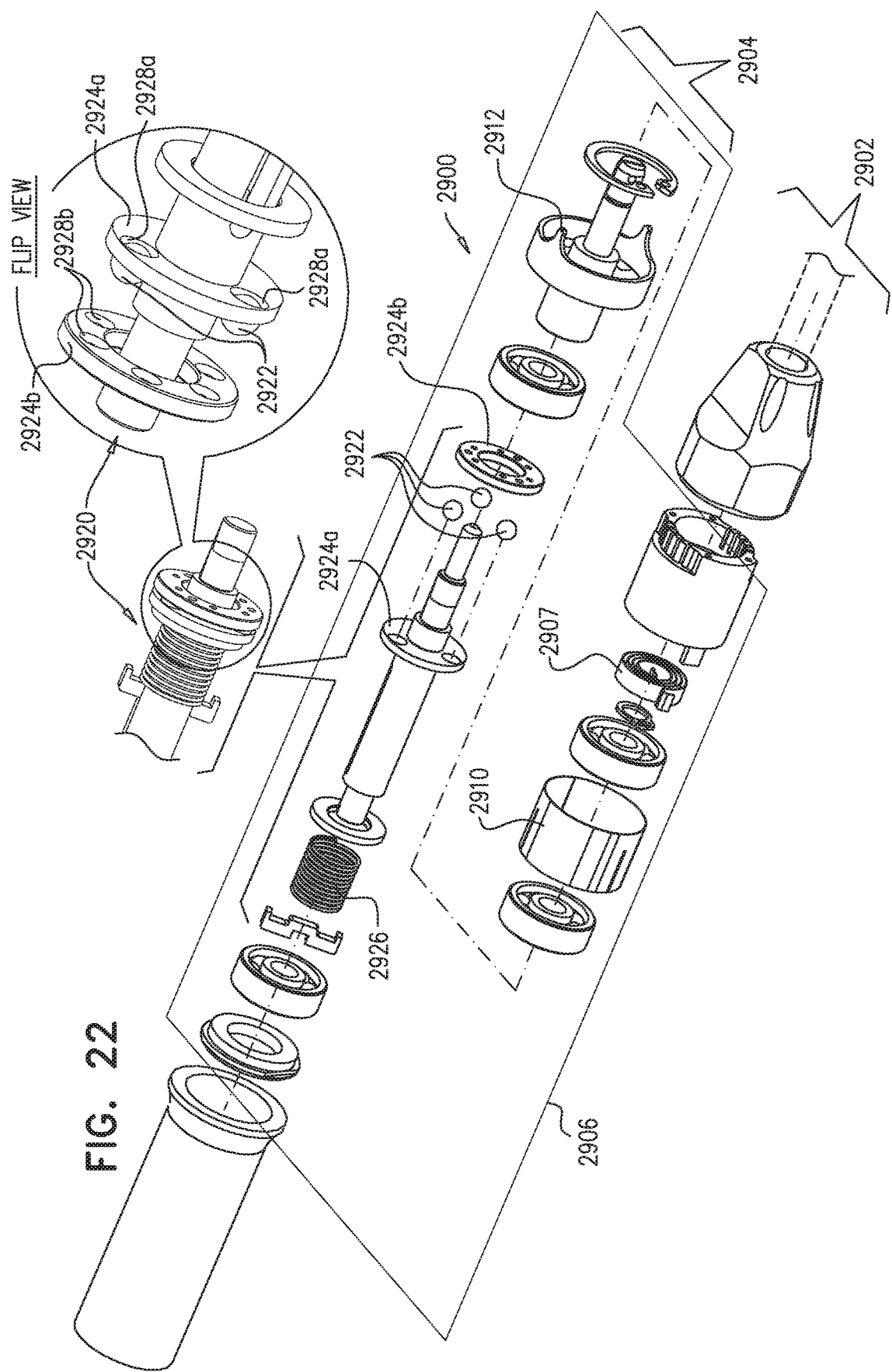

Reference is made to FIGS. 21-24D, which are schematic illustrations of a tool 2900 for use with anchor driver 36 (described hereinabove) for manipulating anchor 32 (e.g., anchoring the anchor in tissue of the annulus), in accordance with some applications of the invention. FIG. 21 shows a perspective view and a cross-sectional view of tool 2900, and FIG. 22 shows an exploded view of the tool. Tool 2900 comprises (i) a distal portion 2902, configured to be coupled to anchor driver 36 (e.g., a proximal end thereof) of deployment manipulator 61, and/or to housing 135, (ii) a proximal portion 2904, rotatably coupled to the distal portion, and (iii) a variable-resistance mechanism 2906. Typically, proximal portion 2904 is rotatably coupled to distal portion 2902 via mechanism 2906. An indicator 2908, typically disposed close to the interface between proximal portion 2904 and distal portion 2902, indicates the present rotational position of proximal portion 2904 with respect to distal portion 2902. For example, and as shown in FIG. 21, indicator 2908 may comprise a gauge 2910 (e.g., a circumferential gauge), fixedly coupled to distal portion 2902, and a pointer 2912, fixedly coupled to proximal portion 2904 (or vice versa).

FIG. 21 shows proximal portion 2904 in a rest rotational position with respect to distal portion 2902 (indicated by the position of pointer 2912 with respect to gauge 2910). Mechanism 2906 is configured to progressively inhibit rotation of proximal portion 2904 with respect to distal portion 2902, correspondingly with a rotational distance, from the rest rotational position, of the proximal portion with respect to the distal portion. That is, as proximal portion 2904 rotates with respect to distal portion 2902, resistance to such rotation increases. For example, mechanism 2906 may comprise a torsion spring 2907 (e.g., a spiral torsion spring) that provides this functionality (e.g., by coupling proximal portion 2902 to distal portion 2904 and/or being functionally disposed therebetween).

FIGS. 23A-H show the use of tool 2900 to facilitate using deployment manipulator 61 to screw an anchor 32 into a tissue 5 (e.g., the annulus of mitral valve 230), in accordance with some applications of the invention. Anchor 32 is transluminally advanced to the tissue while coupled, via deployment element 38, to a distal end of deployment manipulator 61 (e.g., anchor driver 36 thereof). Typically, anchor 32 is advanced via channel 18 and into sleeve 26, as described hereinabove; however, for clarity, FIGS. 23A-H and 24A-D do not show sleeve 26 (nor many other elements of system 10). Distal portion 2902 of tool 2900 is coupled (before or after advancing of anchor 32) to a proximal end of manipulator 61 (e.g., driver 36 thereof), typically such that portion 2902 is rotationally locked with respect to manipulator 61 and anchor 32. For example, portion 2902 may define a driver-receiving socket 2903, configured to receive a proximal portion of anchor driver 36 and/or housing 135.

Gauge 2910 is shown in FIGS. 21-24D as defining three zones 2914: first zone 2914a, second zone 2914b, and third zone 2914c, but it is to be noted that the gauge may define more or fewer zones, graduation marks, and/or other markings. FIG. 23A shows a resting state of tool 2900, with pointer 2912 in first zone 2914a.

Figure 23A:
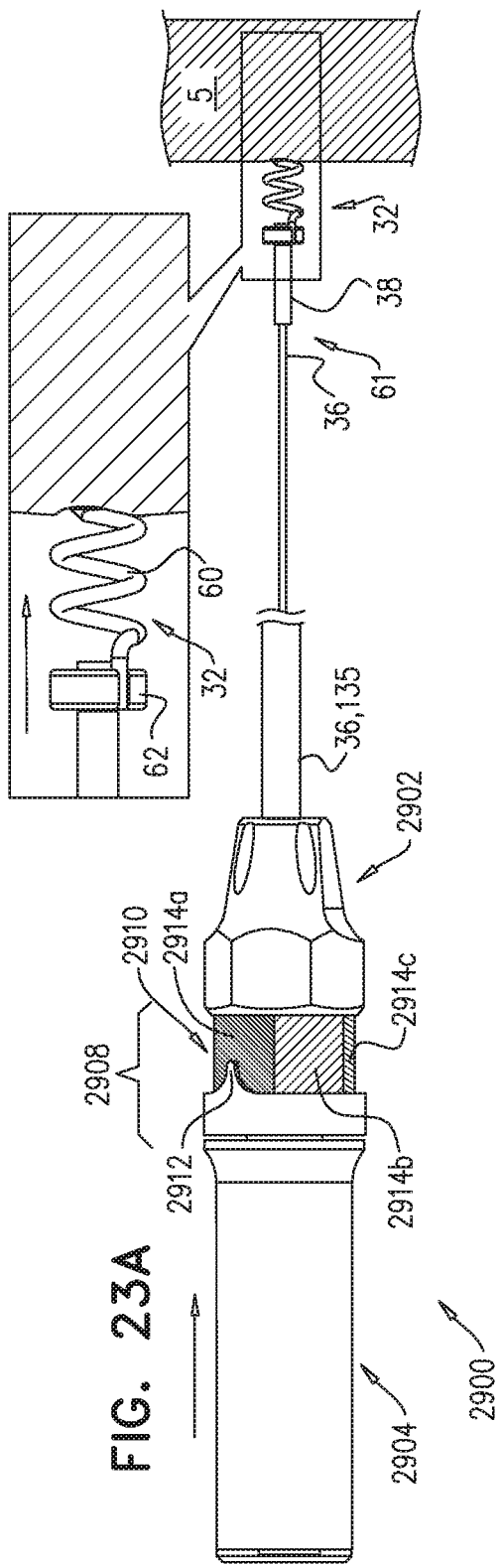
Figure 23B:
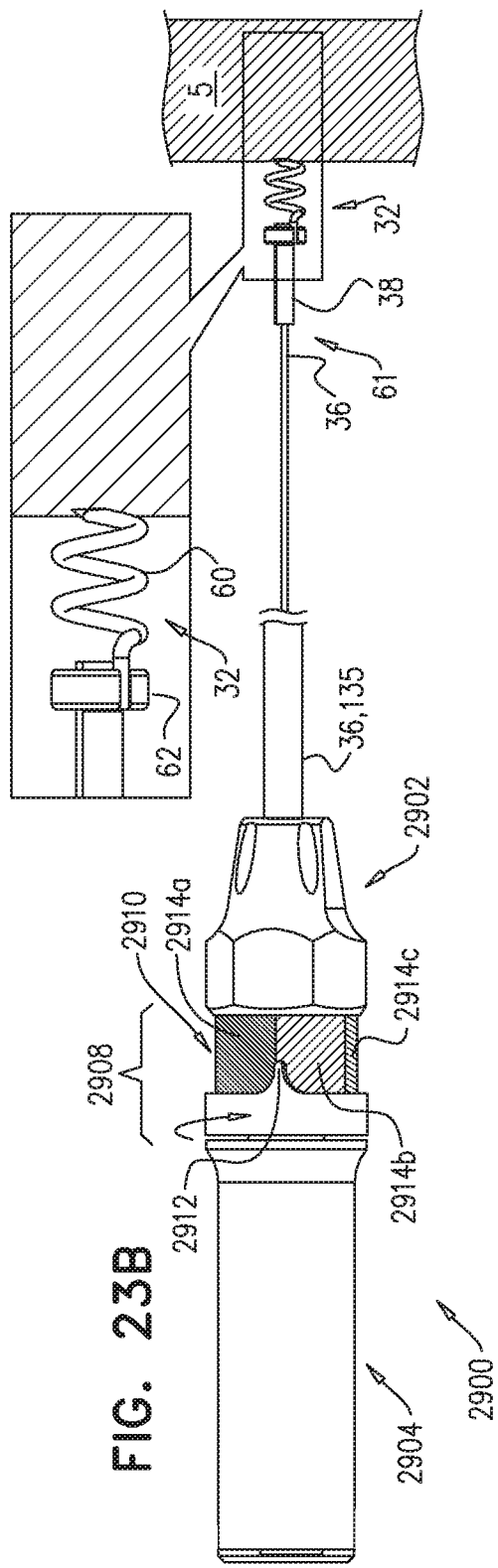
Figure 23C:
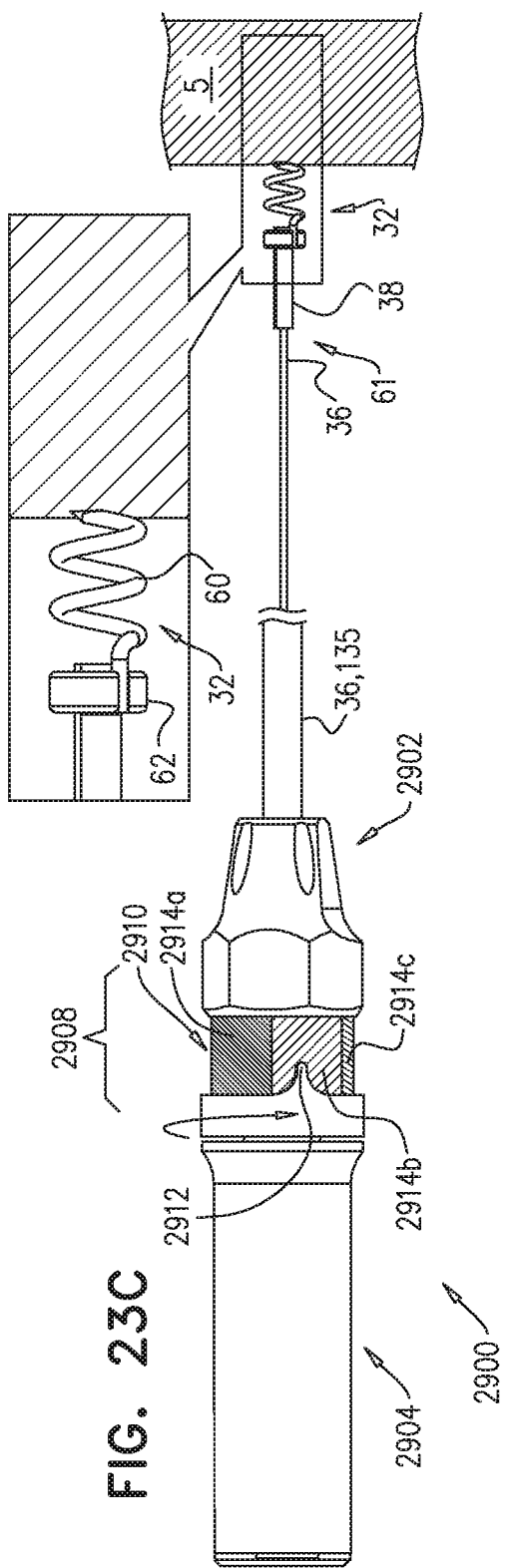

Tissue-engaging element 60 of tissue anchor 32 is placed against tissue 5, typically while proximal portion 2904 is in the rest rotational position (FIG. 23A). Subsequently, proximal portion 2904 is rotated. Initially, resistance imparted by tissue 5 inhibits (e.g., prevents) tissue-engaging element 60 from penetrating the tissue. This resistance thereby inhibits (e.g., prevents) anchor 32, and thus also distal portion 2902, from rotating. Thus, proximal portion 2904 rotates with respect to distal portion 2902, and pointer 2912 thereby moves with respect to gauge 2910. FIG. 23B shows pointer 2912 moving into second zone 2914b, and FIG. 23C shows movement of pointer 2912 further into second zone 2914b, following additional rotation of proximal portion 2904.

Figure 23D:
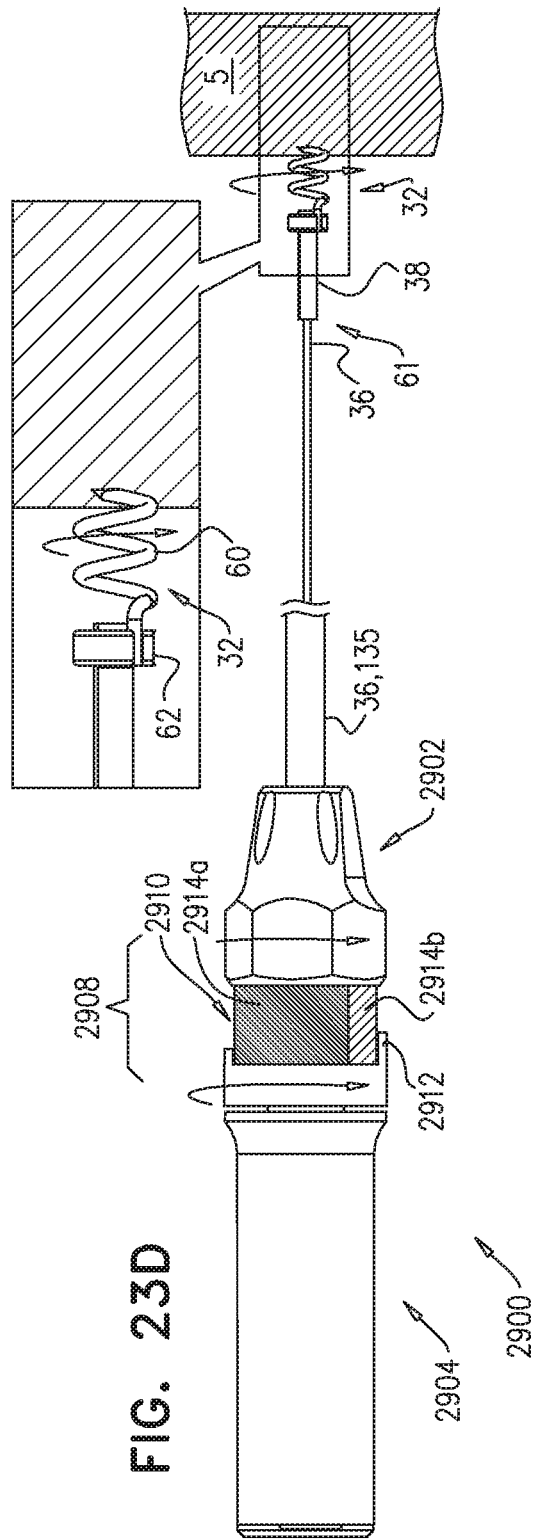

As described hereinabove, mechanism 2906 is configured such that as proximal portion 2904 rotates with respect to distal portion 2902, resistance to such rotation increases. Once mechanism 2906 applies sufficient resistance such that sufficient force (e.g., torque) is transferred from proximal portion 2904 to distal portion 2902 and anchor 32, resistance imparted by tissue 5 is overcome, and tissue-engaging element 60 begins to penetrate the tissue (FIG. 23D). Tool 2900 is configured such that indicator 2908 indicates when mechanism 2906 is providing this sufficient resistance, and thereby when this sufficient force is being applied. For example, and as shown in FIGS. 21-24D, this indication is provided by pointer 2912 pointing within second zone 2914b.

FIGS. 23E-F show continued rotation of proximal portion 2904, and responsive rotation of distal portion 2902 and anchor 32, such that the sufficient force is maintained (e.g., pointer 2912 is maintained within second zone 2914b). If the operating physician were to stop rotating proximal portion 2904 during this stage, rotation of anchor 32 would either stop immediately (pointer 2912 immediately becoming stationary with respect to gauge 2910), or continue rotating briefly and then stop (gauge 2910 also continuing to rotate briefly, such that pointer 2912 briefly moves "in reverse" toward first zone 2914*a* of gauge 2910, before stopping). Typically, if the operating physician were to rotate proximal portion 2904 too quickly during this stage, due to resistance from tissue 5, pointer 2912 would move toward, into, and/or past third zone 2914*c*, which indicates that excess force is being applied, and typically protects tissue 5 from becoming damaged by such excess force, as described hereinbelow with respect to FIGS. 23G-H. Thus, tissue-engaging portion 60 of anchor 32 is typically screwed into tissue 5 by rotating proximal portion 2904 so as to maintain indicator 2908 indicating that sufficient but not excessive force is being applied—e.g., by maintaining pointer 2912 within second zone 2914*b*.

Tool 2900 (e.g., mechanism 2906 thereof) is configured (and/or configurable) according to the tissue to which anchor 32 is to be anchored. For example, a pre-determined torque range may be determined and/or selected for screwing tissue-engaging element 60 into the annulus of the mitral valve, and tool 2900 is configured such that this pre-determined torque range is indicated by pointer 2912 being disposed within second zone 2914*b*. In this example, first zone 2914*a* would thereby indicate that the torque applied is smaller than the pre-determined torque range, and third zone 2914*c* would indicate that the torque applied is at the higher end of, and/or greater than, the pre-determined torque range.

For some applications (e.g., for some applications in which tool 2900 is used to anchor anchor 2332, described with reference to FIGS. 18A-C), the pre-determined torque range for screwing tissue-engaging element 60 into the annulus of the mitral valve has a lower limit of 0.3-1.0 Ncm (e.g., 0.3-0.6 Ncm, or 0.6-0.9 Ncm), and/or an upper limit of 0.8-1.5 Ncm (e.g., 0.8-1.3 Ncm, or 1.0-1.5 Ncm, such as 1.2 Ncm).

FIG. 23G shows anchor 32 having been fully screwed into tissue 5, such that coupling head 62 abuts against the tissue. As described hereinabove, for clarity, FIGS. 23A-H and 24A-D do not show sleeve 26, nor many other elements of system 10. It is to be noted that when tool 2900 is used to facilitate implantation of sleeve 26, at this stage of anchoring, the portion of the sleeve that is anchored by anchor 32 is typically sandwiched between coupling head 62 and the tissue. Resistance to rotation of anchor 32 due to the abutment of coupling head 62 against the tissue (either directly or through sleeve 26) inhibits rotation of distal portion 2902, and continued rotation of proximal portion 2904 moves to point to third zone 2914*c*, indicating that torque applied is at the higher end of, and/or greater than, the pre-determined torque range. Typically, mechanism 2906 is configured such that further rotation of proximal portion 2904 results in the proximal portion "jumping" (e.g., with a "click"), as shown in FIG. 23H. For example, portion 2902, portion 2904 and/or mechanism 2906 may temporarily rotationally disengage. This may be considered a clutch functionality. For example, pointer 2912 may "jump" from third zone 2914*c* back into first zone 2914*a*, in which little or no torque is transferred to anchor 32. Further rotation of portion 2904 begins to apply torque to portion 2902 again. Alternatively or additionally, tool 2900 may be configured such that a permanent disengagement occurs (e.g., as described hereinbelow for tool 2950 with reference to FIGS. 25A-E). Mechanism 2906 thereby typically provides a torque-limiting mechanism (e.g., a safety mechanism) that prevents over-tightening of anchor 32, and damage to tissue 5, sleeve 26, and/or the anchor that may otherwise be caused by such over-tightening.

For some applications, tool 2900 comprises a clutch mechanism 2920 that is configured to provide the temporary rotational disengagement (e.g., the clutch functionality) described in the above paragraph. For example, clutch mechanism 2920 may comprise one or more bearings 2922 disposed between two clutch plates 2924 (e.g., a first clutch plate 2924*a* and a second clutch plate 2924*b*), at least one of the clutch plates shaped to define one or more sockets 2928 in which bearings 2922 are configured to be seated. For some applications, clutch plate 2924*a* defines a first one or more sockets 2928*a* and clutch plate 2924*b* defines a second one or more sockets 2928*b*. A spring 2926 provides an engaging force that pushes the clutch plates together, sandwiching bearings 2922 therebetween such that each bearing is seated in a respective socket 2928*a* and a respective socket 2928*b*. In this state, torque applied to proximal portion 2904 is transferred to distal portion 2902.

When mechanism 2920 experiences torque that exceeds the pre-determined torque range, rotational disengagement occurs by the engaging force being overcome, each bearing 2922 exiting at least one of its respective sockets 2928, and becoming free to roll over the plate that defines the at least one respective socket. Further rotation of the proximal portion of the tool (in the same or opposite direction) allows each bearing to enter another or the same socket, thereby rotationally re-engaging the proximal and distal portions of the tool.

FIGS. 24A-D show tool 2900 being used when tissue 5 is not engaged by anchor 32, tissue 5 being the tissue to which anchor 32 is intended to be anchored (e.g., the annulus of the mitral valve). FIGS. 24A-D show anchor 32 not engaging any solid tissue, but also apply to situations in which anchor 32 engages a solid tissue that is more easily penetrated than tissue 5 (e.g., leaflet tissue of the mitral valve). Because anchor 32 does not experience resistance to rotation thereof (e.g., tissue 5, which is not in contact with the anchor does not provide resistance), or experiences only insufficient resistance to rotation thereof (e.g., resistance provided by leaflet tissue to penetration of tissue-engaging element 60), when proximal portion 2904 is rotated, distal portion 2902 also rotates, and indicator 2908 does not indicate torque within the pre-determined torque range (e.g., pointer 2912 does not reach second zone 2914*b*).

For some applications of the invention, respective pre-determined torque ranges for non-target tissues may also be indicated on gauge 2910. For example, a pre-determined torque range for leaflet tissue may be indicated such that the operating physician may distinguish between penetration of no tissue, penetration of leaflet tissue, and penetration of annulus tissue. Similarly, tool 2900 may alternatively or additionally indicate and/or prevent undesired penetration of a folded portion of sleeve 26. FIGS. 24A-D show tool 2900 experiencing no resistance to rotation of anchor 32, and pointer 2912 remaining in first zone 2914*a* throughout.

For some applications, the deeper into tissue 5 that tissue-engaging portion 60 penetrates, the greater torque is required to continue to drive the anchor into the tissue. Thus, for such applications, the number of rotations that portion 2902 has completed at a given time may be taken into account when distinguishing between penetration (or not) of various tissue/materials. For example, movement of pointer 2912 close to third zone 2914*c* upon initial rotation of portion 2904 may indicate that tissue-engaging portion 60 has engaged a hard material that is not the annulus, whereas movement of the pointer close to the third zone after two complete rotations of portion 2902 (and therefore of anchor 32) may indicate that the tissue-engaging portion has penetrated two turns-deep into the annulus.

For some applications, tool 2900 indicates the number of rotations completed by portion 2902. For some applications, tool 2900 (e.g., indicator 2908 thereof) adjusts (e.g., calibrates) in real-time, according to number of rotations completed by portion 2902, such that despite a change (e.g., an increase) in absolute torque, pointer 2912 continues to point to second zone 2914b throughout the screwing in of tissue-engaging portion 60.

Reference is made to FIGS. 25A-E, which are schematic illustrations of a tool 2950 for use with anchor driver 36 (described hereinabove) for manipulating anchor 32 (e.g., anchoring the anchor in tissue of the annulus), in accordance with some applications of the invention. FIG. 25A shows a perspective view and an exploded view of tool 2950, FIG. 25B shows a cutaway view of the tool, and FIGS. 25C-E shows functionality of the tool. Typically, tool 2950 has similar functionality, and is used in a similar way and for similar purpose, as tool 2900 described hereinabove, mutatis mutandis.

Tool 2950 is configured to indicate, control and/or limit torque applied to anchor 32. Tool 2950 comprises (i) a distal portion 2952, configured to be coupled to anchor driver 36 (e.g., a proximal end thereof) of deployment manipulator 61, and/or to housing 135, (ii) a proximal portion 2954, rotatably coupled to the distal portion, and (iii) a variable-resistance mechanism 2956. Typically, proximal portion 2954 is rotatably coupled to distal portion 2952 via mechanism 2956. An indicator 2908, typically disposed close to the interface between proximal portion 2954 and distal portion 2952, indicates the present rotational position of proximal portion 2954 with respect to distal portion 2952. For example, indicator 2958 may comprise a gauge 2960 (e.g., a circumferential gauge), fixedly coupled to distal portion 2952, and a pointer 2962, fixedly coupled to proximal portion 2954 (or vice versa).

Mechanism 2956 is configured to progressively inhibit rotation of proximal portion 2954 with respect to distal portion 2952, correspondingly with a rotational distance, from a rest rotational position, of the proximal portion with respect to the distal portion (e.g., as described hereinabove with respect to tool 2900, mutatis mutandis). That is, as proximal portion 2954 rotates with respect to distal portion 2952, resistance to such rotation increases. For example, mechanism 2956 may comprise one or more torsion springs 2957 (e.g., spiral torsion springs) that provides this functionality (e.g., by coupling proximal portion 2952 to distal portion 2954 and/or being functionally disposed therebetween).

Typically, tool 2950 is used in a similar way and for similar purpose (e.g., driving anchors 32), as tool 2900 described hereinabove, mutatis mutandis. For example, the variable and/or progressive inhibition of rotation of the proximal portion with respect to the distal portion, in combination with the indicator, facilitates controlled torque application to anchors 32, e.g., as described with reference to FIGS. 23A-24D, mutatis mutandis.

Similarly, like tool 2900, tool 2950 is configured to provide torque-limiting functionality. However, rather than temporarily rotationally disengaging in response to torque in excess of the pre-determined torque range, portions 2952 and 2954 permanently disengage. This may be considered a fuse functionality.

For some applications, tool 2950 (e.g., mechanism 2956 thereof) comprises a shear pin 2970 that is configured to provide the rotational disengagement functionality. Shear pin 2970 is disposed laterally through a first axle portion 2974a and a second axle portion 2974b, rotationally locking the portions such that they act as a single axle 2974. FIGS. 25C-D show tool 2950 being rotated while axle portions 2794a and 2974b are rotationally locked by shear pin 2970. Shear pin 2970 is configured to shear in response to experiencing torque in excess of the pre-determined torque range, thereby rotationally disengaging axle portions 2974b and 2974b, and thus also rotationally disengaging proximal portion 2954 from distal portion 2952. FIG. 25E shows shear pin having sheared, and proximal portion 2954 having rotated independently of distal portion 2952. Shear pin 2970 thereby typically provides a torque-limiting mechanism (e.g., a safety mechanism) that prevents over-tightening of anchor 32, and damage to tissue 5, sleeve 26, and/or the anchor that may otherwise be caused by such over-tightening.

Reference is again made to FIGS. 1-2, and 21-25E. For some applications, an electronic extracorporeal controller is provided that provides similar functionality to tool 2900 and/or tool 2950, and may further provide at least some of the functionality described hereinabove as being provided by the physician. For example, the electronic extracorporeal controller may measure (e.g., continuously) both (1) the number of rotations of anchor driver 36, and (2) the torque required for further rotation of the anchor driver. The electronic extracorporeal controller typically couples to anchor driver 36 and/or housing 135.

As described hereinabove (e.g., with reference to FIGS. 21-25E), the relationship between (1) the number of rotations that anchor 32 is screwed into tissue, and (2) torque required to screw the anchor further into tissue, may indicate the nature of the material into which the anchor is being driven (e.g., whether the anchor is inadvertently being driven into leaflet tissue or through a kink in sleeve 26).

For example, the electronic extracorporeal controller may:
- detect an initial increase in torque that indicates initial penetration of tissue,
- indicate that an anchor is well placed if a threshold torque is detected in fewer than a given number of rotations since the initial penetration,
- indicate that an anchor is well placed if (1) a threshold torque is detected in fewer than a given number of rotations since the initial penetration, and (2) torque is maintained within a given difference of that detected torque for another given number of rotations,
- indicate that an anchor may not be well placed if a threshold torque is detected within an unexpectedly low number of rotations since the initial penetration, and/or
- indicate that an anchor may not be well placed if a threshold torque is not detected within a given number of rotations.

For some applications, the controller drives (e.g., rotates) driver 36 (e.g., the controller comprises an electric motor). For some such applications, the controller automatically drives, or is automatically driven to drive, driver 36 in response to the detected rotations and/or torque, e.g., as described with reference to FIG. 34. For some applications, the controller only provides a readout for the operating physician.

Reference is made to FIGS. 26A-G, which are schematic illustrations of steps in the implantation of an annuloplasty ring structure to repair a mitral valve, in accordance with some applications of the invention. In general, the implantation shown in FIGS. 26A-G is similar to that described with reference to FIGS. 10A-I, with differences described herein.

Figure 26A:
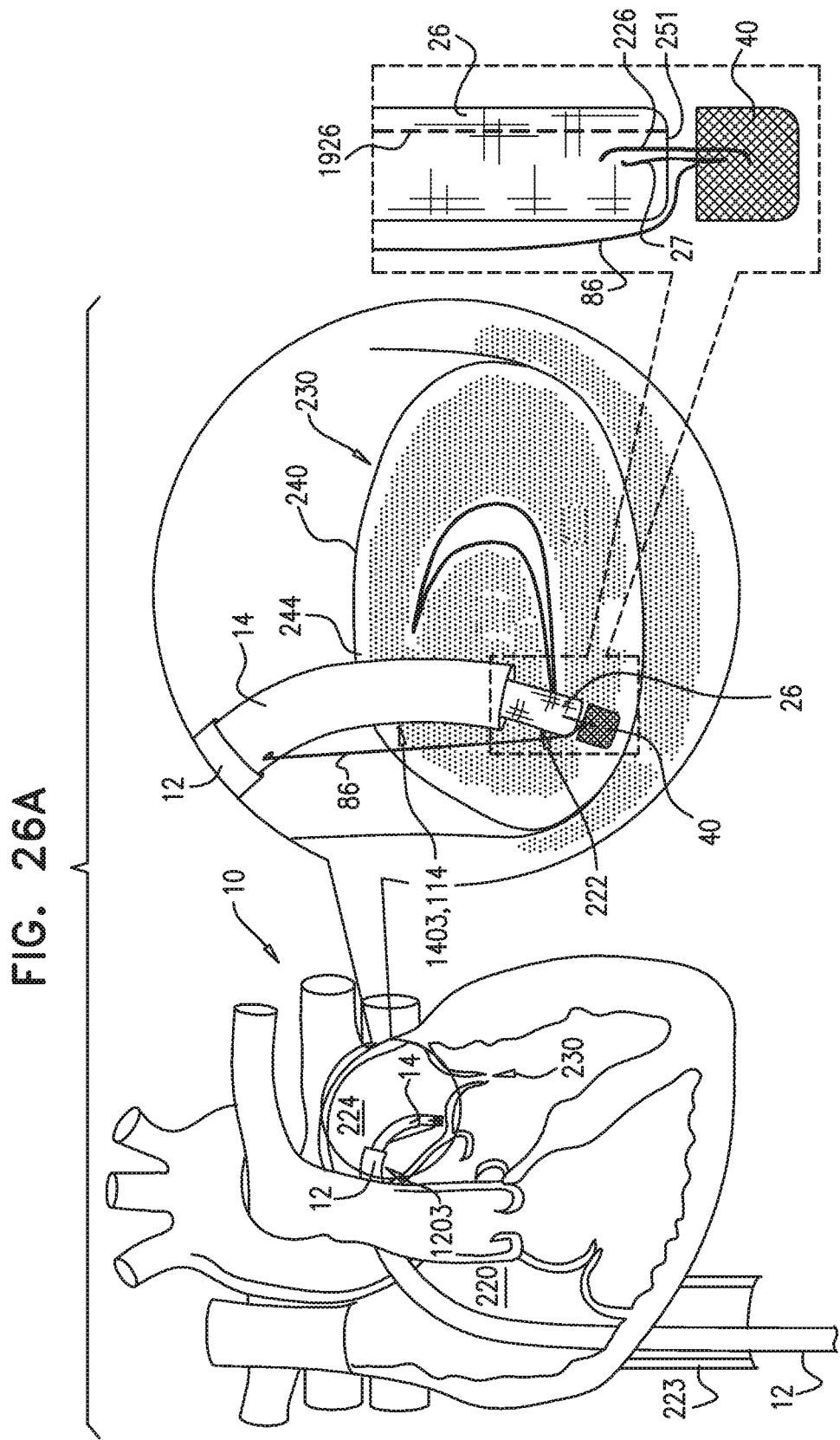

FIG. 26A shows annuloplasty ring structure 222, comprising sleeve 26 and adjustment mechanism 40, having been advanced, via catheter 14, to mitral valve 230. For some applications, the steps shown in FIGS. 26A-C correspond to the step described with respect to FIG. 10G, mutatis mutandis. For example, for some applications, the steps prior to that shown in FIG. 26A are typically the same as those described with reference to FIGS. 10A-F, mutatis mutandis.

As shown in FIG. 26A, and as described hereinabove, during advancement of structure 222, adjustment mechanism 40 is disposed distal to (i.e., in front of) sleeve 26. In this way, adjustment mechanism 40 is disposed on the longitudinal axis of sleeve 26 (e.g., collinearly with the sleeve), so as to advantageously maintain a small cross-sectional diameter of the implant for transluminal delivery. Mechanism 40 is typically coupled to sleeve 26 via one or more connectors 27, such as sutures, which provide flexible and/or articulated coupling. Guide member 86, described hereinabove, typically extends distally from catheter 14, between distal end 251 of sleeve 26 and adjustment mechanism 40, and there is coupled to the adjustment mechanism.

Figure 26C:
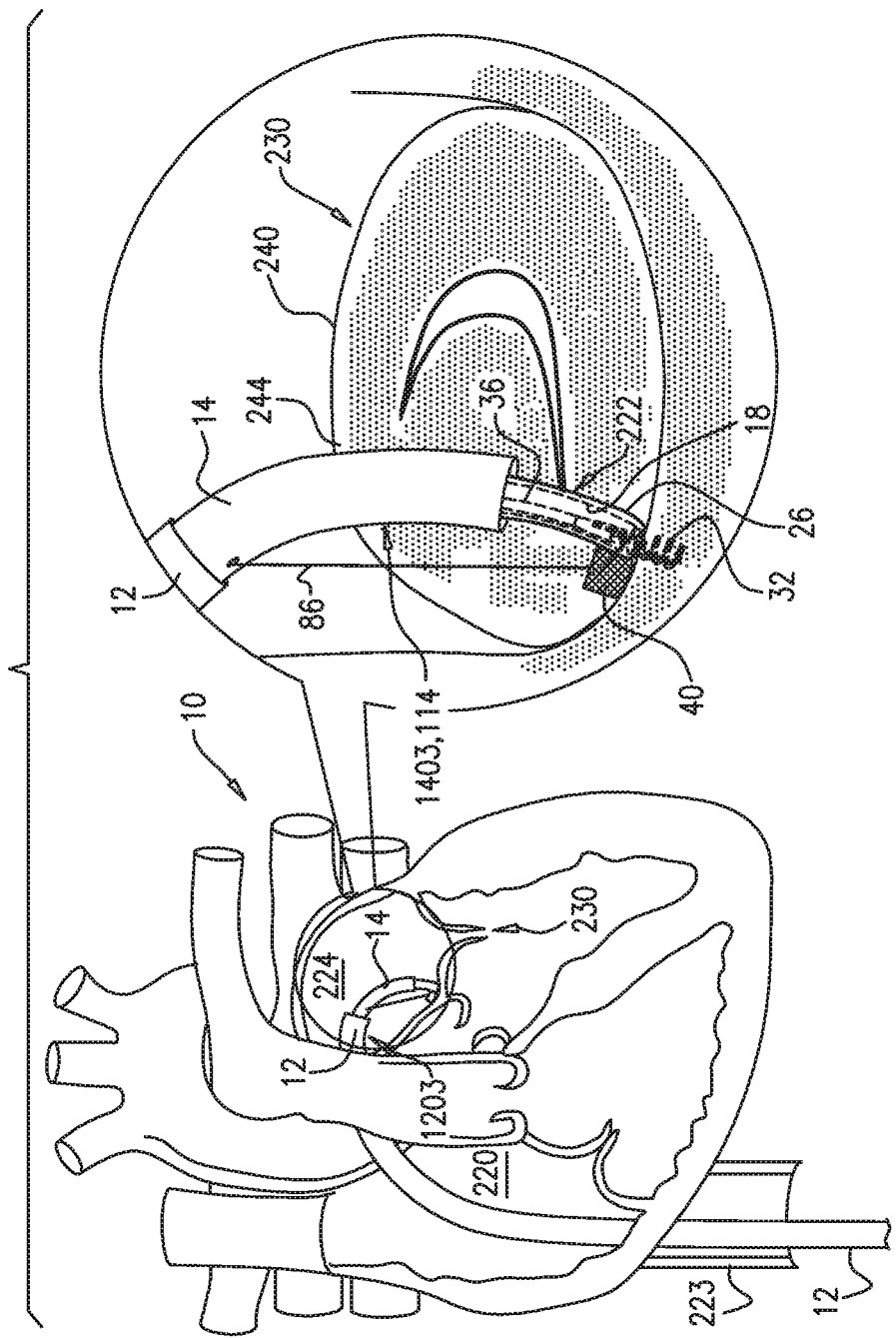

Subsequent to exposure of at least adjustment mechanism 40 (and typically at least distal end 251 of sleeve 26) from catheter 14, the adjustment mechanism is moved away from distal end 251. Typically, this is achieved by guide member 86 being proximally such that mechanism 40 moves (e.g., translates, deflects, and/or rotates) away from the longitudinal axis of the sleeve, typically to become disposed laterally from sleeve 26. FIG. 26B shows mechanism 40 having translated to such a position. The movement of mechanism 40 away from distal end 251 of sleeve 26 advantageously allows the distal end of the sleeve to be placed against annulus 240, and a first anchor 38 to be driven through the distal end of the sleeve and into the annulus (FIG. 26C).

Figure 26D:
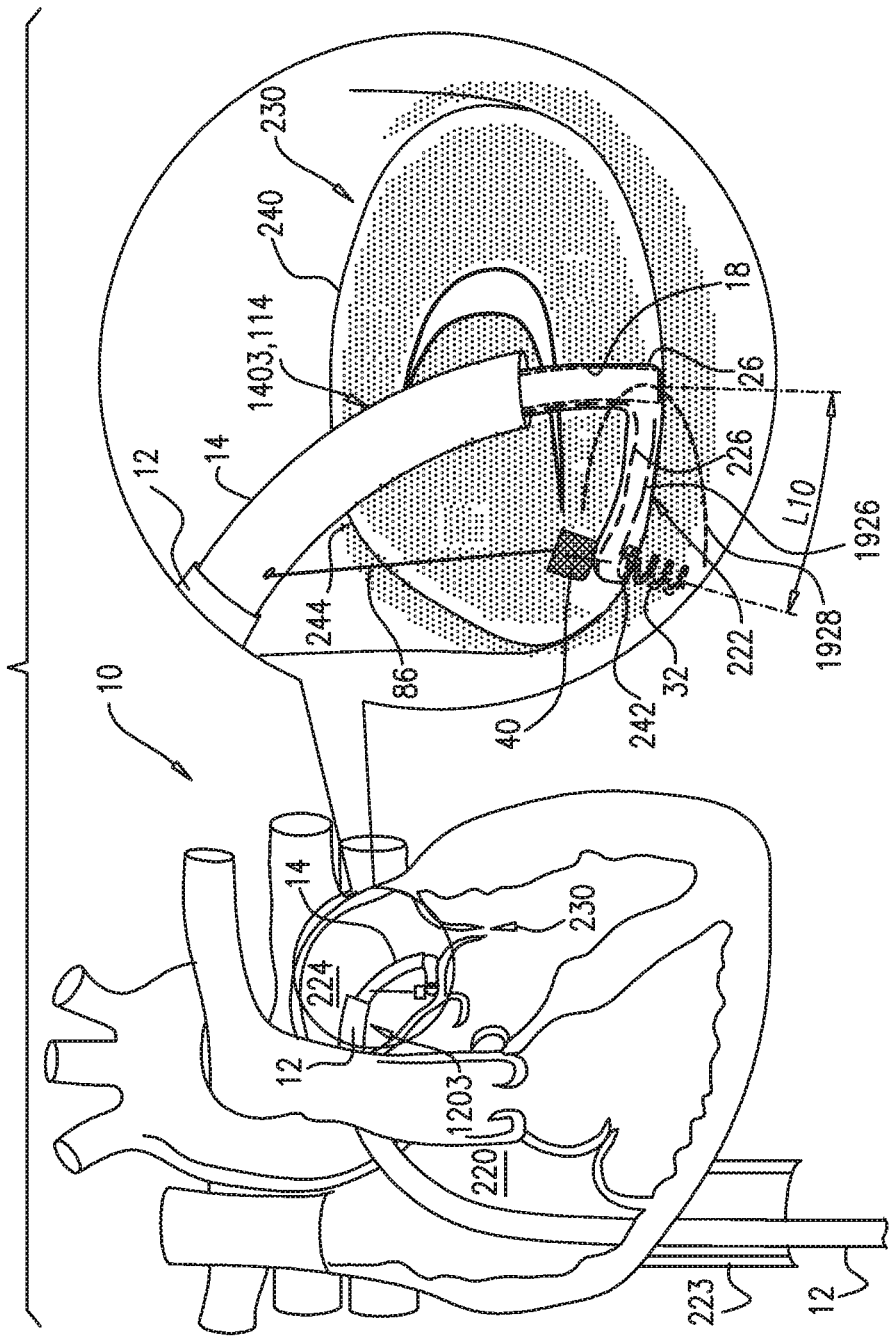
Figure 26E:
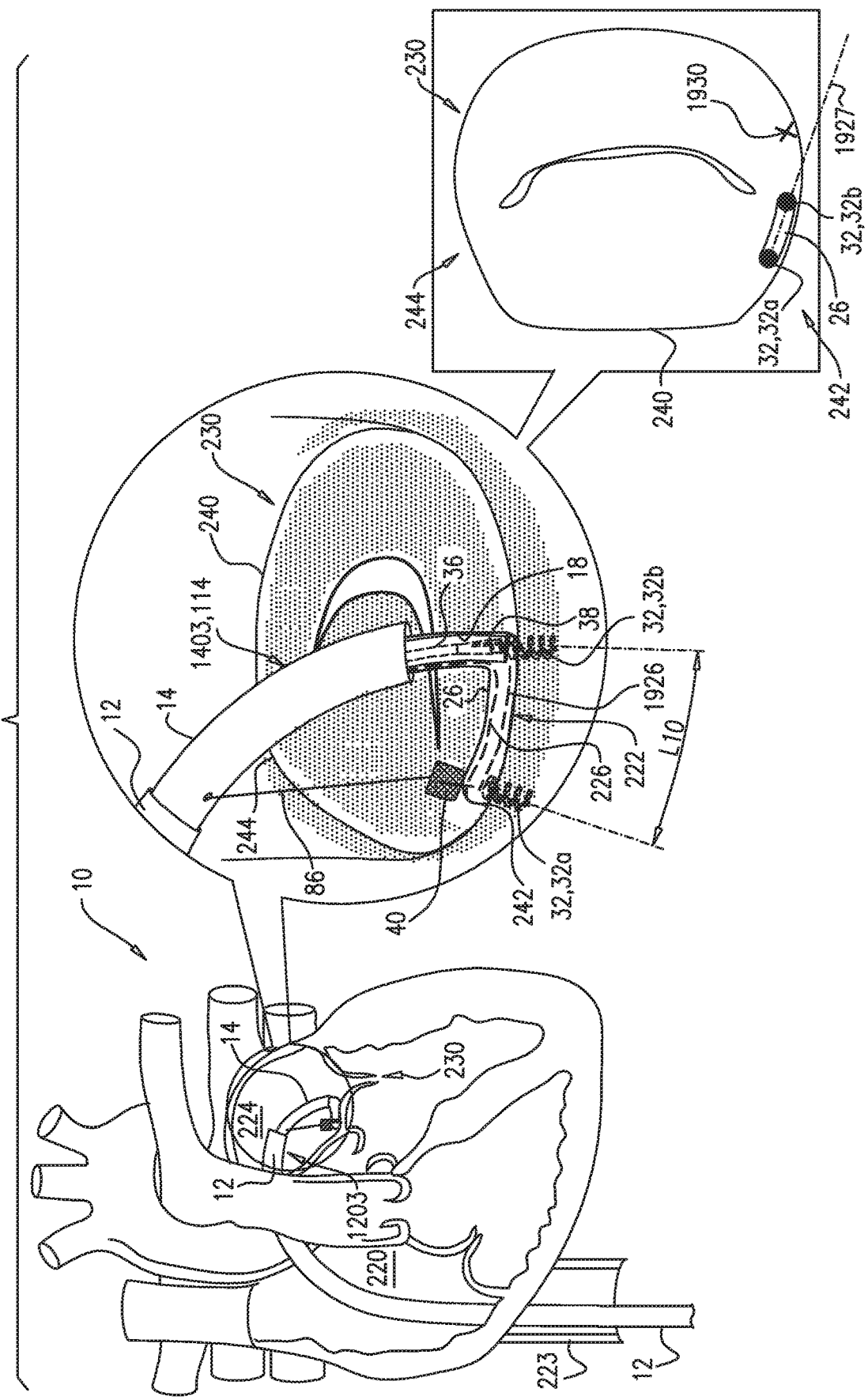

FIG. 26D shows a distal portion of sleeve 26 having been decoupled from a portion of channel 18 by retracting the channel proximally, as described hereinabove (e.g., with reference to FIG. 10G, mutatis mutandis). The position of the distal end of channel 18 within the sleeve defines a portion of the sleeve that will next be anchored. FIG. 26E shows a second anchor being deployed through a lateral wall of sleeve 26 at the defined portion of the sleeve. For some applications, the steps shown in FIGS. 26D-E correspond to the step described with respect to FIG. 10H, mutatis mutandis. For example, for some applications, the steps prior to that shown in FIG. 26D are typically the same as those described with reference to FIGS. 10A-G, mutatis mutandis.

For some applications, a maximum distance L10 between a first anchor and a point of anchoring of a second anchor is provided by the length of sleeve 26 that has been decoupled from the portion of channel 18 (e.g., by the distance that channel 18 has been retracted from sleeve 26). That is, for some applications, a second anchor may be placed anywhere within a circle having a radius that equals L10, centered on the first anchor.

As described hereinabove (e.g., with reference to FIGS. 16A-B, and 19), for some applications, a stiffening element 1926 is provided during the implantation of sleeve 26, and for some applications, the stiffening element facilitates positioning of portions of the sleeve and/or anchors 32, such as positioning of subsequent portions and/or anchors following positioning of previous portions and/or anchors. For example, and as shown in FIG. 26D, by resisting compression, stiffening element 1926 biases the positioning of the distal end of channel 18 (and thereby the position at which the second anchor will be deployed) toward the perimeter of the circle described hereinabove that is centered on the first anchor. That is, by resisting compression, stiffening element 1926 biases the second anchor toward being disposed a distance L10 from the first anchor. Due to, or independently from, this compression-resisting feature of stiffening element 1926, stiffening element 1926 typically maintains an overall length of sleeve 26, the length of the sleeve having typically been selected in response to measurement of the annulus on which it is to be implanted.

By resisting bending, stiffening element 1926 may further bias the positioning of the distal end of channel 18 (and thereby the position at which the second anchor will be deployed) toward a particular sector of the circle. For some applications, by resisting compression and bending, stiffening element 1926 biases the positioning of the distal end of channel 18 (and thereby the position at which the second anchor will be deployed) toward a particular sector of the perimeter of the circle, i.e., toward an arc (e.g., a circular arc) 1928.

For some applications, by resisting bending, stiffening element 1926 biases sleeve 26 (and portions thereof) toward being straight, and thereby biases positioning of the distal end of channel 18 (and thereby the position at which the next anchor will be deployed) toward being on a line defined by at least the two preceding anchors (e.g., the two preceding anchors define a line segment of the line therebetween). FIG. 26E includes a schematic view illustrating a first anchor 32$a$, a second anchor 32$b$, and a corresponding portion of sleeve 26 having been anchored to annulus 240. A line 1927 is defined by the anchors 32$a$ and 32$b$, stiffening element 1926 (not shown in this view) biasing a subsequent portion of sleeve 26 (and thereby subsequent anchors) to be disposed along line 1927. A desired position of a subsequent anchor is shown by cross 1930. This desired position is at the annulus, rather than closer to the center of the valve (e.g., the leaflets of the valve). Anatomical constraints and/or application of force by the operating physician oppose this biasing, such that the subsequent anchor is anchored at cross 1930. For such applications, the presence of stiffening element 1926 thereby facilitates placement of the subsequent anchor at annulus 240, as opposed to placement closer to the center of valve 230. It is to be noted that stiffening element 1926 biases structure 222 (e.g., sleeve 26 thereof) to assume a shape that is different to that of the native valve and/or native annulus. That is, stiffening element 1926 biases structure 222 (e.g., sleeve 26 thereof) to not conform to the shape of the native valve and/or native annulus.

Figure 26G:
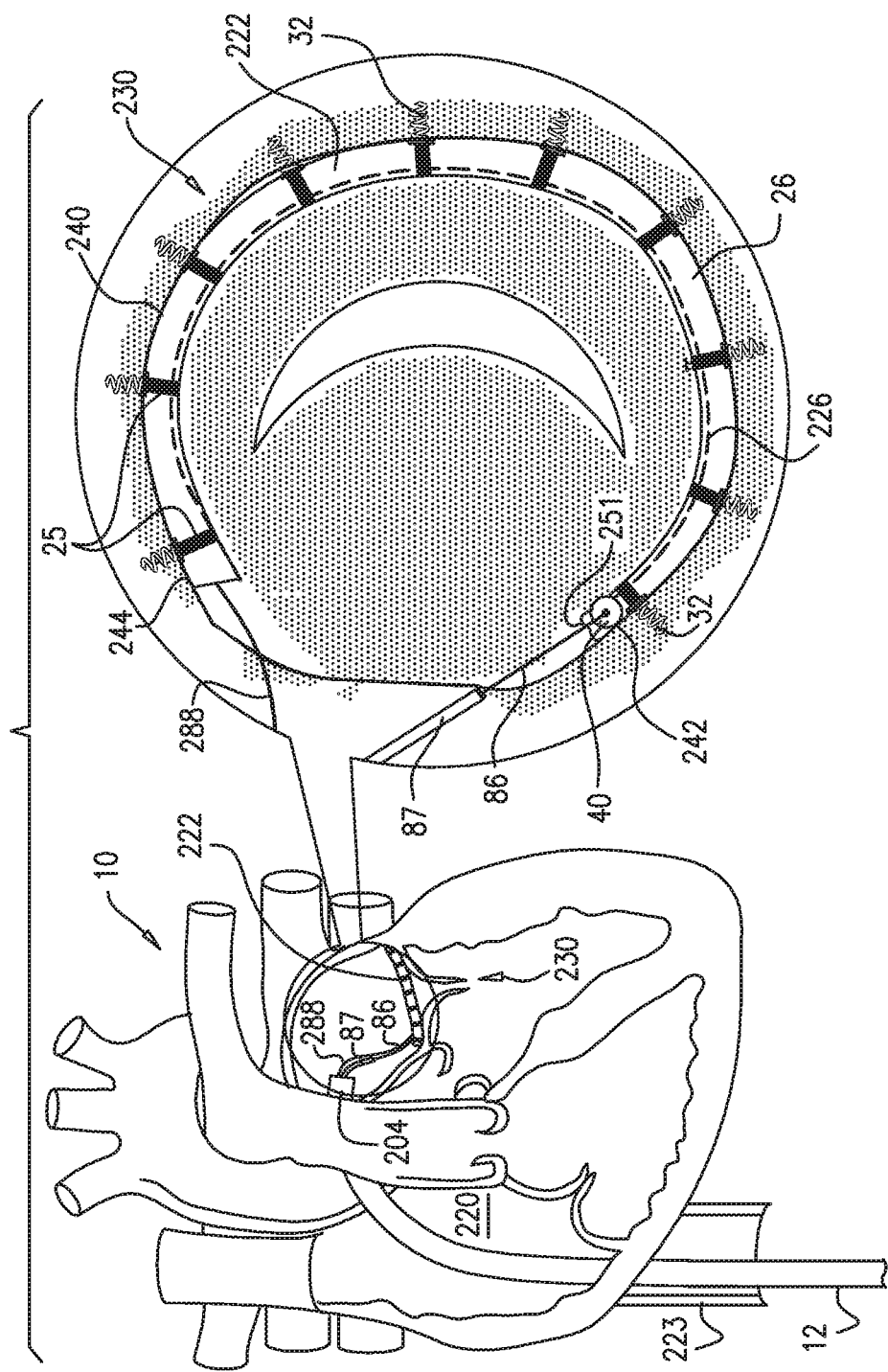

FIG. 26F shows the entire length of sleeve 26 having been anchored, via a plurality of anchors 32, to annulus 240, as described hereinabove (e.g., with reference to FIG. 10I, mutatis mutandis). FIG. 26G shows an adjustment tool 87 being advanced over guide member 86, as described hereinabove (e.g., with respect to FIG. 10I, mutatis mutandis). For some applications, the steps shown in FIGS. 26F-G correspond to the step described with respect to FIG. 10I, mutatis mutandis. For example, for some applications, the steps prior to that shown in FIG. 26F typically correspond to those described with reference to FIGS. 10A-H, mutatis mutandis.

Adjustment tool 87 typically comprises a rotation tool, and is configured to actuate (e.g., rotate) adjustment mechanism 40, so as to contract contracting member 226, and thereby sleeve 26, as described hereinabove.

Reference is again made to FIGS. 26G and 10I. For anatomical reasons, a transluminal (e.g., transfemoral) approach to the mitral valve via transseptal puncture typically provides access more directly and/or easily to the region of the anterior commissure (e.g., including left fibrous trigone 242) than to the region of the posterior commissure (e.g., including right fibrous trigone 244). It may therefore be advantageous to position and anchor distal end 251 of sleeve 26 in the vicinity of the left fibrous trigone; the positioning of the first point of anchoring of structure 222 may be more difficult than the positioning of subsequent points of anchoring (e.g., due to guidance provided by sleeve 26 and/or stiffening element 1928; FIG. 26D). Due to this same reason of accessibility, it may also be advantageous to deliver adjustment tool 87 to the region of the anterior commissure (as shown in FIG. 26G).

System 10 (e.g., structure 222 thereof) is configured to facilitate exploitation of these two advantages: By adjustment mechanism 40 being disposed at a distal end of sleeve 26, and being movable away from the longitudinal axis of the sleeve, (1) the first anchor may be driven through distal portion 251 into the region of the anterior commissure, despite the adjustment mechanism having previously been obstructively positioned, and (2) the adjustment tool may be delivered to the region of the anterior commissure because the adjustment mechanism is disposed in that region.

Figure 27A:
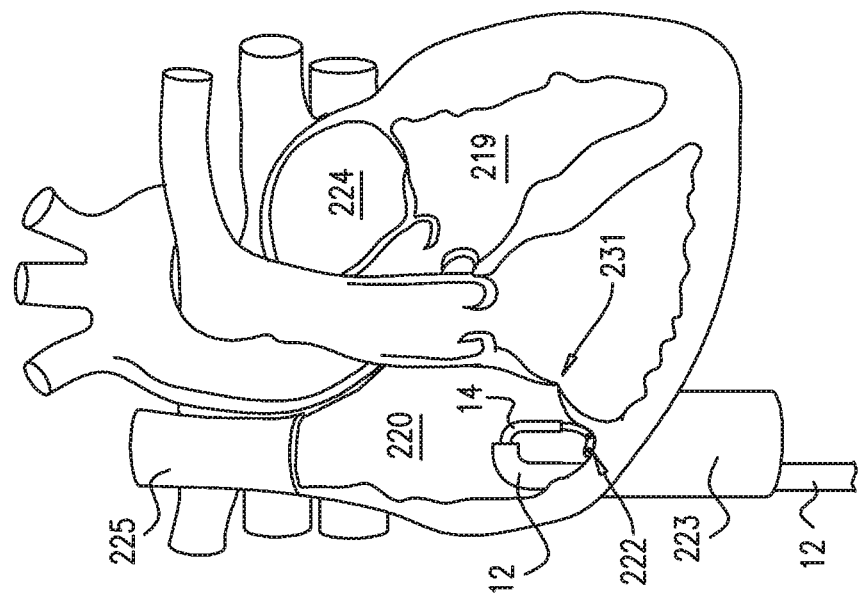
FIGS. 27A-B are schematic illustrations of respective systems and procedures for transluminally implanting an annuloplasty ring structure at a tricuspid valve, in accordance with some applications of the present invention.
Figure 27B:
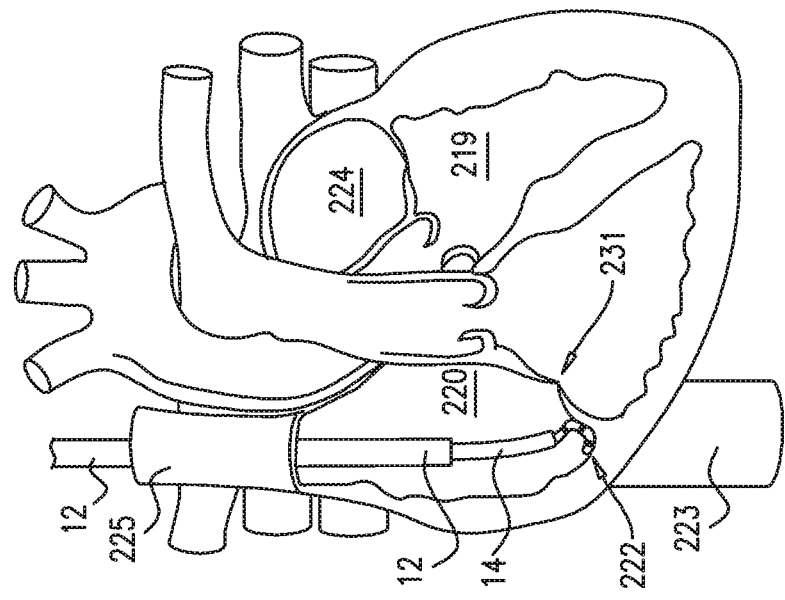

Reference is made to FIGS. 27A-B, which are schematic illustrations of respective systems and procedures for transluminally implanting annuloplasty ring structure at a tricuspid valve, in accordance with some applications of the invention. For some applications of the present invention, annuloplasty ring structure 222 is used to treat an atrioventricular valve other than the mitral valve, i.e., tricuspid valve 231, using system 10 in a similar method as described hereinabove with reference to FIGS. 10A-I, in accordance with some applications of the present invention.

For these applications, ring structure 222 and other components of system 10 described hereinabove as being placed in the left atrium are instead placed in the right atrium 220. For example, and as shown in FIG. 27A, right atrium 220 may be accessed via a superior vena cava 225 of the patient, e.g., via the subclavian vein, such as following access via the basilic vein or the external jugular vein. Alternatively, and as shown in FIG. 27B, right atrium 220 may be accessed via inferior vena cava 223, e.g., via a transfemoral approach.

For some applications in which structure 222 is implanted at tricuspid valve 231 via superior vena cava 225, catheter 12 is not significantly steered, and may in fact comprise a non-steerable catheter.

When structure 222 is implanted at tricuspid valve 231 via inferior vena cava 223, the distal end of catheter 12 is typically advanced to a position superior to the tricuspid valve, and catheters 12 and 14 are steered to provide a turn of at least 100 degrees (e.g., at least 120 degrees, such as at least 150 degrees) so as to face the valve annulus.

Although annuloplasty ring structure 222 is described hereinabove as being placed in an atrium, for some application the ring is instead placed in either the left or right ventricle.

Accordingly, it is noted that, annuloplasty ring structure 222 and other components of system 10 described hereinabove and methods shown in the application can be used on any cardiac valve (e.g., the mitral, tricuspid, aortic, and/or pulmonary).

Reference is now made to FIG. 28, which is a schematic illustration of a system 2100 used to implant annuloplasty ring structure 222 transapically, in accordance with some applications of the present invention. Catheters 12 and 14 are used to guide the implantation of structure 222 in a manner as described hereinabove with reference to FIGS. 10E-I, with the exception that catheters 12 and 14 are advanced through apex 218 and ventricle 219.

Catheter 12 is advanced into ventricle 219 via apex 218 (e.g., via a trocar 217, following transapical puncture using the trocar). Catheter 12 may be advanced only until it enters ventricle 219, may be advanced until it reaches mitral valve 230, or may be advanced into left atrium 224 (as shown in FIG. 28). For some applications in which a transapical approach is used, catheter 12 is not significantly steered, and may in fact comprise a non-steerable catheter.

Catheter 14 is advanced through catheter 12, and is steered such that the distal end thereof faces annulus 240 of the mitral valve. Such steering typically requires a bend of at least 100 degrees (e.g., at least 120 degrees, such as at least 150 degrees). For some applications, such bending is facilitated by steering of the distal end of catheter 12, disposed in atrium 224 (e.g., as shown in FIG. 28). For some applications in which catheter 12 is not steered and/or is not steerable, such bending is provided by catheter 14 alone. When implant structure is delivered transapically, the distal end of sleeve 26 may be anchored by the first anchor to tissue in a vicinity of right fibrous trigone 244 of the subject, or in a vicinity of a left fibrous trigone 242 of the subject.

It is to be noted that such a transapical approach may be used to implant structure 222 at the tricuspid valve, mutatis mutandis.

Reference is made to FIG. 29, which is a schematic illustration of a multi-component tubular system 3000 providing one or more rotationally-controlled steering catheters configured for delivering an implant to a heart of a patient, in accordance with some applications of the invention. System 3000 and components thereof are generally identical to system 10 and components thereof, described hereinabove, except where specifically noted. Typically, system 3000 is generally identical to system 10 except for a proximal handle portion 3001 of system 3000, which provides similar functionality to proximal handle portion 101 of system 10. The apparatus and methods described herein relating to system 10 are typically compatible with system 3000, mutatis mutandis.

Whereas FIG. 1 shows the proximal end of guide member 86 of system 10 exits the catheter system via a lateral wall of catheter 14 distal to handle 24, in system 3000, the proximal end of guide member 86 exits the catheter system via an opening 85 in handle 24.

Reference is made to FIGS. 30A-D, which are schematic illustrations of a telescopic introducer 3100, for facilitating introduction of catheter 14 and/or structure 222 into a proximal end of catheter 12, in accordance with some applications of the invention. Introducer 3100 comprises a first tubular member 3102, and a second tubular member 3104 which is slidably coupled to member 3102 such that introducer 3100 is telescopically extendable and compactable between an extended state and a compact state. Typically, first tubular member 3102 is slidable into second tubular member 3104.

First tubular member 3102 is configured to receive a distal end of catheter 14 containing at least part of structure 222. Typically, following the advancing of catheter 12 toward and into left atrium 224, catheter 14 is introduced into a proximal end of catheter 12 while structure 222 is disposed within a distal portion of catheter 14. Typically, at least a distal portion of structure 222 (e.g., adjusting mechanism 40) is disposed outside of the distal end of catheter 14 during this introduction. For applications of the invention in which guidewire 2244 is used, a distal portion of the guidewire is typically also disposed outside of the distal end of catheter 14. Introducer 3100 is configured to facilitate the introduction of catheter 14 and structure 222 into the proximal end of catheter 12, such as by protecting the distal portion of structure 222 (e.g., adjusting mechanism 40).

Typically, catheter 12 comprises at least one valve 3106 (e.g., a reed valve, a duckbill valve, or similar), configured to prevent blood from migrating from the heart of the subject, out of the proximal end of catheter 12 before catheter 14 and/or other components of system 10 are introduced into catheter 12. Typically, valve 3106 is configured to be openable by inserting (e.g., pushing) an element, such as catheter 14, distally through the valve such that sealing is maintained throughout the placing of the element in fluid communication with the blood of the subject. However, for some applications, it is advantageous to provide reinforcement during such insertion. For example, for applications in which catheter 14 is introduced with the distal portion of structure 222 exposed from the distal end thereof, it may be advantageous to protect the structure (e.g., adjusting mechanism 40 thereof) from being pushed against valve 3106. For applications in which guidewire 2244 is used, it may be advantageous to similarly protect the distal end of the guidewire.

Introducer 3100 (e.g., member 3102 thereof) comprises an O-ring 3108, configured to provide sealing around catheter 14. Catheter 14 is inserted into introducer 3100 prior to insertion of the introducer into catheter 12 (and thus prior to placing the catheter and the introducer in fluid communication with blood of the subject) (FIG. 30A). Therefore a valve that provides sealing throughout insertion of catheter 14 into introducer 3100 is typically not required. Typically therefore, O-ring 3108 advantageously (1) provides sufficient sealing, and (2) does not require pushing of structure 222 (e.g., adjusting mechanism 40 thereof) thereagainst.

Subsequently, a distal end of introducer 3100 (e.g., of member 3104 thereof) is inserted into catheter 12, typically pushing against and through valve 3106 (FIG. 30B). Valve 3106 is typically configured to seal around member 3104. It will be noted that (i) adjustment mechanism 40 and guidewire 2244 do not directly contact valve 3106, and (ii) only at this stage is catheter 14 in fluid communication with blood of the subject, and thus typically only at this stage is the sealing provided by O-ring 3108 required.

Subsequently, introducer 3100 is typically telescopically compacted, such that catheter 14 and structure 222 (and for some applications, guidewire 2244) slide through member 3104 and into catheter 12, typically while remaining stationary with respect to member 3102 (FIG. 30C). Subsequently, and as shown in FIG. 30D, catheter 14 and structure 222 are advanced further, to the heart of the subject, as described hereinabove.

In addition to the sliding described with respect to FIG. 30C, the telescopic nature of introducer 3100 allows the introducer, (1) while in the extended state, to contain (and thereby protect) portions of structure 222 and guidewire 2244 that are exposed from catheter 14, and (2) while in the compacted state, to fit between handles 22 and 24, e.g., as shown in FIG. 29.

Reference is made to FIGS. 31A-C, which are schematic illustrations of an annuloplasty ring structure 3222, comprising sleeve 26 and adjusting mechanism 40, in accordance with some applications of the invention. Structure 3222 is identical to structure 222, described hereinabove, except for where noted. Similarly, techniques described herein for use with structure 222 (e.g., sleeve 26 and/or mechanism 40 thereof) may be used with structure 3222 (e.g., sleeve 26 and/or mechanism 40 thereof). As described hereinabove (e.g., with reference to FIGS. 26A-C), for some applications it is advantageous to (1) advance the structure to the mitral valve while mechanism 40 is disposed on the longitudinal axis of sleeve 26 (e.g., collinearly with the sleeve), so as to maintain a small cross-sectional diameter of the structure for transluminal delivery; and (2) to subsequently move mechanism 40 away from the longitudinal axis, e.g., so as to allow distal end 251 of the sleeve to be placed against the annulus, and/or so as to allow an anchor to be driven through the distal end of the sleeve. Structure 222 facilitates this technique by mechanism 40 being flexibly and/or articulatably coupled to sleeve 26 (e.g., via suture). Structure 3222 also facilitates this technique, but in a different manner.

Adjustment mechanism 40 of structure 3222 is coupled to the lateral wall of sleeve 26 of structure 3222, as shown in FIG. 31C (which shows the adjustment mechanism and sleeve of structure 3222 in a similar juxtaposition to that of the adjustment mechanism and sleeve of structure 222 shown in FIG. 26B). For delivery of structure 3222, channel 18 is not disposed throughout the entire lumen of sleeve 26. Rather, a region 3224 (e.g., a distal region) of sleeve 26 is provided in which channel 18 is not disposed in the lumen of the sleeve, and mechanism 40 is pressed laterally into region 3224, such that the sleeve is compressed at region 3224, and mechanism 40 is disposed on the longitudinal axis of the sleeve (e.g., collinearly with the sleeve). Typically, region 3224 includes distal end 251 of sleeve 26. It is to be noted, however, that region 3224 may be provided at another position along the longitudinal axis of sleeve 26. Typically, mechanism 40 is fixedly coupled to the lateral wall of sleeve 26 at region 3224. In this state, structure 3222 is disposed within catheter 14 for delivery.

Structure 3222 is advanced out of catheter 14 as described hereinabove for structure 222. Once at least adjustment mechanism 40 and/or portion 3222 is exposed from catheter 14, the adjustment mechanism moves (e.g., translates) away from the longitudinal axis of sleeve 26 (e.g., laterally), typically by channel 18 being moved distally such that it pushes laterally the portion of the lateral wall of the sleeve to which the adjustment mechanism is coupled (FIG. 31B). FIG. 31C shows channel 18 having been moved all the way to distal end 251 of sleeve 26, and mechanism 40 having been moved away from the longitudinal axis of the sleeve, so as to allow the distal end of the sleeve to be placed against the annulus, and/or so as to allow an anchor to be driven through the distal end of the sleeve (e.g., as described with reference to FIG. 26C for structure 222, mutatis mutandis).

Figure 32B:
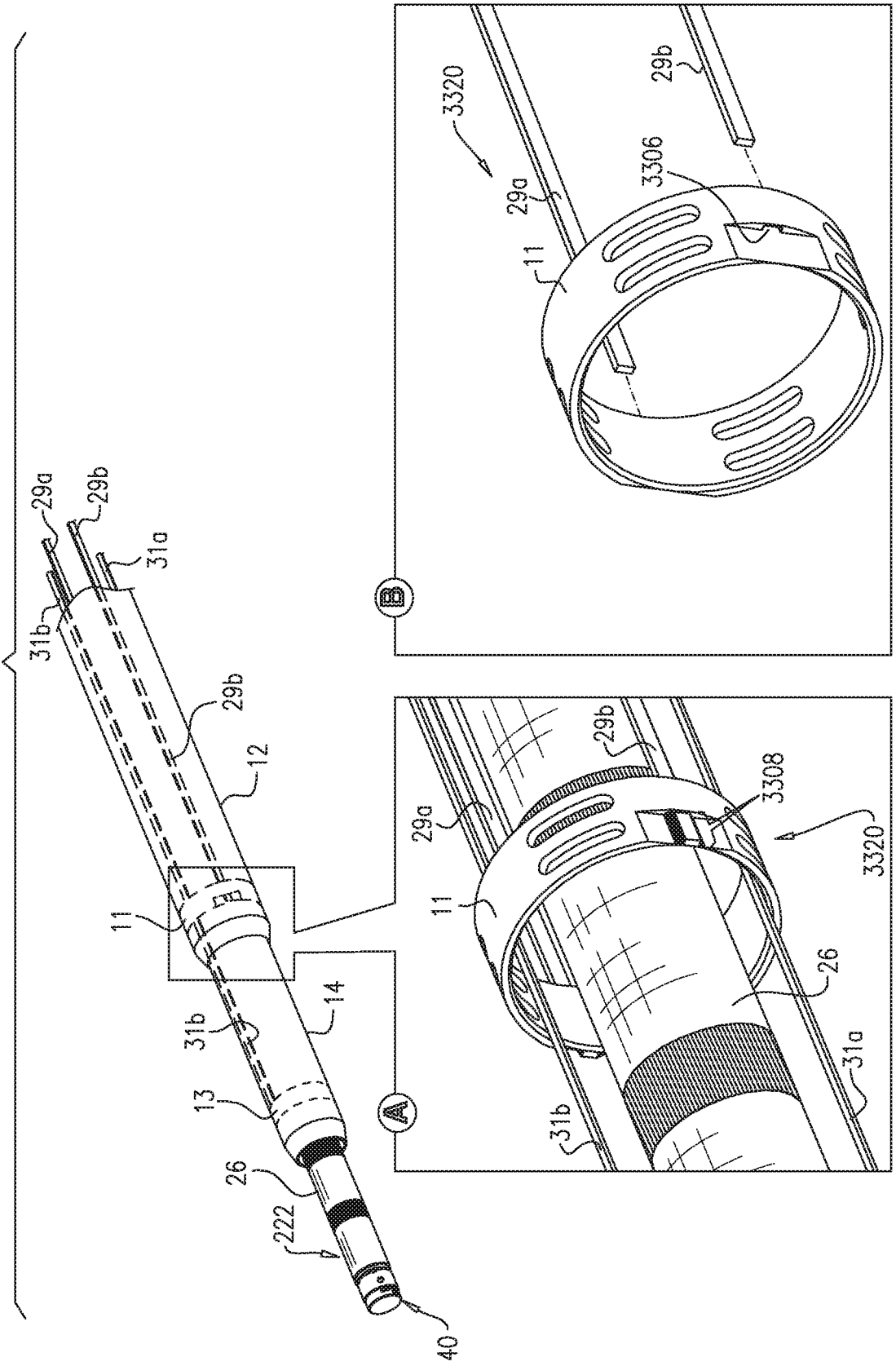

Reference is made to FIGS. 32A-B, which are schematic illustrations of systems 3300 and 3320, respectively, for coupling pull ring 11 of catheter 12 to pull wires 29a and 29b, in accordance with some applications of the invention. View A of FIG. 32A shows system 3300 with catheters 12 and 14 themselves removed (e.g., to illustrate the relative positioning of the pull ring and pull wires), and view B shows an exploded view of system 3300. As described hereinabove (e.g., with reference to FIGS. 1-2), pull ring 11 and pull wires 29a and 29b are disposed within catheter 12, and configured such that adjusting a degree of tension of the pull wires (e.g., by rotating knob 210) applies a force to the pull ring, which thereby steers the catheter (i.e., the distal end thereof). For example, increasing tension on pull wire 29a steers the catheter toward the side on which pull wire 29a is disposed.

Typically, the pull wires are coupled to the pull ring by welding. For some applications, the pull ring defines two or more receptacles, such as recesses 3304 in which a respective pull wire (e.g., a distal end thereof) is disposed, so as to increase the surface area of contact between the pull ring and the pull wire, and thereby to facilitate the coupling therebetween.

For some applications, and as shown in FIG. 32A, a the coupling of each pull wire to the pull ring is further facilitated (e.g., reinforced) by at least one cap 3302 (e.g., a respective cap, such as a cap 3302a and a cap 3302b). Cap 3302 bridges at least part of recess 3304, and thereby further holds the respective pull wire within the recess. Thus, each cap 3302 and ring 11 together form an opening through which pull wire 29 is disposed. Cap 3302 is typically welded to the pull ring, and further may also be welded to the pull wire. Typically, a distal end 3308 of each pull wire 29 is coupled (e.g., welded) to ring 11 distal to cap 3302. For some applications, a single cap is used for both pull wires 29. For example, a ring may be slid over the pull ring and guide wires, and thereby act as an annular cap for both pull wires.

It is hypothesized that system 3300 provides a strong coupling between the pull wires and the pull ring, and thereby advantageously facilitates the application of strong tensile forces by the pull wires on the pull ring, and/or a large angle of steering of the catheter. For example, cap 3302 may protect welding material that welds end 3308 to the pull ring from fatigue, e.g., by isolating end 3308 from bending experienced by more proximal portions of the pull wire.

System 3320, shown FIG. 32B, is generally identical to system 3300, and is used in generally the same way as system 3300, except where noted. In system 3320, pull ring 11 is shaped to define a respective receptacle, such as an opening 3306 therethrough for each guidewire 29. The respective guidewire is passed through the opening such that distal end 3308 is exposed distal to the opening. End 3308 is typically welded to the pull ring in this position, as described for system 3300, mutatis mutandis. Opening 3306 thereby effectively defines a cap and recess similar to cap 3302 and recess 3304 of system 3300, and/or has similar functionality thereto.

It is to be noted that systems 3300 and 3320 may be used to couple other pull wires to other pull rings, such as to couple pull wires 31a and 31b to pull ring 13, mutatis mutandis. It is to be further noted that, although FIGS. 32A-B shows the coupling wires being coupled to a recess in the outer surface of the pull ring, for some applications, the coupling wires are coupled to a recess in the inner surface of the pull ring.

With reference again to FIGS. 1-7B and 15A-D, reference is now made to FIG. 33, which is a schematic illustration of an adjustment mechanism 3400 for adjusting a relative axial position of catheter 14 with respect to catheter 12, in accordance with some applications of the invention. As described hereinabove (e.g., with reference to FIGS. 15A-D) locking system 1700 is configured to rotationally, and typically axially, lock catheters 12 and 14 by locking handles 22 and 24. Adjustment mechanism 3400 facilitates adjustment (e.g., fine-tuning) of the relative axial position of catheter 14 with respect to catheter 12 while the catheters are locked via locking system 1700. Adjustment mechanism 3400 typically comprises, or is associated with, locking system 1700 (described with reference to FIGS. 15A-D), or components thereof. For example, adjustment mechanism typically comprises a control wheel 3402 (or another controller) and protrusion 1724.

For clarity, the right-hand portion of each part (i.e., parts A, B and C) of FIG. 33 shows handle 24 decoupled from other elements of handle portion 101, such as handle 22, whereas the left-hand portion shows catheter 14 disposed within catheter 12 and extending out of distal end 102 thereof. It is to be understood (e.g., from descriptions hereinabove and hereinbelow) that, in reality, when catheters 12 and 14 are in such an arrangement, handle 22 is typically coupled to handle 24 (e.g., via system 1700 and/or mechanism 3400; e.g., via protrusion 1724 being coupled to housing 1702).

Control wheel 3402 facilitates adjustment of a distance between at least a portion of protrusion 1724 and another portion of handle 24, thereby facilitating adjustment of a distance between handle 24 and handle 22, while the handles are locked via system 1700. For example, (1) turning control wheel 3402 in a first direction may extend protrusion 1724 distally, thereby (a) increasing the distance between the handles, and (b) retract the distal portion of catheter 14 into the distal end of catheter 12, while (2) turning the control wheel in a second opposite direction may retract the protrusion proximally, thereby (a) reducing the distance between the handles, and (b) advancing the distal portion of catheter 14 out of the distal end of catheter 12. For some applications, adjustment mechanism 3400 further comprises an indicator 3404, such as a scale, that indicates a degree of axial adjustment of catheters 12 and 14 that has been provided by the adjustment mechanism. An illustrative example of when the adjustability provided by mechanism 3400 may be desirable is provided here:

As described hereinabove, at least a portion of the steerable distal end portion of catheter 14 is exposed from distal end 102 of catheter 12 and is thus free for steering toward the annulus of the mitral valve. Typically, this portion comprises exposed bending section 1403. When catheter 12 is bent (e.g., steered), the length of at least a portion of the catheter (e.g., the overall length of the catheter) may be reduced, e.g., due to compressive forces applied by proximal pulling of a pull-wire 29 (not visible in FIG. 33) in order to produce the bend. Thus, distal end 104 of catheter 14 is typically disposed further out of distal end 102 of catheter 12 when catheter 12 is bent, than when catheter 12 is straight (compare FIG. 33 part A to FIG. 33 part B).

For some applications, it is desirable to move distal end 104 of catheter 14 distally when catheter 12 is straight, such as to move and/or maintain portion 1403 out of distal end 102 of catheter 12 in order to facilitate steering of portion 1403. Alternatively or additionally, it may be desirable to move distal end 104 of catheter 14 distally when catheter 14 is bent (e.g., due to steering-induced shortening of catheter 14 as described hereinabove for catheter 12, mutatis mutandis).

FIG. 33 part A shows catheter 12 in a bent state; catheter 12 may be bent in this way during deployment of a first anchor 32 through sleeve 26, e.g., as described with reference to FIG. 10G. It is to be noted that in FIG. 33 part A, portion 1403 of catheter 14 is shown entirely exposed out of distal end 102 of catheter 12. FIG. 33 part B shows catheter 12 in a relatively straight state; catheter 12 may be in this state during deployment of a last anchor 32 through sleeve 26. It is to be noted that in FIG. 33 part B, a proximal part of portion 1403 of catheter 14 is shown disposed within catheter 12, due to lengthening of catheter 12 in the absence of pulling steering forces via pull-wires 29. For some applications, this may disadvantageously limit steerability of catheter 14, by catheter 12 restricting bending of portion 1403. Adjustment mechanism 3400 allows real-time advancement of catheter 14 (e.g., portion 1403 thereof) distally out of catheter 12. Thus, for some applications, adjustment mechanism 3400 may be used to compensate for the change, due to steering of the catheters, in the amount of catheter 14 that is exposed out of the distal end of catheter 12 (e.g., to facilitate maintenance of the amount of catheter 14 that is exposed out of the distal end of catheter 12).

Therefore, a method is provided in which (1) a steerable (e.g., bendable) distal portion of catheter 12 is advanced transluminally, (2) catheter 14 is advanced through catheter 12, such that at least part of portion 1403 is exposed from distal end 102 of catheter 12, (3) while the distal portion of catheter 12 is bent, an anchor (e.g., a first anchor) is driven through sleeve 26 and into the valve annulus, (4) the distal portion of catheter 12 is subsequently at least partly straightened, adjustment mechanism 3400 is used to move the distal end of catheter 14 distally away from the distal end of catheter 12, so as to expose more of portion 1403, and (6) another anchor (e.g., a final anchor) is subsequently driven through sleeve 26 and into the valve annulus.

Figure 34:
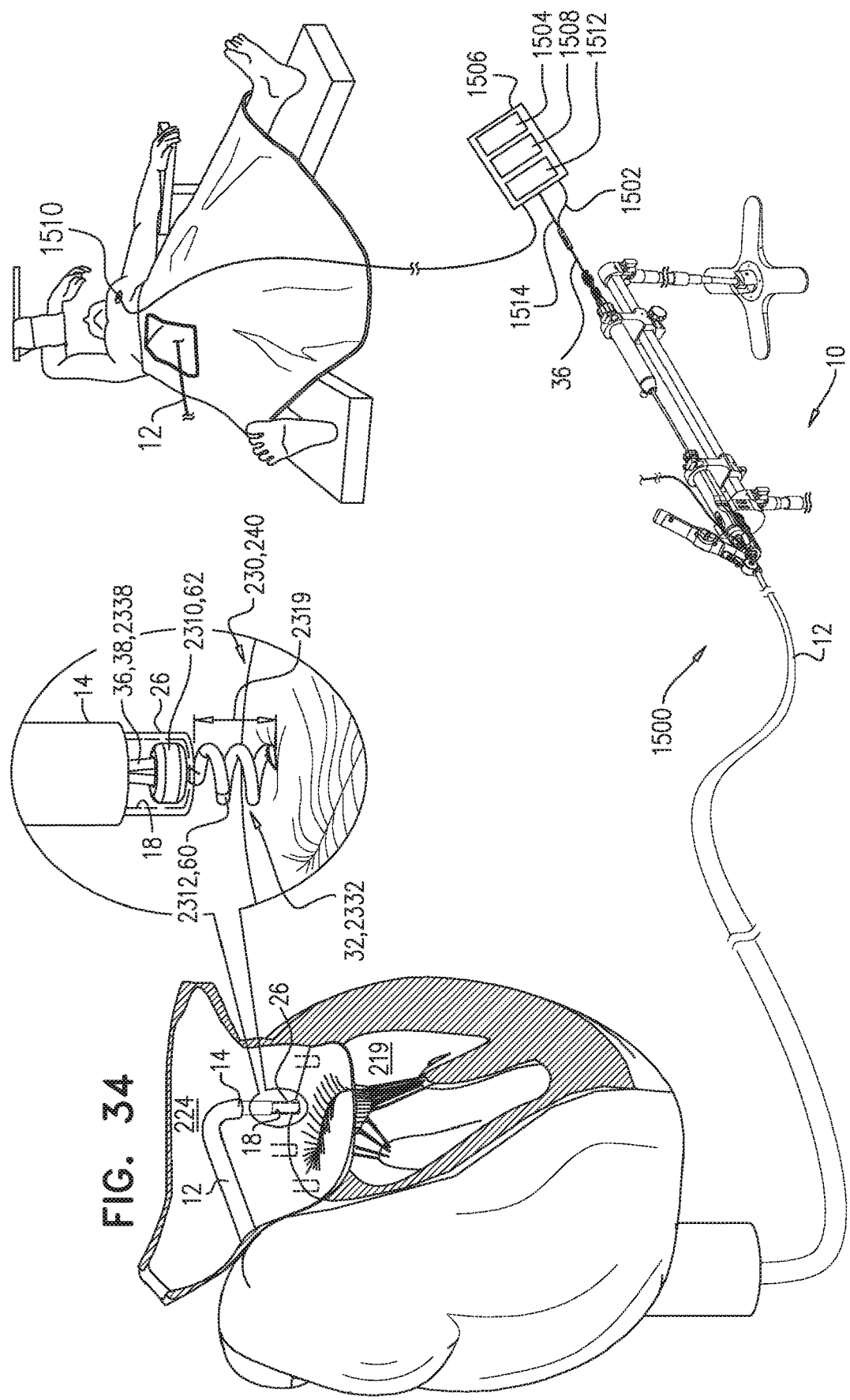
FIG. 34 is a schematic illustration of a guidance-based system which employs electrophysiological determining of the positioning of the distal end of a multi-component tubular system with respect to the annulus of the valve, in accordance with some applications of the present invention.

Reference is made to FIG. 34, which is a schematic illustration of a guidance-based system 1500 which employs electrophysiological determining of the positioning of the distal end of multi-component tubular system 10 (as described hereinabove with reference to FIGS. 1-3) with respect to the annulus of the valve, in accordance with some applications of the present invention.

System 1500 comprises a control unit 1506 that comprises a display 1504 and circuitry 1508. Control unit 1506 is electrically coupled to a distal portion of system 10. Typically, control unit 1506 is electrically coupled, via anchor driver 36, to a tissue anchor (e.g. tissue anchor 32 or tissue anchor 2332). Further typically, control unit 1506 is electrically coupled, via the anchor driver, to the tissue-engaging element of the tissue anchor (e.g., tissue-engaging element 60 or tissue-engaging element 2312). For example, control unit 1506 may be electrically coupled to anchor driver 36 via a wire 1502, and anchor driver 36 (including deployment element 38 thereof) may itself be electrically conductive, as may the coupling head of the tissue anchor (e.g., coupling head 62 or coupling head 2310). Alternatively or additionally, wire 1502 may extend from control unit 1506, through or alongside anchor driver 36 (e.g., within channel 18), to the tissue anchor.

Control unit 1506 is also electrically coupled to at least one electrode 1510 (e.g., an electrocardiographic electrode), which is typically configured to be placed on the skin of the subject (although alternatively may be configured to be placed internally).

System 1500 is configured to facilitate positioning of anchors prior at the native valve annulus. Control unit 1506 (e.g., circuitry 1508 thereof) is configured to receive electrical signals from the anchor and the electrode 1510, and responsively to the electrical signals, to provide information regarding the location of the anchor, via display 1504, to the operating physician. That is, the anchor acts as a second electrode.

It is to be noted that display 1504 may comprise a visual display (e.g., a screen), but may alternatively or additionally provide audio and/or tactile feedback.

For some applications, control unit 1506 is configured to receive electrophysiological signals (e.g., electrocardiographic signals). For some applications, control unit 1506 is configured to receive artificial signals (e.g., to apply an electrical signal via the electrode and to detect the signal via the tissue anchor, and/or vice versa).

As described hereinabove with reference to FIGS. 18A-C, tissue anchor 2332 is configured (e.g., by comprising proximal stem portion 2314) to allow tissue-engaging element 2312 to engage cardiac tissue while protruding from sleeve 26, and for the resulting gap between the sleeve and the tissue to be subsequently closed when the anchor is driven into the tissue. To facilitate the electrical guidance techniques described with reference to FIG. 34, it is typically advantageous to advance the tissue-engaging element of the tissue anchor through sleeve 26, so that the tissue-engaging element can be placed in direct electrical contact with tissue of the subject. It is therefore hypothesized that tissue anchor 2332 facilitates such navigation techniques by facilitating such advancement of the tissue-engaging element (i.e., tissue-engaging element 2312) through sleeve 26 prior to engaging the tissue with the tissue-engaging element. Tissue-engaging element 2312 is shown as having been advanced through sleeve 26 and placed in contact with tissue (e.g., annulus 240). It is to be noted that gap 2319 (described with reference to FIGS. 18A-C) exists between sleeve 26 and tissue 5.

Therefore, a method is described in which: (1) electrode 1510 is placed in contact with a first anatomical site of a subject; (2) a portion of sleeve 26 (e.g., with tissue anchor 2332 disposed therethrough) is advanced toward a second anatomical site of the subject (e.g., within the heart of the subject); (3) control unit 1506 (e.g., circuitry 1508 thereof) detects the electrical signal and provides, via display 1504, an indication of the location of the anchor; (4) in response to the indication, the operating physician moves the portion of the sleeve and the anchor to another (e.g., a third) anatomical site of the subject (e.g., within the heart of the subject); (5) detection of the electrical signal and indication of the position are performed again; (6) in response to the second detection of step 5, the operating physician anchors the portion of the sleeve by driving the tissue anchor into tissue at the third anatomical site.

Subsequent to the anchoring of the portion of the sleeve, anchor driver 36 is mechanically and electrically decoupled from the tissue anchor. Typically, the above procedure is repeated for more than one anchor (e.g., for all the anchors) during implantation of annuloplasty ring structure 222.

It is to be noted that, in contrast to implantable electrodes that are configured to conduct current to and/or from tissue for extended periods of time, and which typically comprise a noble metal and/or an inert coating, anchors 32 and/or 2332 typically comprise stainless steel, which provides mechanical strength, but typically becomes tarnished and less conductive over time.

Regarding steps 3 and 4 above, the operating physician typically moves the anchor to another anatomical site when it is determined that the anchor is in an undesired location. For example, the electrical signal may indicate that the tissue-engaging element of the anchor is not in direct contact with solid tissue.

For some applications, the electrical signal is indicative of a position, in contact with solid tissue, of the anchor. For example, a relative intensity between (i) electrical activity associated with atrial depolarization and/or repolarization, and (ii) electrical activity associated with ventricular depolarization and/or repolarization, may be interpreted by control unit 1506 as a position of the anchor with respect to the atrium and the ventricle (e.g., a position of the anchor on an atrial-ventriclar axis).

For some applications, rather than the tissue anchor acting as a electrode through which the electrical signal is received, channel 18 may act as the electrode by being electrically coupled to control unit 1506. It is to be noted that for such applications, the electrical signal is typically detected through sleeve 26.

For some applications, control unit 1506 further comprises an electric motor 1512, and is configured to drive (e.g., rotate) anchor driver 36, such as in response to the detected electronic signal. For example, control unit 1506 may be mechanically coupled to driver 36 via a shaft 1514. Although wire 1502 and shaft 1514 are shown as distinct, separate elements, wire 1502 may be coupled to or integrated with shaft 1514, or shaft 1514 may itself be conductive, and may act as wire 1502.

Although motor 1512 is shown as an integrated component of control unit 1506, it may alternatively or additionally be used with torque-limiting apparatus described hereinabove (e.g., with reference to FIGS. 21-25E). For example, circuitry 1508 may be configured to receive torque and/or rotation information, and to responsively drive motor 1512 to drive driver 36, e.g., automatically providing some or all of the functions described with reference to FIGS. 21-25E as being performed by the operating physician, mutatis mutandis. Similarly, control unit 1506 may be configured to automatically drive motor 1512 responsively to a temporary electrocardiographic abnormality and/or an absence thereof, e.g., thereby automating at least part of the method described hereinbelow with reference to FIG. 36, mutatis mutandis. Alternatively, motor 1512 may be used independently of torque-limiting apparatus or electrophysiological guidance.

For some applications, control unit 1506 detects anchoring strength by providing a proximal pulling force to driver 36, e.g., providing functionality described hereinabove for gauge 2800.

Reference is made to FIGS. 35A-C, which are schematic illustrations of a technique for sizing before implantation of an adjustable annuloplasty structure 2550, in accordance with some applications of the invention. For illustration, FIGS. 39A-C use the example of mitral valve 230 of the patient, but the scope of the present invention includes the repair of other valves of the patient, mutatis mutandis. Annuloplasty structure 2550 may comprise any of the annuloplasty structures described herein, or another adjustable annuloplasty structure.

Using one or more imaging techniques known in the art (e.g., fluoroscopy, transesophageal echo, and/or echocardiography), the circumference 2552 around the posterior portion of annulus 2240 (e.g., the portion of the annulus to which posterior leaflet 2246*p* is attached), is measured (FIG. 35A). That is, the circumference of the posterior portion of annulus 2240 is measured in the diseased state of the valve. The circumference is typically measured around the posterior annulus, between sites in the vicinity of respective commissures and/or respective fibrous trigones (the sites are labeled A and B in FIG. 35A). According to the measured circumference, an annuloplasty structure 2550 is selected. Typically, an annuloplasty structure is selected that has an uncontracted length that is generally similar to (e.g., within 30 percent of, e.g., within 10 percent of, such as equal to) the measured circumference. The annuloplasty structure is subsequently implanted and adjusted (e.g., contracted), so as to repair the valve (FIGS. 35B and 35C, respectively).

It is to be noted that, whereas some techniques known in the art comprise selecting an annuloplasty structure based on a target (e.g., desired, calculated, and/or physiological) circumference of the posterior portion of the annulus, applications of the present invention comprise selecting an annuloplasty structure based on an existing (e.g., pathological) circumference of the annulus or a portion thereof (e.g., a posterior portion of the annulus).

Reference is made to FIG. 36, which is a flow chart of at least some steps in a method for use with an implant, such as annuloplasty ring structure 222, and a tissue anchor for anchoring the implant, in accordance with some applications of the invention. Electrocardiography of the subject during implantation of structure 222 has resulted in the observation, by the inventors, that when a tissue anchor is driven through sleeve 26 and into tissue of the subject, a temporary electrocardiographic change, e.g., an abnormality, such as a premature impulse (e.g., a premature ventricular contraction (PVC) and/or a premature atrial contraction (PAC)), typically occurs. The electrocardiographic change typically occurs when while the tissue anchor is placed in contact with the tissue or driven into the tissue, or shortly thereafter (e.g., within 5 seconds and/or 5 heartbeats of the driving of the anchor). It is hypothesized that the PVC is initiated by, and indicative of, the distal end of the tissue-engaging element of the tissue anchor penetrating heart muscle tissue (e.g., of the ventricle) after having passed all the way through the annulus. It is further hypothesized that an absence of the abnormality (e.g., the PVC) at the time of anchoring a tissue anchor is indicative of the tissue-engaging element not having penetrated the heart muscle tissue. For some applications it is advantageous for the distal end of the tissue-engaging element to pass all the way through the annulus.

Therefore a method 400 is described in which:

(1) A tissue anchor is advanced through channel 18 and into the lumen of sleeve 26, e.g., as described hereinabove, mutatis mutandis (step 402).

(2) The tissue anchor is driven, from the lumen of the sleeve, through the fabric of the sleeve, and into a site of tissue of the heart of the subject (e.g., into the annulus), e.g., as described hereinabove, mutatis mutandis (step 404).

(3) An electrocardiographic signal is observed (step 406).

(4a) If a temporary electrocardiographic abnormality (e.g., a PVC) is observed (step 410), the anchor driver is decoupled from the tissue anchor (step 412) and withdrawn from the implant, and for some applications another tissue anchor is subsequently advanced into the lumen of the sleeve (step 414; optional, and therefore shown with broken line).

(4b) If the temporary electrocardiographic abnormality is not observed (step 410), the tissue anchor is moved with respect to the tissue of the heart (step 416). For example, the tissue anchor may be driven deeper into the original tissue site, or may be withdrawn (e.g., de-anchored) from the original tissue site, and driven into another tissue site.

Typically, observation step 406 is performed generally at the same time as tissue anchor driving step 404; this is indicated by the grouping of steps 404 and 406 within box 408.

It is to be noted that, although method 400 is described as a sequence of steps and/or actions, the operating physician may take into account factors other than the temporary electrocardiographic abnormality, and may choose to perform a different action to that described hereinabove. That is, the operating physician may use the presence or absence of the temporary electrocardiographic abnormality as an indicator (e.g., as one of a plurality of indicators) of anchoring quality. For example, the operating physician may choose to move the anchor despite observing a PVC, or may choose to decouple the anchor driver from the anchor despite not observing a PVC.

It is to be noted that tissue anchor 2332, described hereinabove with reference to FIGS. 18A-C, may advantageously facilitate method 400 because, as described with reference to FIG. 18C, anchor 2332 facilitates (1) withdrawal of tissue-engaging element 2312 thereof from tissue without withdrawal of the tissue-engaging element from sleeve 26, and (2) subsequent driving of the tissue-engaging element into another tissue site.

Reference is again made to FIGS. 1-36. It is to be noted that following implantation of the annuloplasty structures described herein, the dimensions of the annuloplasty structures may be adjusted remotely and while the patient is not on a cardio-pulmonary bypass pump (i.e., with a beating heart), under fluoroscopy and/or echo guidance.

It is to be further noted that systems 10, 1500, 1600, 1700, 2600, and 3000, and catheters 12, 14, 1012 and 1014 may be advanced using (1) a trans-septal procedure in which the system is advanced through vasculature of the patient at any suitable access location (e.g., femoral vein), (2) a minimally-invasive transapical approach (as shown in FIG. 28), (3) a minimally-invasive transatrial approach (e.g., an intercostal approach), or (4) a surgical, open-heart approach. Furthermore, for some applications, the systems described herein are not steerable and may comprise straight elements (e.g., in a surgical, open-heart procedure).

It is to be further noted that systems 10, 1500, 1600, 1700, 2600, and 3000, and catheters 12, 14, 1012, and 1014 for repairing a dilated annulus of the patient may be used to treat any cardiac valve of the patient, e.g., the aortic valve, the pulmonary valve, the mitral valve, and the tricuspid valve. It is to be still further noted that systems described herein for treatment of valves may be used to treat other annular muscles within the body of the patient. For example, the systems described herein may be used in order to treat a sphincter muscle within a stomach of the patient.

It is further noted that the scope of the present invention includes the use systems 10, 1500, 1600, 1700, 2600, and 3000, and catheters 12, 14, 1012, and 1014 (or subcomponents thereof) and methods described hereinabove on any suitable tissue of the patient (e.g., stomach tissue, urinary tract, and prostate tissue).

Reference is again made to FIGS. 1-36. It is to be noted that any sleeve 26 shown in any of the figures shown herein may be used with any one of the systems described herein.

Reference is again made to FIGS. 1-36. It is to be noted that the rotational position of coupling 152 with respect to catheter 12 and the steering plane thereof, and the rotational position of coupling 154 with respect to catheter 14 and the steering plane thereof, are shown in various figures by way of illustration and not limitation.

Additionally, the scope of the present invention includes applications described in one or more of the following:

- U.S. patent application Ser. No. 12/435,291 to Maisano et al., entitled, "Adjustable repair chords and spool mechanism therefor," filed on May 4, 2009, which published as US Patent Application Publication 2010/0161041, which issued as U.S. Pat. No. 8,147,542;
- U.S. patent application Ser. No. 12/437,103 to Zipory et al., entitled, "Annuloplasty ring with intra-ring anchoring," filed on May 7, 2009, which published as US Patent Application Publication 2010/0286767, which issued as U.S. Pat. No. 8,715,342;
- U.S. patent application Ser. No. 12/548,991 to Maisano et al., entitled, "Implantation of repair chords in the heart," filed on Aug. 27, 2009, which published as US Patent Application Publication 2010/0161042, which issued as U.S. Pat. No. 8,808,368;
- PCT Patent Application PCT/IL2009/001209 to Cabiri et al., entitled, "Adjustable annuloplasty devices and mechanisms therefor," filed on Dec. 22, 2009, which published as PCT Publication WO 10/073246;
- PCT Patent Application PCT/IL2010/000357 to Maisano et al., entitled, "Implantation of repair chords in the heart," filed on May 4, 2010, which published as WO 10/128502;
- PCT Patent Application PCT/IL2010/000358 to Zipory et al., entitled, "Deployment techniques for annuloplasty ring and over-wire rotation tool," filed on May 4, 2010, which published as WO 10/128503; and/or
- PCT Patent Application PCT/IL2012/050451 to Sheps et al., entitled, "Controlled steering functionality for implant-delivery tool," filed on Nov. 8, 2012, which published as WO 2013/069019.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A system, comprising:
   an implant, comprising a tissue anchor comprising:
      a coupling head, and
      a distal helical tissue-engaging element,
   a multi-component tubular system:
      comprising:
         a catheter, and
         a channel, slidable within the catheter, the tissue anchor being slidable through the channel,
      transluminally advanceable into a heart of a subject, and
      configured to deliver the implant inside the heart;
   an anchor driver having a distal end that is reversibly couplable to the coupling head of the tissue anchor in a manner that configures the anchor driver to:
      drive the tissue anchor through the multi-component tubular system and out of a distal end of the multi-component tubular system, and
      anchor the distal helical tissue-engaging element to tissue of the heart;
   a first electrode configured to contact the subject;
   a second electrode configured to be positioned inside the heart of the subject; and
   a control unit electrically coupled to the first electrode and the second electrode, the control unit comprising a display and circuitry configured, while the first electrode is in contact with the subject and the second electrode is inside the heart of the subject, to:
      receive an electrical signal from the first electrode and the second electrode, and
      based on the electrical signal, provide, via the display, information indicative of a position of the second electrode inside the heart;
   wherein the channel is electrically coupled to the control unit such that the channel provides the second electrode.

2. The system of claim 1, wherein the distal helical tissue-engaging element of the tissue anchor is electrically-conductive and electrically coupled to the control unit, such that the tissue anchor serves as the second electrode.

3. The system of claim 2, wherein the coupling head is electrically conductive and electrically coupled to the distal helical tissue-engaging element.

4. The system of claim 3, wherein the anchor driver is electrically conductive and has a proximal end, and the distal end of the anchor driver is mechanically and electrically couplable to and decouplable from the coupling head, wherein the control unit is couplable to the distal helical tissue-engaging element via the coupling head and the anchor driver.

5. The system of claim 3, wherein the tissue anchor further comprises a stem portion that couples the distal helical tissue-engaging element to the coupling head, and that is collinear with a central longitudinal axis of the distal helical tissue-engaging element.

6. The system of claim 5, wherein:
the implant comprises a sleeve shaped to define a lumen therethrough,
the distal helical tissue-engaging element is configured to be screwed through the sleeve from the lumen such that at least a portion of the distal helical tissue-engaging element is (i) disposed outside of the lumen, and (ii) configured to be placed in contact with the tissue of the heart while (a) the coupling head is disposed within the lumen, and (b) a gap exists between the sleeve and the tissue,
the control unit is configured to receive the electrical signal while the at least the portion of the distal helical tissue-engaging element is in contact with the tissue and the coupling head is disposed within the lumen, and
the tissue anchor is configured to be subsequently screwed, by the anchor driver, into the tissue, and to responsively reduce the gap.

7. The system of claim 1, wherein the control unit is configured to receive artificial electrical signals, wherein an artificial electrical signal is applied via one of the first and second electrodes and detected via the other of the first and second electrodes.

8. The system of claim 1, further comprising an electric motor configured to drive the anchor driver.

9. The system of claim 8, wherein the control unit is configured to drive the anchor driver in response to the electrical signal received.

10. The system of claim 1, wherein the control unit is configured to detect an anchoring strength of the tissue anchor to the tissue of the heart by providing a proximal pulling force to the anchor driver.

11. The system of claim 1, wherein the control unit is further configured to provide feedback responsively to the position of the second electrode inside the heart, the feedback being selected from the group consisting of: audio feedback and tactile feedback.

12. A system, comprising:
a multi-component tubular system transluminally advanceable into a heart of a subject;
a first electrode configured to contact skin of the subject;
an implant, usable to change a shape of an annulus of a valve of the heart, and comprising:
a contraction wire, and
a tissue anchor comprising a coupling head and an electrically-conductive helical tissue-engaging element, wherein the tissue anchor is configured to act as a second electrode;
an anchor driver having a distal end that is reversibly couplable to the tissue anchor and configured to advance the tissue anchor through the multi-component tubular system and out of a distal end of the multi-component tubular system, and to anchor the distal helical tissue-engaging element to tissue inside the heart;
a first radiopaque marker, movable with respect to the tissue anchor and the anchor driver;
a second radiopaque marker, movable with the tissue anchor, the anchor driver, the implant, and the first radiopaque marker; and
a control unit electrically coupled to the first electrode and the tissue anchor, the control unit comprising circuitry configured, while the first electrode is in contact with the subject and the tissue anchor is located inside the heart of the subject, to receive an electrical signal from the first electrode and the tissue anchor, and provide information indicative of a location of the tissue anchor inside the heart based on the electrical signal.

13. The system of claim 12, wherein the anchor driver is electrically-conductive and the distal end of the anchor driver is mechanically and electrically couplable to and decouplable from the coupling head, and wherein the control unit is couplable to the distal helical tissue-engaging element via the coupling head and the anchor driver.

14. The system of claim 12, further comprising a first constraining member configured to engage the tissue and inhibit movement of at least a distal end of the anchor driver, along a first axis between (1) the distal end of the anchor driver, and (2) a site at which the first constraining member engages the tissue of the subject; and a second constraining member configured to inhibit movement of at least the distal end of the anchor driver, along a second axis that is different from the first axis.

15. The system of claim 12, wherein the multi-component tubular system comprises:
a first catheter having a steerable distal end portion, and comprising a first coupling at a longitudinal site of the first catheter, configured to be advanced transluminally into a subject; and
a second catheter having a steerable distal end portion configured to be advanced through the first catheter in any rotational orientation of the second catheter with respect to the first catheter, and to be advanced out of a distal end of the first catheter, the second catheter comprising a second coupling at a longitudinal site of the second catheter, the second coupling being configured to be advanced through the first catheter to the first coupling, and to be automatically intracorporeally locked to the first coupling upon the second catheter assuming a given rotational and longitudinal alignment with respect to the first catheter, the first coupling and the second coupling defining a distal locking mechanism having:
an unlocked state in which the first coupling is not locked to the second coupling, and in which the second catheter is rotatable and longitudinally slidable within the first catheter, and
a locked state in which the first coupling is locked to the second coupling, and in which the longitudinal site of the second catheter is (1) inhibited from rotating with respect to the longitudinal site of the first catheter, and (2) longitudinally slidable with respect to the longitudinal site of the first catheter.

16. The system of claim 12, further comprising:
an implant structure configured to treat a native atrioventricular valve of a patient, the implant structure comprising a sleeve having a lumen and at least a proximal end, the proximal end being shaped so as to define an opening; and a closure element coupled to the implant structure in a vicinity of the at least one end, the closure element comprising a flap having (1) an open state and (2) a closed state in which the lumen is in reduced fluid communication with outside of the implant structure compared to when the flap is in the open state, and configured to be biased toward assuming the closed state.

17. The system of claim 12, further comprising a tool comprising a distal portion that is couplable to a proximal end of the anchor driver, a proximal portion, and a variable-resistance mechanism; wherein the proximal portion is rotatably coupled to the distal portion and has a rest rotational position with respect to the distal portion; and wherein the variable-resistance mechanism is configured to progressively inhibit rotation of the proximal portion with respect to the distal portion, correspondingly with a rotational distance, from the rest rotational position, of the proximal portion with respect to the distal portion.

18. The system of claim 1, wherein the first electrode is configured to contact skin of the subject.

19. A system, comprising:
   an implant, comprising a tissue anchor comprising:
      a coupling head, and
      a distal helical tissue-engaging element,
   a multi-component tubular system:
      comprising:
         a catheter, and
         a channel, slidable within the catheter, the tissue anchor being slidable through the channel,
      transluminally advanceable into a heart of a subject, and
      configured to deliver the implant inside the heart;
   an anchor driver having a distal end that is reversibly couplable to the coupling head of the tissue anchor;
   an electric motor configured to drive the anchor driver to:
      drive the tissue anchor through the multi-component tubular system and out of a distal end of the multi-component tubular system, and
      anchor the distal helical tissue-engaging element to tissue of the heart;
   a first electrode configured to contact the subject;
   a second electrode configured to be positioned inside the heart of the subject; and
   a control unit electrically coupled to the first electrode and the second electrode, the control unit comprising a display and circuitry configured, while the first electrode is in contact with the subject and the second electrode is inside the heart of the subject, to:
      receive an electrical signal from the first electrode and the second electrode, and
      based on the electrical signal:
         provide, via the display, information indicative of a position of the second electrode inside the heart, and
         via the electric motor, drive the anchor driver.

20. The system according to claim 19, wherein the control unit is configured to receive artificial electrical signals, wherein an artificial electrical signal is applied via one of the first and second electrodes and detected via the other of the first and second electrodes.

21. The system according to claim 19, wherein the control unit is configured to detect an anchoring strength of the tissue anchor to the tissue of the heart by providing a proximal pulling force to the anchor driver.

22. The system according to claim 19, wherein the first electrode is configured to contact skin of the subject.

23. A system, comprising:
   a multi-component tubular system transluminally advanceable into a heart of a subject;
   a first electrode configured to contact skin of the subject;
   an implant configured to treat a native atrioventricular valve of a patient by changing a shape of an annulus of a valve of the heart, and comprising:
      a sleeve having a lumen and at least a proximal end, the proximal end being shaped so as to define an opening,
      a closure element coupled to the sleeve in a vicinity of at least one end, the closure element comprising a flap having (1) an open state and (2) a closed state in which the lumen is in reduced fluid communication with outside of the sleeve compared to when the flap is in the open state, and configured to be biased toward assuming the closed state,
      a contraction wire, and
      a tissue anchor comprising a coupling head and an electrically-conductive helical tissue-engaging element, wherein the tissue anchor is configured to act as a second electrode;
   an anchor driver having a distal end that is reversibly couplable to the tissue anchor and configured to advance the tissue anchor through the multi-component tubular system and out of a distal end of the multi-component tubular system, and to anchor the distal helical tissue-engaging element to tissue inside the heart; and
   a control unit electrically coupled to the first electrode and the tissue anchor, the control unit comprising circuitry configured, while the first electrode is in contact with the subject and the tissue anchor is located inside the heart of the subject, to receive an electrical signal from the first electrode and the tissue anchor, and provide information indicative of a location of the tissue anchor inside the heart based on the electrical signal.

24. The system of claim 23, wherein the anchor driver is electrically-conductive and the distal end of the anchor driver is mechanically and electrically couplable to and decouplable from the coupling head, and wherein the control unit is couplable to the distal helical tissue-engaging element via the coupling head and the anchor driver.

25. The system of claim 23, further comprising a first constraining member configured to engage the tissue and inhibit movement of at least a distal end of the anchor driver, along a first axis between (1) the distal end of the anchor driver, and (2) a site at which the first constraining member engages the tissue of the subject; and a second constraining member configured to inhibit movement of at least the distal end of the anchor driver, along a second axis that is different from the first axis.

26. The system of claim 23, wherein the multi-component tubular system comprises:
   a first catheter having a steerable distal end portion, and comprising a first coupling at a longitudinal site of the first catheter, configured to be advanced transluminally into a subject; and
   a second catheter having a steerable distal end portion configured to be advanced through the first catheter in any rotational orientation of the second catheter with respect to the first catheter, and to be advanced out of a distal end of the first catheter, the second catheter comprising a second coupling at a longitudinal site of the second catheter, the second coupling being configured to be advanced through the first catheter to the first coupling, and to be automatically intracorporeally locked to the first coupling upon the second catheter assuming a given rotational and longitudinal alignment with respect to the first catheter, the first coupling and the second coupling defining a distal locking mechanism having:
- an unlocked state in which the first coupling is not locked to the second coupling, and in which the second catheter is rotatable and longitudinally slidable within the first catheter, and
- a locked state in which the first coupling is locked to the second coupling, and in which the longitudinal site of the second catheter is (1) inhibited from rotating with respect to the longitudinal site of the first catheter, and (2) longitudinally slidable with respect to the longitudinal site of the first catheter.

27. The system of claim 23, further comprising a tool comprising a distal portion that is couplable to a proximal end of the anchor driver, a proximal portion, and a variable-resistance mechanism; wherein the proximal portion is rotatably coupled to the distal portion and has a rest rotational position with respect to the distal portion; and wherein the variable-resistance mechanism is configured to progressively inhibit rotation of the proximal portion with respect to the distal portion, correspondingly with a rotational distance, from the rest rotational position, of the proximal portion with respect to the distal portion.

28. A system, comprising:
an implant, comprising a tissue anchor comprising:
  a coupling head, and
  a distal helical tissue-engaging element,
a multi-component tubular system:
  comprising:
    a catheter, and
    a channel, slidable within the catheter, the tissue anchor being slidable through the channel, transluminally advanceable into a heart of a subject, and
  configured to deliver the implant inside the heart;
an anchor driver having a distal end that is reversibly couplable to the coupling head of the tissue anchor in a manner that configures the anchor driver to:
  drive the tissue anchor through the multi-component tubular system and out of a distal end of the multi-component tubular system, and
  anchor the distal helical tissue-engaging element to tissue of the heart;
a first electrode configured to contact the subject;
a second electrode configured to be positioned inside the heart of the subject; and
a control unit electrically coupled to the first electrode and the second electrode, the control unit comprising a display and circuitry configured, while the first electrode is in contact with the subject and the second electrode is inside the heart of the subject, to:
  receive an electrical signal from the first electrode and the second electrode, and
  based on the electrical signal, provide, via the display, information indicative of a position of the second electrode inside the heart;
wherein the control unit is further configured to provide feedback responsively to the position of the second electrode inside the heart, the feedback being selected from the group consisting of: audio feedback and tactile feedback.

29. The system of claim 28, wherein the control unit is configured to receive artificial electrical signals, wherein an artificial electrical signal is applied via one of the first and second electrodes and detected via the other of the first and second electrodes.

30. The system of claim 28, wherein the control unit is configured to detect an anchoring strength of the tissue anchor to the tissue of the heart by providing a proximal pulling force to the anchor driver.

31. The system of claim 28, wherein the first electrode is configured to contact skin of the subject.

* * * * *